United States Patent
Muehlebach et al.

(10) Patent No.: US 10,494,366 B2
(45) Date of Patent: *Dec. 3, 2019

(54) PESTICIDALLY ACTIVE AMIDE HETEROCYCLIC DERIVATIVES WITH SULPHUR CONTAINING SUBSTITUENTS

(71) Applicant: Syngenta Participations AG, Basel (CH)

(72) Inventors: Michel Muehlebach, Stein (CH); Andrew Edmunds, Stein (CH); Andre Jeanguenat, Stein (CH); Pierre Joseph Marcel Jung, Stein (CH); Peter Renold, Stein (CH); Ottmar Franz Hueter, Stein (CH)

(73) Assignee: SYNGENTA PARTICIPATIONS AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 15/531,638

(22) PCT Filed: Nov. 24, 2015

(86) PCT No.: PCT/EP2015/077417
§ 371 (c)(1),
(2) Date: May 30, 2017

(87) PCT Pub. No.: WO2016/087257
PCT Pub. Date: Jun. 9, 2016

(65) Prior Publication Data
US 2018/0327398 A1 Nov. 15, 2018

(30) Foreign Application Priority Data
Dec. 1, 2014 (EP) .................... 14195573

(51) Int. Cl.
*A01N 43/82* (2006.01)
*C07D 417/12* (2006.01)
*C07D 213/75* (2006.01)
*C07D 213/79* (2006.01)
*C07D 213/82* (2006.01)
*C07D 285/135* (2006.01)
*C07D 401/12* (2006.01)
*C07D 401/14* (2006.01)
*C07D 417/14* (2006.01)

(52) U.S. Cl.
CPC ........ *C07D 417/12* (2013.01); *A01N 43/82* (2013.01); *C07D 213/75* (2013.01); *C07D 213/79* (2013.01); *C07D 213/82* (2013.01); *C07D 285/135* (2013.01); *C07D 401/12* (2013.01); *C07D 401/14* (2013.01); *C07D 417/14* (2013.01)

(58) Field of Classification Search
None
See application file for complete search history.

(56) References Cited

U.S. PATENT DOCUMENTS

2008/0312435 A1 12/2008 Saito

FOREIGN PATENT DOCUMENTS

| CN | 102367240 B | 6/2014 |
|---|---|---|
| EP | 2595981 A1 | 5/2013 |
| WO | 02092584 A1 | 11/2002 |
| WO | 2012028579 A1 | 3/2012 |
| WO | 2013018928 A1 | 2/2013 |
| WO | 2014002754 A1 | 1/2014 |
| WO | 2014021468 A1 | 2/2014 |
| WO | 2015177063 A1 | 11/2015 |

OTHER PUBLICATIONS

Extended European Search Report for EP14195573.2, dated Mar. 16, 2015.
Partial international search for PCT/EP2015/077417, dated Feb. 10, 2016.
International Search Report and Written Opinion for PCT/EP2015/077417, dated Apr. 29, 2016.

*Primary Examiner* — Samantha L Shterengarts
(74) *Attorney, Agent, or Firm* — BakerHostetler LLP; Toni-Junell Herbert

(57) ABSTRACT

Compounds of formula I wherein the substituents are as defined in claim 1, and the agrochemically acceptable salts, stereoisomers, enantiomers, tautomers and N-oxides of those compounds, can be used as insecticides and can be prepared in a manner known per se.

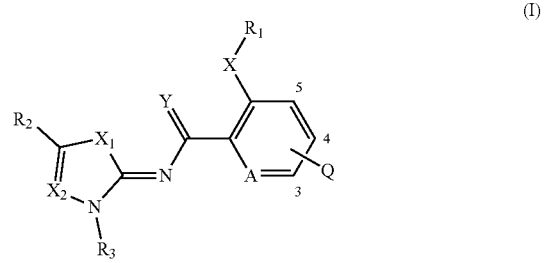

13 Claims, No Drawings

PESTICIDALLY ACTIVE AMIDE HETEROCYCLIC DERIVATIVES WITH SULPHUR CONTAINING SUBSTITUENTS

RELATED APPLICATION INFORMATION

This application is a 371 of International Application No. PCT/EP2015/077417, filed 24 Nov. 2015, which claims priority to EP 14195573.2, filed 1 Dec. 2014, the contents of which are incorporated herein by reference herein.

The present invention relates to pesticidally active, in particular insecticidally active amide heterocyclic derivatives containing sulphur substituents, to intermediates for the preparation of those compounds, to compositions comprising those compounds, and to their use for controlling animal pests (including arthropods and in particular insects or representatives of the order Acarina).

Amide heterocyclic compounds with pesticidal action are known and described, for example, in WO 2013/191041, WO 2014/002754 and WO 2014/021468.

There have now been found novel pesticidally active amide heterocyclic ring derivatives with sulphur substituents.

The present invention accordingly relates to compounds of formula I,

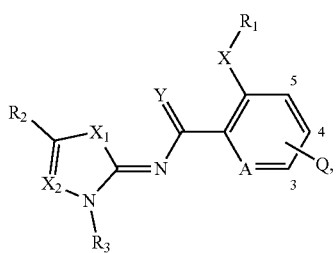

(I)

wherein

A is CH or N;

Q is attached to the 3- or 4-position; and is phenyl which can be mono- or polysubstituted by substituents selected from the group consisting of halogen, cyano, $C_1$-$C_4$alkyl, $C_1$-$C_4$haloalkyl, $C_1$-$C_4$haloalkoxy, $C_1$-$C_4$alkoxy, $C_1$-$C_4$haloalkylsulfanyl, $C_1$-$C_4$haloalkylsulfinyl, $C_1$-$C_4$haloalkylsulfonyl and —C(O)$C_1$-$C_4$haloalkyl; or Q is a five- to ten-membered monocyclic or fused bicyclic ring system linked via a carbon atom to the ring which contains the group A, said ring system can be aromatic, partially saturated or fully saturated and contains 1 to 4 hetero atoms selected from the group consisting of nitrogen, oxygen and sulfur, it not being possible for each ring system to contain more than 2 oxygen atoms and more than 2 sulfur atoms, said five- to ten-membered ring system can be mono- to polysubstituted by substituents independently selected from the group consisting of halogen, cyano, $C_1$-$C_4$alkyl, $C_1$-$C_4$haloalkyl, $C_1$-$C_4$haloalkoxy, $C_1$-$C_4$alkoxy, $C_1$-$C_4$alkylsulfanyl, $C_1$-$C_4$alkylsulfinyl, $C_1$-$C_4$alkylsulfonyl, —C(O)$C_1$-$C_4$alkyl, $C_1$-$C_4$haloalkylsulfanyl, $C_1$-$C_4$haloalkylsulfinyl, $C_1$-$C_4$haloalkylsulfonyl and —C(O)$C_1$-$C_4$haloalkyl; or Q is a five- to six-membered, aromatic, partially saturated or fully saturated ring system linked via a nitrogen atom to the ring which contains the group A, said ring system can be mono- or polysubstituted by substituents selected from the group consisting of halogen, cyano, $C_1$-$C_4$alkyl, $C_1$-$C_4$haloalkyl, $C_1$-$C_4$haloalkoxy, $C_1$-$C_4$alkoxy, $C_1$-$C_4$alkylsulfanyl, $C_1$-$C_4$alkylsulfinyl, $C_1$-$C_4$alkylsulfonyl, —C(O)$C_1$-$C_4$alkyl, $C_1$-$C_4$haloalkylsulfanyl, $C_1$-$C_4$haloalkylsulfinyl, $C_1$-$C_4$haloalkylsulfonyl and —C(O)$C_1$-$C_4$haloalkyl; and said ring system contains 1, 2 or 3 heteroatoms selected from the group consisting of nitrogen, oxygen and sulfur, where said ring system may not contain more than one oxygen atom and not more than one sulfur atom; or Q is $C_3$-$C_6$cycloalkyl, or $C_3$-$C_6$cycloalkyl mono- or polysubstituted by substituents selected from the group consisting of halogen, cyano, $C_1$-$C_4$alkyl, $C_1$-$C_4$haloalkyl, $C_3$-$C_6$cycloalkyl and phenyl, wherein said phenyl can be mono- or polysubstituted by substituents selected from the group consisting of halogen, cyano, $C_1$-$C_4$alkyl, $C_1$-$C_4$haloalkyl, $C_1$-$C_4$haloalkoxy, $C_1$-$C_4$alkoxy, $C_1$-$C_4$haloalkylsulfanyl, $C_1$-$C_4$haloalkylsulfinyl, $C_1$-$C_4$haloalkylsulfonyl and —C(O)$C_1$-$C_4$haloalkyl; or Q is $C_2$-$C_6$alkenyl, or $C_2$-$C_6$alkenyl mono- or polysubstituted by substituents selected from the group consisting of halogen, cyano, $C_1$-$C_4$alkyl, $C_1$-$C_4$haloalkyl, $C_1$-$C_4$alkoxy, $C_3$-$C_6$cycloalkyl and phenyl, wherein said phenyl can be mono- or polysubstituted by substituents selected from the group consisting of halogen, cyano, $C_1$-$C_4$alkyl, $C_1$-$C_4$haloalkyl, $C_1$-$C_4$haloalkoxy, $C_1$-$C_4$alkoxy, $C_1$-$C_4$haloalkylsulfanyl, $C_1$-$C_4$halo-alkylsulfinyl, $C_1$-$C_4$haloalkylsulfonyl and —C(O)$C_1$-$C_4$haloalkyl; or Q is $C_2$-$C_6$alkynyl, or $C_2$-$C_6$alkynyl mono- or polysubstituted by substituents selected from the group consisting of halogen, cyano, $C_1$-$C_4$alkyl, $C_1$-$C_4$haloalkyl, $C_3$-$C_6$cycloalkyl, tri($C_1$-$C_4$alkyl)silyl and phenyl, wherein said phenyl can be mono- or polysubstituted by substituents selected from the group consisting of halogen, cyano, $C_1$-$C_4$alkyl, $C_1$-$C_4$haloalkyl, $C_1$-$C_4$haloalkoxy, $C_1$-$C_4$alkoxy, $C_1$-$C_4$halo-alkylsulfanyl, $C_1$-$C_4$haloalkylsulfinyl, $C_1$-$C_4$haloalkylsulfonyl and -C(O)$C_1$-$C_4$haloalkyl; or Q is $C_1$-$C_6$haloalkylsulfanyl, $C_1$-$C_6$haloalkylsulfinyl, $C_1$-$C_6$haloalkylsulfonyl, $C_1$-$C_6$haloalkoxy, —C(O)$C_1$-$C_4$haloalkyl, $C_1$-$C_6$alkylsulfanyl, $C_1$-$C_6$alkylsulfinyl, or $C_1$-$C_6$alkylsulfonyl;

X is S, SO or $SO_2$;

$R_1$ is $C_1$-$C_4$alkyl, $C_1$-$C_4$haloalkyl, $C_3$-$C_6$cycloalkyl, $C_3$-$C_6$cycloalkyl-$C_1$-$C_4$alkyl; or $R_1$ is $C_3$-$C_6$cycloalkyl mono - or polysubstituted by substituents selected from the group consisting of halogen, cyano and $C_1$-$C_4$alkyl; or $R_1$ is $C_3$-$C_6$cycloalkyl-$C_1$-$C_4$alkyl mono- or polysubstituted by substituents selected from the group consisting of halogen, cyano and $C_1$-$C_4$alkyl; or $R_1$ is $C_2$-$C_6$alkenyl, $C_2$-$C_6$haloalkenyl or $C_2$-$C_6$alkynyl;

$X_1$ is O, S or $CR_6$=CH, wherein $R_6$ is hydrogen, halogen, $C_1$-$C_6$haloalkyl or $C_1$-$C_6$haloalkyl substituted by one or two substituents selected from the group consisting of hydroxyl, methoxy and cyano; or $R_6$ is $C_1$-$C_4$haloalkylsulfanyl, $C_1$-$C_4$haloalkylsulfinyl, $C_1$-$C_4$haloalkylsulfonyl, O($C_1$-$C_4$haloalkyl), or —C(O)$C_1$-$C_4$haloalkyl;

or $X_1$ is N—$R_4$, wherein $R_4$ is $C_1$-$C_4$alkyl;

$X_2$ is N or C—$R_5$, wherein $R_5$ is hydrogen, $C_1$-$C_4$alkyl, $C_1$-$C_4$haloalkyl, halogen or cyano;

$R_2$ is hydrogen, halogen, cyano, $C_1$-$C_6$haloalkyl, or $C_1$-$C_6$haloalkyl substituted by one or two substituents selected from the group consisting of hydroxyl, methoxy and cyano; or $R_2$ is $C_1$-$C_4$haloalkylsulfanyl, $C_1$-$C_4$haloalkylsulfinyl, $C_1$-$C_4$haloalkylsulfonyl, O($C_1$-$C_4$haloalkyl), or —C(O)$C_1$-$C_4$haloalkyl;

$R_3$ is $C_1$-$C_4$alkyl, $C_2$-$C_6$alkenyl, $C_2$-$C_6$alkynyl, $C_1$-$C_4$alkoxy-$C_1$-$C_4$alkyl or $C_3$-$C_6$cycloalkyl;

Y is O or S;

and agrochemically acceptable salts, stereoisomers, enantiomers, tautomers and N-oxides of those compounds.

Compounds of formula I which have at least one basic centre can form, for example, acid addition salts, for example with strong inorganic acids such as mineral acids, for example perchloric acid, sulfuric acid, nitric acid, a phosphorus acid or a hydrohalic acid, with strong organic carboxylic acids, such as $C_1$-$C_4$alkanecarboxylic acids which are unsubstituted or substituted, for example by halogen, for example acetic acid, such as saturated or unsaturated dicarboxylic acids, for example oxalic acid, malonic acid, succinic acid, maleic acid, fumaric acid or phthalic acid, such as hydroxycarboxylic acids, for example ascorbic acid, lactic acid, malic acid, tartaric acid or citric acid, or such as benzoic acid, or with organic sulfonic acids, such as $C_1$-$C_4$alkane- or arylsulfonic acids which are unsubstituted or substituted, for example by halogen, for example methane- or p-toluenesulfonic acid. Compounds of formula I which have at least one acidic group can form, for example, salts with bases, for example mineral salts such as alkali metal or alkaline earth metal salts, for example sodium, potassium or magnesium salts, or salts with ammonia or an organic amine, such as morpholine, piperidine, pyrrolidine, a mono-, di- or tri-lower-alkylamine, for example ethyl-, diethyl-, triethyl- or dimethylpropylamine, or a mono-, di- or trihydroxy-lower-alkylamine, for example mono-, di- or triethanolamine.

The alkyl groups occurring in the definitions of the substituents can be straight-chain or branched and are, for example, methyl, ethyl, n-propyl, isopropyl, n-butyl, sec-butyl, iso-butyl, tert-butyl, pentyl, hexyl, nonyl, decyl and their branched isomers. Alkylsulfanyl, alkylsulfinyl, alkylsulfonyl, alkoxy, alkenyl and alkynyl radicals are derived from the alkyl radicals mentioned. The alkenyl and alkynyl groups can be mono- or polyunsaturated. $C_1$-di-alkylamino is dimethylamino.

Halogen is generally fluorine, chlorine, bromine or iodine. This also applies, correspondingly, to halogen in combination with other meanings, such as haloalkyl or halophenyl.

Haloalkyl groups preferably have a chain length of from 1 to 6 carbon atoms. Haloalkyl is, for example, fluoromethyl, difluoromethyl, trifluoromethyl, chloromethyl, dichloromethyl, trichloromethyl, 2,2,2-trifluoroethyl, 2-fluoroethyl, 2-chloroethyl, pentafluoroethyl, 1,1-difluoro-2,2,2-trichloroethyl, 2,2,3,3-tetrafluoroethyl and 2,2,2-trichloroethyl; preferably trichloromethyl, difluorochloromethyl, difluoromethyl, trifluoromethyl and dichlorofluoromethyl.

Alkoxy groups preferably have a preferred chain length of from 1 to 6 carbon atoms. Alkoxy is, for example, methoxy, ethoxy, propoxy, i-propoxy, n-butoxy, isobutoxy, sec-butoxy and tert-butoxy and also the isomeric pentyloxy and hexyloxy radicals; preferably methoxy and ethoxy.

Alkoxyalkyl groups preferably have a chain length of 1 to 6 carbon atoms. Alkoxyalkyl is, for example, methoxymethyl, methoxyethyl, ethoxymethyl, ethoxyethyl, n-propoxymethyl, n-propoxyethyl, isopropoxymethyl or isopropoxyethyl.

Alkoxycarbonyl is for example methoxycarbonyl (which is $C_1$alkoxycarbonyl), ethoxycarbonyl, propoxycarbonyl, isopropoxycarbonyl, n-butoxycarbonyl, tert-butoxycarbonyl, n-pentoxycarbonyl or hexoxycarbonyl.

Alkylsulfanyl is for example methylsulfanyl, ethylsulfanyl, propylsulfanyl, isopropylsulfanyl, butylsulfanyl, pentylsulfanyl, and hexylsulfanyl.

Alkylsulfinyl is for example methylsulfinyl, ethylsulfinyl, propylsulfinyl, isopropylsulfinyl, a butylsulfinyl, pentylsulfinyl, and hexylsulfinyl.

Alkylsulfonyl is for example methylsulfonyl, ethylsulfonyl, propylsulfonyl, isopropylsulfonyl, butylsulfonyl, pentylsulfonyl, and hexylsulfonyl.

The cycloalkyl groups preferably have from 3 to 6 ring carbon atoms, for example cyclopropyl, cyclobutyl, cyclopentyl and cyclohexyl.

Haloalkoxy groups preferably have a chain length of from 1 to 4 carbon atoms. Haloalkoxy is, for example, difluoromethoxy, trifluoromethoxy or 2,2,2-trifluoroethoxy.

Haloalkylsulfanyl groups preferably have a chain length of from 1 to 4 carbon atoms. Haloalkylsulfanyl is, for example, difluoromethylsulfanyl, trifluoromethylsulfanyl or 2,2,2-trifluoroethylsulfanyl. Similar considerations apply to the radicals $C_1$-$C_4$haloalkylsulfinyl and $C_1$-$C_4$haloalkylsulfonyl, which may be, for example, trifluoromethylsulfinyl, trifluoromethylsulfonyl or 2,2,2-trifluoroethylsulfonyl.

In the context of this invention, examples of a five- to six-membered, aromatic, partially saturated or fully saturated ring system that are linked via a nitrogen atom to the ring which contains the group A, are selected from pyrazole, pyrrole, pyrrolidine, pyrrolidine-2-one, piperidine, morpholine, imidazole, triazole and pyridine-2-one.

In the context of this invention "mono- to polysubstituted" in the definition of the substituents, means typically, depending on the chemical structure of the substituents, monosubstituted to seven-times substituted, preferably monosubstituted to five-times substituted, more preferably mono-, double- or triple-substituted.

Free radicals represents methyl groups.

The compounds of formula I according to the invention also include hydrates which may be formed during the salt formation.

Depending on the nature of substituents, compounds of formula I in the context of this invention may exist in different double bond isomeric forms (cis- and/or trans-, or (E) and/or (Z) double bond configurations), as illustrated by the compounds of formula I and I' below. This invention covers all such isomers and mixtures thereof in all proportions. Existence of multiple double bond configurations may also be represented by a structure of formula I".

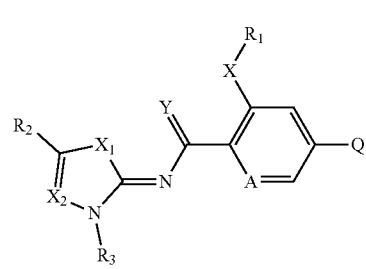

I

-continued

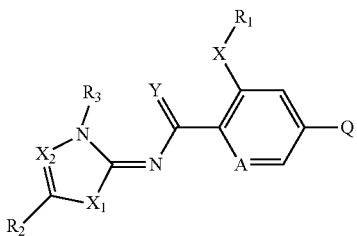

I'

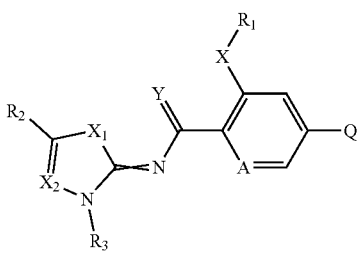

I''

Similar double bond geometry considerations also apply to the compounds of the formula I-A.

According to the present invention, Q as a five- to ten-membered monocyclic or fused bicyclic ring system that is linked via a carbon atom to the ring which contains the group A, said ring system can be aromatic, partially saturated or fully saturated and contains 1 to 4 hetero atoms selected from the group consisting of nitrogen, oxygen and sulfur, it not being possible for each ring system to contain more than 2 oxygen atoms and more than 2 sulfur atoms, or Q as a three- to ten-membered, monocyclic or fused bicyclic ring system which may be aromatic, partially saturated or fully saturated;

is, depending of the number of ring members, is for example, selected from the group consisting of the following heterocyclic groups:

pyrrolyl; pyrazolyl; isoxazolyl; furanyl; thienyl; imidazolyl; oxazolyl; thiazolyl; isothiazolyl; triazolyl; oxadiazolyl; thiadiazolyl; tetrazolyl; furyl; pyridyl; pyrimidyl; pyrazinyl; pyridazinyl; triazinyl, pyranyl; quinazolinyl; isoquinolinyl; indolinyl; isobenzofuranylnaphthyridinyl; quinoxalinyl; cinnolinyl; phthalazinyl; benzothiazolyl; benzoxazolyl; benzotriazolyl; indazolyl; indolyl; (1H-pyrrol-1-yl)-; (1H-pyrrol-2-yl)-; (1H-pyrrol-3-yl)-; (1H-pyrazol-1-yl)-; (1H-pyrazol-3-yl)-; (3H-pyrazol-3-yl)-; (1H-pyrazol-4-yl)-; (3-isoxazolyl)-; (5-isoxazolyl)-; (2-furanyl)-; (3-furanyl)-; (2-thienyl)-; (3-thienyl)-; (1H-imidazol-2-yl)-; (1H- imidazol-4-yl)-; (1H-imidazol-5-yl)-; (2-oxazol-2-yl)-; (oxazol-4-yl)-; (oxazol-5-yl)-; (thiazol-2-yl)-; (thiazol-4-yl)-; (thiazol-5-yl)-; (isothiazol-3-yl)-; (isothiazol-5-yl)-; (1H-1,2,3-triazol-1-yl)-; (1H-1,2,4-triazol-3-yl)-; (4H-1,2,4-triazol-4-yl)-; (1H-1,2,4-triazol-1-yl)-(1,2,3-oxadiazol-2-yl)-; (1,2,4-oxadiazol-3-yl)-; (1,2,4-oxadiazol-4-yl)-; (1,2,4-oxadiazol-5-yl)-; (1,2,3-thiadiazol-2-yl)-; (1,2,4-thiadiazol-3-yl)-; (1,2,4-thiadiazol-4-yl)-; (1,3,4-thiadiazol-5-yl)-; (1H-tetrazol-1-yl)-; (1H-tetrazol-5-yl)-; (2H-tetrazol-5-yl)-; (2-pyridyl)-; (3-pyridyl)-; (4-pyridyl)-; (2-pyrimidinyl)-; (4-pyrimidinyl)-; (5-pyrimidinyl)-; (2-pyrazinyl)-; (3-pyridazinyl)-; (4-pyridazinyl)-; (1,3,5-triazin-2-yl)-; (1,2,4-triazin-5-yl)-; (1,2,4-triazin-6-yl)-; (1,2,4-triazin-3-yl)-; (furazan-3-yl)-; (2-quinolinyl)-; (3-quinolinyl)-; (4-quinolinyl)-; (5-quinolinyl)-; (6-quinolinyl)-; (3-isoquinolnyl)-; (4-isoquinolnyl)-; (2-quinozolinyl)-; (2-quinoxalinyl)-; (5-quinoxalinyl)-; (pyrido[2,3-b]pyrazin-7-yl)-; (benzoxazol-5-yl)-; (benzothiazol-5-yl)-; (benzo[b]thien-2-yl) and (benzo[1,2,5]oxadiazol-5-yl)-; indolinyl and tetrahydroquinolynyl.

Preferably, Q is always in the 4-position and is phenyl which can be mono- or polysubstituted by substituents selected from the group consisting of halogen, cyano, $C_1$-$C_4$alkyl, $C_1$-$C_4$haloalkyl, $C_1$-$C_4$haloalkoxy, $C_1$-$C_4$alkoxy, $C_1$-$C_4$haloalkylsulfanyl, $C_1$-$C_4$haloalkylsulfinyl, $C_1$-$C_4$haloalkylsulfonyl and —C(O) $C_1$-$C_4$haloalkyl; or Q is a five- to ten-membered monocyclic or fused bicyclic ring system linked via a carbon atom to the ring which contains the group A, said ring system can be aromatic, partially saturated or fully saturated and can contain 1 to 4 hetero atoms selected from the group consisting of nitrogen, oxygen and sulfur, it not being possible for each ring system to contain more than 2 oxygen atoms and more than 2 sulfur atoms, said five- to ten-membered ring system can be mono- to polysubstituted by substituents independently selected from the group consisting of halogen, cyano, $C_1$-$C_4$alkyl, $C_1$-$C_4$haloalkyl, $C_1$-$C_4$haloalkoxy, $C_1$-$C_4$alkoxy, $C_1$-$C_4$alkylsulfanyl, $C_1$-$C_4$alkylsulfinyl, $C_1$-$C_4$alkylsulfonyl, —C(O)$C_1$-$C_4$alkyl, $C_1$-$C_4$haloalkylsulfanyl, $C_1$-$C_4$haloalkylsulfinyl, $C_1$-$C_4$haloalkylsulfonyl and —C(O) $C_1$-$C_4$haloalkyl; or Q is a five- to six-membered, aromatic, partially saturated or fully saturated ring system linked via a nitrogen atom to the ring which contains the group A, said ring system can be mono- or polysubstituted by substituents selected from the group consisting of halogen, cyano, $C_1$-$C_4$alkyl, $C_1$-$C_4$haloalkyl, $C_1$-$C_4$haloalkoxy, $C_1$-$C_4$alkoxy, $C_1$-$C_4$alkylsulfanyl, $C_1$-$C_4$alkylsulfinyl, $C_1$-$C_4$alkylsulfonyl, —C(O)$C_1$-$C_4$alkyl, $C_1$-$C_4$haloalkylsulfanyl, $C_1$-$C_4$haloalkylsulfinyl, $C_1$-$C_4$haloalkylsulfonyl and —C(O) $C_1$-$C_4$haloalkyl; and said ring system contains 1, 2 or 3 heteroatoms selected from the group consisting of nitrogen, oxygen and sulfur, where said ring system may not contain more than one oxygen atom and not more than one sulfur atom.

In preferred compounds of formula I, Q is selected from the group consisting of J-1 to J-45 (where the arrow represents the pount of attachment of the heterocycle to the radical Q):

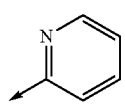

J-1

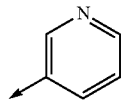

J-2

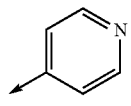

J-3

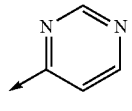

J-4

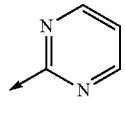

J-5

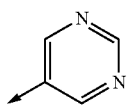
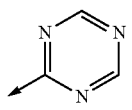
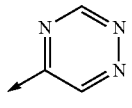
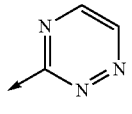
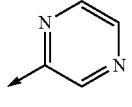
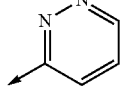
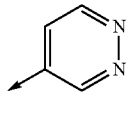
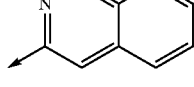
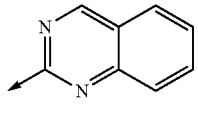
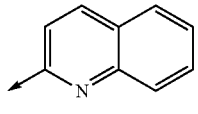
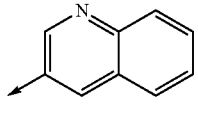
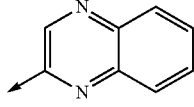
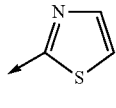
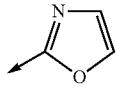
J-6
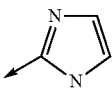
J-7
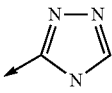
J-8
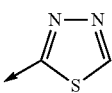
J-9
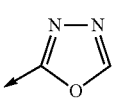
J-10
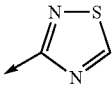
J-11
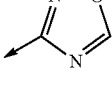
J-12
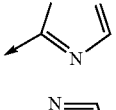
J-13
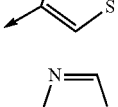
J-14
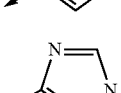
J-15
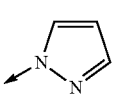
J-16
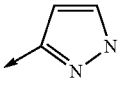
J-17
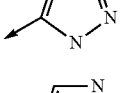
J-18
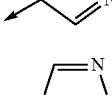
J-19
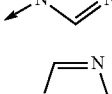
J-20
J-21
J-22
J-23
J-24
J-25
J-26
J-27
J-28
J-29
J-30
J-31
J-32
J-33
J-34
J-35

-continued

J-36 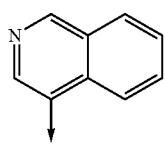

J-37 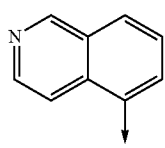

J-38 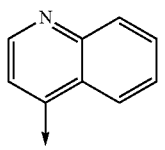

J-39 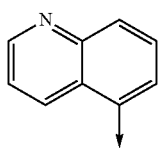

J-40 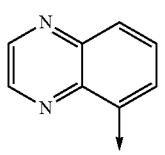

J-41 

J-42 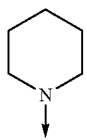

J-43 

J-44 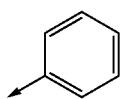

J-45 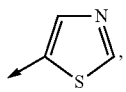

in particular selected from J-1 to J-42;

wherein each group J-1 to J-45 is mono- di- or trisubstituted with Rx, wherein each Rx is, independently selected from the group consisting of hydrogen, halogen, cyano, $C_1$-$C_4$alkyl, $C_1$-$C_4$haloalkyl, $C_1$-$C_4$haloalkoxy, $C_1$-$C_4$alkoxy, $C_1$-$C_4$alkylsulfanyl, $C_1$-$C_4$alkylsulfinyl, $C_1$-$C_4$alkylsulfonyl, —C(O)$C_1$-$C_4$alkyl, $C_1$-$C_4$haloalkylsulfanyl, $C_1$-$C_4$haloalkylsulfinyl, $C_1$-$C_4$haloalkylsulfonyl and —C(O)$C_1$-$C_4$haloalkyl.

A preferred group of compounds of formula I is represented by the compounds of formula I-1

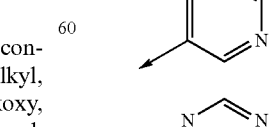
(I-1)

wherein Y, $R_2$, $R_3$, $X_2$ and Q are as defined under formula I above; $Xa_1$ is S, SO or $SO_2$; $Ra_1$ is methyl, ethyl, n-propyl, i-propyl or cyclopropylmethyl; and agrochemically acceptable salts, stereoisomers, enantiomers, tautomers and N-oxides of those compounds. In this preferred group of compounds of formula I-1, $Xa_1$ is preferably S or $SO_2$, in particular $SO_2$, and $Ra_1$ is preferably ethyl, Y is preferably O, $R_2$ is in particular pentafluoroethyl or trifluoromethyl, preferably trifluoromethyl, $R_3$ is in particular methyl or ethyl, preferably methyl, when $X_2$ is N or CH.

In said preferred compounds of formula I-1, Q is selected from the group consisting of J-1 to J-45 (where the arrow represents the point of attachment of the heterocycle to the radical Q):

J-1 

J-2 

J-3 

J-4 

J-5

J-6

J-7

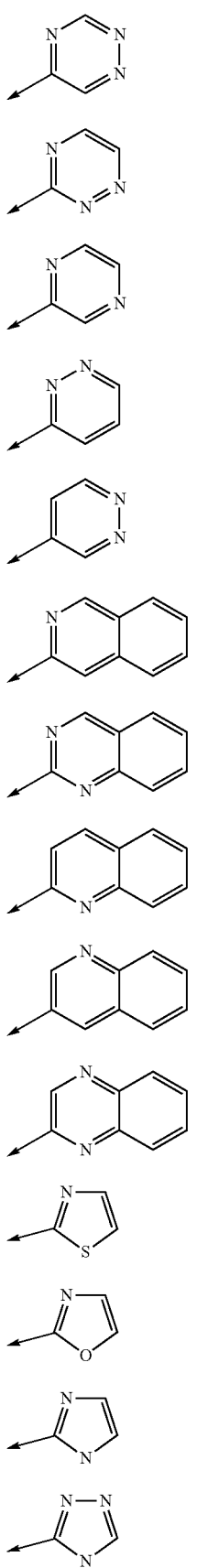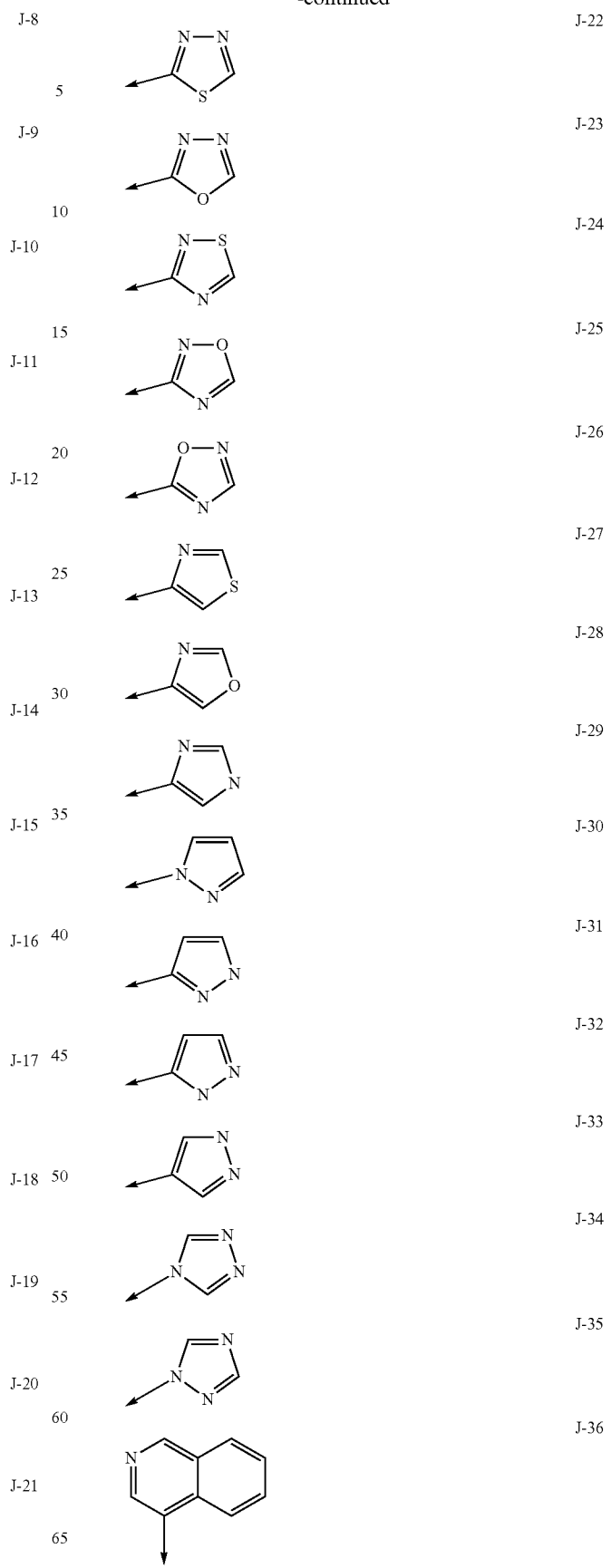

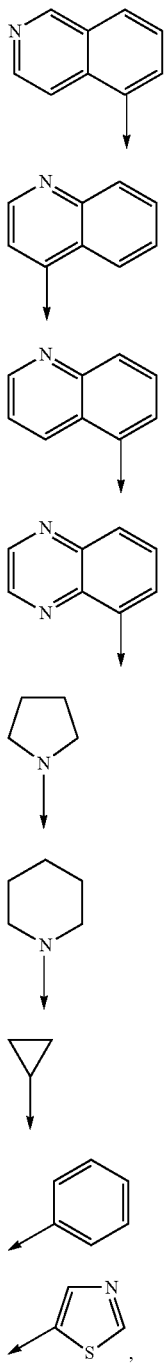

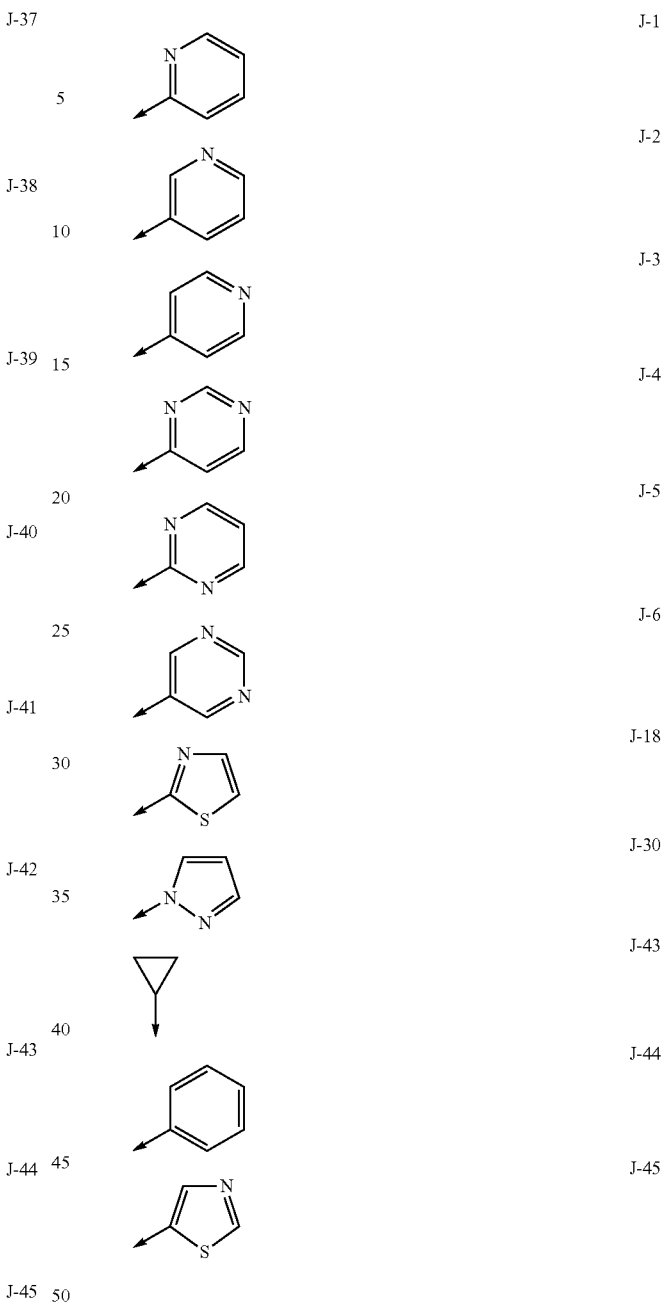

in particular selected from J-1 to J-42;

wherein each group J-1 to J-45 is mono- di- or trisubstituted with Rx, wherein each Rx is, independently selected from the group consisting of hydrogen, halogen, cyano, $C_1$-$C_4$alkyl, $C_1$-$C_4$haloalkyl, $C_1$-$C_4$haloalkoxy, $C_1$-$C_4$alkoxy, $C_1$-$C_4$alkylsulfanyl, $C_1$-$C_4$alkylsulfinyl, $C_1$-$C_4$alkylsulfonyl, —C(O)$C_1$-$C_4$alkyl, $C_1$-$C_4$haloalkylsulfanyl, $C_1$-$C_4$haloalkylsulfinyl, $C_1$-$C_4$haloalkylsulfonyl and —C(O)$C_1$-$C_4$haloalkyl.

In compounds of formula I-1 and all of the preferred embodiments of compounds of formula I-1 mentioned above, Q is preferably selected from the group consisting of wherein each group J-1 to J-45 is mono- di- or trisubstituted with Rx, wherein each Rx is,I independently selected from the group consisting of hydrogen, halogen, cyano, $C_1$-$C_4$alkyl, $C_1$-$C_4$haloalkyl, $C_1$-$C_4$haloalkoxy, $C_1$-$C_4$alkoxy, $C_1$-$C_4$alkylsulfanyl, $C_1$-$C_4$alkylsulfinyl, $C_1$-$C_4$alkylsulfonyl, —C(O)$C_1$-$C_4$alkyl, $C_1$-$C_4$haloalkylsulfanyl, $C_1$-$C_4$haloalkylsulfinyl, $C_1$-$C_4$haloalkylsulfonyl and —C(O)$C_1$-$C_4$haloalkyl.

Preferably each Rx is, independently selected from hydrogen, halogen, cyano, $C_1$-$C_4$haloalkyl, $C_1$-$C_4$haloalkoxy, $C_1$-$C_4$alkylsulfanyl and $C_1$-$C_4$alkylsulfonyl, preferably selected from hydrogen, fluorine, chlorine, cyano, trifluoromethyl, trifluoromethoxy, methylsulfanyl and ethylsulfonyl.

Another preferred group of compounds of formula I is represented by the compounds of formula I-2

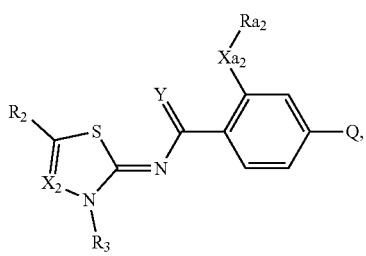
(I-2)

wherein Y, R$_2$, R$_3$, X$_2$ and Q are as defined under formula I above; Xa$_2$ is S, SO or SO$_2$; Ra$_2$ is methyl, ethyl, n-propyl, i-propyl or cyclopropylmethyl; and agrochemically acceptable salts, stereoisomers, enantiomers, tautomers and N-oxides of those compounds. In this preferred group of compounds of formula I-2, Xa$_2$ is preferably SO$_2$ and Ra$_2$ is preferably ethyl, Y is preferably O, R$_2$ is in particular pentafluoroethyl or trifluoromethyl, preferably trifluoromethyl, R$_3$ is in particular methyl or ethyl, preferably methyl, when X$_2$ is N or CH.

In said preferred compounds of formula I-2, Q is selected from the group consisting of J-1 to J-45 (where the arrow represents the point of attachment of the heterocycle to the radical Q):

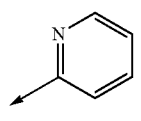
J-1

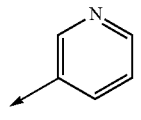
J-2

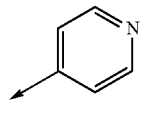
J-3

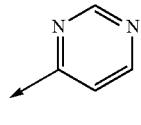
J-4

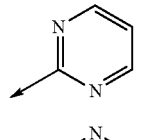
J-5

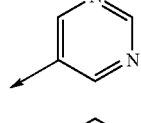
J-6

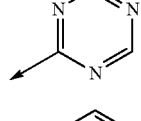
J-7

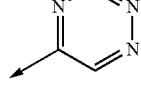
J-8

-continued

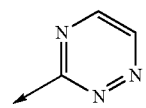
J-9

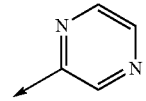
J-10

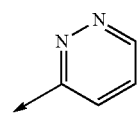
J-11

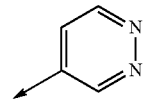
J-12

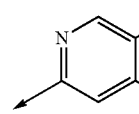
J-13

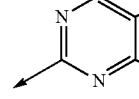
J-14

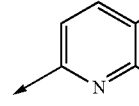
J-15

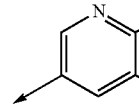
J-16

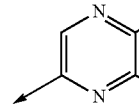
J-17

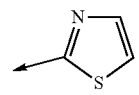
J-18

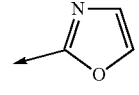
J-19

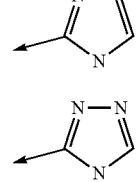
J-20

J-21

J-22

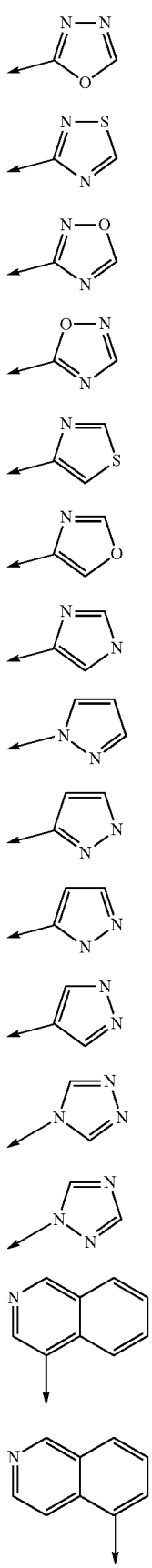

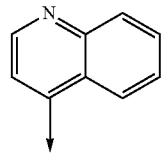

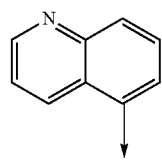

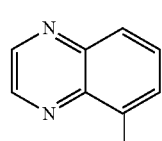

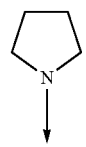

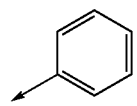

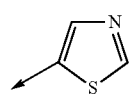

in particular selected from J-1 to J-42;

wherein each group J-1 to J-45 is mono- di- or trisubstituted with Rx, wherein each Rx is, independently selected from the group consisting of hydrogen, halogen, cyano, $C_1$-$C_4$alkyl, $C_1$-$C_4$haloalkyl, $C_1$-$C_4$haloalkoxy, $C_1$-$C_4$alkoxy, $C_1$-$C_4$alkylsulfanyl, $C_1$-$C_4$alkylsulfinyl, $C_1$-$C_4$alkylsulfonyl, —C(O)$C_1$-$C_4$alkyl, $C_1$-$C_4$haloalkylsulfanyl, $C_1$-$C_4$haloalkylsulfinyl, $C_1$-$C_4$haloalkylsulfonyl and —C(O)$C_1$-$C_4$haloalkyl.

In compounds of formula I-2 and all of the preferred embodiments of compounds of formula I-2 mentioned above, Q is preferably

J-44

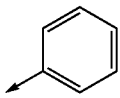

wherein J-44 is mono- di- or trisubstituted with Rx, wherein each Rx is, independently selected from the group consisting of hydrogen, halogen, cyano, $C_1$-$C_4$alkyl, $C_1$-$C_4$haloalkyl, $C_1$-$C_4$haloalkoxy, $C_1$-$C_4$alkoxy, $C_1$-$C_4$alkylsulfanyl, $C_1$-$C_4$alkylsulfinyl, $C_1$-$C_4$alkylsulfonyl, —C(O)$C_1$-$C_4$alkyl, $C_1$-$C_4$haloalkylsulfanyl, $C_1$-$C_4$haloalkylsulfinyl, $C_1$-$C_4$haloalkylsulfonyl and —C(O)$C_1$-$C_4$haloalkyl. Preferably each Rx is, independently selected from hydrogen and $C_1$-$C_4$haloalkyl, preferably selected from hydrogen and trifluoromethyl.

Especially preferred compounds of formula I are represented by the compounds of formula Ia-1

(Ia-1)

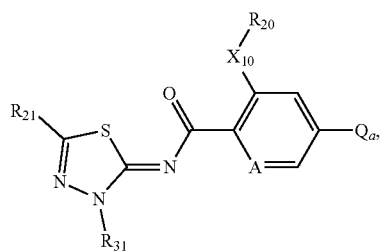

wherein

A is CH or N;

$X_{10}$ is S or $SO_2$;

$R_{20}$ is $C_1$-$C_4$alkyl;

$R_{21}$ is $C_1$-$C_4$haloalkyl;

$R_{31}$ is $C_1$-$C_4$alkyl; and $Q_a$ is selected from the group consisting of the heterocycles J-0a

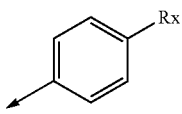

J-0b

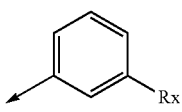

J-0c

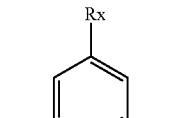

J-0d

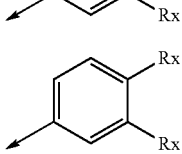

J-0e

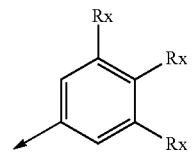

J-0f

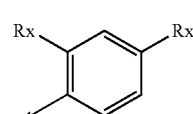

J-0g

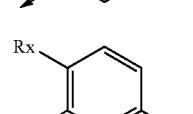

J-1a

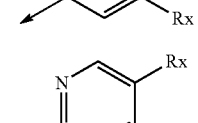

J-1b

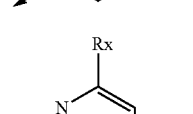

J-1c

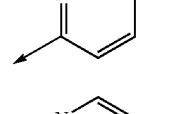

J-1d

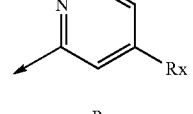

J-1e

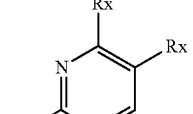

J-2a

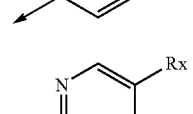

J-2b

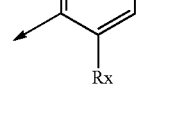

J-2c

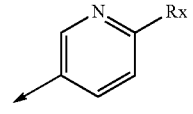

J-3a

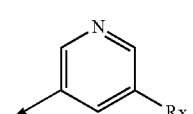

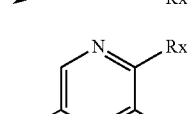

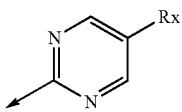
J-5a

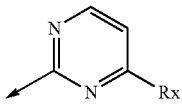
J-5b

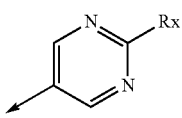
J-6a

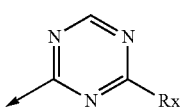
J-7a

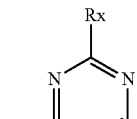
J-4a

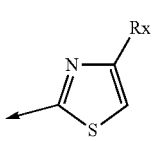
J-18a

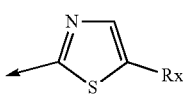
J-18b

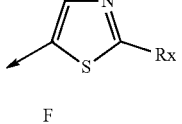
J-45a

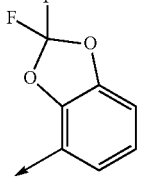
J-0h

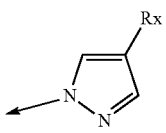
J-30a

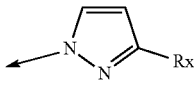
J-30b

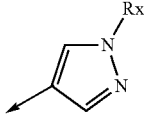
J-33a

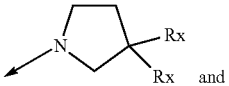
J-41a

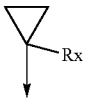
J-43a in particular selected from J-0a, J-0b, J-0c, J-0d, J-0e, J-1a, J-2a, J-2b, J-2c, J-3a, J-5a, J-6a, J-7a, J-30a, J-30b, J-33a and J-41a;

wherein each preferred group $Q_a$ is mono- di- or trisubstituted with Rx, wherein each Rx is, independently selected from the group consisting of hydrogen, halogen, cyano, $C_1$-$C_4$alkyl, $C_1$-$C_4$haloalkyl, $C_1$-$C_4$haloalkoxy, $C_1$-$C_4$alkoxy, $C_1$-$C_4$alkylsulfanyl, $C_1$-$C_4$alkylsulfinyl, $C_1$-$C_4$alkylsulfonyl, —C(O)$C_1$-$C_4$alkyl, $C_1$-$C_4$haloalkylsulfanyl, $C_1$-$C_4$haloalkylsulfinyl, $C_1$-$C_4$haloalkylsulfonyl and —C(O)$C_1$-$C_4$haloalkyl.

In said preferred compounds of formula Ia-1, $Q_a$ is preferably mono- or disubstituted with Rx, whereby each Rx is, independently preferably selected from hydrogen, halogen, cyano, $C_1$-$C_4$alkyl, $C_1$-$C_4$haloalkyl, $C_1$-$C_4$alkoxy, $C_1$-$C_4$haloalkoxy, $C_1$-$C_4$alkylsulfanyl and $C_1$-$C_4$alkylsulfonyl; in particular from hydrogen, halogen, $C_1$-$C_4$alkyl, $C_1$-$C_4$haloalkyl, $C_1$-$C_4$alkoxy, and $C_1$-$C_4$haloalkoxy.

Even more preferred compounds of formula I are represented by the compounds of formula Ia-2

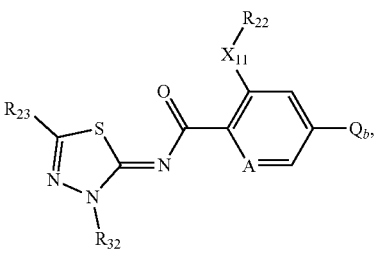

(Ia-2)

wherein
A is CH or N;
$X_{11}$ is S or SO$_2$;
$R_{22}$ is $C_1$-$C_4$alkyl;
$R_{23}$ is $C_1$-$C_4$haloalkyl;
$R_{32}$ is $C_1$-$C_4$alkyl; and
$Q_b$ is is preferably selected from the group consisting of the heterocycles

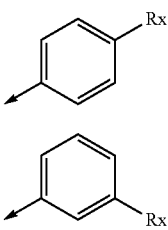
J-0a

J-0b

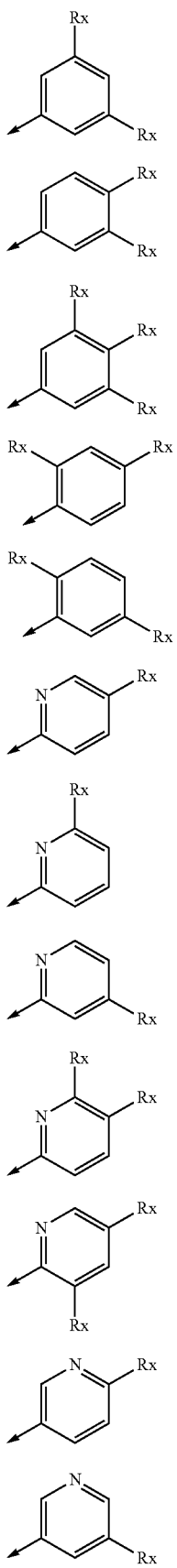
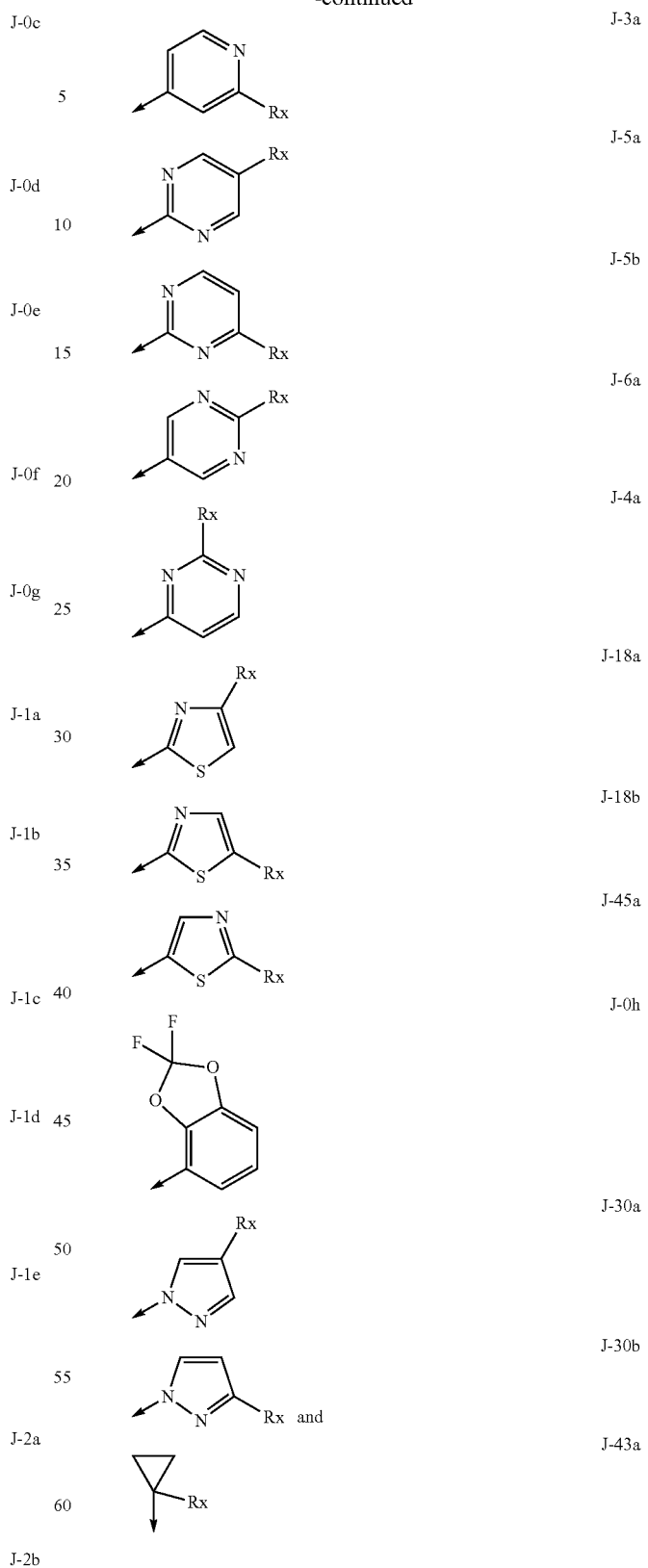
in particular selected from J-0a, J-5a, J-30a and J-30b;
wherein each Rx is, independently selected from the group consisting of hydrogen, halogen, cyano, $C_1$-$C_4$alkyl, $C_1$-$C_4$haloalkyl, $C_1$-$C_4$haloalkoxy, $C_1$-$C_4$alkoxy, $C_1$-$C_4$alkylsulfanyl, $C_1$-$C_4$alkylsulfinyl, $C_1$-$C_4$alkylsulfonyl, —C(O)$C_1$-$C_4$alkyl, $C_1$-$C_4$haloalkylsulfanyl, $C_1$-$C_4$haloalkylsulfinyl, $C_1$-$C_4$haloalkylsulfonyl and —C(O)$C_1$-$C_4$haloalkyl.

In said preferred compounds of formula Ia-2, Rx is independently especially preferably selected from the group consisting of hydrogen, halogen, cyano, $C_1$-$C_4$alkyl, $C_1$-$C_4$haloalkyl, $C_1$-$C_4$alkoxy, $C_1$-$C_4$haloalkoxy, $C_1$-$C_4$alkyl-sulfanyl and $C_1$-$C_4$alkylsulfonyl; in particular from hydrogen, halogen, $C_1$-$C_4$alkyl, $C_1$-$C_4$haloalkyl, $C_1$-$C_4$alkoxy, and $C_1$-$C_4$haloalkoxy.

In each of the compounds of formula I-1, I-2, Ia-1 and Ia-2, Q is most preferably selected from the group consisting of the heterocycles

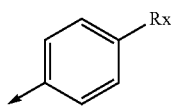

J-0a

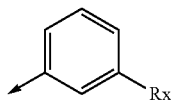

J-0b

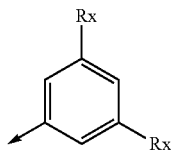

J-0c

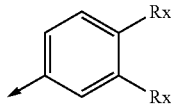

J-0d

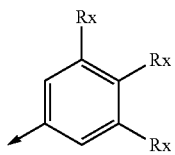

J-0e

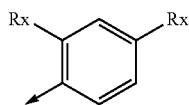

J-0f

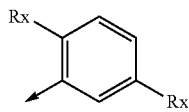

J-0g

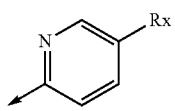

J-1a

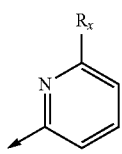

J-1b

-continued

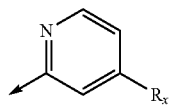

J-1c

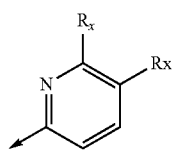

J-1d

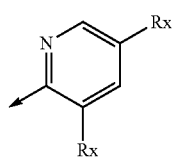

J-1e

J-2a

J-2b

J-3a

J-5a

J-5b

J-6a

J-4a

J-18a

J-18b in particular Q is most preferably J-0a or J-30b;

wherein Rx is independently selected from the group consisting of hydrogen, halogen, cyano, $C_1$-$C_4$haloalkyl, $C_1$-$C_4$haloalkoxy, $C_1$-$C_4$alkylsulfanyl and $C_1$-$C_4$alkylsulfonyl; in particular from halogen or $C_1$-$C_4$haloalkyl. Preferably each Rx is, independently selected from the group consisting of hydrogen, fluorine, chlorine, cyano, trifluoromethyl, trifluoromethoxy, methylsulfanyl and ethylsulfonyl.

An especially preferred group of compounds of formula I are represented by the compounds of formula Ia-3

(Ia-3)

wherein
- A is CH or N;
- $R_{24}$ is $C_1$-$C_4$haloalkyl;
- $R_{33}$ is $C_1$-$C_4$alkyl; and
- $Q_c$ is selected from the group consisting of the heterocycles

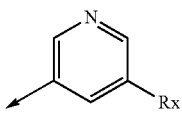 J-2b

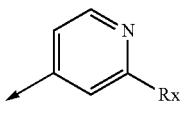 J-3a

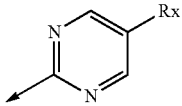 J-5a

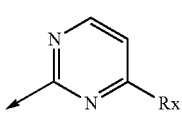 J-5b

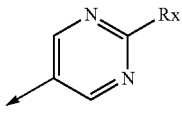 J-6a

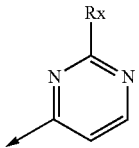 J-4a

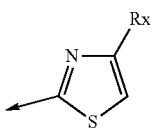 J-18a

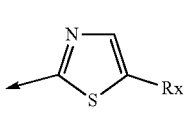 J-18b

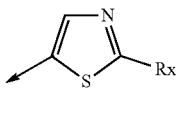 J-45a

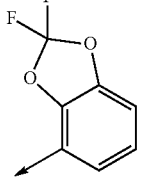 J-0h

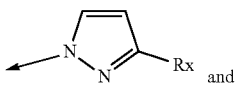 J-30b and

 J-43a wherein Rx is independently selected from the group consisting of hydrogen, halogen, cyano, $C_1$-$C_4$alkyl, $C_1$-$C_4$haloalkyl, $C_1$-$C_4$alkoxy, $C_1$-$C_4$haloalkoxy, $C_1$-$C_4$alkylsulfanyl and $C_1$-$C_4$alkylsulfonyl; in particular Rx is hydrogen, halogen, $C_1$-$C_4$alkyl, $C_1$-$C_4$haloalkyl, $C_1$-$C_4$alkoxy and $C_1$-$C_4$haloalkoxy. Even more preferably Rx is independently selected from the group consisting of hydrogen, halogen, cyano, $C_1$-$C_4$haloalkyl, $C_1$-$C_4$haloalkoxy, $C_1$-$C_4$alkylsulfanyl and $C_1$-$C_4$alkylsulfonyl. In said more preferred compounds of formula Ia-3, Rx is preferably independently selected from the group consisting of hydrogen, fluorine, chlorine, cyano, trifluoromethyl, trifluoromethoxy, methylsulfanyl and ethylsulfonyl; in particular from halogen and $C_1$-$C_4$haloalkyl.

In particular $Q_c$ in formula Ia-3 is selected from the group consisting of J-0a or J-30b;

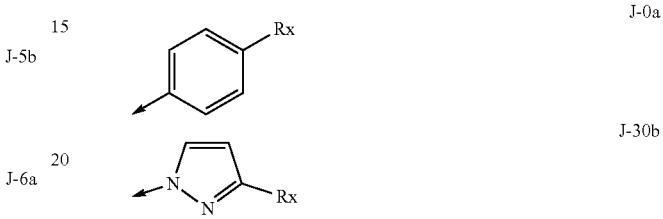

wherein

Rx is independently selected from the group consisting of hydrogen, halogen, $C_1$-$C_4$alkyl, $C_1$-$C_4$haloalkyl, $C_1$-$C_4$alkoxy and $C_1$-$C_4$haloalkoxy.

Another preferred group of compounds of formula I is represented by the compounds of formula I-4

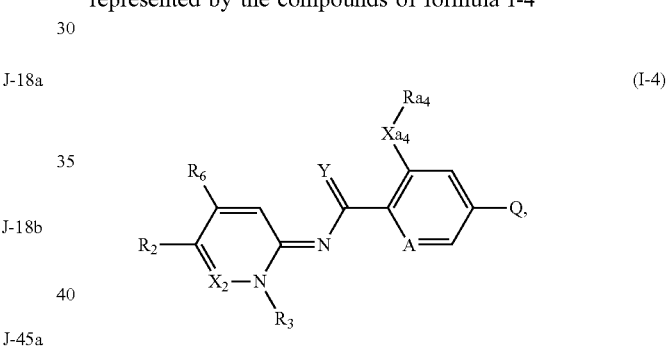

wherein A, Y, $R_2$, $R_3$, $R_6$, Q and $X_2$ are as defined under formula I above; $Xa_4$ is S, SO or $SO_2$; $Ra_4$ is methyl, ethyl, n-propyl, i-propyl or cyclopropylmethyl; and agrochemically acceptable salts and N-oxides of those compounds. In this preferred group of compounds of formula I-4, A is preferably N, $Xa_4$ is preferably S or $SO_2$, in particular $SO_2$, and $Ra_4$ is preferably ethyl, Y is preferably O, $R_2$ is in particular trifluoromethylsulfanyl, trifluoromethylsulfinyl, trifluoromethylsulfonyl, preferably trifluoromethylsulfanyl, $R_6$ is preferably hydrogen, $R_3$ is in particular methyl or ethyl, preferably methyl, and $X_2$ is N or CH, preferably CH.

In said preferred compounds of formula I-4, Q is selected from the group consisting of J-1 to J-45, wherein J-1 to J-45, and Rx, is as defined in Q in formula I-1 above.

In compounds of formula I-4 and all of the preferred embodiments of compounds of formula I-4 mentioned above, Q is preferably selected from the group consisting of

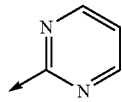 J-5

-continued

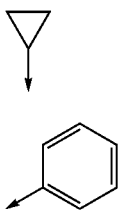
J-43

J-44 wherein each group J-5 to J-44 is mono- di- or trisubstituted with Rx, wherein each Rx is, independently selected from the group consisting of hydrogen, halogen, cyano, $C_1$-$C_4$alkyl, $C_1$-$C_4$haloalkyl, $C_1$-$C_4$haloalkoxy, $C_1$-$C_4$alkoxy, $C_1$-$C_4$alkylsulfanyl, $C_1$-$C_4$alkylsulfinyl, $C_1$-$C_4$alkylsulfonyl, —C(O)$C_1$-$C_4$alkyl, $C_1$-$C_4$haloalkylsulfanyl, $C_1$-$C_4$haloalkylsulfinyl, $C_1$-$C_4$haloalkylsulfonyl and —C(O)$C_1$-$C_4$haloalkyl.

Preferably each Rx is independently selected from hydrogen and $C_1$-$C_4$haloalkyl, preferably selected from hydrogen and trifluoromethyl.

Another preferred embodiment of the invention comprises compounds of formula I represented by the compounds of formula Ia-4

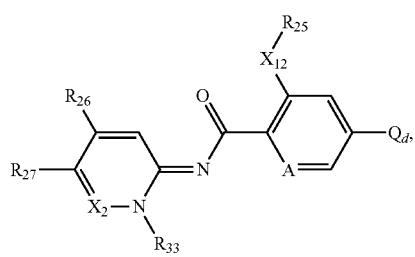
(Ia-4)

wherein
A is N or CH, in particular N;
$R_{26}$ is hydrogen;
$R_{27}$ is trifluoromethylsulfanyl, trifluoromethylsulfinyl or trifluoromethylsulfonyl, in particular trifluoromethylsulfanyl;
$X_2$ is N or CH, in particular CH;
$X_{12}$ is S, SO or $SO_2$, in particular S or $SO_2$;
$R_{25}$ is $C_1$-$C_4$alkyl, in particular methyl or ethyl;
$R_{33}$ is $C_1$-$C_4$alkyl, in particular methyl or ethyl; and
$Q_d$ is selected from the group consisting of the heterocycles

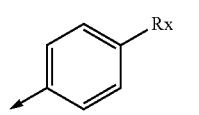
J-0a

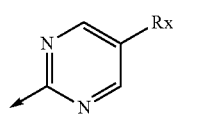
J-5a and

J-43a wherein each group J is monosubstituted with Rx, wherein each Rx is independently selected from the group consisting of hydrogen, halogen, cyano, $C_1$-$C_4$alkyl, $C_1$-$C_4$haloalkyl, $C_1$-$C_4$haloalkoxy, $C_1$-$C_4$alkoxy, $C_1$-$C_4$alkylsulfanyl, $C_1$-$C_4$alkylsulfinyl, $C_1$-$C_4$alkylsulfonyl, —C(O)$C_1$-$C_4$alkyl, $C_1$-$C_4$haloalkylsulfanyl, $C_1$-$C_4$haloalkylsulfinyl, $C_1$-$C_4$haloalkylsulfonyl and —C(O) $C_1$-$C_4$haloalkyl; and agrochemically acceptable salts, stereoisomers, enantiomers, tautomers and N-oxides of the compounds of formula Ia-4.

In said preferred compounds of formula Ia-4, Rx is independently selected from hydrogen and $C_1$-$C_4$haloalkyl; in particular from hydrogen and trifluoromethyl.

An especially preferred group of compounds of formula I are represented by the compounds of formula Ia-5

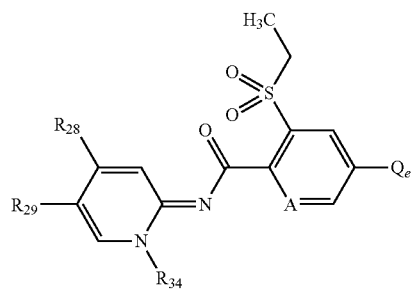
(Ia-5)

wherein
A is N or CH, in particular N;
$R_{28}$ is hydrogen;
$R_{29}$ is trifluoromethylsulfanyl, trifluoromethylsulfinyl or trifluoromethylsulfonyl, in particular trifluoromethylsulfanyl;
$R_{34}$ is $C_1$-$C_4$alkyl, in particular methyl or ethyl; and
$Q_e$ is selected from the group consisting of the heterocycles

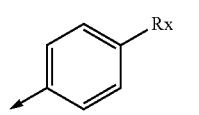
J-0a

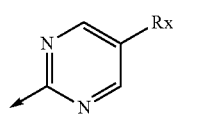
J-5a and

J-43a wherein each Rx is independently selected from hydrogen and $C_1$-$C_4$haloalkyl.

In said more preferred compounds of formula Ia-5, Rx is preferably independently selected from hydrogen and trifluoromethyl.

A further preferred group of compounds of formula I is represented by the compounds of formula I-5

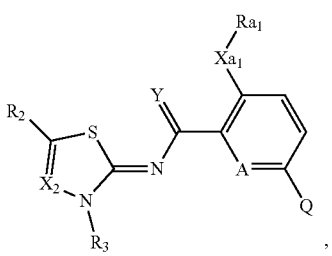

(I-5)

wherein A, Y, $R_2$, $R_3$, $X_2$ and Q are as defined under formula I above; and wherein $Xa_1$ is S, SO or $SO_2$; $Ra_1$ is methyl, ethyl, n-propyl, i-propyl or cyclopropylmethyl; and agrochemically acceptable salts, stereoisomers, enantiomers, tautomers and N-oxides of those compounds. In this preferred group of compounds of formula I-5, $Xa_1$ is preferably $SO_2$, and $Ra_1$ is preferably ethyl, Y is preferably O, $R_2$ is in particular pentafluoroethyl or trifluoromethyl, preferably trifluoromethyl, $R_3$ is in particular methyl or ethyl, preferably methyl, and $X_2$ is N or CH, preferably N.

In said preferred compounds of formula I-5, Q is selected from the group consisting of J-1 to J-45, wherein J-1 to J-45, and Rx, is as defined in Q in formula I-1 above.

In compounds of formula I-5 and all of the preferred embodiments of compounds of formula I-5 mentioned above, Q is preferably selected from

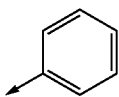

J-44 wherein J-44 is mono- di- or trisubstituted with Rx, wherein each Rx is, independently selected from the group consisting of hydrogen, halogen, cyano, $C_1$-$C_4$alkyl, $C_1$-$C_4$haloalkyl, $C_1$-$C_4$haloalkoxy, $C_1$-$C_4$alkoxy, $C_1$-$C_4$alkyl-sulfanyl, $C_1$-$C_4$alkylsulfinyl, $C_1$-$C_4$alkylsulfonyl, —C(O)$C_1$-$C_4$alkyl, $C_1$-$C_4$haloalkylsulfanyl, $C_1$-$C_4$haloalkylsulfinyl, $C_1$-$C_4$haloalkylsulfonyl and —C(O)$C_1$-$C_4$haloalkyl.

Preferably each Rx is independently selected from hydrogen and $C_1$-$C_4$haloalkyl, preferably selected from hydrogen and trifluoromethyl.

Another preferred embodiment of the invention comprises compounds of formula I represented by the compounds of formula Ia-6

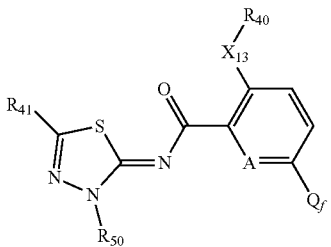

(Ia-6)

wherein
A is N or CH, in particular N;
$X_{13}$ is S or $SO_2$, in particular $SO_2$;
$R_{40}$ is $C_1$-$C_4$alkyl;
$R_{41}$ is $C_1$-$C_4$haloalkyl;
$R_{50}$ is $C_1$-$C_4$alkyl; and
$Q_f$ is

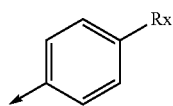

J-0a wherein J-0a is monosubstituted with Rx, wherein
Rx is hydrogen, halogen, cyano, $C_1$-$C_4$alkyl, $C_1$-$C_4$haloalkyl, $C_1$-$C_4$haloalkoxy, $C_1$-$C_4$alkoxy, $C_1$-$C_4$alkylsulfanyl, $C_1$-$C_4$alkylsulfinyl, $C_1$-$C_4$alkylsulfonyl, —C(O)$C_1$-$C_4$alkyl, $C_1$-$C_4$haloalkylsulfanyl, $C_1$-$C_4$haloalkylsulfinyl, $C_1$-$C_4$haloalkylsulfonyl or —C(O)$C_1$-$C_4$haloalkyl; and agrochemically acceptable salts, stereoisomers, enantiomers, tautomers and N-oxides of the compounds of formula Ia-6.

In said preferred compounds of formula Ia-6, Rx is independently preferably selected from hydrogen and $C_1$-$C_4$haloalkyl; in particular from hydrogen and trifluoromethyl.

An especially preferred group of compounds of formula I are represented by the compounds of formula Ia-7

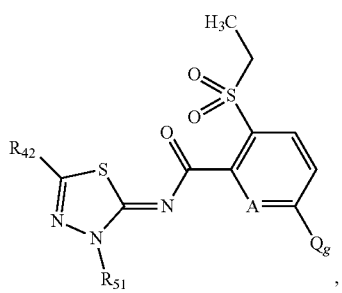

(Ia-7)

wherein
A is N or CH, in particular N;
$R_{42}$ is $C_1$-$C_4$haloalkyl;
$R_{51}$ is $C_1$-$C_4$alkyl; and
$Q_g$ is

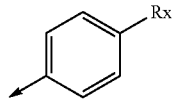

J-0a wherein Rx is hydrogen or $C_1$-$C_4$haloalkyl. In said more preferred compounds of formula Ia-7, Rx is preferably hydrogen and trifluoromethyl.

In an outstanding group of compounds of formula I,
$R_1$ is $C_1$-$C_4$alkyl;
$R_2$ is $C_1$-$C_4$haloalkyl or $C_1$-$C_4$haloalkylsulfanyl;
$R_3$ is $C_1$-$C_4$alkyl;
X is S or $SO_2$;
$X_1$ is S; or $X_1$ is $CR_6$=CH, wherein $R_6$ is hydrogen; preferably $X_1$ is S;

$X_2$ is N; or $X_2$ is C—$R_5$, wherein $R_5$ is hydrogen; preferably $X_2$ is N;

Y is O;

A is CH or N;

Q is phenyl, which is unsubstituted or mono- or polysubstituted by substituents selected from the group consisting of halogen, $C_1$-$C_4$alkysulfonyl, $C_1$-$C_4$haloalkyl, $C_1$-$C_4$haloalkoxy, cyano and $C_1$-$C_4$alkylsulfanyl;

or Q is pyrazolyl, which can be mono-substituted by $C_1$-$C_4$haloalkyl;

or Q is pyridyl, which can be mono- or polysubstituted by substituents selected from the group consisting of halogen, $C_1$-$C_4$haloalkyl and cyano;

or Q is pyrimidinyl, which can be mono-substituted by halogen, $C_1$-$C_4$haloalkyl or cyano;

or Q is $C_3$-$C_6$cycloalkyl which can be mono-substituted by cyano;

or Q is 2,2-difluoro-1,3-benzodioxolyl; or is thiazolyl which can be mono-substituted by $C_1$-$C_4$haloalkyl and halogen; and Q can be in the 3- or 4-position; and the N-oxides of said outstanding compounds of formula I.

The process according to the invention for preparing compounds of formula I is carried out by methods known to those skilled in the art. The following processes describe the prepartion of compounds of formula I, wherein Q is in the 4-position. Compounds of formula I, wherein Q is in the 3-position can be prepared analogously.

The subgroup of compounds of formula I, wherein X is SO (sulfoxide) and/or $SO_2$ (sulfone), may be obtained by means of an oxidation reaction of the corresponding sulfide compounds of formula I, wherein X is S, involving reagents such as, for example, m-chloroperoxybenzoic acid (mCPBA), hydrogen peroxide, oxone, sodium periodate, sodium hypochlorite or tert-butyl hypochlorite amongst other oxidants. The oxidation reaction is generally conducted in the presence of a solvent. Examples of the solvent to be used in the reaction include aliphatic halogenated hydrocarbons such as dichloromethane and chloroform; alcohols such as methanol and ethanol; acetic acid; water; and mixtures thereof. The amount of the oxidant to be used in the reaction is generally 1 to 3 moles, preferably 1 to 1.2 moles, relative to 1 mole of the sulfide compounds Ito produce the sulfoxide compounds I, and preferably 2 to 2.2 moles of oxidant, relative to 1 mole of of the sulfide compounds I to produce the sulfone compounds I. Such oxidation reactions are disclosed, for example, in WO 2013/018928.

The subgroup of compounds of formula I, wherein X is S, SO or $SO_2$ and Y is O, and wherein A, Q, $X_1$, $X_2$, $R_1$, $R_2$ and $R_3$ are as defined above,

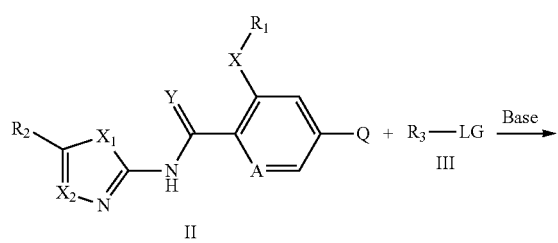

may be prepared by reacting a compound of formula II, wherein X is S, SO or $SO_2$ and Y is O, and wherein A, Q, $X_1$, $X_2$, $R_1$ and $R_2$ are as defined above, with an alkylating agent of formula III, wherein $R_3$ are as defined above and wherein LG is a leaving group such as a halogen (especially bromine or iodine), a sulfonate $OSO_2R_{38}$ (especially mesylate or tosylate), wherein $R_{38}$ is $C_1$-$C_6$alkyl, $C_1$-$C_6$haloalkyl, or phenyl optionally substituted by nitro or $C_1$-$C_3$alkyl, or a sulfate (such as dimethylsulfate), preferably in the presence of a suitable base, such as alkali metal carbonates, for example sodium carbonate or potassium carbonate, or alkali metal hydrides such as sodium hydride, or alkali metal hydroxides such as sodium hydroxide and potassium hydroxide, in an inert solvent at temperatures between −20 and 150° C., preferably between 0 and 80° C. Examples of solvent to be used include ethers such as tetrahydrofuran, ethylene glycol dimethyl ether, tert-butylmethyl ether, and 1,4-dioxane, aromatic hydrocarbons such as toluene and xylene, nitriles such as acetonitrile or polar aprotic solvents such as N,N-dimethylformamide, N,N-dimethylacetamide, N-methyl-2-pyrrolidone or dimethyl sulfoxide.

The subgroup of compounds of formula II, wherein X is S, SO or $SO_2$ and Y is O, and wherein A, Q, $X_1$, $X_2$, $R_1$ and $R_2$ are as defined above,

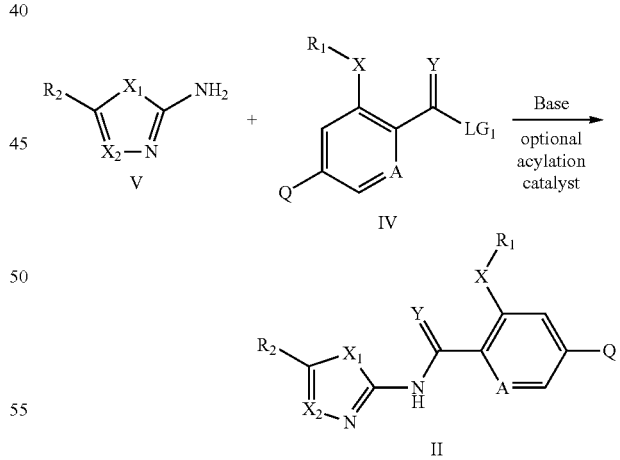

may be prepared by reacting a compound of formula V, or a salt thereof (such as a hydrohalide salt, preferably a hydrochloride or a hydrobromide salt, or any other equivalent salt), wherein $X_1$, $X_2$ and $R_2$ are as defined above, with a compound of formula IV, wherein X is S, SO or $SO_2$ and Y is O, and wherein A, $R_1$ and Q are as defined above, and wherein $LG_1$ is a leaving group such as a halogen (especially chlorine), optionally in presence of an acylating catalyst, such as 4-dimethylaminopyridine (DMAP), preferably in

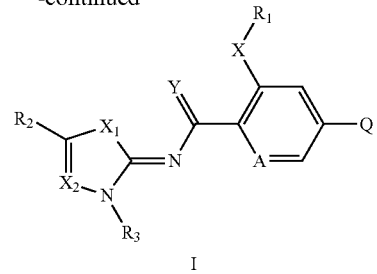

presence of a base, such as triethylamine, diisopropylethylamine or pyridine, in an inert solvent at temperatures between 0 and 50° C. Examples of solvent to be used include ethers such as tetrahydrofuran, ethylene glycol dimethyl ether, tert-butylmethyl ether, and 1,4-dioxane, aromatic hydrocarbons such as toluene and xylene, halogenated hydrocarbons such as dichloromethane and chloroform, nitriles such as acetonitrile or polar aprotic solvents such as N,N-dimethylformamide, N,N-dimethylacetamide, N-methyl-2-pyrrolidone or dimethyl sulfoxide.

Compounds of formula V, or salts thereof, wherein $X_1$, $X_2$ and $R_2$ are as described above are known compounds or can be prepared by known methods, described in the literature.

The compounds of formula II

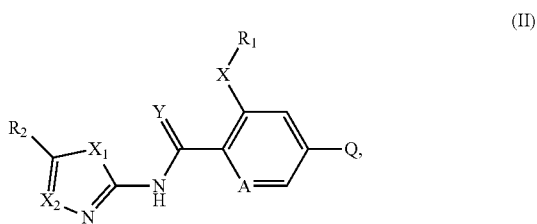

(II)

wherein

Q, Y, $R_1$, $R_2$, X, $X_1$, $X_2$ and A are as defined under formula I, are novel, especially developed for the preparation of the compounds of formula I according to the invention and therefore represent a further object of the invention. The preferences and preferred embodiments of the substituents of the compounds of formula I are also valid for the compounds of formula II.

The subgroup of compounds of formula IV, wherein X is S, SO or $SO_2$ and Y is O, and wherein A, $R_1$ and Q are as defined above, and wherein $LG_1$ is a leaving group such as a halogen (especially chlorine), may be prepared by activation of compound of formula IVa,

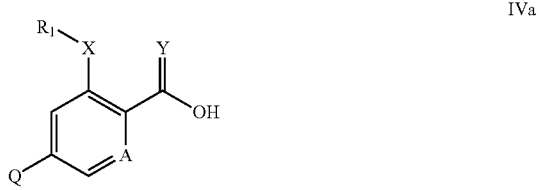

IVa wherein X is S, SO or $SO_2$ and Y is O, and wherein A, $R_1$ and Q are as defined above, by methods known to those skilled in the art and described in, for example, Tetrahedron, 2005, 61 (46), 10827-10852. For example, compounds IV where LG, is halogen, preferably chlorine, are formed by treatment of IVa with, for example, oxalyl chloride $(COCl)_2$ or thionyl chloride $SOCl_2$ in the presence of catalytic quantities of N,N-dimethylformamide DMF in inert solvents such as methylene chloride $CH_2Cl_2$ or tetrahydrofuran THF at temperatures between 20 to 100° C., preferably 25° C.

The subgroup of compounds of formula II, wherein X is SO (sulfoxide) and/or $SO_2$ (sulfone), may be obtained by means of an oxidation reaction of the corresponding sulfide compounds of formula II, wherein X is S, involving reagents such as, for example, m-chloroperoxy-benzoic acid (mCPBA), hydrogen peroxide, oxone, sodium periodate, sodium hypochlorite or tert-butyl hypochlorite amongst other oxidants. The oxidation reaction is generally conducted in the presence of a solvent. Examples of the solvent to be used in the reaction include aliphatic halogenated hydrocarbons such as dichloromethane and chloroform; alcohols such as methanol and ethanol; acetic acid; water; and mixtures thereof. The amount of the oxidant to be used in the reaction is generally 1 to 3 moles, preferably 1 to 1.2 moles, relative to 1 mole of the sulfide compounds II to produce the sulfoxide compounds II, and preferably 2 to 2.2 moles of oxidant, relative to 1 mole of of the sulfide compounds II to produce the sulfone compounds II. Such oxidation reactions are disclosed, for example, in WO 2013/018928.

Alternatively, compounds of formula I, wherein X is S, SO or $SO_2$ and Y is O, and wherein A, Q, $X_1$, $X_2$, $R_1$, $R_2$ and $R_3$ are as defined above,

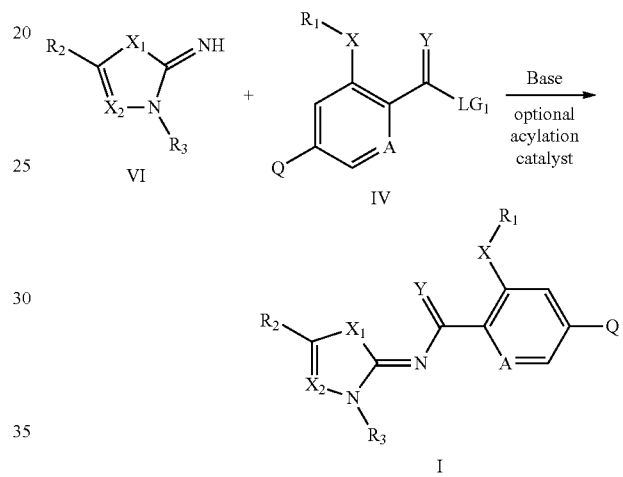

may be prepared by reacting a compound of formula VI, or a salt thereof (such as a hydrohalide salt, preferably a hydrochloride, hydrobromide or a hydroiodide salt, or any other equivalent salt), wherein $X_1$, $X_2$, $R_2$ and $R_3$ are as defined above, with a compound of formula IV, wherein X is S, SO or $SO_2$ and Y is O, and wherein A, $R_1$ and Q are as defined above, and wherein $LG_1$ is a leaving group such as a halogen (especially chlorine), optionally in presence of an acylating catalyst, such as 4-dimethylaminopyridine (DMAP), preferably in presence of a base, such as triethylamine, diisopropylethylamine or pyridine, in an inert solvent at temperatures between 0 and 50° C. Examples of solvent to be used include ethers such as tetrahydrofuran, ethylene glycol dimethyl ether, tert-butylmethyl ether, and 1,4-dioxane, aromatic hydrocarbons such as toluene and xylene, halogenated hydrocarbons such as dichloromethane and chloroform, nitriles such as acetonitrile or polar aprotic solvents such as N,N-dimethylformamide, N,N-dimethylacetamide, N-methyl-2-pyrrolidone or dimethyl sulfoxide.

Compounds of formula VI, or salts thereof (such as a hydrohalide salt, preferably a hydrochloride, hydrobromide or a hydroiodide salt, or any other equivalent salt), wherein $X_1$, $X_2$, $R_2$ and $R_3$ are as described above, are known compounds or can be prepared by known methods, described in the literature, such as, for example, U.S. Pat. No. 4,264,616A. In particular, compounds of formula VI, or salts thereof, wherein $X_1$, $X_2$, $R_2$ and $R_3$ are as described above,

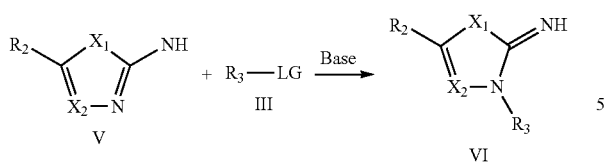

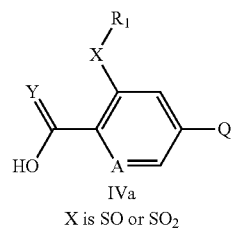

IVa
X is SO or SO$_2$ may be prepared by reacting a compound of formula V, or a salt thereof (such as a hydrohalide salt, preferably a hydrochloride or a hydrobromide salt, or any other equivalent salt), wherein $X_1$, $X_2$ and $R_2$ are as defined above, with an alkylating agent of formula III, wherein $R_3$ are as defined above and wherein LG is a leaving group such as a halogen (especially bromine or iodine), a sulfonate $OSO_2R_{38}$ (especially mesylate or tosylate), wherein $R_{38}$ is $C_1$-$C_6$alkyl, $C_1$-$C_6$haloalkyl, or phenyl optionally substituted by nitro or $C_1$-$C_3$alkyl, or a sulfate (such as dimethylsulfate), optionally in the presence of a suitable base, such as alkali metal carbonates, for example sodium carbonate or potassium carbonate, or alkali metal hydrides such as sodium hydride, or alkali metal hydroxides such as sodium hydroxide and potassium hydroxide, in an inert solvent at temperatures between −20 and 150° C., preferably between 0 and 80° C. Examples of solvent to be used include ethers such as tetrahydrofuran, ethylene glycol dimethyl ether, tert-butylmethyl ether, and 1,4-dioxane, aromatic hydrocarbons such as toluene and xylene, nitriles such as acetonitrile or polar aprotic solvents such as N,N-dimethylformamide, N,N-dimethylacetamide, N-methyl-2-pyrrolidone or dimethyl sulfoxide.

N-oxides of compounds of the formula I can be prepared by reacting a compound of the formula I with a suitable oxidizing agent, such as, for example, m-chloroperoxybenzoic acid (mCPBA), hydrogen peroxide, oxone, sodium periodate, sodium hypochlorite or tert-butyl hypochlorite amongst other oxidants. The oxidation reaction is generally conducted in the presence of a solvent. Examples of the solvent to be used in the reaction include aliphatic halogenated hydrocarbons such as dichloromethane and chloroform; alcohols such as methanol and ethanol; acetic acid or trifluoroacetic acid; water; and mixtures thereof. Another option involves, for example, the $H_2O_2$/urea adduct in the presence of an acid anhydride, e.g. trifluoroacetic anhydride. Such oxidations are known from the literature, for example from J. Med. Chem. 1989, 32, 2561 or WO 2000/15615. Optionally, the oxidation reaction is conducted in the presence of a catalyst such as, for example, sodium tungstate, and the like.

The subgroup of compounds of formula IVa, wherein X is S and Y is O, and wherein A, $R_1$ and Q are as defined above,

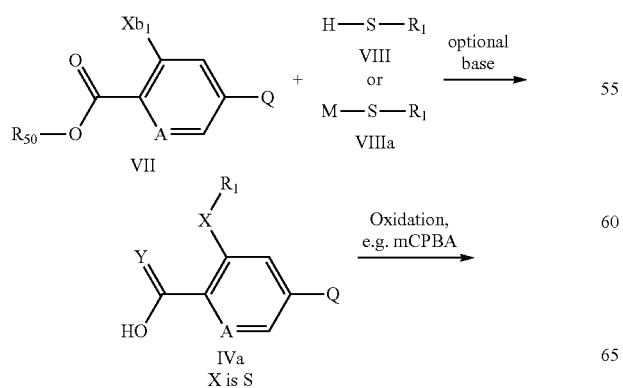

may be prepared by reacting a compound of formula VII, wherein A and Q are as defined above, and wherein $R_{50}$ is $C_1$-$C_4$alkyl and in which $Xb_1$ is a leaving group such as, for example, a halogen (preferably fluorine, chlorine or bromine) or nitro, with a compound of formula VIII, or a salt thereof VIIIa, wherein $R_1$ is as defined in formula I, optionally in the presence of a suitable base, such as alkali metal carbonates, for example sodium carbonate and potassium carbonate, or alkali metal hydrides such as sodium hydride, or alkali metal hydroxides such as sodium hydroxide and potassium hydroxide, optionally in the presence of a catalytic amount of an additive, such as an ammonium salt (for example tetrabutylammonium bromide TBAB), in an inert solvent at temperatures preferably between 25-120° C. Examples of solvent to be used include ethers such as THF, ethylene glycol dimethyl ether, tert-butylmethyl ether, and 1,4-dioxane, aromatic hydrocarbons such as toluene and xylene, nitriles such as acetonitrile, polar aprotic solvents such as N,N-dimethylformamide, N,N-dimethylacetamide, N-methyl-2-pyrrolidone or dimethyl sulfoxide, or water. Examples of salts of the compound of formula VIII include compounds of the formula VIIIa $$R_1\text{—S—M} \qquad \text{(VIIIa)},$$

wherein $R_1$ is as defined above and wherein M is, for example, sodium or potassium. Oxidation of compounds of formula IVa, wherein X is S and Y is O, and wherein A, $R_1$ and Q are as defined above, with a suitable oxidizing agent, into compounds of formula IVa, wherein X is SO or SO$_2$ may be achieved under conditions already described above.

Compounds of formula VII, wherein A and Q are as defined above, and wherein $R_{50}$ is $C_1$-$C_4$alkyl and in which $Xb_1$ is a leaving group such as, for example, a halogen (preferably fluorine, chlorine or bromine) or nitro,

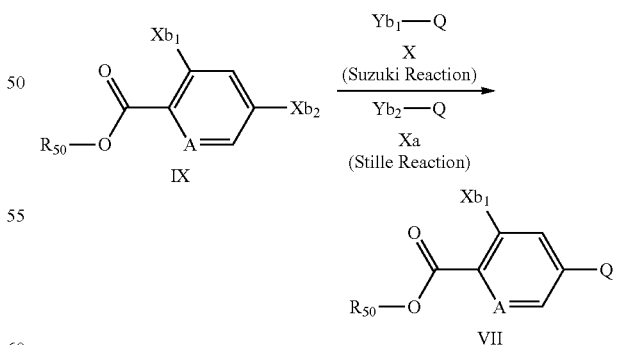

may be prepared by a Suzuki reaction, which involves for example, reacting compounds of formula IX, wherein A, $R_{50}$ and $Xb_1$ are as defined above, and wherein $Xb_2$ is a leaving group like, for example, chlorine, bromine or iodine (preferably bromine), or an aryl- or alkylsulfonate such as trifluoromethane-sulfonate, with compounds of formula X, wherein Q is as defined above, and wherein $Y_{b1}$ can be a boron-derived functional group, such as for example $B(OH)_2$ or $B(OR_{b1})_2$ wherein $R_{b1}$ can be a $C_1$-$C_4$alkyl group or the two groups $OR_{b1}$ can form together with the boron atom a five membered ring, as for example a pinacol boronic ester. The reaction may be catalyzed by a palladium based catalyst, for example tetrakis(triphenylphosphine)-palladium(0), or bis(triphenylphosphine)palladium(II) dichloride, or (1,1'bis(diphenylphosphino)ferrocene)dichloro-palladium-dichloromethane (1:1 complex), in presence of a base, like sodium carbonate or cesium fluoride, in a solvent or a solvent mixture, like, for example a mixture of 1,2-dimethoxyethane and water or of dioxane and water, preferably under inert atmosphere. The reaction temperature can preferentially range from room temperature to the boiling point of the reaction mixture. Such Suzuki reactions are well known to those skilled in the art and have been reviewed, for example, in *J. Orgmet. Chem.* 576, 1999, 147-168.

Alternatively compounds of formula VII, wherein A, Q, $R_{50}$ and $Xb_1$ are as defined above, may be prepared by a Stille reaction between compounds of formula Xa, wherein Q is as defined above, and wherein $Y_{b2}$ is a trialkyl tin derivative, preferably tri-n-butyl tin, and compounds of formula IX, wherein A, $R_{50}$ and $Xb_1$ are as defined above, and wherein $Xb_2$ is a leaving group like, for example, chlorine, bromine or iodine (preferably bromine), or an aryl- or alkylsulfonate such as trifluoromethane-sulfonate. Such Stille reactions are usually carried out in the presence of a palladium catalyst, for example tetrakis(triphenylphosphine) palladium(0), or bis(triphenylphosphine)palladium(II) dichloride, in an inert solvent such as N,N-dimethylformamide, acetonitrile, toluene or dioxane, optionally in the presence of an additive, such as cesium fluoride, or lithium chloride, and optionally in the presence of a further catalyst, for example copper(I)iodide. Such Stille couplings are also well known to those skilled in the art, and have been described in for example *J. Org. Chem.*, 2005, 70, 8601-8604, *J. Org. Chem.*, 2009, 74, 5599-5602, and *Angew. Chem. Int. Ed.*, 2004, 43, 1132-1136.

A large number of compounds of the formula X and Xa are commercially available or can be prepared by those skilled in the art.

Ester compounds of formula IX, wherein A, $R_{50}$, $Xb_1$ and $Xb_2$ are as defined above,

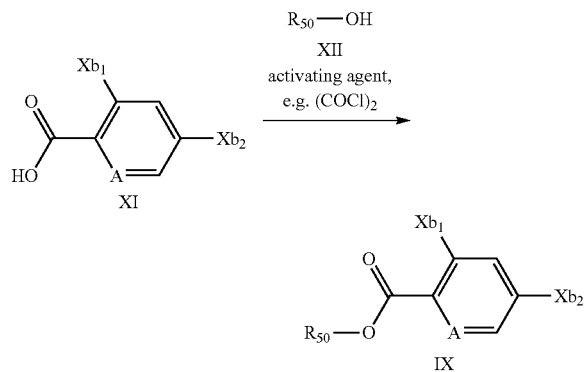

may be prepared from the corresponding carboxylic acid compounds of formula XI, wherein A, $Xb_1$ and $Xb_2$ are as defined above, by reaction with an alcohol of formula XII, wherein $R_{50}$ is $C_1$-$C_4$alkyl, optionally in the presence of an acid (such as sulfuric acid), or alternatively optionally in presence of an activating agent, such as for example oxalyl chloride $(COCl)_2$. Such esterification methods are well known to a person skilled in the art.

When Q is a five- to six-membered, aromatic, partially saturated or fully saturated ring system linked via a nitrogen atom to the ring which contains the group A, then compounds of formula VII, wherein A, $R_{50}$ and $Xb_1$ are as defined above, may be prepared from compounds of formula IX, wherein A, $R_{50}$ and $Xb_1$ are as defined above, and wherein $Xb_2$ is a leaving group like, for example, chlorine, bromine or iodine (preferably bromine), or an aryl- or alkylsulfonate such as trifluoromethane-sulfonate, by reaction with a heterocycle Q-H (which contains an appropriate NH functionality) Xaa, wherein Q is as defined above, in the presence of a base, such as potassium carbonate $K_2CO_3$ or cesium carbonate $Cs_2CO_3$, optionally in the presence of a copper catalyst, for example copper(I) iodide, with or without an additive such as L-proline, N,N'-dimethylcyclohexane-1,2-diamine or N,N'-dimethylethylene-diamine, in an inert solvent such as N-methylpyrrolidone NMP or N,N-dimethylformamide DMF at temperatures between 30-150° C.

Such a reaction (C—N Bond Formation) is illustrated below for the heterocycle Q-H J-30b, wherein J30b and Rx are as defined above,

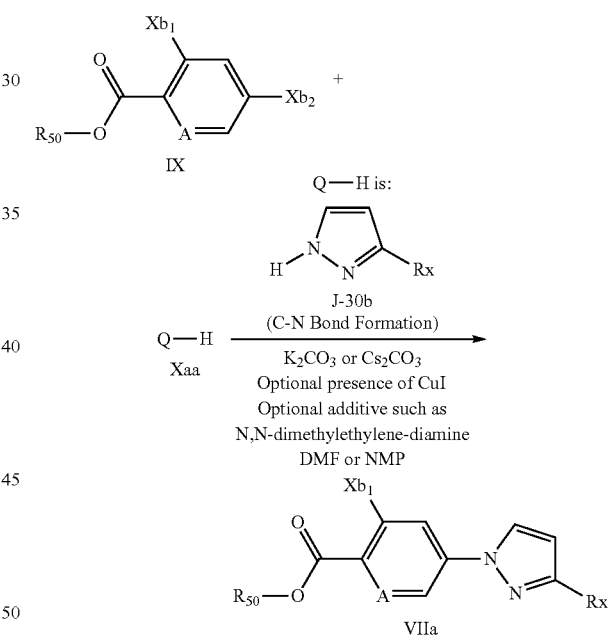

to give compounds of formula VIIa, a particular sub-group of compounds of formula VII, wherein Rx, A, $R_{50}$ and $Xb_1$ are as previously defined.

Alternatively, compounds of formula I may be prepared from compounds of formula VII and compounds of formula VI involving the same chemistry as described above, but by changing the order of the steps. Such an alternative route is summarized in scheme 1. Saponification of a compound of formula VII, wherein A, Q, $R_{50}$ and $Xb_1$ are as defined above, into compounds of formula XIII, wherein A, Q and $Xb_1$ are as defined above, are known to a person skilled in the art (using for example conditions such as: aqueous sodium, potassium or lithium hydroxide in methanol, ethanol or dioxane at room temperature or up to refluxing conditions).

Scheme 1:

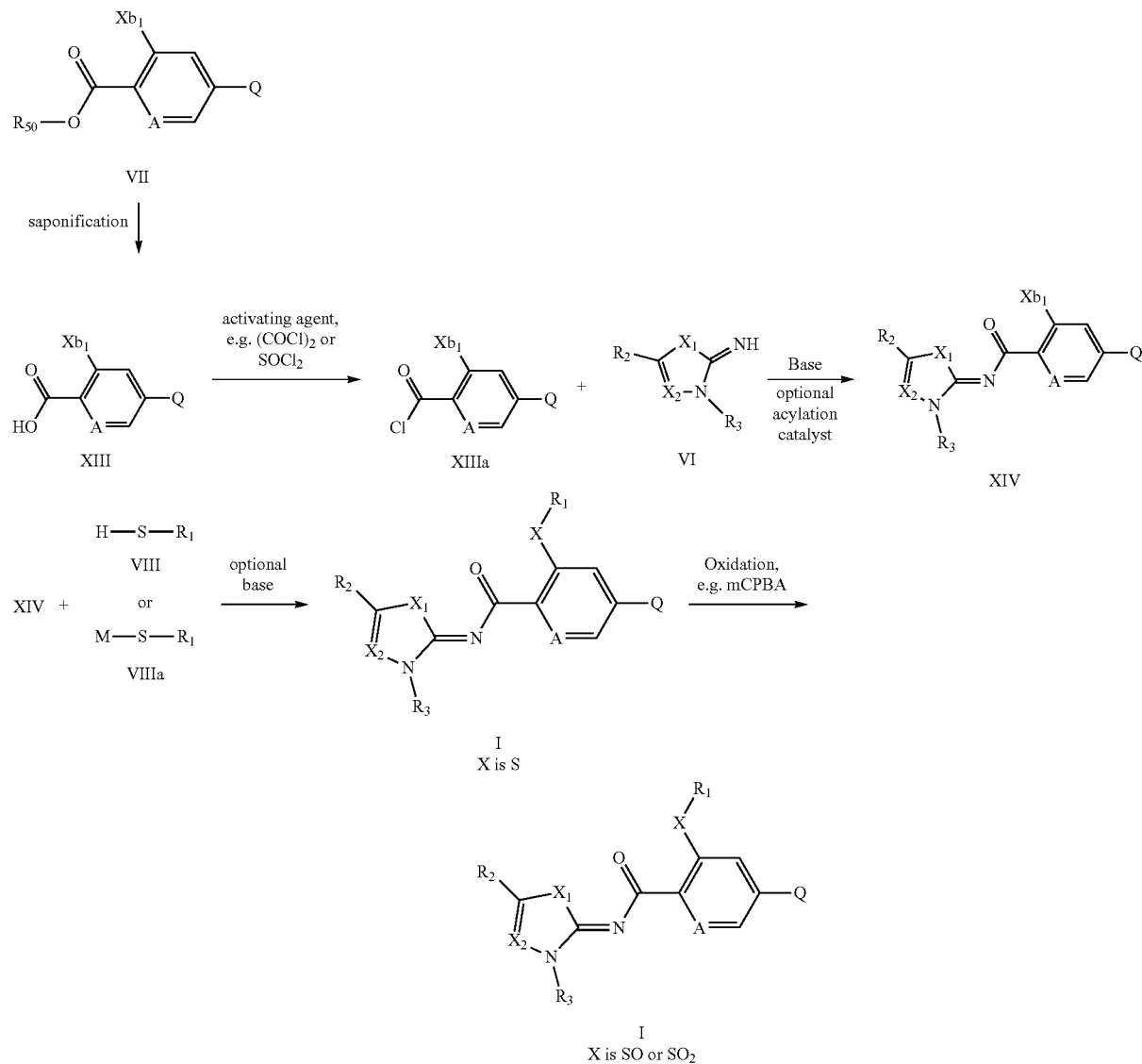

When Q is a five- to six-membered, aromatic, partially saturated or fully saturated ring system linked via a nitrogen atom to the ring which contains the group A, the same considerations apply in analogy. For example, when Q is the fragment J-30b, compounds of the formula VII in scheme 1 may be replaced with compounds of the formula VIIa.

Yet another method to produce compounds of formula I uses again the same reactions previously described but changes their order to produce the final compounds. This is described in scheme 2, and illustrates the preparation of compounds of formula I from compounds of formula XV and compounds of formula VI.

Scheme 2:

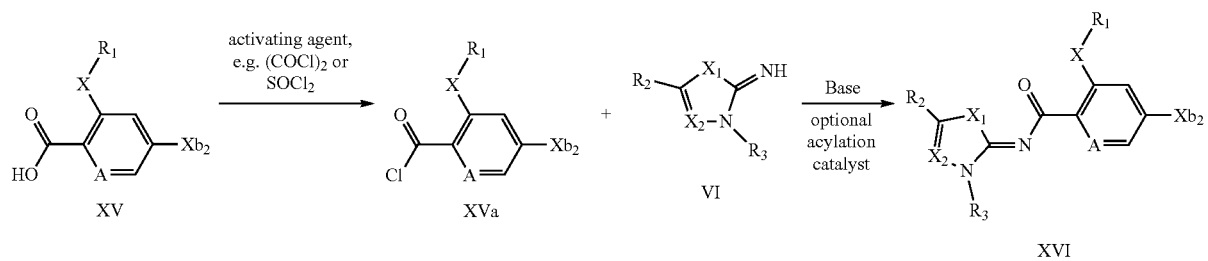

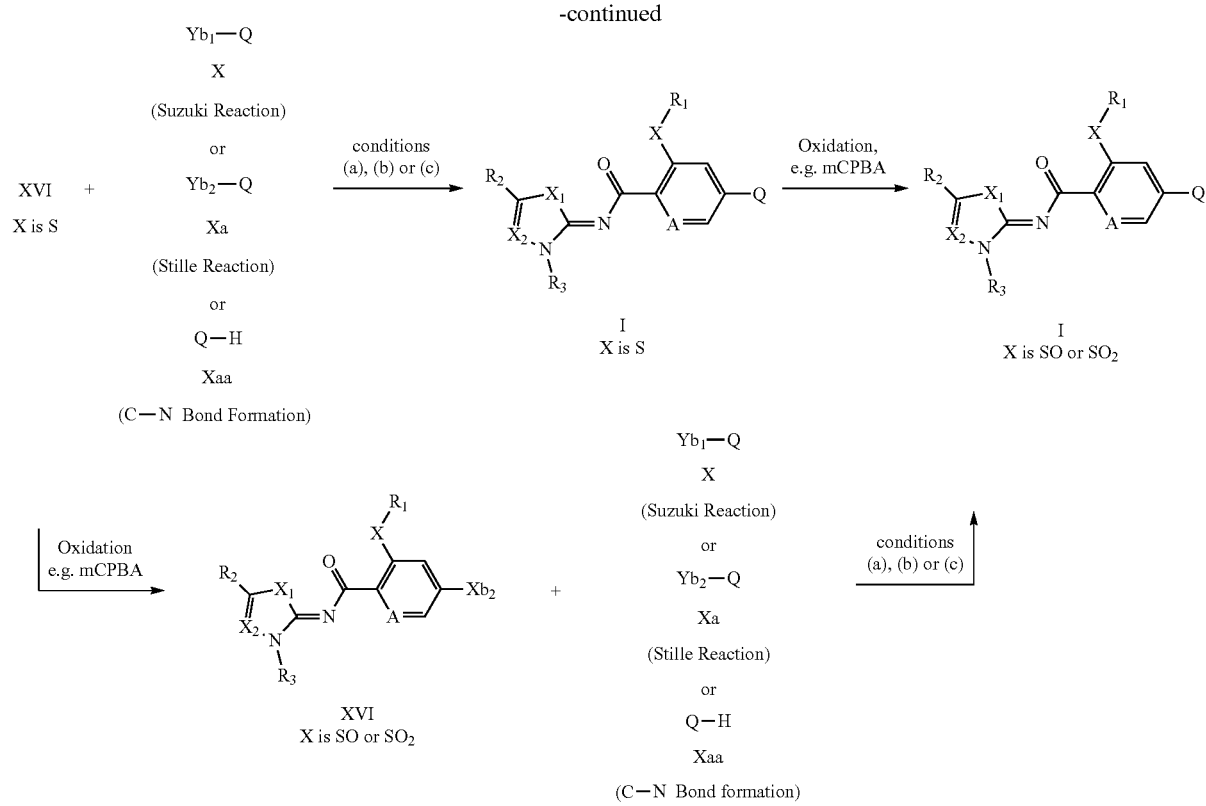

(a) Suzuki reaction: Pd cat. (e.g. Pd(PPh₃)₄ or Pd(dppf)Cl₂), base (e.g. Na₂CO₃), solvent (e.g 1,2-dimethoxyethane/water), 25-180° C.
(b) Stille reaction: Pd cat. (e.g. Pd(PPh₃)₄ or Pd(PPh₃)Cl₂), solvent (e.g toluene), 25-180° C.
(c) C—N bond formation: Base (e.g. K₂CO₃ or Cs₂CO₃), optional presence of CuI, optional additive (such as N,N'-dimethylethylene-diamine), solvent (e.g. N,N-dimethylformamide DMF or N-methylpyrrolidone NMP, 25-180° C.

The substituent definitions in compounds of formula XV, XVa, VI (which may be used as a salt or as the free base), XVI and I, and in reagents of formula X, Xa and Xaa, are as previously described. Key reaction in scheme 2 is the preparation of compounds of formula I, wherein X is S, SO or SO₂ and Y is O, and wherein A, Q, $X_1$, $X_2$, $R_1$, $R_2$ and $R_3$ are as defined above, from compounds of formula XVI, wherein X is S, SO or SO₂, and wherein A, $X_1$, $X_2$, $R_1$, $R_2$ and $R_3$ are as defined above, and in which $Xb_2$ is a leaving group like, for example, chlorine, bromine or iodine (preferably bromine), or an aryl- or alkylsulfonate such as trifluoromethanesulfonate, and a reagent of formula X, Xa or Xaa, (wherein $Yb_1$, $Yb_2$ and Q are as described above) incorporating the fragment Q. This key step is coupled to an additional oxidation step, which was already described before.

Compounds of formula XV, wherein X is S, and wherein A, $R_1$ and $Xb_2$ are as defined above,

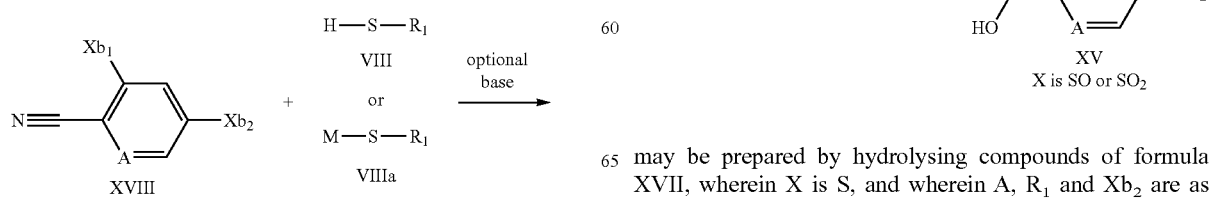

may be prepared by hydrolysing compounds of formula XVII, wherein X is S, and wherein A, $R_1$ and $Xb_2$ are as defined above, for example through heating in concentrated acid, such as concentrated hydrochloric acid HCl conc., optionally in the presence of an inert solvent, such as ethers (for example tetrahydrofuran, ethylene glycol dimethyl ether, or 1,4-dioxane). Such hydrolysis conditions, and variants thereof, are known to a person skilled in the art.

Compounds of formula XVII, wherein X is S, and wherein A, $R_1$ and $Xb_2$ are as defined above, may be prepared by reacting compounds of formula XVIII, wherein A and $Xb_2$ are as defined above, and in which wherein $Xb_1$ is a leaving group such as, for example, a halogen (preferably fluorine, chlorine or bromine) or nitro, with a compound of formula VIII, or a salt thereof VIIIa, wherein $R_1$ is as defined in formula I, optionally in the presence of a suitable base, such as alkali metal carbonates, for example sodium carbonate and potassium carbonate, or alkali metal hydrides such as sodium hydride, or alkali metal hydroxides such as sodium hydroxide and potassium hydroxide, optionally in the presence of a catalytic amount of an additive, such as an ammonium salt (for example tetrabutylammonium bromide TBAB), in an inert solvent at temperatures preferably between 25-120° C. Examples of solvent to be used include ethers such as THF, ethylene glycol dimethyl ether, tert-butylmethyl ether, and 1,4-dioxane, aromatic hydrocarbons such as toluene and xylene, nitriles such as acetonitrile, polar aprotic solvents such as N,N-dimethylformamide, N,N-dimethylacetamide, N-methyl-2-pyrrolidone or dimethyl sulfoxide, or water. Examples of salts of the compound of formula VIII include compounds of the formula VIIIa $R_1$—S-M  (VIIIa), wherein $R_1$ is as defined above and wherein M is, for example, sodium or potassium.

Oxidation of compounds of formula XV, wherein X is S, and wherein A, $R_1$ and $Xb_2$ are as defined above, with a suitable oxidizing agent, into compounds of formula XV, wherein X is SO or $SO_2$ may be achieved under conditions already described above.

Changing order of reaction conditions that have been described above may also allow to convert compounds of the formula XV, or their activated form XVa, into useful compounds of the formula IVa. This is illustrated in scheme 3.

Scheme 3:

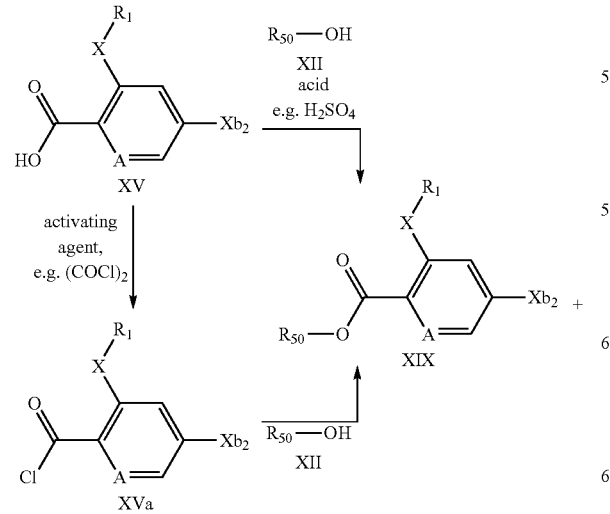

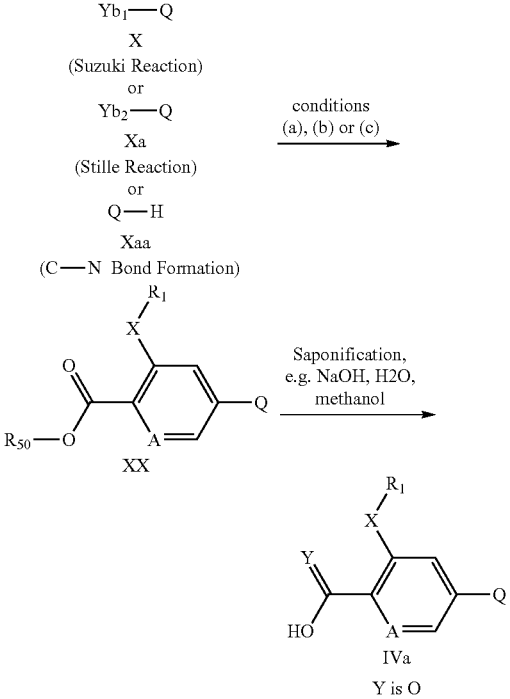

(a) Suzuki reaction: Pd cat. (e.g. Pd(PPh)$_4$ or Pd(dppf)Cl$_2$), base (e.g. Na$_2$CO$_3$), solvent (e.g. 1,2-dimethoxyethane/water), 25-180° C.
(b) Stille reaction: Pd cat. (e.g. Pd(PPh$_3$)$_4$ or Pd(PPh$_3$)Cl$_2$), solvent (e.g. toluene), 25-180° C.
(c) C—N bond formation: Base (e.g. K$_2$CO$_3$ or Cs$_2$CO$_3$), optional presence of CuI, optional additive (such as N,N'-dimethylethylene-diamine), solvent (e.g. N,N-dimethylformamide DMF or N-methylpyrrolidone NMP, 25-180° C.

The substituent definitions in compounds of formula XV, XVa, XIX and XX, and in reagents of formula X, Xa and Xaa, are as previously described.

Compounds of formula I, wherein X is S, SO or $SO_2$,

Scheme 4:

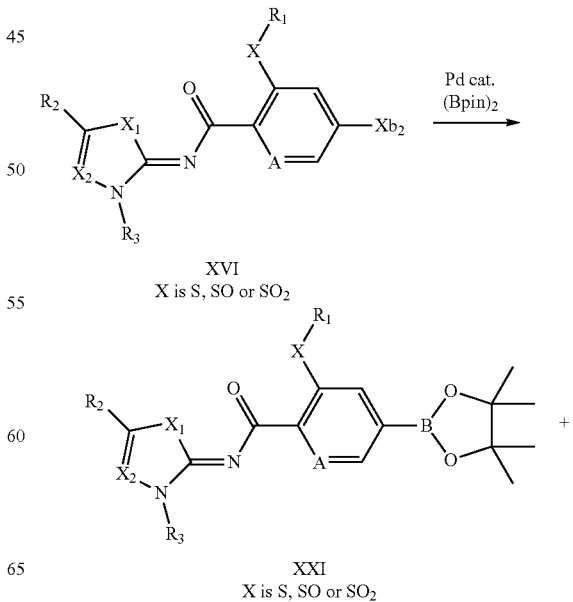

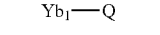

(Suzuki Reaction)

or

Q—H
Xaa (C—N Bond Formation)

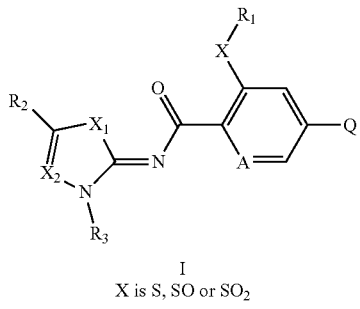

I
X is S, SO or SO$_2$ may alternatively be prepared by a Suzuki reaction (scheme 4), which involves for example, reacting compounds of formula XXI, wherein X is S, SO or SO$_2$, and wherein A, X$_1$, X$_2$, R$_1$, R$_2$ and R$_3$ are as defined above, with compounds of formula X, wherein Q is as defined above, and wherein Yb$_1$ is a leaving group like, for example, chlorine, bromine or iodine (preferably bromine), or an aryl- or alkylsulfonate such as trifluoromethanesulfonate. The reaction may be catalyzed by a palladium based catalyst, for example tetrakis (triphenylphosphine)-palladium(0), (1,1'bis(diphenylphosphino)ferrocene) dichloro-palladium-dichloromethane (1:1 complex) or chloro(2-dicyclohexylphosphino-2',4',6'-triisopropyl-1,1'-biphenyl)[2-(2'-amino-1,1'-biphenyl)]palladium (II) (XPhos palladacycle), in presence of a base, like sodium carbonate, tripotassium phosphate or cesium fluoride, in a solvent or a solvent mixture, like, for example dioxane, acetonitrile, N,N-dimethylformamide, a mixture of 1,2-dimethoxy-ethane and water or of dioxane/water, or of toluene/water, preferably under inert atmosphere. The reaction temperature can preferentially range from room temperature to the boiling point of the reaction mixture, or the reaction may be performed under microwave irradiation. Such Suzuki reactions are well known to those skilled in the art and have been reviewed, for example, in *J. Orgmet. Chem.* 576, 1999, 147-168.

When Q is a five- to six-membered, aromatic, partially saturated or fully saturated ring system linked via a nitrogen atom to the ring which contains the group A, then compounds of formula I, wherein X is S, SO or SO$_2$, may be prepared from compounds of formula XXI, wherein X is S, SO or SO$_2$, and wherein A, X$_1$, X$_2$, R$_1$, R$_2$ and R$_3$ are as defined above, by reaction with a heterocycle Q-H (which contains an appropriate NH functionality) Xaa, wherein Q is as defined above. The reaction, also known as Chan-Lam coupling (P. Y. S. Lam, C. G. Clark, S. Saubern, J. Adams, M. P. Winters, D. M. T. Chan, A. Combs, Tetrahedron Lett. 1998, 39, 2941), is commonly performed with one to two equivalents of a base, like pyridine or triethylamine, in presence of one to two equivalents of a copper derivative, like for example copper (II) acetate and under an oxygen-containing atmosphere. The reaction can be run in an inert solvent, like dichloromethane, dioxane or dimethylformamide, usually at or around room temperature.

Compounds of formula XXI, wherein X is S, SO or SO$_2$, and wherein A, X$_1$, X$_2$, R$_1$, R$_2$ and R$_3$ are as defined above, may be prepared by reacting compounds of formula XVI, wherein X is S, SO or SO$_2$, and wherein A, X$_1$, X$_2$, R$_1$, R$_2$ and R$_3$ are as defined above, and in which Xb$_2$ is a leaving group like, for example, chlorine, bromine or iodine (preferably bromine), or an aryl- or alkylsulfonate such as trifluoromethanesulfonate, with bispinacol diborane (Bpin)$_2$ under palladium catalysis. Such an introduction of a pinacolborate functional group can be performed in an aprotic solvent, such as dioxane, in presence of a base, preferably a weak base, such as potassium acetate KOAc. [1,1'-Bis(diphenylphosphino)ferrocene]dichloropalladium(II), also known as palladium dppf dichloride or Pd(dppf)Cl$_2$, is a common catalyst for this type of reaction. The temperature of the reaction is preferably performed between 0° C. and the boiling point of the reaction mixture, or the reaction may be performed under microwave irradiation.

The compounds of formula XXI-int

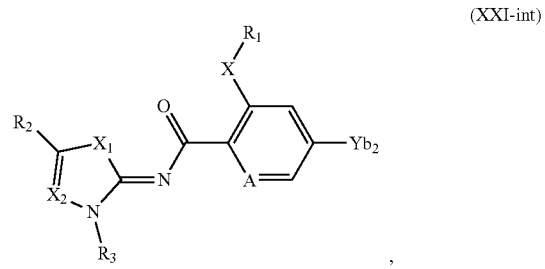

(XXI-int)

wherein

R$_1$, R$_2$, R$_3$, X, X$_1$, X$_2$ and A are as defined under formula I above, and Yb$_2$ is —B(OH)$_2$, —B(OR$_{b2}$)$_2$, in which R$_{b2}$ is a C$_1$-C$_6$alkyl or Yb$_2$ is

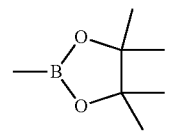

(a 4,4,5,5-tetramethyl-1,3,2-dioxaborolane group), are novel, especially developed for the preparation of the compounds of formula I according to the invention and therefore represent a further object of the invention. The preferences and preferred embodiments of the substituents of the compounds of formula I are also valid for the compounds of formula XXI-int.

Compounds of formula I wherein Q is C$_3$-C$_6$cycloalkyl, mono- or polysubstituted by substituents selected from the group consisting of halogen, cyano, C$_1$-C$_4$haloalkyl, and phenyl, may be prepared by methods described above (in particular, compounds of formula I wherein Q is cyclopropyl may be prepared by a Suzuki reaction involving cyclopropyl-boronic acid according to descriptions made in scheme 2). For the special case of compounds of formula I wherein Q is C$_3$-C$_6$cycloalkyl substituted by cyano (e.g. compounds Iaa) and C$_1$-C$_4$haloalkyl (e.g. compounds Iad), the compounds can be prepared by the methods shown in scheme 5.

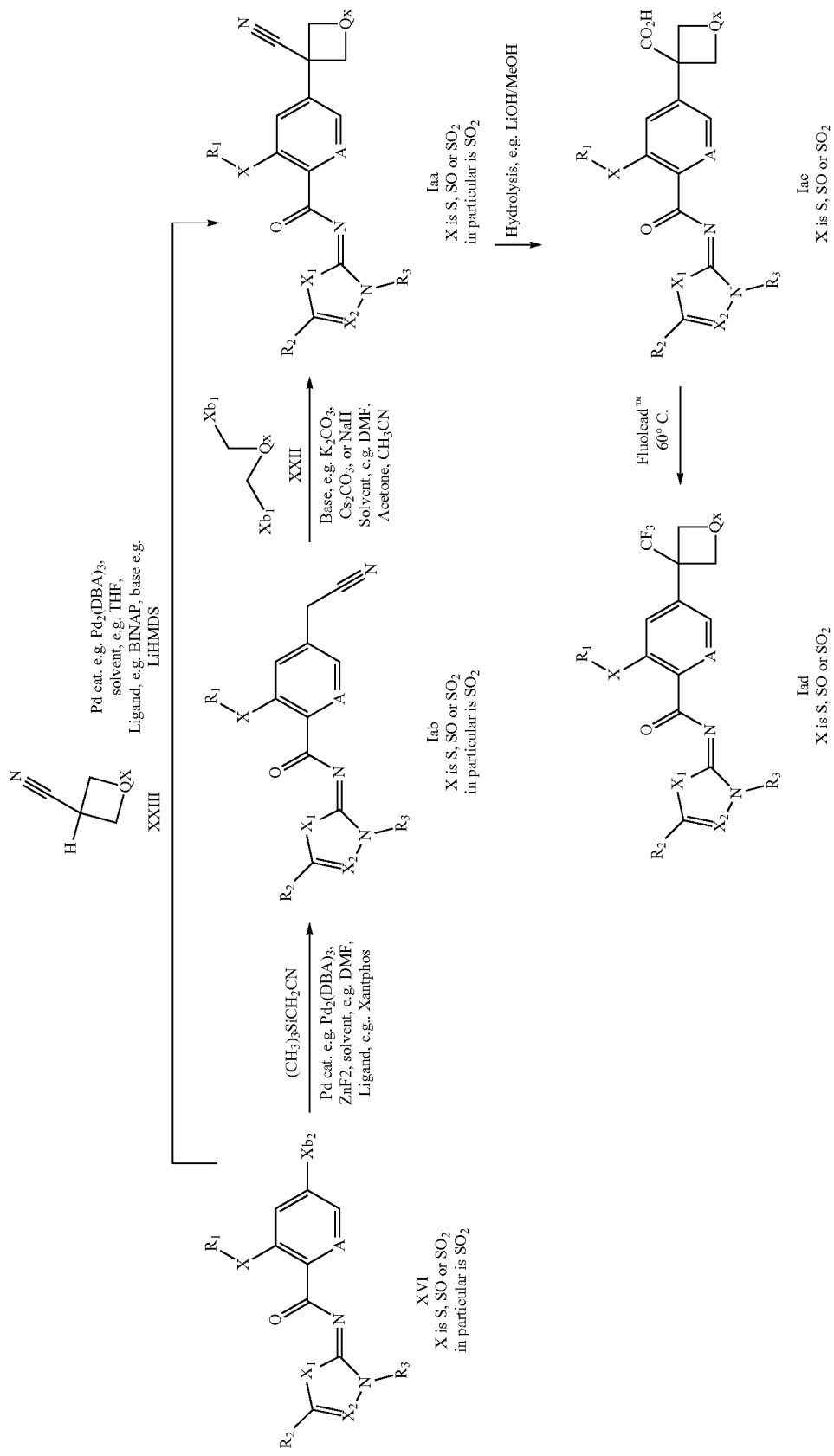

As shown in scheme 5, treatment of compounds of formula XVI, wherein X is S, SO or $SO_2$ (in particular $SO_2$), and wherein A, $X_1$, $X_2$, $R_1$, $R_2$ and $R_3$ are as defined above, and in which $Xb_2$ is a leaving group like, for example, chlorine, bromine or iodine (preferably bromine), or an aryl- or alkylsulfonate such as trifluoromethanesulfonate, with trimethylsilyl-acetonitrile TMSCN, in the presence of zinc (II)fluoride $ZnF_2$, and a palladium(0)catalyst such as tris (dibenzylideneacetone) dipalladium(0)-chloroform adduct $(Pd_2(dba)_3)$, with a ligand, for example Xantphos, in an inert solvent, such as N,N-dimethylformamide DMF at temperatures between 100-180° C., optionally under microwave heating, leads to compounds of formula Iab, wherein X is S, SO or $SO_2$ (in particular $SO_2$). Such chemistry has been described in the literature, e.g. in *Org. Lett.* 16(24), 6314-6317, 2014. Compounds of formula Iab can be treated with compounds of formula XXII, wherein Qx is a direct bond or is $(CH_2)_n$ and n is 1, 2 or 3, and in which $Xb_1$ is a leaving group such as a halogen (preferably chlorine, bromine or iodine), in the presence of a base such as sodium hydride, potassium carbonate $K_2CO_3$, or cesium carbonate $Cs_2CO_3$, in an inert solvent such as N,N-dimethylformamide DMF, acetone, or acetonitrile, at temperatures between 0-120° C., to give compounds of formula Iaa, wherein X is S, SO or $SO_2$ (in particular $SO_2$), and wherein A, $X_1$, $X_2$, $R_1$, $R_2$ and $R_3$ are as defined above and in which Qx is a direct bond or is $(CH_2)$, and n is 1, 2 or 3. Alternatively, compounds of formula Iaa can be prepared directly from compounds of formula XVI by treatment with compounds of formula XXIII, wherein Qx is is as described in XXII, in presence of a catalyst such as $Pd_2(dba)_3$, with a ligand, such as BINAP, a strong base such as lithium hexamethyldisilazane LiH-MDS, in an inert solvent such as tetrahydrofuran THF, at temperatures between 30-80° C. Such chemistry has been described in, for example, *J. Am. Chem. Soc.* 127(45), 15824-15832, 2005.

Compounds of the formula Iaa may further be utilized for the preparation of compounds of formula Iad (scheme 5). Indeed, compounds of formula Iaa, wherein X is S, SO or $SO_2$, and wherein A, $X_1$, $X_2$, $R_1$, $R_2$ and $R_3$ are as defined above and in which Qx is a direct bond or is $(CH_2)$, and n is 1, 2 or 3, may be hydrolyzed, under conditions known to a person skilled in the art (aqueous basic or acidic conditions), to compounds of formula Iac, wherein X is S, SO or $SO_2$, and wherein A, $X_1$, $X_2$, $R_1$, $R_2$ and $R_3$ are as defined above and in which Qx is a direct bond or is $(CH_2)$, and n is 1, 2 or 3. Treatment of compounds of formula Iac with reagents such as sulfur tetrafluoride $SF_4$ or Fluolead (4-tert-butyl-2,6-dimethyl phenylsulfur trifluoride), optionally in the presence of hydrogen fluoride HF, at temperatures between 20-100° C., leads to compounds of formula Iad, wherein X is S, SO or $SO_2$, and wherein A, $X_1$, $X_2$, $R_1$ , $R_2$ and $R_3$ are as defined above and in which Qx is a direct bond or is $(CH_2)$, and n is 1, 2 or 3.

Alternatively compounds of formula Iaa can be prepared as shown in schemes 6 and 7. As shown in scheme 6, the chemistry used is identical to that described in scheme 5, it is just that the substrates for the reactions are different. Thus, reaction of the previously described compound XIX, wherein X is S, SO or $SO_2$ (in particular $SO_2$), and wherein A, R1 are as defined above, and in which $Xb_2$ is a leaving group like, for example, chlorine, bromine or iodine (preferably bromine), or an aryl- or alkylsulfonate such as trifluoromethanesulfonate, and in which $R_{50}$ is $C_1$-$C_4$alkyl, with trimethylsilyl-acetonitrile TMSCN as described in scheme 5, leads to compounds of formula XXIV. These are converted in compounds of formula XXV, wherein X is S, SO or $SO_2$ (in particular $SO_2$), and wherein Qx, A, $R_1$ are as defined above, and in which $R_{50}$ is $C_1$-$C_4$alkyl, by reacting with compounds of formula XXII as described in scheme 5. Similarly, compounds XXV can be prepared directly from XIX by the chemistry discussed in scheme 5. Compounds of formula XXV are readily hydrolysed by methods known to those skilled in the art to give compounds of formula XXVI, wherein X is S, SO or $SO_2$ (in particular $SO_2$), and wherein Qx, A, $R_1$ are as defined above.

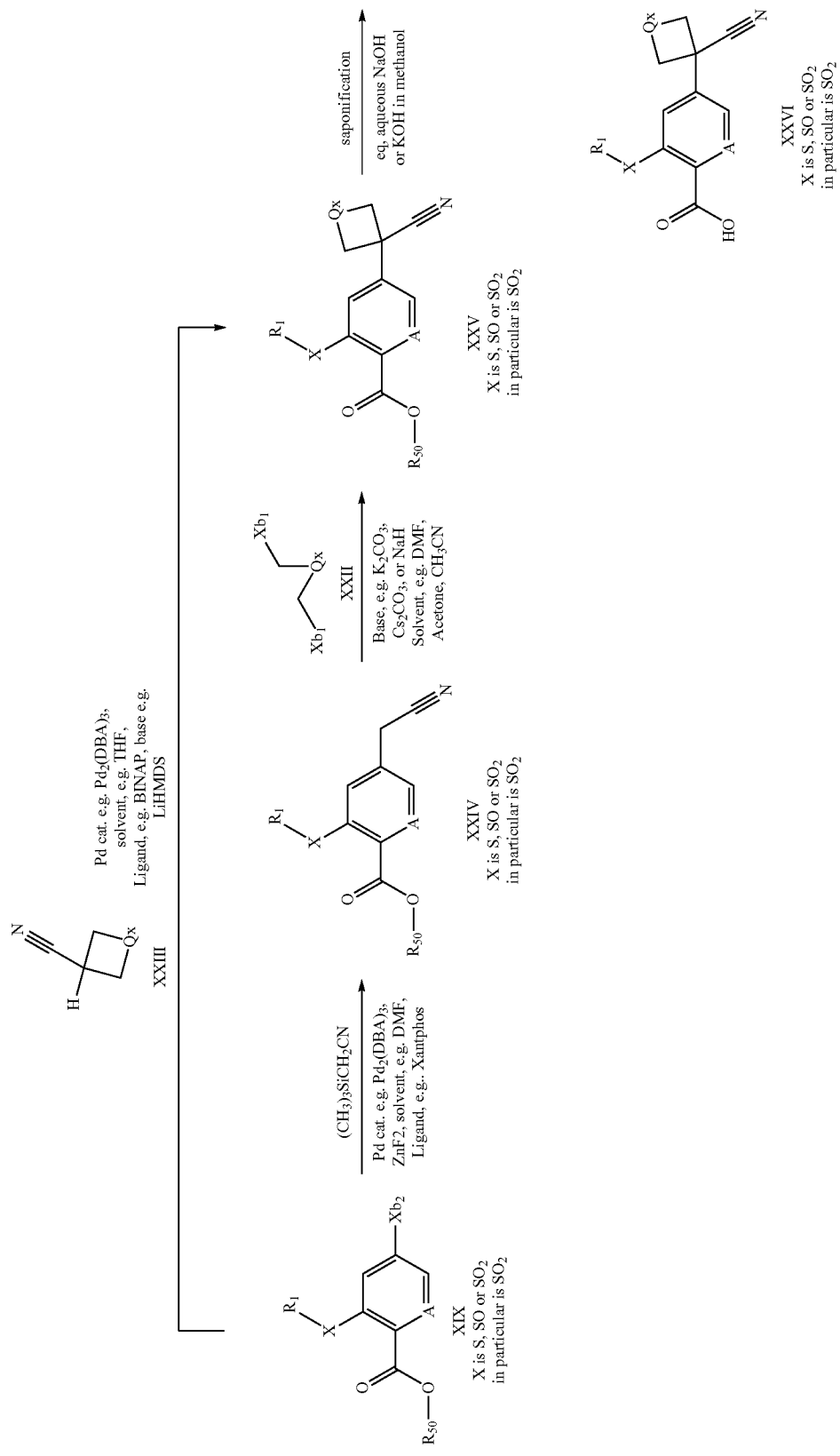

The chemistry shown in scheme 7 has previously been described in detail (see, for example, scheme 2, or text associated to the transformation VI+IV→I). This chemistry involves forming an activated species XXVIa, wherein X is S, SO or $SO_2$ (in particular $SO_2$), and wherein Qx, A, $R_1$ are as defined above, and in which LG, typically is chlorine, followed by amide coupling with a compound of formula VI, or a salt thereof, to give the compounds of formula Iaa, wherein all substituents are as described previously.

Scheme 7

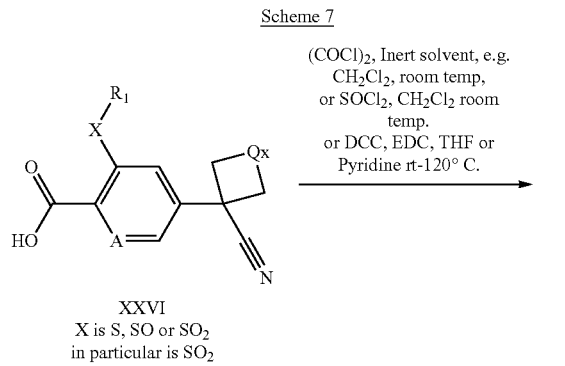

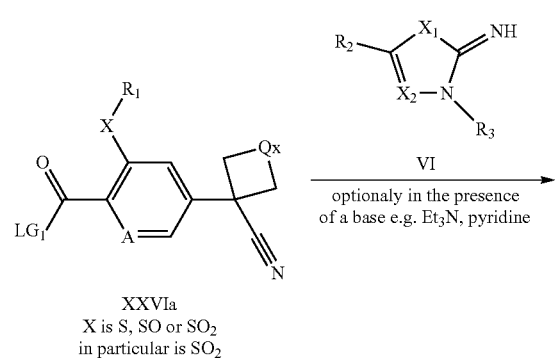

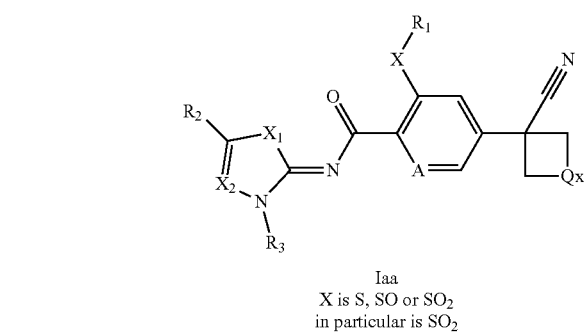

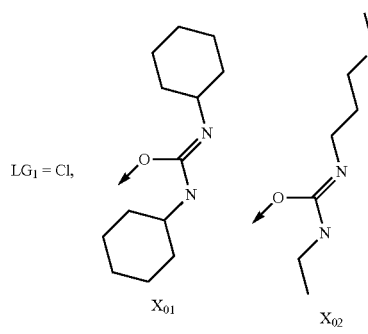

The compounds of formula XXVI-int

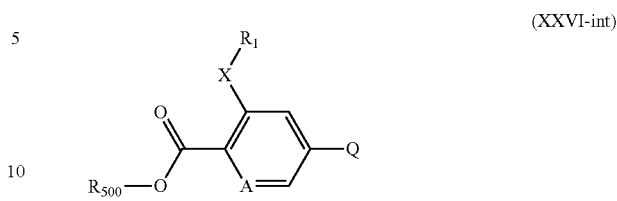

wherein $R_1$, X and A are as defined under formula I above, and $R_{500}$ is hydrogen or $C_1$-$C_4$alkyl, and in which Q is a group wherein $R_{0002}$ is cyano, are novel, especially developed for the preparation of the compounds of formula I according to the invention and therefore represent a further object of the invention. The preferences and preferred embodiments of the substituents of the compounds of formula I are also valid for the compounds of formula XXVI-int.

Compounds of formula I wherein Q is $C_1$-$C_6$haloalkylsulfanyl, $C_1$-$C_6$haloalkylsulfinyl and $C_1$-$C_6$haloalkylsulfonyl (e.g. compounds Iae and/or Iaf) can be prepared by the methods shown in schemes 8.

Scheme 8:

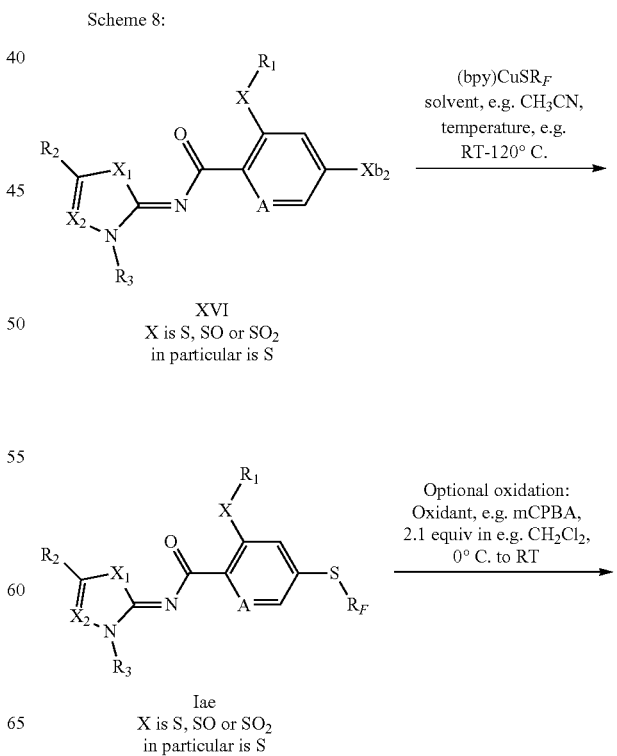

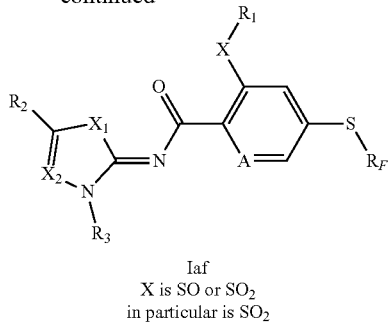

Iaf
X is SO or $SO_2$
in particular is $SO_2$

As shown in scheme 8, treatment of compounds of formula XVI, wherein X is S, SO or $SO_2$ (in particular S), and wherein A, $X_1$, $X_2$, $R_1$, $R_2$ and $R_3$ are as defined above, and in which $Xb_2$ is a leaving group like, for example, chlorine, bromine or iodine (preferably bromine), or an aryl- or alkylsulfonate such as trifluoromethanesulfonate, with a bipyridine copper reagent (bpy)$CuSR_F$, wherein $R_F$ is $C_1$-$C_6$haloalkyl, and in which bpy is bipyridyl, in an inert solvent such as acetonitrile, at temperatures between room temperature and 120° C., optionally under microwave heating, leads to compounds of formula Iae, wherein X is S, SO or $SO_2$ (in particular S), and in which A, $X_1$, $X_2$, $R_1$, $R_2$ and $R_3$ are as defined above and wherein $R_F$ is $C_1$-$C_6$haloalkyl. Such chemistry is known and has been described in the literature, for example, in Angew. Chem. Int. Ed. 2013, 52, 1548-1552. A preferred reagent for this transformation is (bpy)$CuSCF_3$ (CAS 1413732-47-4) for the particular preparation of compounds of formula Iae and Iaf, wherein $R_F$ is trifluoromethyl.

Compounds of formula Iae, wherein X is S or SO, can be further oxidized to, for example, compounds of formula Iaf, wherein X is SO or $SO_2$ (in particular $SO_2$), and in which A, $X_1$, $X_2$, $R_1$, $R_2$ and $R_3$ are as defined above and wherein $R_F$ is $C_1$-$C_6$haloalkyl, by methods known to those skilled in the art and described herein above.

Further adjustment of the oxidation state at sulfur centres can be accomplished by methods known to those skilled in the art and described herein above, for example by using oxidants such as sodium periodate, m-chloroperbenzoic acid and/or hydrogen peroxide (optionally in the presence of catalyst, such as sodium tungstate).

The processes according to the invention for preparing compounds of formula I wherein Q is in the 4-position described above, as well as descriptions on all relevant associated intermediates (see text, descriptions and preparation methods above), may be applied analogously for the preparation of compounds of formula I, wherein Q is in the 3-position, possibly by changing the order of certain steps in a sequence and by slightly adapting reaction conditions in a manner known to a person skilled in the art. In scheme 9, compounds of formula I, wherein Q is in the 3-position, are represented by the compounds of formula I-A

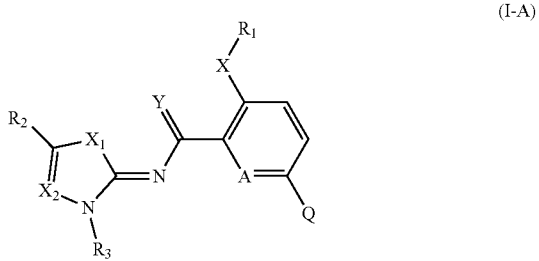

(I-A)

wherein the substituents are as defined as under formula I above.

Such a transposition is illustrated in scheme 9 for the preparation of compounds of formula I-A, wherein Y is O, from intermediate IX-p and VI (or a salt thereof), wherein all substituent definitions mentioned previously are also valid for the compounds shown.

Scheme 9:

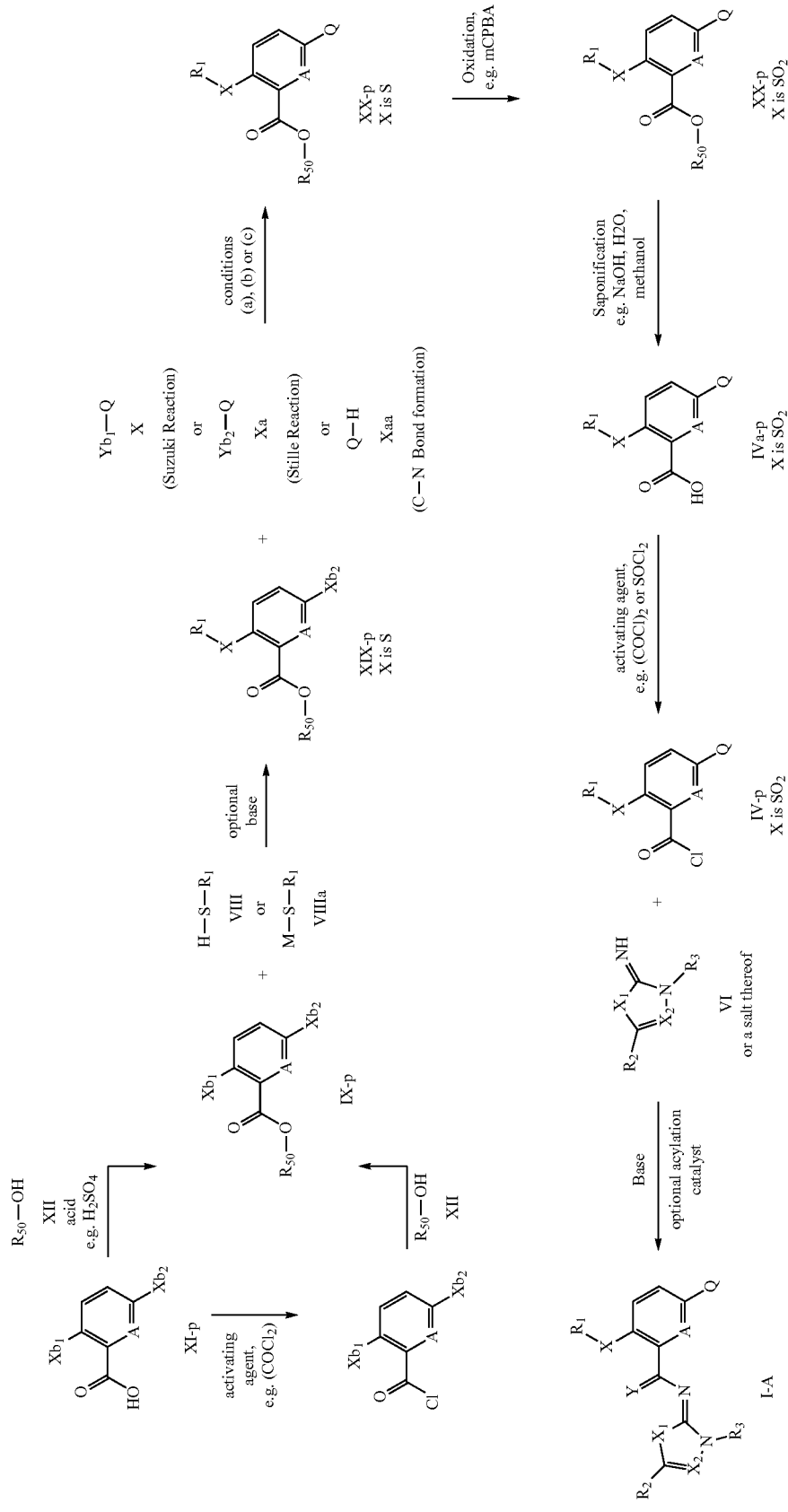

(a) Suzuki reaction: Pd cat. (e.g. Pd(PPh₃)₄ or Pd(dppf)Cl₂), base (e.g. Na₂CO₃), solvent (e.g 1,2-dimethoxyethane/water), 25-180° C.
(b) Stille reaction: Pd cat. (e.g. Pd(PPh₃)₄ or Pd(PPh₃)Cl₂), solvent (e.g toluene), 25-180° C.
(c) C—N bond formation: Base (e.g. K₂CO₃ or Cs₂CO₃), optional presence of CuI, optional additive (such as N,N'-dimethylethylene-diamine), solvent (e.g. N,N-dimethylformamide DMF or N-methylpyrrolidone NMP, 25-180° C.

The reactants can be reacted in the presence of a base. Examples of suitable bases are alkali metal or alkaline earth metal hydroxides, alkali metal or alkaline earth metal hydrides, alkali metal or alkaline earth metal amides, alkali metal or alkaline earth metal alkoxides, alkali metal or alkaline earth metal acetates, alkali metal or alkaline earth metal carbonates, alkali metal or alkaline earth metal dialkylamides or alkali metal or alkaline earth metal alkylsilylamides, alkylamines, alkylenediamines, free or N-alkylated saturated or unsaturated cycloalkylamines, basic heterocycles, ammonium hydroxides and carbocyclic amines. Examples which may be mentioned are sodium hydroxide, sodium hydride, sodium amide, sodium methoxide, sodium acetate, sodium carbonate, potassium tert-butoxide, potassium hydroxide, potassium carbonate, potassium hydride, lithium diisopropylamide, potassium bis(trimethylsilyl)amide, calcium hydride, triethylamine, diisopropylethylamine, triethylenediamine, cyclohexylamine, N-cyclohexyl-N,N-dimethylamine, N,N-diethylaniline, pyridine, 4-(N,N-dimethylamino)pyridine, quinuclidine, N-methylmorpholine, benzyltrimethylammonium hydroxide and 1,8-diazabicyclo [5.4.0]undec-7-ene (DBU).

The reactants can be reacted with each other as such, i.e. without adding a solvent or diluent. In most cases, however, it is advantageous to add an inert solvent or diluent or a mixture of these. If the reaction is carried out in the presence of a base, bases which are employed in excess, such as triethylamine, pyridine, N-methylmorpholine or N,N-diethylaniline, may also act as solvents or diluents.

The reaction is advantageously carried out in a temperature range from approximately −80° C. to approximately +140° C., preferably from approximately −30° C. to approximately +100° C., in many cases in the range between ambient temperature and approximately +80° C.

A compound of formula I can be converted in a manner known per se into another compound of formula I by replacing one or more substituents of the starting compound of formula I in the customary manner by (an)other substituent(s) according to the invention.

Depending on the choice of the reaction conditions and starting materials which are suitable in each case, it is possible, for example, in one reaction step only to replace one substituent by another substituent according to the invention, or a plurality of substituents can be replaced by other substituents according to the invention in the same reaction step.

Salts of compounds of formula I can be prepared in a manner known per se. Thus, for example, acid addition salts of compounds of formula I are obtained by treatment with a suitable acid or a suitable ion exchanger reagent and salts with bases are obtained by treatment with a suitable base or with a suitable ion exchanger reagent.

Salts of compounds of formula I can be converted in the customary manner into the free compounds I, acid addition salts, for example, by treatment with a suitable basic compound or with a suitable ion exchanger reagent and salts with bases, for example, by treatment with a suitable acid or with a suitable ion exchanger reagent.

Salts of compounds of formula I can be converted in a manner known per se into other salts of compounds of formula I, acid addition salts, for example, into other acid addition salts, for example by treatment of a salt of inorganic acid such as hydrochloride with a suitable metal salt such as a sodium, barium or silver salt, of an acid, for example with silver acetate, in a suitable solvent in which an inorganic salt which forms, for example silver chloride, is insoluble and thus precipitates from the reaction mixture.

Depending on the procedure or the reaction conditions, the compounds of formula I, which have salt-forming properties can be obtained in free form or in the form of salts.

The compounds of formula I and, where appropriate, the tautomers thereof, in each case in free form or in salt form, can be present in the form of one of the isomers which are possible or as a mixture of these, for example in the form of pure isomers, such as antipodes and/or diastereomers, or as isomer mixtures, such as enantiomer mixtures, for example racemates, diastereomer mixtures or racemate mixtures, depending on the number, absolute and relative configuration of asymmetric carbon atoms which occur in the molecule and/or depending on the configuration of non-aromatic double bonds which occur in the molecule; the invention relates to the pure isomers and also to all isomer mixtures which are possible and is to be understood in each case in this sense hereinabove and herein below, even when stereochemical details are not mentioned specifically in each case.

Diastereomer mixtures or racemate mixtures of compounds of formula I, in free form or in salt form, which can be obtained depending on which starting materials and procedures have been chosen can be separated in a known manner into the pure diasteromers or racemates on the basis of the physicochemical differences of the components, for example by fractional crystallization, distillation and/or chromatography.

Enantiomer mixtures, such as racemates, which can be obtained in a similar manner can be resolved into the optical antipodes by known methods, for example by recrystallization from an optically active solvent, by chromatography on chiral adsorbents, for example high-performance liquid chromatography (HPLC) on acetyl celulose, with the aid of suitable microorganisms, by cleavage with specific, immobilized enzymes, via the formation of inclusion compounds, for example using chiral crown ethers, where only one enantiomer is complexed, or by conversion into diastereomeric salts, for example by reacting a basic end-product racemate with an optically active acid, such as a carboxylic acid, for example camphor, tartaric or malic acid, or sulfonic acid, for example camphorsulfonic acid, and separating the diastereomer mixture which can be obtained in this manner, for example by fractional crystallization based on their differing solubilities, to give the diastereomers, from which the desired enantiomer can be set free by the action of suitable agents, for example basic agents.

Pure diastereomers or enantiomers can be obtained according to the invention not only by separating suitable isomer mixtures, but also by generally known methods of diastereoselective or enantioselective synthesis, for example by carrying out the process according to the invention with starting materials of a suitable stereochemistry.

N-oxides can be prepared by reacting a compound of the formula I with a suitable oxidizing agent, for example the $H_2O_2$/urea adduct in the presence of an acid anhydride, e.g. trifluoroacetic anhydride. Such oxidations are known from the literature, for example from J. Med. Chem., 32 (12), 2561-73, 1989 or WO 00/15615.

It is advantageous to isolate or synthesize in each case the biologically more effective isomer, for example enantiomer or diastereomer, or isomer mixture, for example enantiomer mixture or diastereomer mixture, if the individual components have a different biological activity.

The compounds of formula I and, where appropriate, the tautomers thereof, in each case in free form or in salt form, can, if appropriate, also be obtained in the form of hydrates and/or include other solvents, for example those which may have been used for the crystallization of compounds which are present in solid form.

The compounds according to the following Tables 1 to 12 below can be prepared according to the methods described above. The examples which follow are intended to illustrate the invention and show preferred compounds of formula I.

Table X: This table discloses 8 substituent definitions X.001 to X.008 of the formula I-1a:

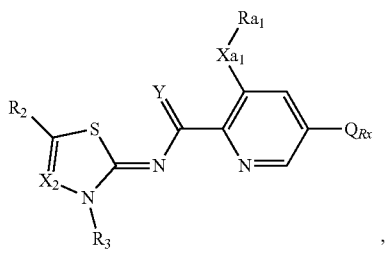

(I-1a)

wherein $Ra_1$, $R_2$, $R_3$, $X_2$ and $Q_{Rx}$ are as defined below:

TABLE X

| Comp. No | $Ra_1$ | $R_2$ | $R_3$ | $X_2$ | $Q_{Rx}$ |
|---|---|---|---|---|---|
| X.001 | —CH$_2$CH$_3$ | CF$_3$ | CH$_3$ | N | —C$_6$H$_5$ |
| X.002 | —CH$_2$CH$_3$ | CF$_3$ | CH$_3$ | N | —C$_6$H$_4$-Cl |
| X.003 | —CH$_2$CH$_3$ | CF$_3$ | CH$_3$ | N | —C$_6$H$_4$-CF$_3$ |
| X.004 | —CH$_2$CH$_3$ | CF$_3$ | CH$_3$ | N | pyrazolyl |
| X.005 | —CH$_2$CH$_3$ | CF$_3$ | CH$_3$ | N | pyrazolyl-CF$_3$ |
| X.006 | —CH$_2$CH$_3$ | CF$_3$ | CH$_3$ | N | pyrazolyl-CF$_3$ |
| X.007 | —CH$_2$CH$_3$ | CF$_3$ | CH$_3$ | N | pyrimidinyl |
| X.008 | —CH$_2$CH$_3$ | CF$_3$ | CH$_3$ | N | pyrimidinyl-Cl | and the N-oxides of the compounds of Table X.

Table 1: This table discloses the 8 compounds 1.001 to 1.008 of the formula I-1a, wherein $Xa_1$ is S, Y is O, and $Ra_1$, $R_2$, $R_3$, $X_2$ and $Q_{Rx}$ are as defined in Table X. For example, compound No. 1.001 has the following structure:

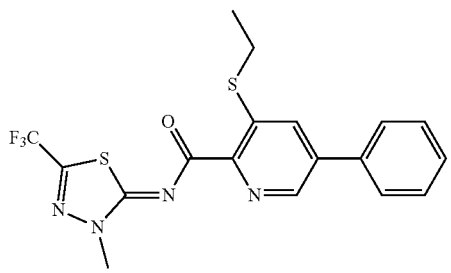

(1.001)

Table 2: This table discloses the 8 compounds 2.001 to 2.008 of the formula I-1a, wherein $Xa_1$ is SO, Y is O, and $Ra_1$, $R_2$, $R_3$, $X_2$ and $Q_{Rx}$ are as defined in Table X.

Table 3: This table discloses the 8 compounds 3.001 to 3.008 of the formula I-1a, wherein $Xa_1$ is SO$_2$, Y is O, and $Ra_1$, $R_2$, $R_3$, $X_2$ and $Q_{Rx}$ are as defined in Table X.

Table Y: This table discloses 8 substituent definitions Y.001 to Y.008 of the formula I-2a:

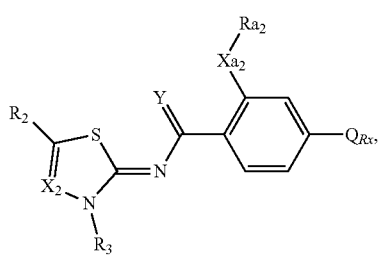

(I-2a)

wherein $Ra_1$, $R_2$, $R_3$, $X_2$ and $Q_{Rx}$ are as defined below:

TABLE Y

| Comp. No | $Ra_1$ | $R_2$ | $R_3$ | $X_2$ | $Q_{Rx}$ |
|---|---|---|---|---|---|
| Y.001 | —CH$_2$CH$_3$ | CF$_3$ | CH$_3$ | N | —C$_6$H$_5$ |
| Y.002 | —CH$_2$CH$_3$ | CF$_3$ | CH$_3$ | N | —C$_6$H$_4$-Cl |
| Y.003 | —CH$_2$CH$_3$ | CF$_3$ | CH$_3$ | N | —C$_6$H$_4$-CF$_3$ |
| Y.004 | —CH$_2$CH$_3$ | CF$_3$ | CH$_3$ | N | pyrazolyl |
| Y.005 | —CH$_2$CH$_3$ | CF$_3$ | CH$_3$ | N | pyrazolyl-CF$_3$ |
| Y.006 | —CH$_2$CH$_3$ | CF$_3$ | CH$_3$ | N | pyrazolyl-CF$_3$ |

TABLE Y-continued

| Comp. No | Ra$_1$ | R$_2$ | R$_3$ | X$_2$ | Q$_{Rx}$ |
|---|---|---|---|---|---|
| Y.007 | —CH$_2$CH$_3$ | CF$_3$ | CH$_3$ | N | 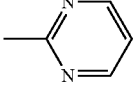 |
| Y.008 | —CH$_2$CH$_3$ | CF$_3$ | CH$_3$ | N | 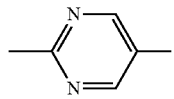 | and the N-oxides of the compounds of Table Y.

Table 4: This table discloses the 8 compounds 4.001 to 4.008 of the formula I-2a, wherein Xa$_2$ is S, Y is O, and Ra$_1$, R$_2$, R$_3$, X$_2$ and Q$_{Rx}$ are as defined in Table Y.

Table 5: This table discloses the 8 compounds 5.001 to 5.008 of the formula I-2a, wherein Xa$_2$ is SO, Y is O, and Ra$_1$, R$_2$, R$_3$, X$_2$ and Q$_{Rx}$ are as defined in Table Y.

Table 6: This table discloses the 8 compounds 6.001 to 6.008 of the formula I-2a, wherein Xa$_2$ is SO$_2$, Y is O, and Ra$_1$, R$_2$, R$_3$, X$_2$ and Q$_{Rx}$ are as defined in Table Y.

Table Z: This table discloses the 10 compounds Z.001 to Z.010 of the formula I-3a:

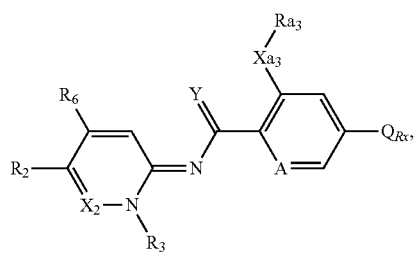

(I-3a)

wherein Ra$_1$, R$_2$, R$_3$, X$_2$ and Q$_{Rx}$ are as defined below:

TABLE Z

| Comp. No | Ra$_3$ | R$_2$ | R$_3$ | X$_2$ | Q$_{Rx}$ |
|---|---|---|---|---|---|
| Z.001 | —CH$_2$CH$_3$ | —SCF$_3$ | CH$_3$ | CH | 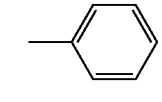 |
| Z.002 | —CH$_2$CH$_3$ | —SCF$_3$ | CH$_3$ | CH | 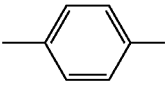 |
| Z.003 | —CH$_2$CH$_3$ | —SCF$_3$ | CH$_3$ | CH | 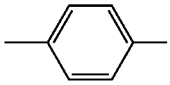 |
| Z.004 | —CH$_2$CH$_3$ | —SCF$_3$ | CH$_3$ | CH | 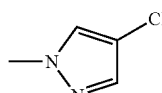 |
| Z.005 | —CH$_2$CH$_3$ | —SCF$_3$ | CH$_3$ | CH | 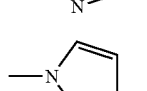 |

TABLE Z-continued

| Comp. No | Ra$_3$ | R$_2$ | R$_3$ | X$_2$ | Q$_{Rx}$ |
|---|---|---|---|---|---|
| Z.006 | —CH$_2$CH$_3$ | —SCF$_3$ | CH$_3$ | CH | 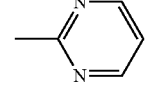 |
| Z.007 | —CH$_2$CH$_3$ | —SO$_2$CF$_3$ | CH$_3$ | CH | 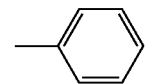 |
| Z.008 | —CH$_2$CH$_3$ | —SO$_2$CF$_3$ | CH$_3$ | CH | 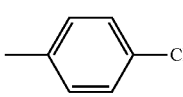 |
| Z.009 | —CH$_2$CH$_3$ | —SO$_2$CF$_3$ | CH$_3$ | CH | 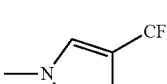 |
| Z.010 | —CH$_2$CH$_3$ | —SO$_2$CF$_3$ | CH$_3$ | CH | 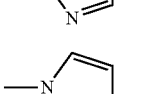 | and the N-oxides of the compounds of Table Z.

Table 7: This table discloses the 10 compounds 7.001 to 7.010 of the formula I-3a, wherein Xa$_3$ is S, Y is O, A is N, R$_6$ is H and Ra$_3$, R$_2$, R$_3$, X$_2$ and Q$_{Rx}$ are as defined in Table Z.

Table 8: This table discloses the 10 compounds 8.001 to 8.010 of the formula I-3a, wherein Xa$_3$ is SO, Y is O, A is N, R$_6$ is H and Ra$_3$, R$_2$, R$_3$, X$_2$ and Q$_{Rx}$ are as defined in Table Z.

Table 9: This table discloses the 10 compounds 9.001 to 9.010 of the formula I-3a, wherein Xa$_3$ is SO$_2$, Y is O, A is N, R$_6$ is H and Ra$_3$, R$_2$, R$_3$, X$_2$ and Q$_{Rx}$ are as defined in Table Z.

Table U: This table discloses the 10 compounds U.001 to U.010 of the formula I-4a:

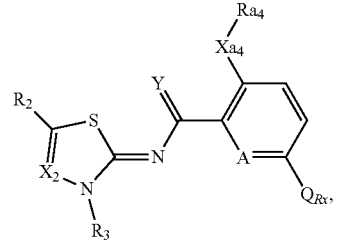

(I-4a)

wherein Ra$_o$, R$_2$, R$_3$, X$_2$ and Q$_{Rx}$ are as defined below:

TABLE U

| Comp. No | Ra$_4$ | R$_2$ | R$_3$ | X$_2$ | Q$_{Rx}$ |
|---|---|---|---|---|---|
| U.001 | —CH$_2$CH$_3$ | CF$_3$ | CH$_3$ | N | 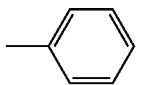 |
| U.002 | —CH$_2$CH$_3$ | CF$_3$ | CH$_3$ | N | 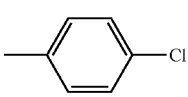 |

TABLE U-continued

| Comp. No | Ra$_4$ | R$_2$ | R$_3$ | X$_2$ | Q$_{Rx}$ |
|---|---|---|---|---|---|
| U.003 | —CH$_2$CH$_3$ | CF$_3$ | CH$_3$ | N | —C$_6$H$_4$—CF$_3$ (para) |
| U.004 | —CH$_2$CH$_3$ | CF$_3$ | CH$_3$ | N | pyrazol-1-yl, 4-CF$_3$ |
| U.005 | —CH$_2$CH$_3$ | CF$_3$ | CH$_3$ | N | pyrazol-1-yl, 3-CF$_3$ |
| U.006 | —CH$_2$CH$_3$ | CF$_3$CF$_2$ | CH$_3$ | N | phenyl |
| U.007 | —CH$_2$CH$_3$ | CF$_3$CF$_2$ | CH$_3$ | N | —C$_6$H$_4$—Cl (para) |
| U.008 | —CH$_2$CH$_3$ | CF$_3$CF$_2$ | CH$_3$ | N | —C$_6$H$_4$—CF$_3$ (para) |
| U.009 | —CH$_2$CH$_3$ | CF$_3$CF$_2$ | CH$_3$ | N | pyrazol-1-yl, 4-CF$_3$ |
| U.010 | —CH$_2$CH$_3$ | CF$_3$CF$_2$ | CH$_3$ | N | pyrazol-1-yl, 3-CF$_3$ | and the N-oxides of the compounds of Table U.

Table 10: This table discloses the 10 compounds 10.001 to 10.010 of the formula I-4a, wherein Xa$_4$ is S, Y is O, A is N, and Ra$_4$, R$_2$, R$_3$, X$_2$ and Q$_{Rx}$ are as defined in Table U.

Table 11: This table discloses the 10 compounds 11.001 to 11.010 of the formula I-4a, wherein Xa$_4$ is SO, Y is O, A is N, and Ra$_4$, R$_2$, R$_3$, X$_2$ and Q$_{Rx}$ are as defined in Table U.

Table 12: This table discloses the 10 compounds 12.001 to 12.010 of the formula I-4a, wherein Xa$_4$ is SO$_2$, Y is O, A is N, and Ra$_4$, R$_2$, R$_3$, X$_2$ and Q$_{Rx}$ are as defined in Table U.

The compounds of formula I according to the invention are preventively and/or curatively valuable active ingredients in the field of pest control, even at low rates of application, which have a very favourable biocidel spectrum and are well tolerated by warm-blooded species, fish and plants. The active ingredients according to the invention act against all or individual developmental stages of normally sensitive, but also resistant, animal pests, such as insects or representatives of the order Acarina. The insecticidal or acaricidal activity of the active ingredients according to the invention can manifest itself directly, i. e. in destruction of the pests, which takes place either immediately or only after some time has elapsed, for example during ecdysis, or indirectly, for example in a reduced oviposition and/or hatching rate.

Examples of the abovementioned animal pests are:
from the order Acarina, for example,

*Acalitus* spp., *Aculus* spp, *Acaricalus* spp., *Aceria* spp., *Acarus* siro, *Amblyomma* spp., *Argas* spp., *Boophilus* spp., *Brevipalpus* spp., *Bryobia* spp, *Calipitrimerus* spp., *Chorioptes* spp., *Dermanyssus gallinae*, *Dermatophagoides* spp., *Eotetranychus* spp, *Eriophyes* spp., *Hemitarsonemus* spp, *Hyalomma* spp., *Ixodes* spp., *Olygonychus* spp, *Ornithodoros* spp., *Polyphagotarsone latus*, *Panonychus* spp., *Phyllocoptruta oleivora*, *Phytonemus* spp, *Polyphagotarsonemus* spp, *Psoroptes* spp., *Rhipicephalus* spp., *Rhizoglyphus* spp., *Sarcoptes* spp., *Steneotarsonemus* spp, *Tarsonemus* spp. and *Tetranychus* spp.;

from the order Anoplura, for example,

*Haematopinus* spp., *Linognathus* spp., *Pediculus* spp., *Pemphigus* spp. and *Phylloxera* spp.; from the order Coleoptera, for example,

*Agriotes* spp., *Amphimallon majale*, *Anomala orientalis*, *Anthonomus* spp., *Aphodius* spp, *Astylus atromaculatus*, *Ataenius* spp, *Atomaria linearis*, *Chaetocnema tibialis*, *Cerotoma* spp, *Conoderus* spp, *Cosmopolites* spp., *Cotinis nitida*, *Curculio* spp., *Cyclocephala* spp, *Dermestes* spp., *Diabrotica* spp., *Diloboderus abderus*, *Epilachna* spp., *Eremnus* spp., *Heteronychus arator*, *Hypothenemus hampei*, *Lagria vilosa*, *Leptinotarsa decemLineata*, *Lissorhoptrus* spp., *Liogenys* spp, *Maecolaspis* spp, *Maladera castanea*, *Megascelis* spp, *Melighetes aeneus*, *Melolontha* spp., *Myochrous armatus*, *Orycaephilus* spp., *Otiorhynchus* spp., *Phyllophaga* spp, *Phlyctinus* spp., *Popillia* spp., *Psylliodes* spp., *Rhyssomatus aubtilis*, *Rhizopertha* spp., *Scarabeidae*, *Sitophilus* spp., *Sitotroga* spp., *Somaticus* spp, *Sphenophorus* spp, *Sternechus subsignatus*, *Tenebrio* spp., *Tribolium* spp. and *Trogoderma* spp.;

from the order Diptera, for example,

*Aedes* spp., *Anopheles* spp, *Antherigona soccata*, *Bactrocea pleas*, *Bibio hortulanus*, *Bradysia* spp, *Calliphora erythrocephala*, *Ceratitis* spp., *Chrysomyia* spp., *Culex* spp., *Cuterebra* spp., *Dacus* spp., *Delia* spp, *Drosophila melanogaster*, *Fannia* spp., *Gastrophilus* spp., *Geomyza tripunctata*, *Glossina* spp., *Hypoderma* spp., *Hyppobosca* spp., *Liriomyza* spp., *Lucilia* spp., *Melanagromyza* spp., *Musca* spp., *Oestrus* spp., *Orseolia* spp., *Oscinella frit*, *Pegomyia hyoscyami*, *Phorbia* spp., *Rhagoletis* spp, *Rivelia quadrifasciata*, *Scatella* spp, *Sciara* spp., *Stomoxys* spp., *Tabanus* spp., *Tannia* spp. and *Tipula* spp.;

from the order Hemiptera, for example,

*Acanthocoris scabrator*, *Acrosternum* spp, *Adelphocoris lineolatus*, *Amblypelta nitida*, *Bathycoelia thalassina*, *Blissus* spp, *Cimex* spp., *Clavigralla tomentosicollis*, *Creontiades* spp, *Distantiella theobroma*, *Dichelops furcatus*, *Dysdercus* spp, *Edessa* spp, *Euchistus* spp., *Eurydema pulchrum*, *Eurygaster* spp., *Halyomorpha halys*, *Horcias nobilellus*, *Leptocorisa* spp., *Lygus* spp, *Margarodes* spp., *Murgantia histrionic*, *Neomegalotomus* spp, *Nesidiocoris tenuis*, *Nezara* spp., *Nysius simulans*, *Oebalus insularis*, *Piesma* spp., *Piezodorus* spp, *Rhodnius* spp., *Sahlbergella singularis*, *Scaptocoris castanea*, *Scotinophara* spp., *Thyanta* spp, *Triatoma* spp., *Vatiga illudens*; *Acyrthosium pisum*, *Adalges* spp, *Agalliana ensigera*, *Agonoscena targionii*, *Aleurodicus* spp, *Aleurocanthus* spp, *Aleurolobus barodensis*, *Aleurothrixus floccosus*, *Aleyrodes brassicae*, *Amarasca biguttula*, *Amritodus atkinsoni*, *Aonidiella* spp., *Aphididae*, *Aphis* spp., *Aspidiotus* spp., *Aulacorthum solani*, *Bactericera cockerelli*, *Bemisia* spp, *Brachycaudus* spp, *Brevicoryne brassicae*, *Cacopsylla* spp, *Cavariella aegopodii* Scop., *Ceroplaster* spp., *Chrysomphalus aonidium*, *Chrysomphalus dictyospermi*, *Cicadella* spp, *Cofana spectra*, *Cryptomyzus* spp, *Cicadulina* spp, *Coccus hesperidum*, *Dalbulus maidis*, *Dialeurodes* spp, *Diaphorina citri*, *Diura-*

*phis noxia, Dysaphis* spp, *Empoasca* spp., *Eriosoma larigerum, Erythroneura* spp., *Gascardia* spp., *Glycaspis brimblecombei, Hyadaphis pseudobrassicae, Hyalopterus* spp, *Hyperomyzus pallidus, Idioscopus clypealis, Jacobiasca lybica, Laodelphax* spp., *Lecanium corni, Lepidosaphes* spp., *Lopaphis erysimi, Lyogenys maidis, Macrosiphum* spp., *Mahanarva* spp, *Metcalfa pruinosa, Metopolophium dirhodum, Myndus crudus, Myzus* spp., *Neotoxoptera* sp, *Nephotettix* spp., *Nilaparvata* spp., *Nippolachnus piri* Mats, *Odonaspis ruthae, Oregma lanigera* Zehnter, *Parabemisia myricae, Paratrioza cockerelli, Parlatoria* spp., *Pemphigus* spp., *Peregrinus maidis, Perkinsiella* spp, *Phorodon humuli, Phylloxera* spp, *Planococcus* spp., *Pseudaulacaspis* spp., *Pseudococcus* spp., *Pseudatomoscelis seriatus, Psylla* spp., *Pulvinaria aethiopica, Quadraspidiotus* spp., *Quesada gigas, Recilia dorsalis, Rhopalosiphum* spp., *Saissetia* spp., *Scaphoideus* spp., *Schizaphis* spp., *Sitobion* spp., *Sogatella furcifera, Spississtilus festinus, Tarophagus Proserpina, Toxoptera* spp, *Trialeurodes* spp, *Tridiscus sporoboli, Trionymus* spp, *Trioza erytreae, Unaspis citri, Zygina flammigera, Zyginidia scutellaris;* from the order Hymenoptera, for example,

*Acromyrmex, Arge* spp, *Atta* spp., *Cephus* spp., *Diprion* spp., *Diprionidae, Gilpinia polytoma, Hoplocampa* spp., *Lasius* spp., *Monomorium pharaonis, Neodiprion* spp., *Pogonomyrmex* spp, *Slenopsis invicta, Solenopsis* spp. and *Vespa* spp.;

from the order Isoptera, for example,

*Coptotermes* spp, *Corniternes* cumulans, *Incisitermes* spp, *Macrotermes* spp, *Mastotermes* spp, *Microtermes* spp, *Reticulitermes* spp.; *Solenopsis geminate* from the order Lepidoptera, for example,

*Acleris* spp., *Adoxophyes* spp., *Aegeria* spp., *Agrotis* spp., *Alabama argillaceae, Amylois* spp., *Anticarsia gemmatalis, Archips* spp., *Argyresthia* spp, *Argyrotaenia* spp., *Autographa* spp., *Bucculatrix thurberiella, Busseola fusca, Cadra cautella, Carposina nipponensis, Chilo* spp., *Choristoneura* spp., *Chrysoteuchia topiaria, Clysia ambiguella, Cnaphalocrocis* spp., *Cnephasia* spp., *Cochylis* spp., *Coleophora* spp., *Colias lesbia, Cosmophila flava, Crambus* spp, *Crocidolomia binotalis, Cryptophlebia leucotreta, Cydalima perspectalis, Cydia* spp., *Diaphania perspectalis, Diatraea* spp., *Diparopsis castanea, Earias* spp., *Eldana saccharina, Ephestia* spp., *Epinotia* spp, *Estigmene acrea, Etiella zinckinella, Eucosma* spp., *Eupoecilia ambiguella, Euproctis* spp., *Euxoa* spp., *Feltia jaculiferia, Grapholita* spp., *Hedya nubiferana, Heliothis* spp., *Hellula undalis, Herpetogramma* spp, *Hyphantria cunea, Keiferia lycopersicella, Lasmopalpus lignosellus, Leucoptera scitella, Lithocollethis* spp., *Lobesia botrana, Loxostege bifidalis, Lymantria* spp., *Lyonetia* spp., *Malacosoma* spp., *Mamestra brassicae, Manduca sexta, Mythimna* spp, *Noctua* spp, *Operophtera* spp., *Orniodes indica, Ostrinia nubilalis, Pammene* spp., *Pandemis* spp., *Panolis flammea, Papaipema nebris, Pectinophora gossypiela, Perileucoptera coffeella, Pseudaletia unipuncta, Phthorimaea operculella, Pieris rapae, Pieris* spp., *Plutella xylostella, Prays* spp., *Pseudoplusia* spp, *Rachiplusia nu, Richia albicosta, Scirpophaga* spp., *Sesamia* spp., *Sparganothis* spp., *Spodoptera* spp., *Sylepta derogate, Synanthedon* spp., *Thaumetopoea* spp., *Tortrix* spp., *Trichoplusia ni, Tuta absoluta*, and *Yponomeuta* spp.;

from the order Mallophaga, for example,

*Damalinea* spp. and *Trichodectes* spp.;

from the order Orthoptera, for example,

*Blatta* spp., *Blattella* spp., *Gryllotalpa* spp., *Leucophaea maderae, Locusta* spp., *Neocurtilla hexadactyla, Periplaneta* spp., *Scapteriscus* spp, and *Schistocerca* spp.;

from the order Psocoptera, for example,

*Liposcelis* spp.;

from the order Siphonaptera, for example,

*Ceratophyllus* spp., *Ctenocephalides* spp. and *Xenopsylla cheopis;* from the order Thysanoptera, for example,

*Calliothrips phaseoli, Frankliniella* spp., *Heliothrips* spp, *Hercinothrips* spp., *Parthenothrips* spp, *Scirtothrips aurantii, Sericothrips variabilis, Taeniothrips* spp., *Thrips* spp;

from the order Thysanura, for example, *Lepisma saccharina.*

The active ingredients according to the invention can be used for controlling, i. e. containing or destroying, pests of the abovementioned type which occur in particular on plants, especially on useful plants and ornamentals in agriculture, in horticulture and in forests, or on organs, such as fruits, flowers, foliage, stalks, tubers or roots, of such plants, and in some cases even plant organs which are formed at a later point in time remain protected against these pests.

Suitable target crops are, in particular, cereals, such as wheat, barley, rye, oats, rice, maize or sorghum; beet, such as sugar or fodder beet; fruit, for example pomaceous fruit, stone fruit or soft fruit, such as apples, pears, plums, peaches, almonds, cherries or berries, for example strawberries, raspberries or blackberries; leguminous crops, such as beans, lentils, peas or soya; oil crops, such as oilseed rape, mustard, poppies, olives, sunflowers, coconut, castor, cocoa or ground nuts; cucurbits, such as pumpkins, cucumbers or melons; fibre plants, such as cotton, flax, hemp or jute; citrus fruit, such as oranges, lemons, grapefruit or tangerines; vegetables, such as spinach, lettuce, asparagus, cabbages, carrots, onions, tomatoes, potatoes or bell peppers; Lauraceae, such as avocado, Cinnamonium or camphor; and also tobacco, nuts, coffee, eggplants, sugarcane, tea, pepper, grapevines, hops, the plantain family and latex plants.

The compositions and/or methods of the present invention may be also used on any ornamental and/or vegetable crops, including flowers, shrubs, broad-leaved trees and evergreens.

For example the invention may be used on any of the following ornamental species: *Ageratum* spp., *Alonsoa* spp., *Anemone* spp., *Anisodontea capsenisis, Anthemis* spp., *Antirrhinum* spp., *Aster* spp., *Begonia* spp. (e.g. *B. elatior, B. semperflorens, B. tubéreux*), *Bougainvillea* spp., *Brachycome* spp., *Brassica* spp. (ornamental), *Calceolaria* spp., *Capsicum annuum, Catharanthus roseus, Canna* spp., *Centaurea* spp., *Chrysanthemum* spp., *Cineraria* spp. (*C. maritime*), *Coreopsis* spp., *Crassula coccinea, Cuphea ignea, Dahlia* spp., *Delphinium* spp., *Dicentra spectabilis, Dorotheantus* spp., *Eustoma grandiflorum, Forsythia* spp., *Fuchsia* spp., *Geranium gnaphalium, Gerbera* spp., *Gomphrena globosa, Heliotropium* spp., *Helianthus* spp., *Hibiscus* spp., *Hortensia* spp., *Hydrangea* spp., *Hypoestes phyllostachya, Impatiens* spp. (*I. Walleriana*), (*resines* spp., *Kalanchoe* spp., *Lantana camara, Lavatera trimestris, Leonotis leonurus, Lilium* spp., *Mesembryanthemum* spp., *Mimulus* spp., *Monarda* spp., *Nemesia* spp., *Tagetes* spp., *Dianthus* spp. (carnation), *Canna* spp., *Oxalis* spp., *Bellis* spp., *Pelargonium* spp. (*P. peltatum, P. Zonale*), *Viola* spp. (pansy), *Petunia* spp., *Phlox* spp., *Plecthranthus* spp., *Poinsettia* spp., *Parthenocissus* spp. (*P. quinquefolia, P. tricuspidata*), *Primula* spp., *Ranunculus* spp., *Rhododendron* spp., *Rosa* spp. (rose), *Rudbeckia* spp., *Saintpaulia* spp., *Salvia* spp., *Scaevola aemola, Schizanthus wisetonensis, Sedum* spp.,

*Solanum* spp., *Surfinia* spp., *Tagetes* spp., *Nicotinia* spp., *Verbena* spp., *Zinnia* spp. and other bedding plants.

For example the invention may be used on any of the following vegetable species: *Allium* spp. (*A. sativum, A., cepa, A. oschaninii, A. Porrum, A. ascalonicum, A. fistulosum*), *Anthriscus cerefolium, Apium graveolus, Asparagus officinalis, Beta vulgarus, Brassica* spp. (*B. Oleracea, B. Pekinensis, B. rapa*), *Capsicum annuum, Cicer arietinum, Cichorium endivia, Cichorum* spp. (*C. intybus, C. endivia*), *Citrillus lanatus, Cucumis* spp. (*C. sativus, C. melo*), *Cucurbita* spp. (*C. pepo, C. maxima*), *Cyanara* spp. (*C. scolymus, C. cardunculus*), *Daucus carota, Foeniculum vulgare, Hypericum* spp., *Lactuca sativa, Lycopersicon* spp. (*L. esculentum, L. lycopersicum*), *Mentha* spp., *Ocimum basilicum, Petroselinum crispum, Phaseolus* spp. (*P. vulgaris, P. coccineus*), *Pisum sativum, Raphanus sativus, Rheum rhaponticum, Rosemarinus* spp., *Salvia* spp., *Scorzonera hispanica, Solanum melongena, Spinacea oleracea, Valerianella* spp. (*V. locusta, V. eriocarpa*) and *Vicia faba.*

Preferred ornamental species include African violet, Begonia, Dahlia, Gerbera, Hydrangea, Verbena, Rosa, Kalanchoe, Poinsettia, Aster, Centaurea, Coreopsis, Delphinium, Monarda, Phlox, Rudbeckia, Sedum, Petunia, Viola, Impatiens, Geranium, Chrysanthemum, Ranunculus, Fuchsia, Salvia, Hortensia, rosemary, sage, St. Johnswort, mint, sweet pepper, tomato and cucumber.

The active ingredients according to the invention are especially suitable for controlling *Aphis craccivora, Diabrotica balteata, Heliothis virescens, Myzus persicae, Plutella xylostella* and *Spodoptera littoralis* in cotton, vegetable, maize, rice and soya crops. The active ingredients according to the invention are further especially suitable for controlling Mamestra (preferably in vegetables), *Cydia pomonella* (preferably in apples), *Empoasca* (preferably in vegetables, vineyards), *Leptinotarsa* (preferably in potatoes) and *Chilo supressalis* (preferably in rice).

In a further aspect, the invention may also relate to a method of controlling damage to plant and parts thereof by plant parasitic nematodes (Endoparasitic-, Semiendoparasitic- and Ectoparasitic nematodes), especially plant parasitic nematodes such as root knot nematodes, *Meloidogyne hapla, Meloidogyne incognita, Meloidogyne javanica, Meloidogyne arenaria* and other *Meloidogyne* species; cyst-forming nematodes, *Globodera rostochiensis* and other *Globodera* species; *Heterodera avenae, Heterodera glycines, Heterodera schachtii, Heterodera trifolii*, and other *Heterodera* species; Seed gall nematodes, *Anguina* species; Stem and foliar nematodes, *Aphelenchoides* species; Sting nematodes, *Belonolaimus longicaudatus* and other *Belonolaimus* species; Pine nematodes, *Bursaphelenchus xylophilus* and other *Bursaphelenchus* species; Ring nematodes, *Criconema* species, *Criconemella* species, *Criconemoides* species, *Mesocriconema* species; Stem and bulb nematodes, *Ditylenchus destructor, Ditylenchus dipsaci* and other *Ditylenchus* species; Awl nematodes, *Dolichodorus* species; Spiral nematodes, *Heliocotylenchus multicinctus* and other *Helicotylenchus* species; Sheath and sheathoid nematodes, *Hemicycliophora* species and *Hemicriconemoides* species; *Hirshmanniella* species; Lance nematodes, *Hoploaimus* species; false rootknot nematodes, *Nacobbus* species; Needle nematodes, *Longidorus elongatus* and other *Longidorus* species; Pin nematodes, *Pratylenchus* species; Lesion nematodes, *Pratylenchus neglectus, Pratylenchus penetrans, Pratylenchus curvitatus, Pratylenchus goodeyi* and other *Pratylenchus* species; Burrowing nematodes, *Radopholus similis* and other *Radopholus* species; Reniform nematodes, *Rotylenchus robustus, Rotylenchus reniformis* and other *Rotylenchus* species; *Scutellonema* species; Stubby root nematodes, *Trichodorus primitivus* and other *Trichodorus* species, *Paratrichodorus* species; Stunt nematodes, *Tylenchorhynchus claytoni, Tylenchorhynchus dubius* and other *Tylenchorhynchus* species; Citrus nematodes, *Tylenchulus* species; Dagger nematodes, *Xiphinema* species; and other plant parasitic nematode species, such as *Subanguina* spp., *Hypsoperine* spp., *Macroposthonia* spp., *Melinius* spp., *Punctodera* spp., and *Quinisulcius* spp..

The compounds of the invention may also have activity against the molluscs. Examples of which include, for example, Ampullariidae; *Arion* (*A. ater, A. circumscriptus, A. hortensis, A. rufus*); Bradybaenidae (*Bradybaena fruticum*); *Cepaea* (*C. hortensis, C. Nemoralis*); ochlodina; *Deroceras* (*D. agrestis, D. empiricorum, D. laeve, D. reticulatum*); *Discus* (*D. rotundatus*); Euomphalia; *Galba* (*G. trunculata*); *Helicelia* (*H. itala, H. obvia*); Helicidae *Helicigona arbustorum*); Helicodiscus; *Helix* (*H. aperta*); *Limax* (*L. cinereoniger, L. flavus, L. marginatus, L. maximus, L. tenellus*); Lymnaea; *Milax* (*M. gagates, M. marginatus, M. sowerbyi*); Opeas; *Pomacea* (*P. canaticulata*); Vallonia and Zanitoides.

The term "crops" is to be understood as including also crop plants which have been so transformed by the use of recombinant DNA techniques that they are capable of synthesising one or more selectively acting toxins, such as are known, for example, from toxin-producing bacteria, especially those of the genus *Bacillus.*

Toxins that can be expressed by such transgenic plants include, for example, insecticidal proteins, for example insecticidal proteins from *Bacillus cereus* or *Bacillus popilliae*; or insecticidal proteins from *Bacillus thuringiensis*, such as δ-endotoxins, e.g. Cry1Ab, Cry1Ac, Cry1F, Cry1Fa2, Cry2Ab, Cry3A, Cry3Bb1 or Cry9C, or vegetative insecticidal proteins (Vip), e.g. Vip1, Vip2, Vip3 or Vip3A; or insecticidal proteins of bacteria colonising nematodes, for example *Photorhabdus* spp. or *Xenorhabdus* spp., such as *Photorhabdus luminescens, Xenorhabdus nematophilus*; toxins produced by animals, such as scorpion toxins, arachnid toxins, wasp toxins and other insect-specific neurotoxins; toxins produced by fungi, such as Streptomycetes toxins, plant lectins, such as pea lectins, barley lectins or snowdrop lectins; agglutinins; proteinase inhibitors, such as trypsin inhibitors, serine protease inhibitors, patatin, cystatin, papain inhibitors; ribosome-inactivating proteins (RIP), such as ricin, maize-RIP, abrin, luffin, saporin or bryodin; steroid metabolism enzymes, such as 3-hydroxysteroidoxidase, ecdysteroid-UDP-glycosyl-transferase, cholesterol oxidases, ecdysone inhibitors, HMG-COA-reductase, ion channel blockers, such as blockers of sodium or calcium channels, juvenile hormone esterase, diuretic hormone receptors, stilbene synthase, bibenzyl synthase, chitinases and glucanases.

In the context of the present invention there are to be understood by δ-endotoxins, for example Cry1Ab, Cry1Ac, Cry1F, Cry1Fa2, Cry2Ab, Cry3A, Cry3Bb1 or Cry9C, or vegetative insecticidal proteins (Vip), for example Vip1, Vip2, Vip3 or Vip3A, expressly also hybrid toxins, truncated toxins and modified toxins. Hybrid toxins are produced recombinantly by a new combination of different domains of those proteins (see, for example, WO 02/15701). Truncated toxins, for example a truncated Cry1Ab, are known. In the case of modified toxins, one or more amino acids of the naturally occurring toxin are replaced. In such amino acid replacements, preferably non-naturally present protease recognition sequences are inserted into the toxin, such as, for example, in the case of Cry3A055, a cathepsin-G-recognition sequence is inserted into a Cry3A toxin (see WO 03/018810). Examples of such toxins or transgenic plants capable of synthesising such toxins are disclosed, for example, in EP-A-0 374 753, WO 93/07278, WO 95/34656, EP-A-0 427 529, EP-A-451 878 and WO 03/052073.

The processes for the preparation of such transgenic plants are generally known to the person skilled in the art and are described, for example, in the publications mentioned above. Cry1-type deoxyribonucleic acids and their preparation are known, for example, from WO 95/34656, EP-A-0 367 474, EP-A-0 401 979 and WO 90/13651.

The toxin contained in the transgenic plants imparts to the plants tolerance to harmful insects. Such insects can occur in any taxonomic group of insects, but are especially commonly found in the beetles (Coleoptera), two-winged insects (Diptera) and moths (Lepidoptera).

Transgenic plants containing one or more genes that code for an insecticidal resistance and express one or more toxins are known and some of them are commercially available. Examples of such plants are: YieldGard® (maize variety that expresses a Cry1Ab toxin); YieldGard Rootworm® (maize variety that expresses a Cry3Bb1 toxin); YieldGard Plus® (maize variety that expresses a Cry1Ab and a Cry3Bb1 toxin); Starlink® (maize variety that expresses a Cry9C toxin); Herculex I® (maize variety that expresses a Cry1Fa2 toxin and the enzyme phosphinothricine N-acetyltransferase (PAT) to achieve tolerance to the herbicide glufosinate ammonium); NuCOTN 33B® (cotton variety that expresses a Cry1Ac toxin); Bollgard I® (cotton variety that expresses a Cry1Ac toxin); Bollgard II® (cotton variety that expresses a Cry1Ac and a Cry2Ab toxin); VipCot@ (cotton variety that expresses a Vip3A and a Cry1Ab toxin); NewLeaf® (potato variety that expresses a Cry3A toxin); NatureGard®, Agrisure® GT Advantage (GA21 glyphosate-tolerant trait), Agrisure® CB Advantage (Bt11 corn borer (CB) trait) and Protecta®.

Further examples of such transgenic crops are:

1. Bt11 Maize from Syngenta Seeds SAS, Chemin de l'Hobit 27, F-31 790 St. Sauveur, France, registration number C/FR/96/05/10. Genetically modified Zea mays which has been rendered resistant to attack by the European corn borer (Ostrinia nubilalis and Sesamia nonagrioides) by transgenic expression of a truncated Cry1Ab toxin. Bt11 maize also transgenically expresses the enzyme PAT to achieve tolerance to the herbicide glufosinate ammonium.

2. Bt176 Maize from Syngenta Seeds SAS, Chemin de l'Hobit 27, F-31 790 St. Sauveur, France, registration number C/FR/96/05/10. Genetically modified Zea mays which has been rendered resistant to attack by the European corn borer (Ostrinia nubilalis and Sesamia nonagrioides) by transgenic expression of a Cry1Ab toxin. Bt176 maize also transgenically expresses the enzyme PAT to achieve tolerance to the herbicide glufosinate ammonium.

3. MIR604 Maize from Syngenta Seeds SAS, Chemin de l'Hobit 27, F-31 790 St. Sauveur, France, registration number C/FR/96/05/10. Maize which has been rendered insect-resistant by transgenic expression of a modified Cry3A toxin. This toxin is Cry3A055 modified by insertion of a cathepsin-G-protease recognition sequence. The preparation of such transgenic maize plants is described in WO 03/018810.

4. MON 863 Maize from Monsanto Europe S.A. 270-272 Avenue de Tervuren, B-1150 Brussels, Belgium, registration number C/DE/02/9. MON 863 expresses a Cry3Bb1 toxin and has resistance to certain Coleoptera insects.

5. IPC 531 Cotton from Monsanto Europe S.A. 270-272 Avenue de Tervuren, B-1150 Brussels, Belgium, registration number C/ES/96/02.

6. 1507 Maize from Pioneer Overseas Corporation, Avenue Tedesco, 7 B-1160 Brussels, Belgium, registration number C/NL/00/10. Genetically modified maize for the expression of the protein Cry1F for achieving resistance to certain Lepidoptera insects and of the PAT protein for achieving tolerance to the herbicide glufosinate ammonium.

7. NK603×MON 810 Maize from Monsanto Europe S.A. 270-272 Avenue de Tervuren, B-1150 Brussels, Belgium, registration number C/GB/02/M3/03. Consists of conventionally bred hybrid maize varieties by crossing the genetically modified varieties NK603 and MON 810. NK603× MON 810 Maize transgenically expresses the protein CP4 EPSPS, obtained from Agrobacterium sp. strain CP4, which imparts tolerance to the herbicide Roundup® (contains glyphosate), and also a Cry1Ab toxin obtained from Bacillus thuringiensis subsp. kurstaki which brings about tolerance to certain Lepidoptera, include the European corn borer.

Transgenic crops of insect-resistant plants are also described in BATS (Zentrum für Biosicherheit and Nachhaltigkeit, Zentrum BATS, Clarastrasse 13, 4058 Basel, Switzerland) Report 2003, (http://bats.ch).

The term "crops" is to be understood as including also crop plants which have been so transformed by the use of recombinant DNA techniques that they are capable of synthesising antipathogenic substances having a selective action, such as, for example, the so-called "pathogenesis-related proteins" (PRPs, see e.g. EP-A-0 392 225). Examples of such antipathogenic substances and transgenic plants capable of synthesising such antipathogenic substances are known, for example, from EP-A-0 392 225, WO 95/33818 and EP-A-0 353 191. The methods of producing such transgenic plants are generally known to the person skilled in the art and are described, for example, in the publications mentioned above.

Crops may also be modified for enhanced resistance to fungal (for example Fusarium, Anthracnose, or Phytophthora), bacterial (for example Pseudomonas) or viral (for example potato leafroll virus, tomato spotted wilt virus, cucumber mosaic virus) pathogens.

Crops also include those that have enhanced resistance to nematodes, such as the soybean cyst nematode.

Crops that are tolerance to abiotic stress include those that have enhanced tolerance to drought, high salt, high temperature, chill, frost, or light radiation, for example through expression of NF-YB or other proteins known in the art.

Antipathogenic substances which can be expressed by such transgenic plants include, for example, ion channel blockers, such as blockers for sodium and calcium channels, for example the viral KP1, KP4 or KP6 toxins; stilbene synthases; bibenzyl synthases; chitinases; glucanases; the so-called "pathogenesis-related proteins" (PRPs; see e.g. EP-A-0 392 225); antipathogenic substances produced by microorganisms, for example peptide antibiotics or heterocyclic antibiotics (see e.g. WO 95/33818) or protein or polypeptide factors involved in plant pathogen defence (so-called "plant disease resistance genes", as described in WO 03/000906).

Further areas of use of the compositions according to the invention are the protection of stored goods and store rooms and the protection of raw materials, such as wood, textiles, floor coverings or buildings, and also in the hygiene sector, especially the protection of humans, domestic animals and productive livestock against pests of the mentioned type.

The present invention also provides a method for controlling pests (such as mosquitoes and other disease vectors; see also http://www.who.int/malaria/vector_control/irs/en/). In one embodiment, the method for controlling pests comprises applying the compositions of the invention to the target pests, to their locus or to a surface or substrate by brushing, rolling, spraying, spreading or dipping. By way of example, an IRS (indoor residual spraying) application of a surface such as a wall, ceiling or floor surface is contemplated by the method of the invention. In another embodiment, it is contemplated to apply such compositions to a substrate such as non-woven or a fabric material in the form of (or which can be used in the manufacture of) netting, clothing, bedding, curtains and tents.

In one embodiment, the method for controlling such pests comprises applying a pesticidally effective amount of the compositions of the invention to the target pests, to their locus, or to a surface or substrate so as to provide effective residual pesticidal activity on the surface or substrate. Such application may be made by brushing, rolling, spraying, spreading or dipping the pesticidal composition of the invention. By way of example, an IRS application of a surface such as a wall, ceiling or floor surface is contemplated by the method of the invention so as to provide effective residual pesticidal activity on the surface. In another embodiment, it is contemplated to apply such compositions for residual control of pests on a substrate such as a fabric material in the form of (or which can be used in the manufacture of) netting, clothing, bedding, curtains and tents.

Substrates including non-woven, fabrics or netting to be treated may be made of natural fibres such as cotton, raffia, jute, flax, sisal, hessian, or wool, or synthetic fibres such as polyamide, polyester, polypropylene, polyacrylonitrile or the like. The polyesters are particularly suitable. The methods of textile treatment are known, e.g. WO 2008/151984, WO 03/034823, U.S. Pat. No. 5,631,072, WO 2005/64072, WO2006/128870, EP 1724392, WO 2005/113886 or WO 2007/090739.

Further areas of use of the compositions according to the invention are the field of tree injection/trunk treatment for all ornamental trees as well all sort of fruit and nut trees.

In the field of tree injection/trunk treatment, the compounds according to the present invention are especially suitable against wood-boring insects from the order Lepidoptera as mentioned above and from the order *Coleoptera*, especially against woodborers listed in the following tables A and B:

TABLE A

Examples of exotic woodborers of economic importance.

| Family | Species | Host or Crop Infested |
|---|---|---|
| Buprestidae | *Agrilus planipennis* | Ash |
| Cerambycidae | *Anoplura glabripennis* | Hardwoods |
|  | *Xylosandrus crassiusculus* | Hardwoods |
| Scolytidae | *X. mutilatus* | Hardwoods |
|  | *Tomicus piniperda* | Conifers |

TABLE B

Examples of native woodborers of economic importance.

| Family | Species | Host or Crop Infested |
|---|---|---|
| Buprestidae | *Agrilus anxius* | Birch |
|  | *Agrilus politus* | Willow, Maple |
|  | *Agrilus sayi* | Bayberry, Sweetfern |
|  | *Agrilus vittaticolllis* | Apple, Pear, Cranberry, Serviceberry, Hawthorn |
|  | *Chrysobothris femorata* | Apple, Apricot, Beech, Boxelder, Cherry, Chestnut, Currant, Elm, Hawthorn, Hackberry, Hickory, Horsechestnut, Linden, Maple, Mountain-ash, Oak, Pecan, Pear, Peach, Persimmon, Plum, Poplar, Quince, Redbud, Serviceberry, Sycamore, Walnut, Willow |
|  | *Texania campestris* | Basswood, Beech, Maple, Oak, Sycamore, Willow, Yellow-poplar |
| Cerambycidae | *Goes pulverulentus* | Beech, Elm, Nuttall, Willow, Black oak, Cherrybark oak, Water oak, Sycamore |
|  | *Goes tigrinus* | Oak |
|  | *Neoclytus acuminatus* | Ash, Hickory, Oak, Walnut, Birch, Beech, Maple, Eastern hophornbeam, Dogwood, Persimmon, Redbud, Holly, Hackberry, Black locust, Honeylocust, Yellow-poplar, Chestnut, Osage-orange, Sassafras, Lilac, Mountain-mahogany, Pear, Cherry, Plum, Peach, Apple, Elm, Basswood, Sweetgum |
|  | *Neoptychodes trilineatus* | Fig, Alder, Mulberry, Willow, Netleaf hackberry |
|  | *Oberea ocellata* | Sumac, Apple, Peach, Plum, Pear, Currant, Blackberry |
|  | *Oberea tripunctata* | Dogwood, Viburnum, Elm, Sourwood, Blueberry, Rhododendron, Azalea, Laurel, Poplar, Willow, Mulberry |
|  | *Oncideres cingulata* | Hickory, Pecan, Persimmon, Elm, Sourwood, Basswood, Honeylocust, Dogwood, Eucalyptus, Oak, Hackberry, Maple, Fruit trees |
|  | *Saperda calcarata* | Poplar |
|  | *Strophiona nitens* | Chestnut, Oak, Hickory, Walnut, Beech, Maple |
| Scolytidae | *Corthylus columbianus* | Maple, Oak, Yellow-poplar, Beech, Boxelder, Sycamore, Birch, Basswood, Chestnut, Elm |
|  | *Dendroctonus frontalis* | Pine |
|  | *Dryocoetes betulae* | Birch, Sweetgum, Wild cherry, Beech, Pear |
|  | *Monarthrum fasciatum* | Oak, Maple, Birch, Chestnut, Sweetgum, Blackgum, Poplar, Hickory, Mimosa, Apple, Peach, Pine |
|  | *Phloeotribus liminaris* | Peach, Cherry, Plum, Black cherry, Elm, Mulberry, Mountain-ash |
|  | *Pseudopityophthorus pruinosus* | Oak, American beech, Black cherry, Chickasaw plum, Chestnut, Maple, Hickory, Hornbeam, Hophornbeam |
| Sesiidae | *Paranthrene simulans* | Oak, American chestnut |
|  | *Sannina uroceriformis* | Persimmon |
|  | *Synanthedon exitiosa* | Peach, Plum, Nectarine, Cherry, Apricot, Almond, Black cherry |
|  | *Synanthedon pictipes* | Peach, Plum, Cherry, Beach, Black Cherry |
|  | *Synanthedon rubrofascia* | Tupelo |

TABLE B-continued

Examples of native woodborers of economic importance.

| Family | Species | Host or Crop Infested |
|---|---|---|
| | Synanthedon scitula | Dogwood, Pecan, Hickory, Oak, Chestnut, Beech, Birch, Black cherry, Elm, Mountain-ash, Viburnum, Willow, Apple, Loquat, Ninebark, Bayberry |
| | Vitacea polistiformis | Grape |

The present invention may be also used to control any insect pests that may be present in turfgrass, including for example beetles, caterpillars, fire ants, ground pearls, millipedes, sow bugs, mites, mole crickets, scales, mealybugs ticks, spittlebugs, southern chinch bugs and white grubs. The present invention may be used to control insect pests at various stages of their life cycle, including eggs, larvae, nymphs and adults.

In particular, the present invention may be used to control insect pests that feed on the roots of turfgrass including white grubs (such as *Cyclocephala* spp. (e.g. masked chafer, *C. lurida*), *Rhizotrogus* spp. (e.g. European chafer, *R. majalis*), *Cotinus* spp. (e.g. Green June beetle, *C. nitida*), *Popillia* spp. (e.g. Japanese beetle, *P. japonica*), *Phyllophaga* spp. (e.g. May/June beetle), *Ataenius* spp. (e.g. Black turfgrass ataenius, *A. spretulus*), *Maladera* spp. (e.g. Asiatic garden beetle, *M. castanea*) and *Tomarus* spp.), ground pearls (*Margarodes* spp.), mole crickets (tawny, southern, and short-winged; *Scapteriscus* spp., *Gryllotalpa africana*) and leatherjackets (European crane fly, *Tipula* spp.).

The present invention may also be used to control insect pests of turfgrass that are thatch dwelling, including armyworms (such as fall armyworm *Spodoptera frugiperda*, and common armyworm *Pseudaletia unipuncta*), cutworms, billbugs (*Sphenophorus* spp., such as *S. venatus verstitus* and *S. parvulus*), and sod webworms (such as *Crambus* spp. and the tropical sod webworm, *Herpetogramma phaeopteralis*).

The present invention may also be used to control insect pests of turfgrass that live above the ground and feed on the turfgrass leaves, including chinch bugs (such as southern chinch bugs, *Blissus insularis*), Bermudagrass mite (*Eriophyes cynodoniensis*), rhodesgrass mealybug (*Antonina graminis*), two-lined spittlebug (*Propsapia bicincta*), leafhoppers, cutworms (Noctuidae family), and greenbugs. The present invention may also be used to control other pests of turfgrass such as red imported fire ants (*Solenopsis invicta*) that create ant mounds in turf.

In the hygiene sector, the compositions according to the invention are active against ectoparasites such as hard ticks, soft ticks, mange mites, harvest mites, flies (biting and licking), parasitic fly larvae, lice, hair lice, bird lice and fleas.

Examples of such parasites are:

Of the order Anoplurida: *Haematopinus* spp., *Linognathus* spp., *Pediculus* spp. and *Phtirus* spp., *Solenopotes* spp.

Of the order Mallophagida: *Trimenopon* spp., *Menopon* spp., *Trinoton* spp., *Bovicola* spp., *Werneckiella* spp., *Lepikentron* spp., *Damalina* spp., *Trichodectes* spp. and *Felicola* spp.

Of the order Diptera and the suborders Nematocerina and Brachycerina, for example *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp. and *Melophagus* spp.

Of the order Siphonapterida, for example *Pulex* spp., *Ctenocephalides* spp., *Xenopsylla* spp., *Ceratophyllus* spp.

Of the order Heteropterida, for example *Cimex* spp., *Triatoma* spp., *Rhodnius* spp., *Panstrongylus* spp..

Of the order Blattarida, for example *Blatta orientalis*, *Periplaneta americana*, *Blattelagermanica* and *Supella* spp.

Of the subclass Acaria (Acarida) and the orders Meta- and Meso-stigmata, for example *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp. and *Varroa* spp.

Of the orders Actinedida (Prostigmata) and Acaridida (Astigmata), for example *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp. and *Laminosioptes* spp.

The compositions according to the invention are also suitable for protecting against insect infestation in the case of materials such as wood, textiles, plastics, adhesives, glues, paints, paper and card, leather, floor coverings and buildings.

The compositions according to the invention can be used, for example, against the following pests: beetles such as *Hylotrupes bajulus*, *Chlorophorus pilosis*, *Anobium punctatum*, *Xestobium rufovillosum*, *Ptilinuspecticornis*, *Dendrobium pertinex*, *Ernobius mollis*, *Priobium carpini*, *Lyctus brunneus*, *Lyctus africanus*, *Lyctus planicollis*, *Lyctus linearis*, *Lyctus pubescens*, *Trogoxylon aequale*, *Minthesrugicollis*, *Xyleborus* spec., *Tryptodendron* spec., *Apate monachus*, *Bostrychus capucins*, *Heterobostrychus brunneus*, *Sinoxylon* spec. and *Dinoderus minutus*, and also hymenopterans such as *Sirex juvencus*, *Urocerus gigas*, *Urocerus gigas taignus* and *Urocerus augur*, and termites such as *Kalotermes flavicollis*, *Cryptotermes brevis*, *Heterotermes indicola*, *Reticulitermes flavipes*, *Reticulitermes santonensis*, *Reticulitermes lucifugus*, *Mastotermes darwiniensis*, *Zootermopsis nevadensis* and *Coptotermes formosanus*, and bristletails such as *Lepisma saccharina*.

The compounds according to the invention can be used as pesticidal agents in unmodified form, but they are generally formulated into compositions in various ways using formulation adjuvants, such as carriers, solvents and surface-active substances. The formulations can be in various physical forms, e.g. in the form of dusting powders, gels, wettable powders, water-dispersible granules, water-dispersible tablets, effervescent pellets, emulsifiable concentrates, microemulsifiable concentrates, oil-in-water emulsions, oil-flowables, aqueous dispersions, oily dispersions, suspoemulsions, capsule suspensions, emulsifiable granules, soluble liquids, water-soluble concentrates (with water or a water-miscible organic solvent as carrier), impregnated polymer films or in other forms known e.g. from the Manual on Development and Use of FAO and WHO Specifications for Pesticides, United Nations, First Edition, Second Revision (2010). Such formulations can either be used directly or diluted prior to use.

The dilutions can be made, for example, with water, liquid fertilisers, micronutrients, biological organisms, oil or solvents.

The formulations can be prepared e.g. by mixing the active ingredient with the formulation adjuvants in order to obtain compositions in the form of finely divided solids, granules, solutions, dispersions or emulsions. The active ingredients can also be formulated with other adjuvants, such as finely divided solids, mineral oils, oils of vegetable or animal origin, modified oils of vegetable or animal origin, organic solvents, water, surface-active substances or combinations thereof.

The active ingredients can also be contained in very fine microcapsules. Microcapsules contain the active ingredients in a porous carrier. This enables the active ingredients to be released into the environment in controlled amounts (e.g. slow-release). Microcapsules usually have a diameter of from 0.1 to 500 microns. They contain active ingredients in an amount of about from 25 to 95% by weight of the capsule weight. The active ingredients can be in the form of a monolithic solid, in the form of fine particles in solid or liquid dispersion or in the form of a suitable solution. The encapsulating membranes can comprise, for example, natural or synthetic rubbers, cellulose, styrene/butadiene copolymers, polyacrylonitrile, polyacrylate, polyesters, polyamides, polyureas, polyurethane or chemically modified polymers and starch xanthates or other polymers that are known to the person skilled in the art. Alternatively, very fine microcapsules can be formed in which the active ingredient is contained in the form of finely divided particles in a solid matrix of base substance, but the microcapsules are not themselves encapsulated.

The formulation adjuvants that are suitable for the preparation of the compositions according to the invention are known per se. As liquid carriers there may be used: water, toluene, xylene, petroleum ether, vegetable oils, acetone, methyl ethyl ketone, cyclohexanone, acid anhydrides, acetonitrile, acetophenone, amyl acetate, 2-butanone, butylene carbonate, chlorobenzene, cyclohexane, cyclohexanol, alkyl esters of acetic acid, diacetone alcohol, 1,2-dichloropropane, diethanolamine, p-diethylbenzene, diethylene glycol, diethylene glycol abietate, diethylene glycol butyl ether, diethylene glycol ethyl ether, diethylene glycol methyl ether, N,N-dimethylformamide, dimethyl sulfoxide, 1,4-dioxane, dipropylene glycol, dipropylene glycol methyl ether, dipropylene glycol dibenzoate, diproxitol, alkylpyrrolidone, ethyl acetate, 2-ethylhexanol, ethylene carbonate, 1,1,1-trichloroethane, 2-heptanone, alpha-pinene, d-limonene, ethyl lactate, ethylene glycol, ethylene glycol butyl ether, ethylene glycol methyl ether, gamma-butyrolactone, glycerol, glycerol acetate, glycerol diacetate, glycerol triacetate, hexadecane, hexylene glycol, isoamyl acetate, isobornyl acetate, isooctane, isophorone, isopropylbenzene, isopropyl myristate, lactic acid, laurylamine, mesityl oxide, methoxypropanol, methyl isoamyl ketone, methyl isobutyl ketone, methyl laurate, methyl octanoate, methyl oleate, methylene chloride, m-xylene, n-hexane, n-octylamine, octadecanoic acid, octylamine acetate, oleic acid, oleylamine, o-xylene, phenol, polyethylene glycol, propionic acid, propyl lactate, propylene carbonate, propylene glycol, propylene glycol methyl ether, p-xylene, toluene, triethyl phosphate, triethylene glycol, xylenesulfonic acid, paraffin, mineral oil, trichloroethylene, perchloroethylene, ethyl acetate, amyl acetate, butyl acetate, propylene glycol methyl ether, diethylene glycol methyl ether, methanol, ethanol, isopropanol, and alcohols of higher molecular weight, such as amyl alcohol, tetrahydrofurfuryl alcohol, hexanol, octanol, ethylene glycol, propylene glycol, glycerol, N-methyl-2-pyrrolidone and the like.

Suitable solid carriers are, for example, talc, titanium dioxide, pyrophyllite clay, silica, attapulgite clay, kieselguhr, limestone, calcium carbonate, bentonite, calcium montmorillonite, cottonseed husks, wheat flour, soybean flour, pumice, wood flour, ground walnut shells, lignin and similar substances. A large number of surface-active substances can advantageously be used in both solid and liquid formulations, especially in those formulations which can be diluted with a carrier prior to use. Surface-active substances may be anionic, cationic, non-ionic or polymeric and they can be used as emulsifiers, wetting agents or suspending agents or for other purposes. Typical surface-active substances include, for example, salts of alkyl sulfates, such as diethanolammonium lauryl sulfate; salts of alkylarylsulfonates, such as calcium dodecylbenzenesulfonate; alkylphenol/alkylene oxide addition products, such as nonylphenol ethoxylate; alcohol/alkylene oxide addition products, such as tridecylalcohol ethoxylate; soaps, such as sodium stearate; salts of alkylnaphthalenesulfonates, such as sodium dibutylnaphthalenesulfonate; dialkyl esters of sulfosuccinate salts, such as sodium di(2-ethylhexyl)sulfosuccinate; sorbitol esters, such as sorbitol oleate; quaternary amines, such as lauryltrimethylammonium chloride, polyethylene glycol esters of fatty acids, such as polyethylene glycol stearate; block copolymers of ethylene oxide and propylene oxide; and salts of mono- and di-alkylphosphate esters; and also further substances described e.g. in McCutcheon's Detergents and Emulsifiers Annual, MC Publishing Corp., Ridgewood New Jersey (1981).

Further adjuvants that can be used in pesticidal formulations include crystallisation inhibitors, viscosity modifiers, suspending agents, dyes, anti-oxidants, foaming agents, light absorbers, mixing auxiliaries, antifoams, complexing agents, neutralising or pH-modifying substances and buffers, corrosion inhibitors, fragrances, wetting agents, take-up enhancers, micronutrients, plasticisers, glidants, lubricants, dispersants, thickeners, antifreezes, microbicides, and liquid and solid fertilisers. The compositions according to the invention can include an additive comprising an oil of vegetable or animal origin, a mineral oil, alkyl esters of such oils or mixtures of such oils and oil derivatives. The amount of oil additive in the composition according to the invention is generally from 0.01 to 10%, based on the mixture to be applied. For example, the oil additive can be added to a spray tank in the desired concentration after a spray mixture has been prepared. Preferred oil additives comprise mineral oils or an oil of vegetable origin, for example rapeseed oil, olive oil or sunflower oil, emulsified vegetable oil, alkyl esters of oils of vegetable origin, for example the methyl derivatives, or an oil of animal origin, such as fish oil or beef tallow. Preferred oil additives comprise alkyl esters of $C_8$-$C_{22}$ fatty acids, especially the methyl derivatives of $C_{12}$-$C_{18}$ fatty acids, for example the methyl esters of lauric acid, palmitic acid and oleic acid (methyl laurate, methyl palmitate and methyl oleate, respectively). Many oil derivatives are known from the Compendium of Herbicide Adjuvants, 10$^{th}$ Edition, Southern Illinois University, 2010.

The inventive compositions generally comprise from 0.1 to 99% by weight, especially from 0.1 to 95% by weight, of compounds of the present invention and from 1 to 99.9% by weight of a formulation adjuvant which preferably includes from 0 to 25% by weight of a surface-active substance.

Whereas commercial products may preferably be formulated as concentrates, the end user will normally employ dilute formulations.

The rates of application vary within wide limits and depend on the nature of the soil, the method of application, the crop plant, the pest to be controlled, the prevailing climatic conditions, and other factors governed by the method of application, the time of application and the target crop. As a general guideline compounds may be applied at a rate of from 1 to 2000 l/ha, especially from 10 to 1000 l/ha.

Preferred formulations can have the following compositions (weight %):

Emulsifiable Concentrates:
active ingredient: 1 to 95%, preferably 60 to 90%
surface-active agent: 1 to 30%, preferably 5 to 20%
liquid carrier: 1 to 80%, preferably 1 to 35%
Dusts:
active ingredient: 0.1 to 10%, preferably 0.1 to 5%
solid carrier: 99.9 to 90%, preferably 99.9 to 99%
Suspension Concentrates:
active ingredient: 5 to 75%, preferably 10 to 50%
water: 94 to 24%, preferably 88 to 30%
surface-active agent: 1 to 40%, preferably 2 to 30%
Wettable Powders:
active ingredient: 0.5 to 90%, preferably 1 to 80%
surface-active agent: 0.5 to 20%, preferably 1 to 15%
solid carrier: 5 to 95%, preferably 15 to 90%
Granules:
active ingredient: 0.1 to 30%, preferably 0.1 to 15%
solid carrier: 99.5 to 70%, preferably 97 to 85%

The following Examples further illustrate, but do not limit, the invention.

| Wettable powders | a) | b) | c) |
| --- | --- | --- | --- |
| active ingredients | 25% | 50% | 75% |
| sodium lignosulfonate | 5% | 5% | — |
| sodium lauryl sulfate | 3% | — | 5% |
| sodium diisobutylnaphthalenesulfonate | — | 6% | 10% |
| phenol polyethylene glycol ether (7-8 mol of ethylene oxide) | — | 2% | — |
| highly dispersed silicic acid | 5% | 10% | 10% |
| Kaolin | 62% | 27% | — |

The combination is thoroughly mixed with the adjuvants and the mixture is thoroughly ground in a suitable mill, affording wettable powders that can be diluted with water to give suspensions of the desired concentration.

| Powders for dry seed treatment | a) | b) | c) |
| --- | --- | --- | --- |
| active ingredients | 25% | 50% | 75% |
| light mineral oil | 5% | 5% | 5% |
| highly dispersed silicic acid | 5% | 5% | — |
| Kaolin | 65% | 40% | — |
| Talcum | — | — | 20 |

The combination is thoroughly mixed with the adjuvants and the mixture is thoroughly ground in a suitable mill, affording powders that can be used directly for seed treatment.

| Emulsifiable concentrate | |
| --- | --- |
| active ingredients | 10% |
| octylphenol polyethylene glycol ether (4-5 mol of ethylene oxide) | 3% |

-continued

| Emulsifiable concentrate | |
| --- | --- |
| calcium dodecylbenzenesulfonate | 3% |
| castor oil polyglycol ether (35 mol of ethylene oxide) | 4% |
| Cyclohexanone | 30% |
| xylene mixture | 50% |

Emulsions of any required dilution, which can be used in plant protection, can be obtained from this concentrate by dilution with water.

| Dusts | a) | b) | c) |
| --- | --- | --- | --- |
| Active ingredients | 5% | 6% | 4% |
| Talcum | 95% | — | — |
| Kaolin | — | 94% | — |
| mineral filler | — | — | 96% |

Ready-for-use dusts are obtained by mixing the combination with the carrier and grinding the mixture in a suitable mill. Such powders can also be used for dry dressings for seed.

| Extruder granules | |
| --- | --- |
| Active ingredients | 15% |
| sodium lignosulfonate | 2% |
| carboxymethylcellulose | 1% |
| Kaolin | 82% |

The combination is mixed and ground with the adjuvants, and the mixture is moistened with water. The mixture is extruded and then dried in a stream of air.

| Coated granules | |
| --- | --- |
| Active ingredients | 8% |
| polyethylene glycol (mol. wt. 200) | 3% |
| Kaolin | 89% |

The finely ground combination is uniformly applied, in a mixer, to the kaolin moistened with polyethylene glycol. Non-dusty coated granules are obtained in this manner.

Suspension Concentrate

| active ingredients | 40% |
| --- | --- |
| propylene glycol | 10% |
| nonylphenol polyethylene glycol ether (15 mol of ethylene oxide) | 6% |
| Sodium lignosulfonate | 10% |
| carboxymethylcellulose | 1% |
| silicone oil (in the form of a 75% emulsion in water) | 1% |
| Water | 32% |

The finely ground combination is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

Flowable Concentrate for Seed Treatment

| active ingredients | 40% |
| --- | --- |
| propylene glycol | 5% |
| copolymer butanol PO/EO | 2% |
| Tristyrenephenole with 10-20 moles EO | 2% |
| 1,2-benzisothiazolin-3-one (in the form of a 20% solution in water) | 0.5% |
| monoazo-pigment calcium salt | 5% |
| Silicone oil (in the form of a 75% emulsion in water) | 0.2% |
| Water | 45.3% |

The finely ground combination is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

Slow Release Capsule Suspension 28 parts of the combination are mixed with 2 parts of an aromatic solvent and 7 parts of toluene diisocyanate/polymethylene-polyphenylisocyanate-mixture (8:1). This mixture is emulsified in a mixture of 1.2 parts of polyvinylalcohol, 0.05 parts of a defoamer and 51.6 parts of water until the desired particle size is achieved. To this emulsion a mixture of 2.8 parts 1,6-diaminohexane in 5.3 parts of water is added. The mixture is agitated until the polymerization reaction is completed. The obtained capsule suspension is stabilized by adding 0.25 parts of a thickener and 3 parts of a dispersing agent. The capsule suspension formulation contains 28% of the active ingredients. The medium capsule diameter is 8-15 microns. The resulting formulation is applied to seeds as an aqueous suspension in an apparatus suitable for that purpose.

Formulation types include an emulsion concentrate (EC), a suspension concentrate (SC), a suspo-emulsion (SE), a capsule suspension (CS), a water dispersible granule (WG), an emulsifiable granule (EG), an emulsion, water in oil (EO), an emulsion, oil in water (EW), a micro-emulsion (ME), an oil dispersion (OD), an oil miscible flowable (OF), an oil miscible liquid (OL), a soluble concentrate (SL), an ultra-low volume suspension (SU), an ultra-low volume liquid (UL), a technical concentrate (TK), a dispersible concentrate (DC), a wettable powder (WP), a soluble granule (SG) or any technically feasible formulation in combination with agriculturally acceptable adjuvants.

PREPARATORY EXAMPLES

"Mp" means melting point in ° C. Free radicals represent methyl groups. $^1$H NMR measurements were recorded on a Brucker 400MHz spectrometer, chemical shifts are given in ppm relevant to a TMS standard. Spectra measured in deuterated solvents as indicated. Either one of the LCMS and/or GCMS methods below was used to characterize the compounds. The characteristic LCMS values obtained for each compound were the retention time ("$R_t$", recorded in minutes) and the measured molecular ion $(M+H)^+$.

LCMS and GCMS Methods:

Method 1:

Spectra were recorded on a Mass Spectrometer from Waters (SQD or ZQ Single quadrupole mass spectrometer) equipped with an electrospray source (Polarity: positive or negative ions, Capillary: 3.00 kV, Cone range: 30-60 V, Extractor: 2.00 V, Source Temperature: 150° C., Desolvation Temperature: 350° C., Cone Gas Flow: 0 L/Hr, Desolvation Gas Flow: 650 L/Hr, Mass range: 100 to 900 Da) and an Acquity UPLC from Waters: Binary pump, heated column compartment and diode-array detector. Solvent degasser, binary pump, heated column compartment and diode-array detector. Column: Waters UPLC HSS T3 , 1.8 µm, 30×2.1 mm, Temp: 60° C., DAD Wavelength range (nm): 210 to 500, Solvent Gradient: A=water+5% MeOH+0.05% HCOOH, B=Acetonitrile+0.05% HCOOH; gradient: 0 min 0% B, 100% A; 1.2-1.5 min 100% B; Flow (ml/min) 0.85.

Method 2:

Spectra were recorded on a Mass Spectrometer from Waters (SQD or ZQ Single quadrupole mass spectrometer) equipped with an electrospray source (Polarity: positive or negative ions, Capillary: 3.00 kV, Cone range: 30-60 V, Extractor: 2.00 V, Source Temperature: 150° C., Desolvation Temperature: 350° C., Cone Gas Flow: 0 L/Hr, Desolvation Gas Flow: 650 L/Hr, Mass range: 100 to 900 Da) and an Acquity UPLC from Waters: Binary pump, heated column compartment and diode-array detector. Solvent degasser, binary pump, heated column compartment and diode-array detector. Column: Waters UPLC HSS T3 , 1.8 µm, 30×2.1 mm, Temp: 60° C., DAD Wavelength range (nm): 210 to 500, Solvent Gradient: A=water+5% MeOH+0.05% HCOOH, B=Acetonitrile+0.05% HCOOH; gradient: 0 min 0% B, 100% A; 2.7-3.0 min 100% B; Flow (ml/min) 0.85.

Method 3:

ACQUITY SQD Mass Spectrometer from Waters (Single quadrupole mass spectrometer) Ionisation method: Electrospray; Polarity: positive ions; Capillary (kV) 3.00, Cone (V) 60.00, Extractor (V) 3.00, Source Temperature (° C.) 150, Desolvation Temperature (° C.) 400, Cone Gas Flow (L/Hr) 60, Desolvation Gas Flow (L/Hr) 700; Mass range: 100 to 800 Da; DAD Wavelength range (nm): 210 to 400. Method Waters ACQUITY UPLC with the following HPLC gradient conditions:

(Solvent A: Water/Methanol 9:1, 0.1% formic acid and Solvent B: Acetonitrile,0.1% formic acid)

| Time (minutes) | A (%) | B (%) | Flow rate (ml/min) |
| --- | --- | --- | --- |
| 0 | 100 | 0 | 0.75 |
| 2.5 | 0 | 100 | 0.75 |
| 2.8 | 0 | 100 | 0.75 |
| 3.0 | 100 | 0 | 0.75 |

Type of column: Waters ACQUITY UPLC HSS T3; Column length: 30 mm; Internal diameter of column: 2.1 mm; Particle Size: 1.8 micron; Temperature: 60° C.

Method 4:

GCMS analyses were performed on a Thermo Electron instrument where a TRACE GC ULTRA gas chromatograph (equipped with a Zebron Phenomenex ZB-5 ms 15 m, diam: 0.25 mm, 0.25 µm column; $H_2$ flow 1.2 mL/min; temp injector: 250° C.; temp detector: 220° C.; method: start at 70° C., then 25° C./min until 320° C., hold 2 min at 320° C.) was linked to a DSQ mass spectrometer characterizing the compounds by electron ionisation (EI).

Example P1

Preparation of (N)-5-(4-chlorophenyl)-3-ethylsulfanyl-N-[3-methyl-5-(trifluoromethyl)-1,3,4-thiadiazol-2-ylidene]pyridine-2-carboxamide (compound P1)

Step 1: Preparation of methyl 5-bromo-3-chloro-pyridine-2-carboxylate

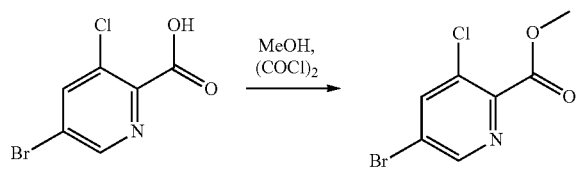

To a slightly cloudy solution of 5-bromo-3-chloro-pyridine-2-carboxylic acid (60 g, 183.2 mmol) in dichloromethane (700 ml) was added dropwise N,N-dimethylformamide (1 ml) and oxalylchloride (24.9 ml, 286.9 mmol). The cloudy solution was stirred for 3 hours at room temperature. The resulting yellow solution was cooled to 10° C. and methanol (30.8 ml, 761.3 mmol) was added dropwise to the mixture, keeping the temperature between 15° and 20° C. The solution was stirred overnight at room temperature. After neutralisation with an aqueous saturated solution of sodium hydrogen carbonate, the organic layer was washed with brine, dried over sodium sulfate, filtrated and evaporated to give methyl 5-bromo-3-chloro-pyridine-2-carboxylate (55 g) as a yellow solid, which was used without further purification. LCMS (method 2): 250/252/254 (M+1)$^+$, retention time 1.12 min.

Step 2: Preparation of methyl 3-chloro-5-(4-chlorophenyl)pyridine-2-carboxylate

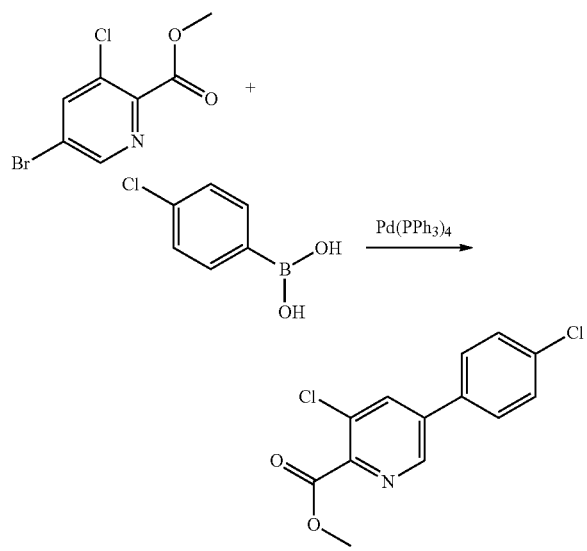

A solution of methyl 5-bromo-3-chloro-pyridine-2-carboxylate (17.33 g, 69.2 mmol), 4-chlorophenyl-boronic acid (11.36 g, 72.7 mmol), sodium carbonate (14.7g, 138.4 mmol) in a mixture of 1,2-di-methoxyethane (500 ml) and water (50 ml) was flushed with argon. Tetrakis(triphenylphosphine) palladium (4.0 g, 3.5 mmol) was added and the mixture was stirred at 90° C. for 7 hours. More catalyst was added (0.5 g, 0.4 mmol) and the mixture was stirred another 2 hours at 90° C. After cooling, the reaction mixture was diluted with water and ethyl acetate. The water phase was separated and washed twice with ethyl acetate. The combined organic phases were dried over magnesium sulfate and evaporated under vacuum. The residue was submitted to flash chromatography to give methyl 3-chloro-5-(4-chlorophenyl)pyridine-2-carboxylate (10.5 g). LCMS (method 2): 282/284 (M+1)$^+$, retention time 1.63 min.

Step 3: Preparation of 5-(4-chlorophenyl)-3-ethylsulfanyl-pyridine-2-carboxylic acid

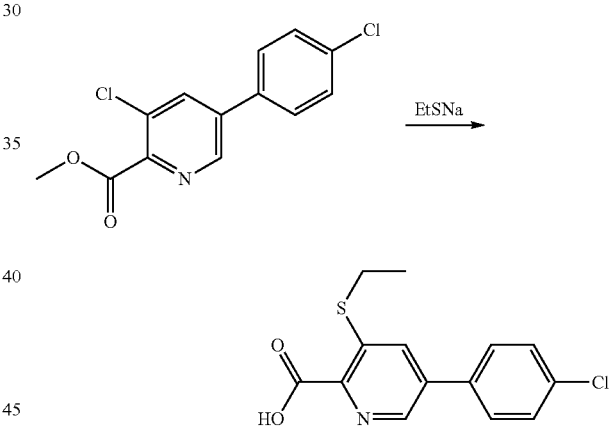

To a solution of methyl 3-chloro-5-(4-chlorophenyl)pyridine-2-carboxylate (2.0 g, 7.1 mmol) in 15 ml N,N-dimethylformamide, sodium ethanethiolate (3.3 g, 35 mmol) was added. The temperature rose to 40° C. and the reaction mixture was stirred 1 hour at room temperature. The solution was diluted with tert-butyl methyl ether and was extracted with ice water. The aqueous phase was separated and neutralized with acetic acid and extracted with tert-butyl methyl ether and ethyl acetate. The combined organic layers were dried over magnesium sulfate and evaporated under vacuum to give 5-(4-chloro-phenyl)-3-ethylsulfanyl-pyridine-2-carboxylic acid (2.0 g) which was used without further purification. LCMS (method 2): 294/296 (M+1)$^+$, retention time 1.42 min.

Step 4: Preparation of (N)-5-(4-chlorophenyl)-3-ethylsulfanyl-N-[3-methyl-5-(trifluoromethyl)-1,3,4-thiadiazol-2-ylidene]pyridine-2-carboxamide (compound P1)

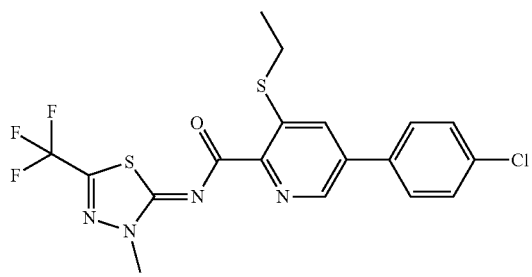

(P1)

(a) To a solution of 5-(4-chlorophenyl)-3-ethylsulfanyl-pyridine-2-carboxylic acid (541 mg, 1.84 mmol) in dichloromethane (7 ml) was added one drop of N,N-dimethylformamide, followed by oxalyl chloride (351 mg, 0.237 ml, 1.5 equiv.). The reaction mixture was shortly heated to 40° C., then at room temperature until end of gas evolution. The mixture was evaporated under reduced pressure at 40° C., the dark residue solubilized in dichloromethane and treated with active charcoal. After short stirring, the mixture was filtered, the fitrate dried over sodium sulfate and evaporated to dryness to afford 5-(4-chloro-phenyl)-3-ethylsulfanyl-pyridine-2-carbonyl chloride as a solid.

(b) To a solution of 3-methyl-5-(trifluoromethyl)-1,3,4-thiadiazol-2-imine (U.S. Pat. No. 4,264,616A) (110 mg, 0.60 mmol) and triethylamine (91 mg, 0.126 ml, 0.90 mmol) in tetrahydrofuran (5 ml) at 0-5° C. was added a solution of 5-(4-chloro-phenyl)-3-ethylsulfanyl-pyridine-2-carbonyl chloride (197 mg, 0.63 mmol) in tetrahydrofuran (5 ml) dropwise. The reaction mixture was stirred at room temperature until judged complete by LCMS analysis, then concentrated to dryness in vacuo. The residue was treated with ethyl acetate, washed twice with a saturated aqueous sodium bicarbonate solution, then with water and brine. The combined organic layers were dried over sodium sulfate and evaporated to dryness. The residue was purified by Combi flash chromatography on silica gel (gradient 0-40% ethyl acetate in cyclohexane) to afford the title compound P1 (160 mg) as a solid, mp 147-148° C. LCMS (method 1): 459/461 (M+H)$^+$, retention time 1.19 min. $^1$H-NMR (CDCl$_3$, ppm) 1.41 (3H), 3.02 (2H), 4.22 (3H), 7.49 (2H), 7.57 (2H), 7.81 (1H), 8.69 (1H).

Example P2

Preparation of (N)-5-(4-chlorophenyl)-3-ethylsulfonyl-N-[3-methyl-5-(trifluoromethyl)-1,3,4-thiadiazol-2-ylidene]pyridine-2-carboxamide (compound P2) and (N)-5-(4-chlorophenyl)-3-ethylsulfonyl-N-[3-methyl-5-(trifluoromethyl)-1,3,4-thiadiazol-2-ylidene]-1-oxido-pyridin-1-ium-2-carboxamide (compound P3)

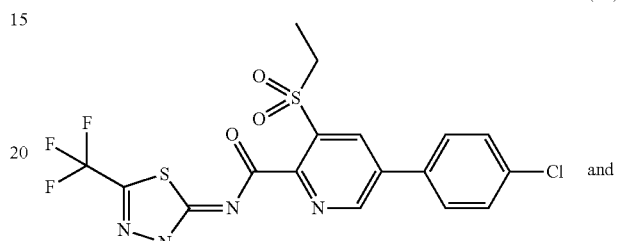

(P2) and

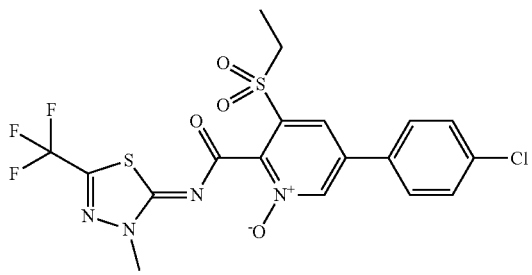

(P3)

To a solution of (N)-5-(4-chlorophenyl)-3-ethylsulfanyl-N-[3-methyl-5-(trifluoromethyl)-1,3,4-thiadiazol-2-ylidene]pyridine-2-carboxamide (160 mg, 0.349 mmol) in dichloromethane (10 ml) at 0-5° C. was added a solution of meta-chloroperoxybenzoic acid (152 mg, mCPBA, ~75%, 0.662 mmol) in dichloromethane (5 ml) dropwise. The white suspension was stirred at 0-5° C. for 2 hours, then poured on water. The organic layer was washed with an aqueous 10% NaHSO$_3$ solution (4×), then with saturated aqueous sodium bicarbonate (4×) and brine, dried over sodium sulfate and evaporated to dryness. The residue was purified by Combi flash chromatography on silica gel (gradient 0-35% ethyl acetate in cyclohexane) to afford the title compound P2 (38 mg) as a white solid, mp 189-191° C. LCMS (method 1): 491/493 (M+H)$^+$, retention time 1.09 min. $^1$H-NMR (CDCl$_3$, ppm) 1.41 (3H), 3.77 (2H), 4.16 (3H), 7.55 (2H), 7.63 (2H), 8.56 (1H), 9.09 (1H).

Further elution (gradient 35-55% ethyl acetate in cyclohexane) delivered (N)-5-(4-chlorophenyl)-3-ethylsulfonyl-N-[3-methyl-5-(trifluoromethyl)-1,3,4-thiadiazol-2-ylidene]-1-oxido-pyridin-1-ium-2-carboxamide (compound P3) as a solid, mp 219-220° C. LCMS (method 2): 507/509 (M+H)$^+$, retention time 1.55 min. $^1$H-NMR (CDCl$_3$, ppm) 1.37 (3H), 3.48 (2H), 4.08 (3H), 7.54 (4H), 7.98 (1H), 8.62 (1H).

Example P3

Preparation of (N)-3-ethylsulfonyl-N-[3-methyl-5-(trifluoromethyl)-1,3,4-thiadiazol-2-ylidene]-5-phenyl-pyridine-2-carboxamide (compound P6)

Step 1: Preparation of 5-bromo-3-ethylsulfanyl-pyridine-2-carbonitrile

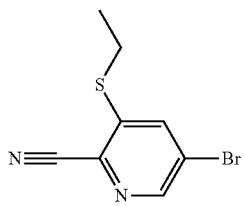

Under nitrogen atmosphere, a solution of 5-bromo-3-fluoro-pyridine-2-carbonitrile (1.005 g, 5.00 mmol) in dry N,N-dimethylformamide (15 ml) was cooled to −50° C. and to this was added dropwise a freshly prepared solution of sodium ethanethiolate (0.429 g, 5.10 mmol) in dry N,N-dimethylformamide (5 ml). After stirring at −50° C. for 30 minutes, the cooling bath was removed and the mixture was allowed to warm to room temperature. Water and brine were added and the aqueous mixture was extracted with ethyl acetate. After separation, the organic layer was washed twice with brine, dried over sodium sulfate and concentrated. The crude product was purified over silica by flash column chromatography (0 to 40% gradient of ethyl acetate in heptane) to afford the title compound (0.93 g) as a solid. GCMS (method 4): 242/244 (M)+, retention time 6.33 min. $^1$H-NMR (CDCl$_3$, ppm) 1.41 (3H), 3.06 (2H), 7.82 (1H), 8.49 (1H).

Alternative preparation method: Under nitrogen atmosphere, a solution of 5-bromo-3-nitro-pyridine-2-carbonitrile (45.35 g, 199 mmol) in dry N,N-dimethylformamide (500 ml) was cooled to −50° C. and to this was added dropwise a freshly prepared solution of sodium ethanethiolate (17.4 g, 207 mmol) in dry N,N-dimethylformamide (200 ml) (not a completely clear solution). After complete addition, stirring was continued at −50° C. for 30 minutes. Water and brine were added and the cooling bath was removed. The aqueous mixture was extracted with ethyl acetate. After separation, the water layer was extracted with ethyl acetate once more. The combined organic layers were washed twice with brine, dried over sodium sulfate and concentrated. The crude product was purified over silica by flash column chromatography (0 to 25% gradient of ethyl acetate in heptane) to afford the title compound (33.9 g) as a solid. LCMS (method 1): 243/245 (M+H)+; retention time: 0.95 min.

Step 2: Preparation of 5-bromo-3-ethylsulfanyl-pyridine-2-carboxylic acid

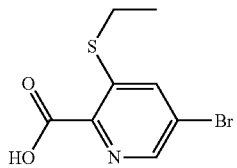

A solution of 5-bromo-3-ethylsulfanyl-pyridine-2-carbonitrile (43 g, 170 mmol, 1.0 eq.) in 800 ml aqueous hydrogen chloride HCl 32% was heated to 60° C. overnight. Dioxane (100 ml) was added and the mixture was further stirred at 60° C. for 48 h. The reaction mixture was cooled to 0-5° C., treated with an aqueous sodium hydroxide solution (NaOH 30%) until pH11 and washed with 2×200 ml tert-butyl methyl ether. The water phase was acidified with HCl 10% back to pH4, the resulting solid was filtrated, washed with water and dried in vacuo. LCMS (method 1): 262, 264 (M+H)+; retention time: 0.77 min. $^1$H NMR (400 MHz, CDCl$_3$) δ ppm: 8.50 (s, 1 H); 8.06 (s, 1 H); 3.03 (q, 2 H); 1.24 (t, 3H).

Step 3: Preparation of (N)-5-bromo-3-ethylsulfanyl-N-[3-methyl-5-(trifluoromethyl)-1,3,4-thiadiazol-2-ylidene]pyridine-2-carboxamide

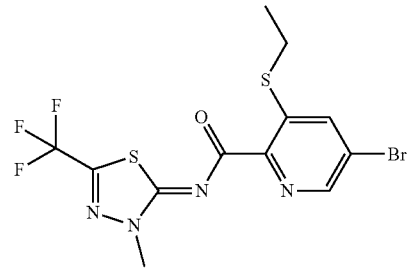 [SMILES: CCSc1cc(Br)cnc1C(=O)/N=c1\sc(C(F)(F)F)nn1C]

(a) To a solution of 5-bromo-3-ethylsulfanyl-pyridine-2-carboxylic acid (4.0 g, 15.26 mmol) in dichloromethane (100 ml) at 5-10° C. was added one drop of N,N-dimethylformamide, followed by oxalyl chloride (2.4 g, 1.647 ml, 1.2 equiv.) dropwise. The reaction mixture was stirred at room temperature overnight and evaporated to dryness in vacuo to afford 5-bromo-3-ethylsulfanyl-pyridine-2-carbonyl chloride as a solid (4.16 g). This material was used without further purification.

(b) To a solution of 3-methyl-5-(trifluoromethyl)-1,3,4-thiadiazol-2-imine (U.S. Pat. No. 4,264,616A) (800 mg, 90%, 3.93 mmol), triethylamine (566 mg, 0.78 ml, 5.60 mmol) and N,N-dimethylpyridin-4-amine (5 mg) in dichloromethane (25 ml) at 0-5° C. was added a solution of 5-bromo-3-ethylsulfanyl-pyridine-2-carbonyl chloride (1.1 g, 95%, 3.72 mmol) in dichloromethane (10 ml) dropwise. The reaction mixture was stirred at 10° C. for two hours, then concentrated to dryness in vacuo. The residue was treated with t-butyl methyl ether and water, the layers separated, the organic phase washed with water (4×) and brine, dried over sodium sulfate and filtered. The dark solution was treated with active charcoal and after short stirring, the mixture was filtered, the fitrate evaporated to dryness to afford (N)-5-bromo-3-ethylsulfanyl-N-[3-methyl-5-(trifluoromethyl)-1,3,4-thiadiazol-2-ylidene]pyridine-2-carboxamide as a pale brown solid (1.35 g), mp 120-123° C. LCMS (method 2): 427/429 (M+H)+, retention time 1.81 min. $^1$H-NMR (CDCl$_3$, ppm) 1.34 (t, 3H), 2.88 (q, 2H), 4.12 (s, 3H), 7.73 (d,1H), 8.46 (d,1H).

Step 4: Preparation of (N)-5-bromo-3-ethylsulfonyl-N-[3-methyl-5-(trifluoromethyl)-1,3,4-thiadiazol-2-ylidene]pyridine-2-carboxamide

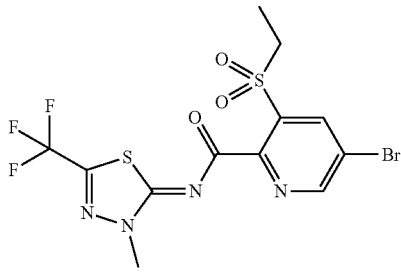 [SMILES: CCS(=O)(=O)c1cc(Br)cnc1C(=O)/N=c1\sc(C(F)(F)F)nn1C]

Obtained from (N)-5-bromo-3-ethylsulfanyl-N-[3-methyl-5-(trifluoromethyl)-1,3,4-thiadiazol-2-ylidene] pyridine-2-carboxamide (1.0 g, 2.34 mmol) and mCPBA (1.104 g, 4.80 mmol, 75%) in dichloro-methane (20 ml) according to procedure Example P2. The mixture was stirred at room temperature. The crude material obtained after extractive workup was suspended and stirred in cold diethyl ether, filtered, the solid washed twice with cold portions of diethyl ether and dried in vacuo to afford (N)-5-bromo-3-ethylsulfonyl-N-[3-methyl-5-(trifluoromethyl)-1,3,4-thiadiazol-2-ylidene]pyridine-2-carboxamide (850 mg) as a white solid, mp 178-180° C. LCMS (method 2): 459/461 (M+H)$^+$; retention time: 1.53 min. $^1$H-NMR (CDCl$_3$, ppm) 1.38 (t, 3H), 3.71 (q, 2H), 4.12 (s, 3H), 8.52 (d, 1H), 8.94 (d, 1H).

Step 5: Preparation of (N)-3-ethylsulfonyl-N-[3-methyl-5-(trifluoromethyl)-1,3,4-thiadiazol-2-ylidene]-5-phenyl-pyridine-2-carboxamide (compound P6)

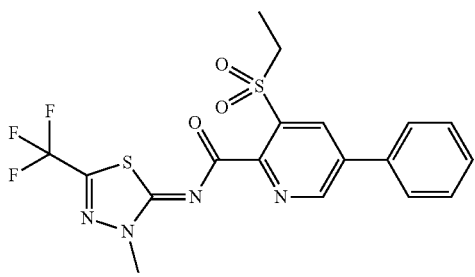 [SMILES: CCS(=O)(=O)c1cc(-c2ccccc2)cnc1C(=O)/N=c1\sc(C(F)(F)F)nn1C]

A solution of (N)-5-bromo-3-ethylsulfonyl-N-[3-methyl-5-(trifluoromethyl)-1,3,4-thiadiazol-2-ylidene]pyridine-2-carboxamide (200 mg, 0.435 mmol), phenyl boronic acid (106.2 mg, 0.871 mmol), sodium carbonate (141 mg, 1.306 mmol) in 1,2-dimethoxyethane (5 ml) was flushed with argon. Bis(triphenylphosphine)palladium(II) dichloride (3.06 mg, 0.004 mmol) was added, and the mixture was stirred in the microwave at 110° C. for 1.5 hours. The reaction mixture was diluted with dichloro-methane, filtered over diatomaceous earth (Hyflo) and the filtrate concentrated to dryness. The residue was purified by flash chromatography on silica gel (cyclohexane /ethyl acetate 8:1) to afford (N)-3-ethylsulfonyl-N-[3-methyl-5-(trifluoromethyl)-1,3,4-thiadiazol-2-ylidene]-5-phenyl-pyridine-2-carboxamide (compound P6) as a solid (105 mg), mp 204-205° C. LCMS (method 1): 457 (M+H)$^+$, retention time 1.06 min. $^1$H-NMR (CDCl$_3$, ppm) 1.40 (t, 3H) 3.74 (q, 2H) 4.14 (s, 3H) 7.55 (m, 3H) 7.67 (m, 2H) 8.56 (d, 1H) 9.10 (d, 1H).

Example P4

Preparation of (N)-5-(6-chloro-2-pyridyl)-3-ethylsulfonyl-N-[3-methyl-5-(trifluoromethyl)-1,3,4-thiadiazol-2-ylidene]pyridine-2-carboxamide (compound P64)

Step 1: Preparation of (N)-3-ethylsulfonyl-N-[3-methyl-5-(trifluoromethyl)-1,3,4-thiadiazol-2-ylidene]-5-(4,4,5,5-tetramethyl-1,3,2-dioxaborolan-2-yl)pyridine-2-carboxamide

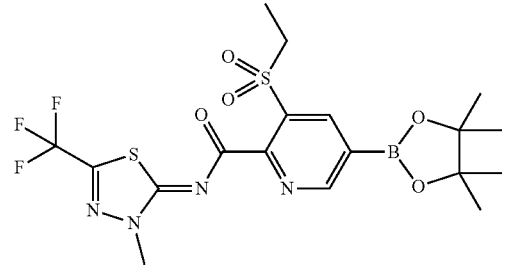 [SMILES: CCS(=O)(=O)c1cc(B2OC(C)(C)C(C)(C)O2)cnc1C(=O)/N=c1\sc(C(F)(F)F)nn1C]

A mixture of (N)-5-bromo-3-ethylsulfonyl-N-[3-methyl-5-(trifluoromethyl)-1,3,4-thiadiazol-2-ylidene]pyridine-2-carboxamide (1.4 g, 3.05 mmol), potassium acetate (0.75 g, 7.64 mmol) and 4,4,5,5-tetramethyl-2-(4,4,5,5-tetramethyl-1,3,2-dioxaborolan-2-yl)-1,3,2-dioxaborolane (1.2 g, 4.63 mmol) in dioxane (15 ml) was purged with argon for 10 minutes. 1,1'-Bis(diphenylphosphino) ferrocene-palladium (II) dichloride dichloromethane complex (1:1; PdCl$_2$(dppf) .CH$_2$Cl$_2$) (110 mg, 0.15 mmol) was then added, and the mixture was stirred in the microwave at 90° C. for 40 minutes. The reaction mixture was filtered over diatomaceous earth (Hyflo), the filtrate dried over sodium sulfate and concentrated under reduced pressure. The residue was triturated with petroleum ether (40-60° C.), the suspension filtered, the solid washed with cold petroleum ether and dried in vacuo at 40° C. to afford (N)-3-ethylsulfonyl-N-[3-methyl-5-(trifluoromethyl)-1,3,4-thiadiazol-2-ylidene]-5-(4,4,5,5-tetramethyl-1,3,2-dioxaborolan-2-yl)pyridine-2-carboxamide as a solid (1.3 g), mp 176-178° C. LCMS (method 1): 425 (M+H)$^+$, retention time 0.80 min [consistent with the corresponding boronic acid of formula C$_{12}$H$_{12}$BF$_3$N$_4$O$_5$S$_2$, MW: 424.18]. $^1$H-NMR (CDCl$_3$, ppm) 1.37 (t, 3H), 1.38 (s, 12H), 3.64 (q, 2H), 4.11 (s, 3H), 8.72 (d, J=1.47 Hz, 1H), 9.16 (d, J=1.47 Hz, 1H).

Step 2: Preparation of (N)-5-(6-chloro-2-pyridyl)-3-ethylsulfonyl-N-[3-methyl-5-(trifluoromethyl)-1,3,4-thiadiazol-2-ylidene]pyridine-2-carboxamide (compound P64)

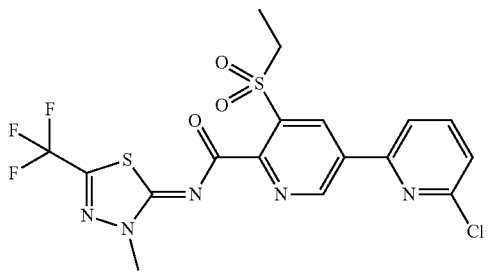 [SMILES: CCS(=O)(=O)c1cc(-c2cccc(Cl)n2)cnc1C(=O)/N=c1\sc(C(F)(F)F)nn1C]

A mixture of (N)-3-ethylsulfonyl-N-[3-methyl-5-(trifluoromethyl)-1,3,4-thiadiazol-2-ylidene]-5-(4,4,5,5-tetramethyl-1,3,2-dioxaborolan-2-yl)pyridine-2-carboxamide (25 mg, 0.049 mmol), 2-bromo-6-chloro-pyridine (23.8 mg, 0.123 mmol) and an aqueous 2M sodium carbonate solution (0.074 ml, 2.0M, 0.148 mmol) in dioxane (1.5 ml) was purged with argon for 10 minutes. Tetrakis(triphenylphosphine) palladium(O) (2.9 mg, 0.0025 mmol) was then added, and the mixture was stirred in the microwave at 90° C. for 30 minutes. The reaction mixture was diluted with ethyl acetate and water, the layers separated, the organic phase washed with brine, dried over sodium sulfate and concentrated. The residue was purified by flash chromatography on silica gel (gradient cyclohexane/ethyl acetate 4:1 to 1:1) to afford (N)-5-(6-chloro-2-pyridyl)-3-ethylsulfonyl-N-[3-methyl-5-(trifluoromethyl)-1,3,4-thiadiazol-2-ylidene]pyridine-2-carboxamide (compound P64) as a solid (19 mg), mp 190-192° C. LCMS (method 1): 492/494 (M+H)$^+$, retention time 1.05 min. $^1$H-NMR (CDCl$_3$, ppm) 1.41 (t, 3H), 3.72 (q, 2H), 4.14 (s, 3H), 7.42 (m, 1H), 7.82 (m, 2H), 8.95 (d, 1H), 9.47 (d, 1H).

Example P5

Preparation of (N)-3-ethylsulfonyl-N-[1-methyl-5-(trifluoromethylsulfanyl)-2-pyridylidene]-5-pyrimidin-2-yl-pyridine-2-carboxamide (compound P17)

Step 1: Preparation of 1-methyl-5-(trifluoromethylsulfanyl)pyridin-2-imine hydroiodide salt

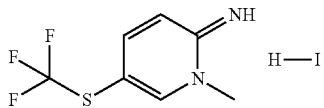

To a solution of 5-(trifluoromethylsulfanyl)pyridin-2-amine (2 g, 10.30 mmol) in N,N-dimethylformamide (20 ml) was added iodomethane (0.962 ml, 15.45 mmol, 1.5 equiv.) under stirring. The clear colorless solution was heated to 50° C. until complete conversion. The clear solution was concentrated under vacuum, the residue treated with diethyl ether, the slurry stirred for 30 minutes, filtered, the solid washed with cold diethyl ether and dried in vacuo to afford 1-methyl-5-(trifluoromethylsulfanyl)pyridin-2-imine hydroiodide salt as a solid (3.1 g), mp 219-221° C.

LCMS (method 1): 209 (M+H)$^+$, retention time 0.34 min [consistent with the corresponding free base of formula C$_7$H$_7$F$_3$N$_2$S, MW: 208.20]. $^1$H-NMR (DMSO-d$_6$, ppm) 3.79 (s, 3H), 7.14 (d, 1H), 8.07 (dd, 1H), 8.74 (d, 1H).

Step 2: Preparation of (N)-5-bromo-3-ethylsulfanyl-N-[1-methyl-5-(trifluoromethylsulfanyl)-2-pyridylidene]pyridine-2-carboxamide

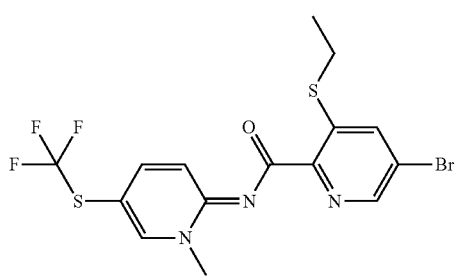 [SMILES: CCSc1cc(Br)cnc1C(=O)/N=c1\ccc(SC(F)(F)F)cn1C]

To a solution of 1-methyl-5-(trifluoromethylsulfanyl) pyridin-2-imine hydroiodide salt (400 mg, 1.19 mmol), triethylamine (307 mg, 2.97 mmol) and 4-dimethylamino pyridine (1.5 mg) in dichloromethane (20 ml) at 0-5° C. was added a solution of 5-bromo-3-ethylsulfanyl-pyridine-2-carbonyl chloride (317 mg, 1.13 mmol) in dichloromethane (5 ml) dropwise. The reaction mixture was stirred at 10° C. for two hours, then evaporated to dryness. The residue was treated with ethylacetate and water, the layers separated, the organic phase washed with water (4×) and brine, dried over sodium sulfate, filtered and concentrated to afford (N)-5-bromo-3-ethylsulfanyl-N-[1-methyl-5-(trifluoromethylsulfanyl)-2-pyridylidene]pyridine-2-carboxamide as a solid (390 mg), mp 131-133° C. LCMS (method 1): 452/454 (M+H)$^+$, retention time 0.93 min. $^1$H-NMR (CDCl$_3$, ppm) 1.38 (t, J=7.52 Hz, 3H), 2.92 (q, J=7.52 Hz, 2H), 3.87 (s, 3H), 7.66 (dd, J=9.54, 1.83 Hz, 1H), 7.75 (d, J=1.83 Hz, 1H), 7.90 (d, J=1.83 Hz, 1H), 8.15 (d, J=9.54 Hz, 1H), 8.44 (d, J=1.83 Hz, 1H).

Step 3: Preparation of (N)-5-bromo-3-ethylsulfonyl-N-[1-methyl-5-(trifluoromethylsulfanyl)-2-pyridylidene]pyridine-2-carboxamide

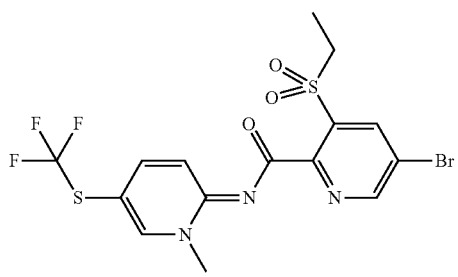 [SMILES: CCS(=O)(=O)c1cc(Br)cnc1C(=O)/N=c1\ccc(SC(F)(F)F)cn1C]

Obtained from (N)-5-bromo-3-ethylsulfanyl-N-[1-methyl-5-(trifluoromethylsulfanyl)-2-pyridylidene] pyridine-2-carboxamide (580 mg, 1.28 mmol) and mCPBA (605 mg, 2.63 mmol, 75%) in dichloro-methane (15 ml) according to procedure Example P3, step 4. The mixture was stirred at 5° C. for two hours. The crude material obtained after extractive workup was purified by flash chromatography (cyclohexane/ethylacetate 1:1) to afford (N)-5-bromo-3-ethylsulfonyl-N-[1-methyl-5-(trifluoromethyl-sulfanyl)-2-pyridylidene]pyridine-2-carboxamide (360 mg) as a solid, mp 150-152° C. LCMS (method 1): 484/486 (M+H)$^+$; retention time: 0.96 min. $^1$H-NMR (CDCl$_3$, ppm) 1.36 (t, 3H), 3.70 (q, 2H), 3.86 (s, 3H), 7.76 (dd, 1H), 7.94 (d, 1H), 8.24 (d, 1H) 8.47 (d, 1H) 8.87 (d, 1H).

Step 4: Preparation of (N)-3-ethylsulfonyl-N-[1-methyl-5-(trifluoromethylsulfanyl)-2-pyridylidene]-5-pyrimidin-2-yl-pyridine-2-carboxamide (compound P17)

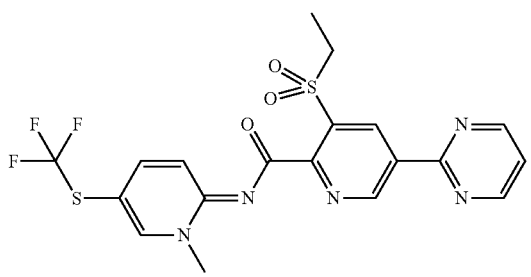 [SMILES: CCS(=O)(=O)c1cc(-c2ncccn2)cnc1C(=O)/N=c1\ccc(SC(F)(F)F)cn1C]

A solution of (N)-5-bromo-3-ethylsulfonyl-N-[1-methyl-5-(trifluoromethylsulfanyl)-2-pyridylidene] pyridine-2-carboxamide (160 mg, 0.33 mmol) in N,N-dimethylformamide (2.5 ml) was purged with argon for 10 minutes. Then tributyl(pyrimidin-2-yl)stannane (183 mg, 0.496 mmol) and bis(triphenyl-phosphine)palladium(II) dichloride (23 mg, 0.033 mmol) were added, and the mixture was stirred in the microwave at 200° C. for 20 minutes. The reaction mixture was concentrated in vacuo and the residue purified by flash chromatography on silica gel (gradient heptane/ethyl acetate 10:1 to 1:2) to afford (N)-3-ethylsulfonyl-N-[1-methyl-5-(trifluoromethylsulfanyl)-2-pyridylidene]-5-pyrimidin-2-yl-pyridine-2-carboxamide (compound P17) as a solid (21 mg), mp 215-217° C. LCMS (method 1): 484 (M+H)$^+$, retention time 0.91 min. $^1$H-NMR (CDCl$_3$, ppm) 1.39 (t, 3H), 3.72 (q, 2H), 3.88 (s, 3H), 7.32 (t, 1H), 7.76 (dd, 1H), 7.94 (d, 1H), 8.28 (d, 1H), 8.88 (d, 2H), 9.34 (d, 1H), 9.83 (d, 1H).

Example P6

Preparation of (N)-5-cyclopropyl-3-ethylsulfonyl-N-[1-methyl-5-(trifluoromethylsulfanyl)-2-pyridylidene]pyridine-2-carboxamide (compound P18)

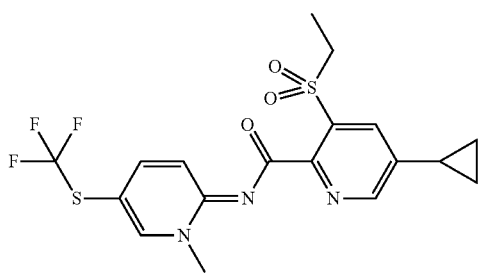 [SMILES: CCS(=O)(=O)c1cc(C2CC2)cnc1C(=O)/N=c1\ccc(SC(F)(F)F)cn1C]

A mixture of (N)-5-bromo-3-ethylsulfonyl-N-[1-methyl-5-(trifluoromethylsulfanyl)-2-pyridylidene] pyridine-2-carboxamide (140 mg, 0.289 mmol), cyclopropylboronic acid (89 mg, 1.041 mmol) and tripotassium phosphate (368 mg, 1.73 mmol) in toluene/water (1.5 ml / 1.5 ml) was purged with argon for 10 minutes. Tetrakis(triphenylphosphine)palladium(O) (33 mg, 0.029 mmol) was then added, and the mixture was stirred in the microwave at 130° C. for 45 minutes. The reaction mixture was concentrated in vacuo, and the residue purified over silica by flash column chromatography (gradient cyclohexane/ethyl acetate 4:1 to 1:1) to afford (N)-5-cyclopropyl-3-ethylsulfonyl-N-[1-methyl-5-(trifluoromethylsulfanyl)-2-pyridylidene]pyridine-2-carboxamide (compound P18) as a gum (50 mg). LCMS (method 1): 446 (M+H)$^+$, retention time 0.93 min. $^1$H-NMR (CDCl$_3$, ppm) 0.83 (m, 2H), 1.15 (m, 2H), 1.33 (t, 3H), 2.03 (m, 1H), 3.68 (q, 2H), 3.84 (s, 3H), 7.70 (dd, 1H), 7.91 (d, 2H), 8.19 (d, 1H), 8.59 (d, 1H).

Example P7

Preparation of (N)-3-ethylsulfonyl-N-[3-methyl-5-(trifluoromethyl)-1,3,4-thiadiazol-2-ylidene]-6-[4-(trifluoromethyl)phenyl]pyridine-2-carboxamide (compound P21)

Step 1: Preparation of methyl 6-chloro-3-ethylsulfanyl-pyridine-2-carboxylate

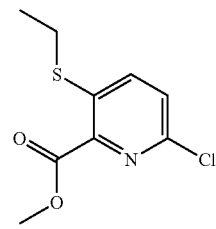

3,6-Dichloro-2-pyridinecarboxylic acid methyl ester (commercially available, 20.0 g, 97.073 mmol) was dissolved in tetrahydrofuran (200 ml) and 18-crown-6-ether (some crystals) was added. Sodium ethanethiolate (9.073 g, 97.073 mmol) was then added in 3 portions at room temperature and the reaction was stirred for 1 hour at room temperature. The reaction mixture was poured on an aqueous saturated ammonium chloride solution (100 ml) and extracted twice with ethyl acetate (2'100 ml). The combined organic layers were washed with an aqueous saturated ammonium chloride solution (2×50 ml) and water (3×100 ml), dried over sodium sulfate, filtered and evaporated under vacuum. The crude was purified by combi flash chromatography (220 g column; gradient cyclohexane +0-10% ethyl acetate) to give the title compound (14.5 g) as a solid, mp 122-124° C. LCMS (method 1): 232/234 (M+H)$^+$, retention time 0.94 min. $^1$H NMR (400 MHz, CDCl$_3$) δ ppm: 1.42 (t, 3H), 2.96 (q, 2H), 4.02 (s, 3H), 7.45 (d, 1H), 7.70 (d, 1H).

Step 2: Preparation of methyl 3-ethylsulfanyl-6-[4-(trifluoromethyl)phenyl]pyridine-2-carboxylate

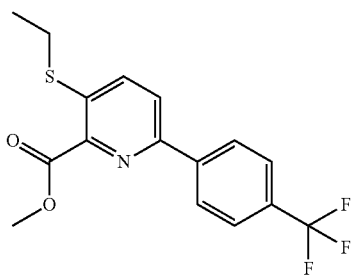 [SMILES: CCSc1ccc(-c2ccc(C(F)(F)F)cc2)nc1C(=O)OC]

A solution of methyl 6-chloro-3-ethylsulfanyl-pyridine-2-carboxylate (0.3 g, 1.29 mmol) in 1,4-dioxane (7.5 ml) was treated with [4-(trifluoromethyl)phenyl]boronic acid (0.32 g, 1.68 mmol) and anhydrous potassium carbonate (0.537 g, 3.88 mmol), and the mixture purged with argon for 10 minutes. To this mixture was added tetrakis(triphenylphosphine)palladium(0) (0.149 g, 0.129 mmol) and the solution heated at 95° C. overnight. The reaction mixture was quenched with water at room temperature and ethyl acetate was added. The aqueous layer was extracted 3 times with ethyl acetate. The combined organic layer was washed with an aqueous saturated NaHCO₃ solution and brine, dried over sodium sulfate, filtered and evaporated under vacuum at 45° C.The crude product was dissolved in dichloromethane and adsorbed on TEFLON BULK SORBENTS. The crude was purified by Combi flash chromatography (24 g column; gradient cyclohexane +0-50% ethyl acetate) to give the title compound (280 mg) as a white solid, mp 67-69° C. LCMS (method 1): 342 (M+H)⁺, retention time 1.21 min. ¹H-NMR (CDCl₃, ppm) 1.41 (t, J=7.34 Hz, 3H), 2.99 (q, J=7.34 Hz, 2H), 4.03 (s, 3H), 7.72 (d, J=8.07 Hz, 2H), 7.80 (m, 2H), 8.13 (d, J=8.07 Hz, 2H).

Step 3: Preparation of methyl 3-ethylsulfonyl-6-[4-(trifluoromethyl)phenyl]pyridine-2-carboxylate

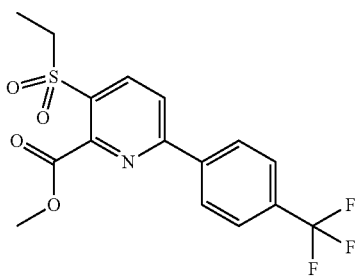 [SMILES: CCS(=O)(=O)c1ccc(-c2ccc(C(F)(F)F)cc2)nc1C(=O)OC]

Obtained from methyl 3-ethylsulfanyl-6-[4-(trifluoromethyl)phenyl]pyridine-2-carboxylate (1.0 g, 2.93 mmol) and mCPBA (1.32 g, 5.89 mmol, 77%) in dichloromethane (15 ml) according to procedure Example P3, step 4. The mixture was stirred at 5° C. for two hours. The crude material obtained after extractive workup was suspended and stirred in hexane/ethyl acetate 4:1, filtered, the solid washed with cold portions of hexane and dried in vacuo to afford methyl 3-ethylsulfonyl-6-[4-(trifluoromethyl) phenyl]pyridine-2-carboxylate (850 mg) as a solid, mp 151-153° C. LCMS (method 1): 374 (M+H)⁺; retention time: 1.19 min. ¹H-NMR (CDCl₃, ppm) 1.40 (t, 3H), 3.55 (q, 2H), 4.10 (s, 3H), 7.80 (d, 2H), 8.05 (d, 1H), 8.23 (d, 2H), 8.44 (d,1H).

Step 4: Preparation of 3-ethylsulfonyl-6-[4-(trifluoromethyl)phenyl]pyridine-2-carboxylic acid

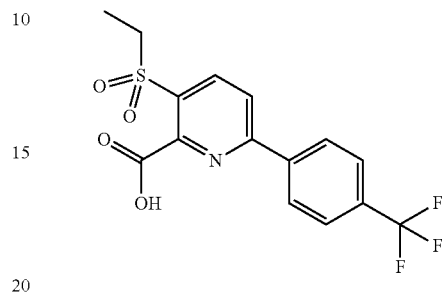

Methyl 3-ethylsulfonyl-6-[4-(trifluoromethyl)phenyl]pyridine-2-carboxylate (850 mg, 2.28 mmol) was dissolved in a mixture dioxane and water (16 ml, 1/1), lithium hydroxide (60 mg, 2.5 mmol) was added and the reaction mixture stirred at room temperature overnight. After complete conversion, ethyl acetate was added, the layers separated, the aqueous phase acidified with hydrochloric acid and the product extracted with ethyl acetate. The combined organic phases were washed with brine, dried over sodium sulfate, filtered and concentrated to afford 3-ethylsulfonyl-6-[4-(trifluoromethyl)phenyl] pyridine-2-carboxylic acid (610 mg) as a solid, mp 140-142° C. LCMS (method 1): 360 (M+H)⁺, 358 (M−H)⁻; retention time: 0.92 min. ¹H-NMR (CDCl₃, ppm) 1.38 (t, 3H), 3.80 (q, 2H), 7.83 (d, 2H), 8.17 (t, 3H), 8.69 (d,1H).

Step 5: Preparation of (N)-3-ethylsulfonyl-N-[3-methyl-5-(trifluoromethyl)-1,3,4-thiadiazol-2-ylidene]-6-[4-(trifluoromethyl)phenyl]pyridine-2-carboxamide (compound P21)

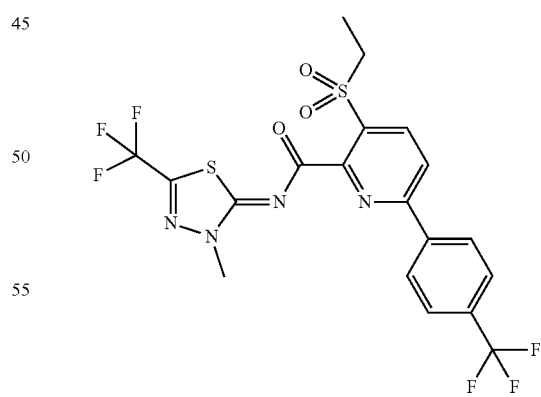

(a) 3-Ethylsulfonyl-6-[4-(trifluoromethyl)phenyl]pyridine-2-carbonyl chloride: obtained from 3-ethyl-sulfonyl-6-[4-(trifluoromethyl)phenyl]pyridine-2-carboxylic acid and oxalyl chloride according to procedure Example P1, step 4 (a).

(b) Compound P21: obtained from 3-ethylsulfonyl-6-[4-(trifluoromethyl)phenyl]pyridine-2-carbonyl chloride (300 mg, 0.794 mmol) and 3-methyl-5-(trifluoromethyl)-1,3,4-thiadiazol-2-imine hydroiodide salt (247 mg, 0.794 mmol) according to procedure Example P1, step 4 (b). The crude material obtained after extractive workup was purified by flash chromatography (0-30% gradient ethyl acetate in cyclohexane) to afford (N)-3-ethylsulfonyl-N-[3-methyl-5-(trifluoromethyl)-1,3,4-thiadiazol-2-ylidene]-6l-[4-(trifluoromethyl)phenyl]pyridine-2-carboxamide (compound P21) as a solid (290 mg), mp 195-197° C. LCMS (method 1): 525 (M+H)⁺; retention time: 1.21 min. ¹H-NMR (CDCl₃, ppm) 1.38 (t, 3H), 3.65 (q, 2H), 4.12 (s, 3H), 7.77 (d, 2H), 8.00 (d, 1H), 8.21 (d, 2H), 8.44 (d, 1H).

Example P8

Preparation of (N)-5-(1-cyanocyclopropyl)-3-ethyl-sulfonyl-N-[3-methyl-5-(1,1,2,2,2-pentafluoroethyl)-1,3,4-thiadiazol-2-ylidene]pyridine-2-carboxamide (compound P20)

Step 1: Preparation of methyl 5-bromo-3-ethylsulfonyl-pyridine-2-carboxylate

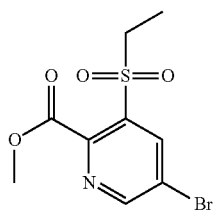 [SMILES: CCS(=O)(=O)c1cc(Br)cnc1C(=O)OC]

Methyl 5-bromo-3-ethylsulfanyl-pyridine-2-carboxylate (24.4 g, 88.4 mmol, step B1 from Example P1) was suspended in dichloromethane (250 mL), cooled to 0° C., and treated portion wise with mCPBA (37.6 g, 185.7 mmol). The mixture was stirred at ambient temperature for 18 hours. The mixture was diluted with water and dichloromethane, the aqueous phase was back extracted with dichloromethane (2×), and the combined organic phases washed with Na₂S₂O₄, dried over Na₂SO₄. Partial concentration of the solvent, led to a solid (the desired title compound) that was filtered. The filtrate was evaporated to dryness, which was purified by chromatography on silica to give further pure title compound as white solid. LCMS (method 1): 308/310 (M+H)⁺; retention time: 0.76 min. ¹H NMR (d⁶-DMSO, 400 MHz): 9.08 (d, J=2.4Hz, 1H), 8.58 (d, J=2.4Hz, 1H), 3.87 (s, 3H), 3.52 (q, J=7.8Hz, 2H), 1.18 (t, J=7.8Hz, 3H).

Step 2: Preparation of methyl 5-(cyanomethyl)-3-ethylsulfonyl-pyridine-2-carboxylate

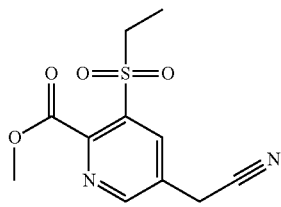 [SMILES: CCS(=O)(=O)c1cc(CC#N)cnc1C(=O)OC]

A solution of methyl 5-bromo-3-ethylsulfonyl-pyridine-2-carboxylate, (2.00 g, 6.49 mmol) in DMF (13.0 mL) was treated with TMS-acetonitrile (2.25 g, 2.71 mL, 19.5 mmol), difluorozinc (0.403 g, 3.89 mmol), XANTPHOS (0.153 g, 0.260 mmol) and Pd₂(dba)₃ (0.119 g, 0.130 mmol) under argon. The resulting mixture was stirred for 5 hours at 100° C. LCMS after this time showed no further reaction progression. The mixture was cooled, diluted with EtOAc, and filtered over hyflo. The filtrate was washed with water/NH₄Cl, brine, dried over Na₂SO₄, filtered and concentrated in vacuo. The crude product was purified by combi flash chromatography with a column of 40 g and a gradient cyclohexane +0-50% ethylacetate. This gave the title compound as yellow oil. LCMS (method 1): 269 (M+H)⁺; retention time: 0.58 min. ¹H NMR (400 MHz, CDCl₃) δ ppm: 1.38 (t, J=7.5 Hz, 3 H), 3.58 (q, J=7.5 Hz, 2 H), 3.95 (s, 2 H), 4.06 (s, 3 H), 8.37 (d, J=2.20 Hz, 1 H), 8.86 (d, J=2.20 Hz, 1 H).

Step 3: Preparation of methyl 5-(1-cyanocyclopropyl)-3-ethylsulfonyl-pyridine-2-carboxylate

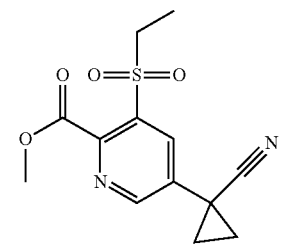 [SMILES: CCS(=O)(=O)c1cc(C2(C#N)CC2)cnc1C(=O)OC]

Methyl 5-(cyanomethyl)-3-ethylsulfonyl-pyridine-2-carboxylate (0.63 g, 2.3 mmol) was dissolved in acetonitrile (19 mL) and cesium carbonate (2.3 g, 7.0 mmol) was added to the colourless solution (solution darkened), followed by addition of 1,2-dibromoethane (0.90 g, 0.41 mL, 4.7 mmol) The brown solution was stirred at 80° C. bath temperature. LC/MS detected desired mass at Rt=0.73 min after 1.5 h. The reaction mixture was concentrated in vacuo and diluted with EtOAc and water. The organic layer was separated, washed successively with water and brine, dried over Na₂SO₄, filtered and concentrated in vacuo. The crude product was dissolved in dichloromethane and adsorbed onto TEFLON BULK SORBENTS. Purification over a silica gel cartridge (Rf200) eluting with Cyclohexane/EtOAc, gave the title compound as a beige resin. LCMS (method 1): 295 (M+H)⁺; retention time: 0.72 min. ¹H NMR (400 MHz, CDCl₃) δ ppm: 1.36 (t, J=7.5 Hz, 3 H), 1.57-1.62 (m, 2 H), 1.95-2.00 (m, 2 H), 2.05 (s, 2 H), 4.04 (s, 4 H), 8.13 (d, J=2.20 Hz, 1 H), 8.87 (d, J=2.20 Hz, 1 H).

Step 4: Preparation of 5-(1-cyanocyclopropyl)-3-ethylsulfonyl-pyridine-2-carboxylic acid

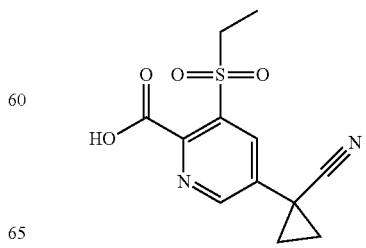

A solution of methyl 5-(1-cyanocyclopropyl)-3-ethylsulfonyl-pyridine-2-carboxylate (0.27 g, 0.92 mmol) was dissolved in THF (4mL) and water (1.5 mL) (red solution), and then treated with LiOH.H$_2$O (0.058 g, 1.4 mmol). The mixture was stirred at ambient temperature for 2 hours by which time LCMS analysis showed reaction completion (only desired product at Rt=0.32 min, method 1). The THF was evaporated in vacuo and the residue was acidified with 1M HCl and extracted with EtOAc. The organic layer was washed with brine, dried over Na$_2$SO$_4$ filtrated and concentrated in vacuo to give pure title product as a beige solid. LCMS (method 1): 281 (M+H)$^+$; retention time: 0.30 min. $^1$H NMR (400 MHz, methanol-d$_4$) δ ppm: 1.31 (t, J=7.3 Hz,3H), 1.71-1.78 (m, 2 H), 1.92-1.98 (m, 2 H), 3.60 (q, J=7.3 Hz, 2 H), 8.28 (d, J=2.20 Hz, 1 H), 8.83 (d, J=2.20 Hz, 1 H).

Step 5: Preparation of 5-(1-cyanocyclopropyl)-3-ethylsulfonyl-N-[5-(1,1,2,2,2-pentafluoroethyl)-1,3,4-thiadiazol-2-yl]pyridine-2-carboxamide

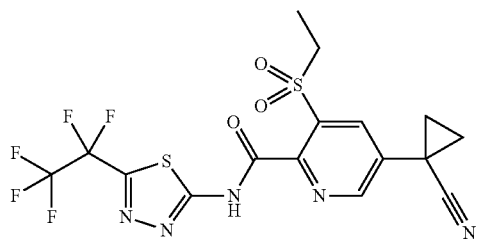 [SMILES: CCS(=O)(=O)c1cc(C2(C#N)CC2)cnc1C(=O)Nc1nnc(C(F)(F)C(F)(F)F)s1]

(a) 5-(1-cyanocyclopropyl)-3-ethylsulfonyl-pyridine-2-carbonyl chloride: obtained from 5-(1-cyano-cyclopropyl)-3-ethylsulfonyl-pyridine-2-carboxylic acid (300 mg, 1.07 mmol) and oxalyl chloride (163 mg, 0.112 ml, 1.2 equiv.) in dichloromethane (10 ml) according to procedure Example P1, step 4. The mixture was stirred at room temperature overnight, then evaporated to dryness to afford the acid chloride (318 mg) as a gum.

(b) To a solution of 5-(1,1,2,2,2-pentafluoroethyl)-1,3,4-thiadiazol-2-amine (147 mg, 0.67 mmol), triethylamine (102 mg, 0.140 ml, 1.004 mmol) and 4-dimethylaminopyridine (1 mg) in dichloromethane (10 ml) at 0-5° C. was added a solution of 5-(1-cyanocyclopropyl)-3-ethylsulfonyl-pyridine-2-carbonyl chloride (200 mg, 0.67 mmol) in dichloromethane (5 ml) dropwise. The reaction mixture was stirred at 10° C. for two hours, then concentrated to dryness in vacuo. The residue was treated with t-butyl methyl ether and water, the layers separated, the organic phase washed with water (4×) and brine, dried over sodium sulfate and concentrated. The crude material was purified by flash chromatography on silica gel (cyclohexane/ethyl acetate 3:1) to afford 5-(1-cyanocyclopropyl)-3-ethylsulfonyl-N-[5-(1,1,2,2,2-pentafluoroethyl)-1,3,4-thiadiazol-2-yl]pyridine-2-carboxamide (167 mg) as a solid, mp 149-151° C. LCMS (method 1): 482 (M+H)$^+$, retention time 1.02 min. $^1$H-NMR (CDCl$_3$, ppm) 1.40 (t, J=7.52 Hz, 3H), 1.65-1.71 (m, 2H), 2.03-2.09 (m, 2H), 3.87 (q, J=7.52 Hz, 2H), 8.35 (d, J=2.20 Hz,1H), 8.99 (d, J=2.20 Hz, 1H), 12.79 (br s, 1H).

Step 6: Preparation of (N)-5-(1-cyanocyclopropyl)-3-ethylsulfonyl-N-[3-methyl-5-(1,1,2,2,2-pentafluoroethyl)-1,3,4-thiadiazol-2-ylidene]pyridine-2-carboxamide (compound P20)

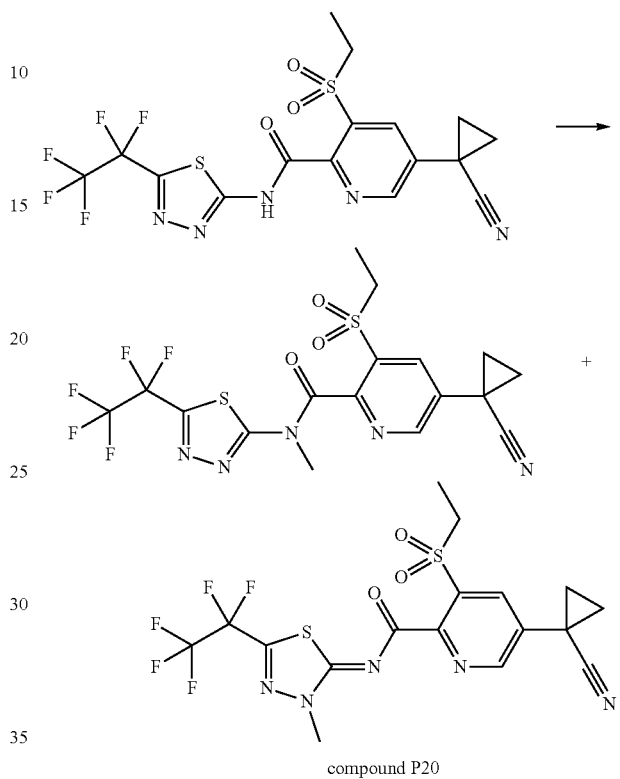

compound P20

To a solution of 5-(1-cyanocyclopropyl)-3-ethylsulfonyl-N-[5-(1,1,2,2,2-pentafluoroethyl)-1,3,4-thiadiazol-2-yl] pyridine-2-carboxamide (120 mg, 0.240 mmol) and potassium carbonate (103.4 mg, 0.748 mmol) in N,N-dimethylformamide (1.5 ml) at 0-5° C. was added a solution of iodomethane (37 mg, 0.016 ml, 0.259 mmol) in N,N-dimethylformamide (0.5 ml) dropwise. The reaction was stirred at 0-5° C. for two hours and at room temperature overnight, then concentrated to dryness in vacuo. The residue was treated with ethyl acetate and water, the layers separated, the organic phase washed with water (2×) and brine, dried over sodium sulfate and concentrated. The crude material was purified by flash chromatography on silica gel (cyclohexane/ethyl acetate 2:1) to first afford 5-(1-cyanocyclo-propyl)-3-ethylsulfonyl-N-methyl-N-[5-(1,1,2,2,2-pentafluoroethyl)-1,3,4-thiadiazol-2-yl]pyridine-2-carboxamide (40 mg) as a solid, mp 187-189° C. LCMS (method 1): 496 (M+H)$^+$, retention time 1.10 min. $^1$H-NMR (CDCl$_3$, ppm) 1.37 (t, J=7.52 Hz, 3H), 1.63-1.69 (m, 2H), 1.98-2.10 (m, 2H), 3.45 (q, J=7.52 Hz, 2H), 3.66 (s, 3H), 8.16 (d, J=2.20 Hz, 1H), 8.94 (d, J=2.20 Hz, 1H).

Further elution delivered the desired title compound P20 (N)-5-(1-cyanocyclopropyl)-3-ethylsulfonyl-N-[3-methyl-5-(1,1,2,2,2-pentafluoroethyl)-1,3,4-thiadiazol-2-ylidene] pyridine-2-carboxamide (7 mg) as a solid, mp 170-172° C. LCMS (method 1): 496 (M+H)$^+$, retention time 1.05 min. $^1$H-NMR (CDCl$_3$, ppm) 1.37 (t, J=7.34 Hz, 3H), 1.58-1.62 (m, 2H), 1.92-1.99 (m, 2H), 3.71 (q, J=7.34 Hz, 2H), 4.13 (s, 3H), 8.15 (d, J=2.20 Hz, 1H), 8.86-8.95 (m, 1H).

Example P9

Preparation of (N)-3-ethylsulfonyl-N-[3-methyl-5-(1,1,2,2,2-pentafluoroethyl)-1,3,4-thiadiazol-2-ylidene]-5-[3-(trifluoromethyppyrazol-1-yl]pyridine-2-carboxamide (compound P9)

Step A-1: Preparation of 3-methyl-5-(1,1,2,2,2-pentafluoroethyl)-1,3,4-thiadiazol-2-imine hydroiodide salt

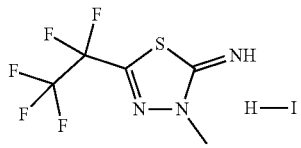

To a solution of 5-(1,1,2,2,2-pentafluoroethyl)-1,3,4-thiadiazol-2-amine (2.0 g, 9.13 mmol) in N,N-dimethylformamide (20 ml) was added iodomethane (1.94 g, 0.852 ml, 13.69 mmol) and the reaction was stirred at 50° C. for 16 hours, then concentrated to dryness in vacuo. The residue was triturated with diethyl ether, the slurry stirred for 30 minutes, the suspension filtered, the solid washed with cold diethyl ether and dried in vacuo at 40° C. to afford 3-methyl-5-(1,1,2,2,2-pentafluoroethyl)-1,3,4-thiadiazol-2-imine hydroiodide salt as a solid (2.85 g), mp 180° C. (decomposition). LCMS (method 1): 234 (M+H)$^+$, retention time 0.47 min [consistent with the corresponding free base of formula $C_5H_4F_6N_3S$, MW: 233.16]. $^1$H-NMR (DMSO-d$_6$, ppm) 3.88 (s, 3H), 10.30 (br s, 2H).

Step B-1: Preparation of methyl 3-chloro-5-[3-(trifluoromethyl)pyrazol-1-yl]pyridine-2-carboxylate

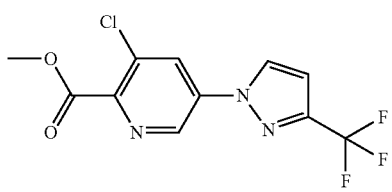 [SMILES: COC(=O)c1ncc(-n2ccc(C(F)(F)F)n2)cc1Cl]

To a solution of methyl 5-bromo-3-chloro-pyridine-2-carboxylate (preparation described before, 40.0 g, 160 mmol) in dioxane (1000 ml) was added 3-trifluoromethyl-1H-pyrazole (32.6 g, 240 mmol), (1R,2R)-N1,N2-dimethylcyclohexane-1,2-diamine (4.78 g, 5.30 ml), potassium carbonate (48.4 g, 479 mmol) and copper(I) iodide (15.2 g, 79.8 mmol). The reaction mixture was stirred under reflux for 24 hours. The reaction mixture was filtered through a Hyflo pad, which was rinsed with MeOH, then the solvent was evaporated under vaccum. The solid was dissolved in AcOEt and washed with HCl 0.5N, the organic phase was dried on magnesium sulfate, filtered and concentrated under vacuum. The residue was subjected to column chromatography over silica gel, eluting with ethyl acetate/cyclohexane. The selected fractions were evaporated to yield the title compound as colorless solid (18 g). LCMS (method 1): 305/307 (M+H)$^+$, retention time 0.99 min.

Step B-2: Preparation of 3-ethylsulfanyl-5-[3-(trifluoromethyppyrazol-1-yl]pyridine-2-carboxylic acid

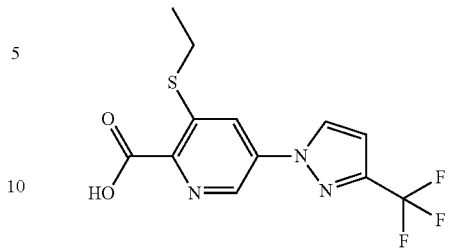

To a solution of methyl 3-chloro-5-[3-(trifluoromethyppyrazol-1-yl]pyridine-2-carboxylate (18.0 g, 58.9 mmol) in N,N-dimethylformamide (200 ml) was added sodium ethanethiolate (27.4 g, 290 mmol). The reaction mixture was stirred for one hour at ambient temperature. The solution was diluted with tert-butyl methyl ether and ice water, the aqueous phase was separated and neutralized with acetic acid. The precipitate formed was filtered off and washed with diethyl ether. The solid was suspended in 80 ml of iPrOH and refluxed for 1.5 hours. It was filtered (hot) and the filtrate was allowed to cool down under stirring, then filtered to give the desired 3-ethylsulfanyl-5-[3-(trifluoromethyl)pyrazol-1-yl]pyridine-2-carboxylic acid (4.13 g). LCMS (method 1): 318 (M+H)$^+$, 316 on-Hy, retention time 0.92 min.

Step C-1: Preparation of (N)-3-ethylsulfanyl-N-[3-methyl-5-(1,1,2,2,2-pentafluoroethyl)-1,3,4-thiadiazol-2-ylidene]-5-[3-(trifluoromethyl)pyrazol-1-yl]pyridine-2-carboxamide (compound P10)

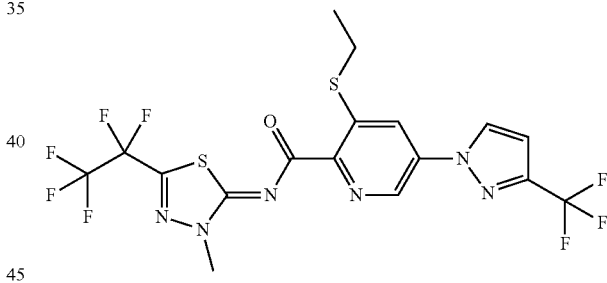

(a) To a solution of 3-ethylsulfanyl-5-[3-(trifluoromethyppyrazol-1-yl]pyridine-2-carboxylic acid (300 mg, 0.9 mmol) in dichloromethane (2 ml) was added one drop of N,N-dimethylformamide, followed by oxalyl chloride (200 mg, 2 mmol). The reaction mixture was stirred 30 minutes at room temperature then 30 minutes to reflux. The solvent was removed in vacuo and the residue dried under vacuum to afford 3-ethylsulfanyl-5-[3-(trifluoromethyppyrazol-1-yl] pyridine-2-carbonyl chloride.

(b) To a solution of 3-methyl-5-(1,1,2,2,2-pentafluoroethyl)-1,3,4-thiadiazol-2-imine hydroiodide salt (250 mg, 0.692 mmol), triethylamine (175 mg, 0.241 ml, 1.73 mmol) and 4-dimethylaminopyridine (1 mg) in dichloromethane (10 ml) at 0-5° C. was added a solution of 3-ethylsulfanyl-5-[3-(trifluoromethyl) pyrazol-1-yl]pyridine-2-carbonyl chloride (232.4 mg, 0.692 mmol) in dichloromethane (2.5 ml) dropwise. The reaction mixture was stirred at 10° C. for three hours, then concentrated to dryness in vacuo. The residue was treated with t-butyl methyl ether and water, the layers separated, the organic phase washed with water (4×) and brine, dried over sodium sulfate and concentrated to afford (N)-3-ethylsulfanyl-N-[3-methyl-5-(1,1,2,2,2-pentafluoroethyl)-1,3,4-thiadiazol-2-ylidene]-5-[3-(trifluoromethyl) pyrazol-1-yl]pyridine-2-carboxamide (compound P10) as a solid (190 mg), mp 219-221° C. LCMS (method 2): 533 (M+H)⁺, retention time 2.09 min. ¹H-NMR (CDCl₃, ppm) 1.46 (t, J=7.34 Hz, 3H), 3.07 (q, J=7.34 Hz, 2H), 4.24 (s, 3H), 6.82 (d, J=2.20 Hz, 1H), 8.10 (m, 2H), 8.17 (s, 2H), 8.77 (s, 1H).

Step C-2: Preparation of (N)-3-ethylsulfonyl-N-[3-methyl-5-(1,1,2,2,2-pentafluoroethyl)-1,3,4-thiadiazol-2-ylidene]-5-[3-(trifluoromethyppyrazol-1-yl]pyridine-2-carboxamide (compound P9)

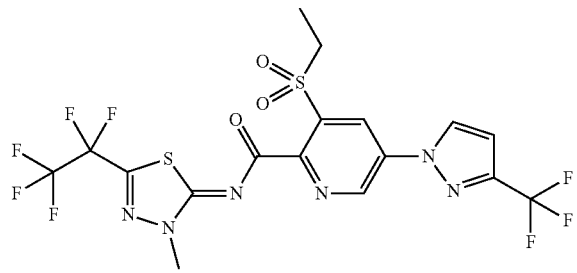 [SMILES: CCS(=O)(=O)c1cc(-n2ccc(C(F)(F)F)n2)cnc1C(=O)/N=c1\sc(C(F)(F)C(F)(F)F)nn1C]

Obtained from (N)-3-ethylsulfanyl-N-[3-methyl-5-(1,1,2,2,2-pentafluoroethyl)-1,3,4-thiadiazol-2-ylidene]-5-[3-(trifluoromethyppyrazol-1-yl]pyridine-2-carboxamide (compound P10) (180 mg, 0.338 mmol) and mCPBA (159.5 mg, 0.693 mmol, 75%) in dichloromethane (5 ml) according to procedure Example P3, step 4. The mixture was stirred at room temperature overnight. The crude material obtained after extractive workup was triturated with diethyl ether, the suspension filtered, the solid washed with cold diethyl ether and dried in vacuo to afford (N)-3-ethylsulfonyl-N-[3-methyl-5-(1,1,2,2,2-pentafluoroethyl)-1,3,4-thiadiazol-2-ylidene]-5-[3-(trifluoromethyl)pyrazol-1-yl]pyridine-2-carboxamide (compound P9) as a solid (155 mg), mp 183-185° C. LCMS (method 1): 565 (M+H)⁺; retention time: 1.17 min. ¹H-NMR (CDCl₃, ppm) 1.42 (t, J=7.52 Hz, 3H), 3.78 (q, J=7.52 Hz, 2H), 4.16 (s, 3H), 6.87 (d, J=2.57 Hz, 1H), 8.15 (d, J=2.57 Hz, 1H), 8.70 (d, J=2.57 Hz, 1H), 9.31 (d, J=2.57 Hz, 1H).

TABLE P

Examples of compounds of formula (I)

| Entry No. | Compound | Ret. Time (min) | (M + H)⁺ Measured | Method | Mp. ° C. |
|---|---|---|---|---|---|
| P1 | | 1.19 | 459/461 | 1 | 147-148 |
| P2 | | 1.09 | 491/493 | 1 | 189-191 |
| P3 | | 1.55 | 507/509 | 2 | 219-220 |

TABLE P-continued
Examples of compounds of formula (I)
| Compound No. | Structures | LCMS $R_t$ (min) | [M + H]⁺ (measured) | Method | Mp (° C.) |
|---|---|---|---|---|---|
| P4 | 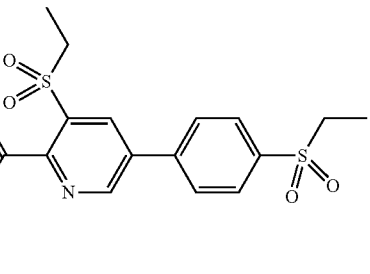 | 1.52 | 549 | 2 | 206-208 |
| P5 | 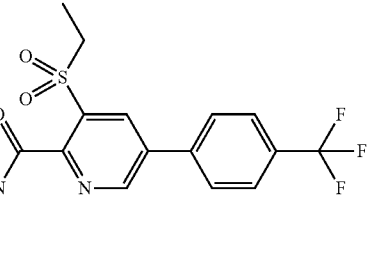 | 1.13 | 525 | 1 | 196-197 |
| P6 | 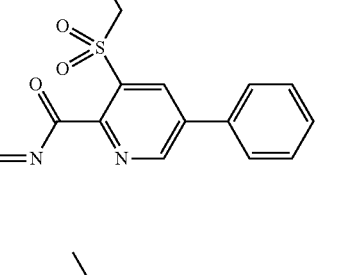 | 1.06 | 457 | 1 | 204-205 |
| P7 | 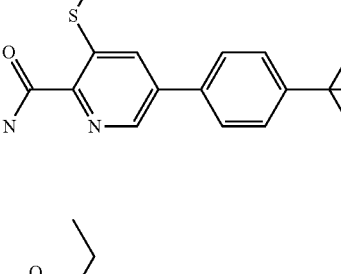 | 1.28 | 543 | 1 | 173-175 |
| P8 | 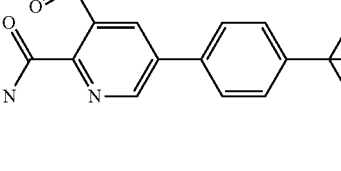 | 1.17 | 575 | 1 | 161-163 |

TABLE P-continued

| | | | | | |
|---|---|---|---|---|---|
| P9 | (structure) | 1.17 | 565 | 1 | 183-185 |
| P10 | (structure) | 2.09 | 533 | 2 | 219-221 |
| P11 | (structure) | 1.15 | 541/543 | 1 | 179-181 |
| P12 | (structure) | 1.31 | 509/511 | 1 | 166-168 |
| P13 | (structure) | 1.21 | 483 | 1 | 224-226 |
| P14 | (structure) | 1.12 | 515 | 1 | 177-179 |

TABLE P-continued

| | | | | | |
|---|---|---|---|---|---|
| P15 | | 1.08 | 518 | 1 | 138-140 |
| P16 | | 1.09 | 550 | 1 | 174-175 |
| P17 | | 0.91 | 484 | 1 | 215-217 |
| P18 | | 0.93 | 446 | 1 | |
| P19 | | 0.96 | 446 | 1 | 171-172 |
| P20 | | 1.05 | 496 | 1 | 170-172 |

TABLE P-continued
| P21 | 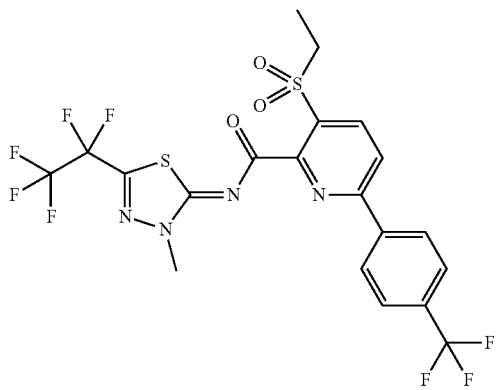 [SMILES: CCS(=O)(=O)c1ccc(-c2ccc(C(F)(F)F)cc2)nc1C(=O)/N=c1\sc(C(F)(F)C(F)(F)F)nn1C] | 1.21 | 525 | 1 | 195-197 |
| P22 | 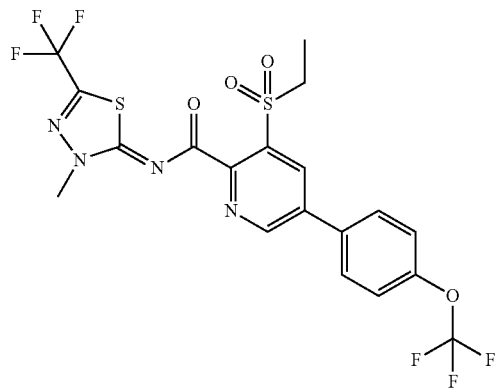 [SMILES: CCS(=O)(=O)c1cc(-c2ccc(OC(F)(F)F)cc2)cnc1C(=O)/N=c1\sc(C(F)(F)F)nn1C] | 1.86 | 541 | 3 | |
| P23 | 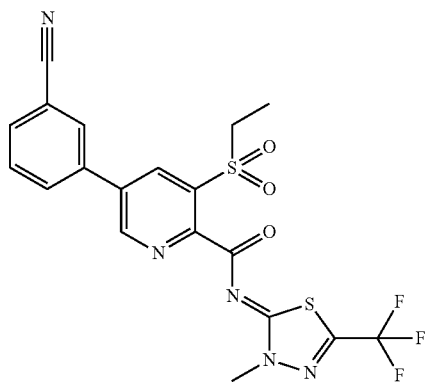 [SMILES: CCS(=O)(=O)c1cc(-c2cccc(C#N)c2)cnc1C(=O)/N=c1\sc(C(F)(F)F)nn1C] | 1.57 | 482 | 3 | |
| P24 | 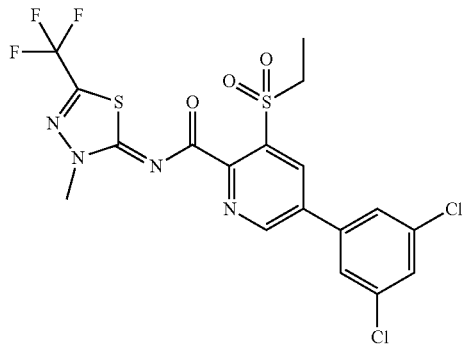 [SMILES: CCS(=O)(=O)c1cc(-c2cc(Cl)cc(Cl)c2)cnc1C(=O)/N=c1\sc(C(F)(F)F)nn1C] | 1.92 | 525/527 | 3 | |

TABLE P-continued

| | | | | |
|---|---|---|---|---|
| P25 | (structure) | 1.71 | 493 | 3 |
| P26 | (structure) | 1.69 | 475 | 3 |
| P27 | (structure) | 1.92 | 543/545 | 3 |
| P28 | (structure) | 1.57 | 482 | 3 |
| P29 | (structure) | 1.83 | 537 | 3 |

TABLE P-continued

| | | | | |
|---|---|---|---|---|
| P30 | (structure) | 1.78 | 503 | 3 |
| P31 | (structure) | 1.86 | 541 | 3 |
| P32 | (structure) | 1.68 | 475 | 3 |
| P33 | (structure) | 1.71 | 493 | 3 |
| P34 | (structure) | 1.90 | 525/527 | 3 |

TABLE P-continued

| | | | | |
|---|---|---|---|---|
| P35 | (structure) | 1.73 | 493 | 3 |
| P36 | (structure) | 1.88 | 525/527 | 3 |
| P37 | (structure) | 1.82 | 525 | 3 |
| P38 | (structure) | 1.77 | 503 | 3 |

TABLE P-continued
| | | | | |
|---|---|---|---|---|
| P39 | 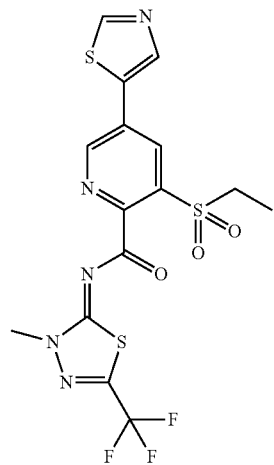 [SMILES: CCS(=O)(=O)c1cc(-c2cncs2)cnc1C(=O)/N=c1\sc(C(F)(F)F)nn1C] | 1.37 | 464 | 3 |
| P40 | 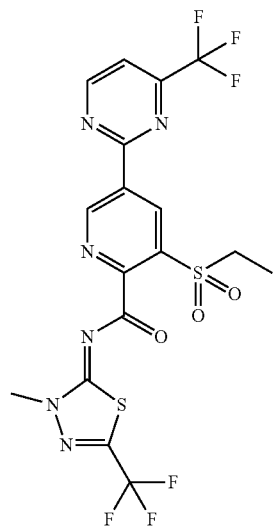 [SMILES: CCS(=O)(=O)c1cc(-c2nccc(C(F)(F)F)n2)cnc1C(=O)/N=c1\sc(C(F)(F)F)nn1C] | 1.72 | 527 | 3 |
| P41 | 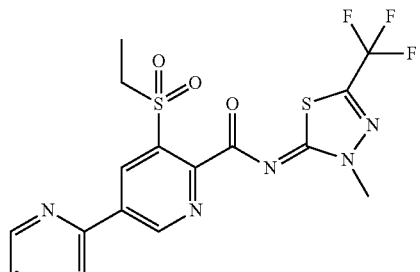 | 1.65 | 492/494 | 3 |
| P42 | 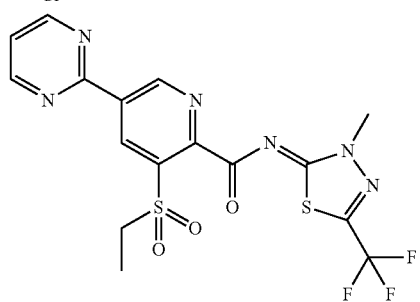 | 1.44 | 459 | 3 |

TABLE P-continued
| P43 | 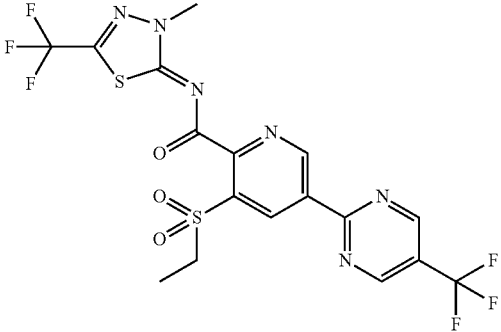 | 1.73 | 527 | 3 |
| P44 | 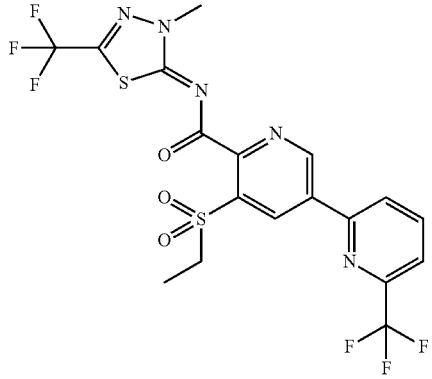 [SMILES: CCS(=O)(=O)c1cc(-c2cccc(C(F)(F)F)n2)cnc1C(=O)/N=c1\sc(C(F)(F)F)nn1C] | 1.74 | 526 | 3 |
| P45 | 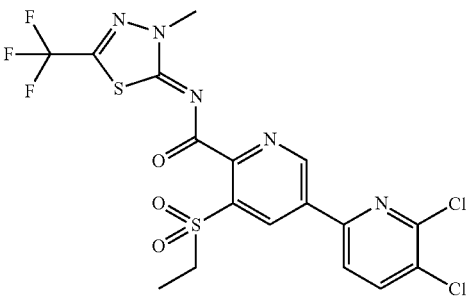 [SMILES: CCS(=O)(=O)c1cc(-c2ccc(Cl)c(Cl)n2)cnc1C(=O)/N=c1\sc(C(F)(F)F)nn1C] | 1.81 | 526/528 | 3 |
| P46 | 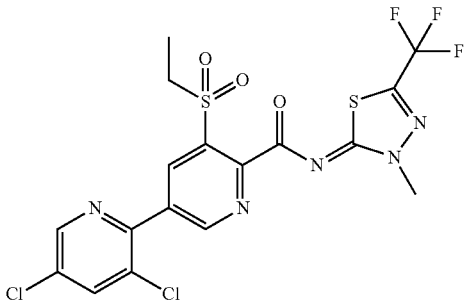 [SMILES: CCS(=O)(=O)c1cc(-c2ncc(Cl)cc2Cl)cnc1C(=O)/N=c1\sc(C(F)(F)F)nn1C] | 1.76 | 526/528 | 3 |
| P47 | 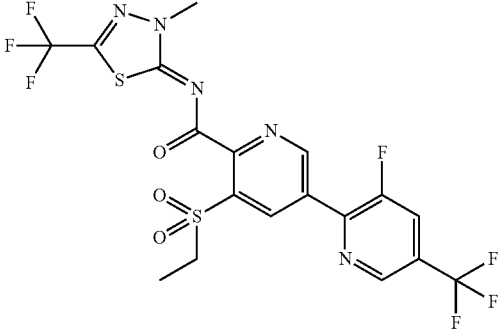 [SMILES: CCS(=O)(=O)c1cc(-c2ncc(C(F)(F)F)cc2F)cnc1C(=O)/N=c1\sc(C(F)(F)F)nn1C] | 1.78 | 544 | 3 |

TABLE P-continued

| | | | | |
|---|---|---|---|---|
| P48 | (structure) | 1.52 | 483 | 3 |
| P49 | (structure) | 1.68 | 492/494 | 3 |
| P50 | (structure) | 1.74 | 526 | 3 |
| P51 | (structure) | 1.46 | 458 | 3 |

TABLE P-continued
| | | | | |
|---|---|---|---|---|
| P52 | 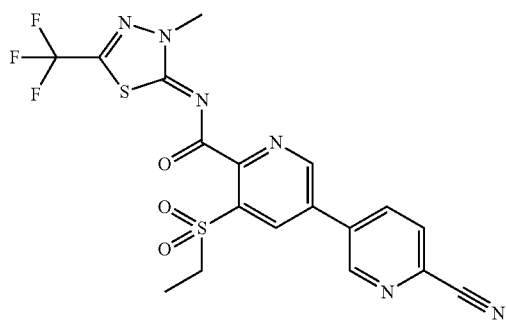 [SMILES: CCS(=O)(=O)c1cc(-c2ccc(C#N)nc2)cnc1C(=O)/N=c1\sc(C(F)(F)F)nn1C] | 1.45 | 483 | 3 |
| P53 | 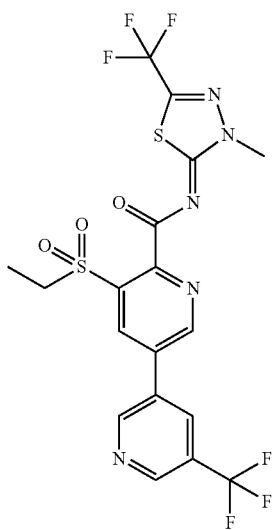 [SMILES: CCS(=O)(=O)c1cc(-c2cncc(C(F)(F)F)c2)cnc1C(=O)/N=c1\sc(C(F)(F)F)nn1C] | 1.62 | 526 | 3 |
| P54 | 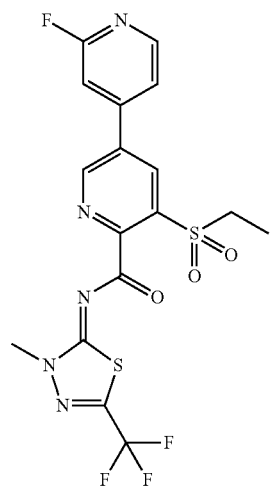 [SMILES: CCS(=O)(=O)c1cc(-c2ccnc(F)c2)cnc1C(=O)/N=c1\sc(C(F)(F)F)nn1C] | 1.49 | 476 | 3 |
| P55 | 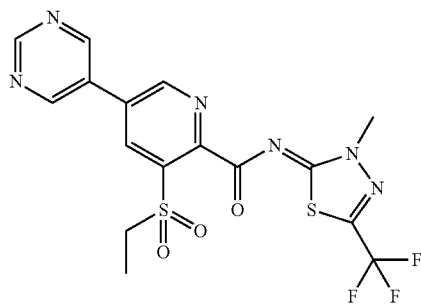 [SMILES: CCS(=O)(=O)c1cc(-c2cncnc2)cnc1C(=O)/N=c1\sc(C(F)(F)F)nn1C] | 1.23 | 459 | 3 |

TABLE P-continued

| | | | | | |
|---|---|---|---|---|---|
| P56 | (structure) | | 1.73 | 532 | 3 |
| P57 | (structure) | | 1.71 | 498/500 | 3 |
| P58 | (structure) | | 1.79 | 532 | 3 |
| P59 | (structure) | | 1.66 | 498/500 | 3 |
| P60 | (structure) | | 1.73 | 532 | 3 |

TABLE P-continued
| | | | | | |
|---|---|---|---|---|---|
| P61 | 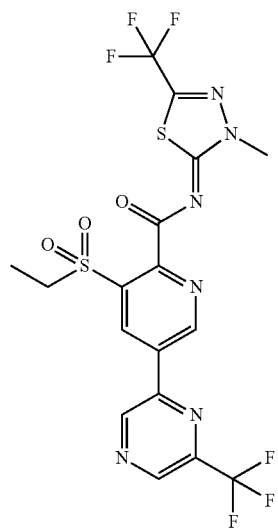 [SMILES: CCS(=O)(=O)c1cc(-c2cncc(C(F)(F)F)n2)cnc1C(=O)/N=c1\sc(C(F)(F)F)nn1C] | 1.65 | 527 | 3 | |
| P62 | 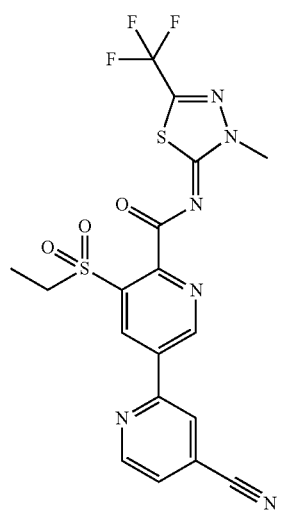 [SMILES: CCS(=O)(=O)c1cc(-c2cc(C#N)ccn2)cnc1C(=O)/N=c1\sc(C(F)(F)F)nn1C] | 1.52 | 483 | 3 | |
| P63 | 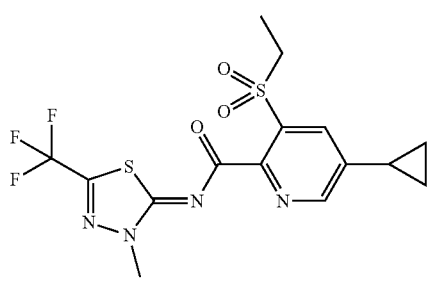 [SMILES: CCS(=O)(=O)c1cc(C2CC2)cnc1C(=O)/N=c1\sc(C(F)(F)F)nn1C] | 0.97 | 421 | 1 | 150-151 |
| P64 | 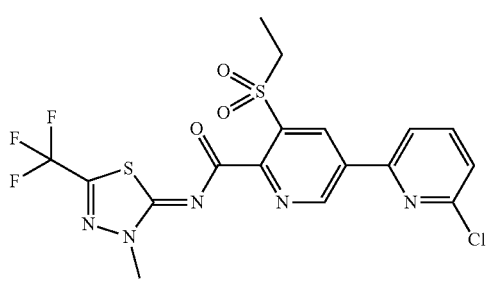 [SMILES: CCS(=O)(=O)c1cc(-c2cccc(Cl)n2)cnc1C(=O)/N=c1\sc(C(F)(F)F)nn1C] | 1.05 | 492/494 | 1 | 190-192 |

TABLE P-continued

| | Structure | | | | |
|---|---|---|---|---|---|
| P65 | 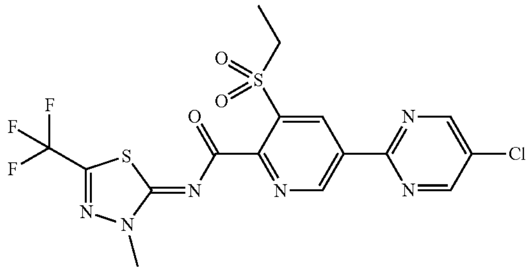 [SMILES: CCS(=O)(=O)c1cc(-c2ncc(Cl)cn2)cnc1C(=O)/N=c1\sc(C(F)(F)F)nn1C] | 1.05 | 493/495 | 1 | 239-241 |
| P66 | 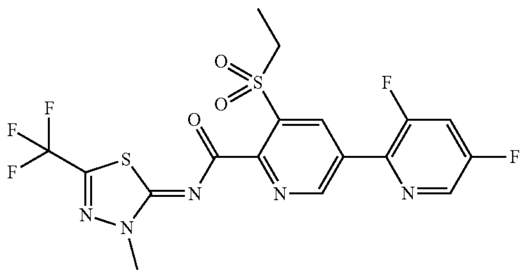 [SMILES: CCS(=O)(=O)c1cc(-c2ncc(F)cc2F)cnc1C(=O)/N=c1\sc(C(F)(F)F)nn1C] | 1.04 | 494 | 1 | 191-193 |
| P67 | 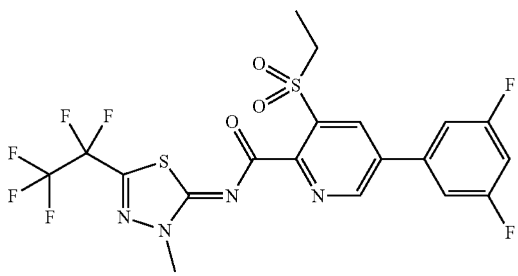 [SMILES: CCS(=O)(=O)c1cc(-c2cc(F)cc(F)c2)cnc1C(=O)/N=c1\sc(C(F)(F)C(F)(F)F)nn1C] | 1.13 | 543 | 1 | 174-176 |
| P68 | 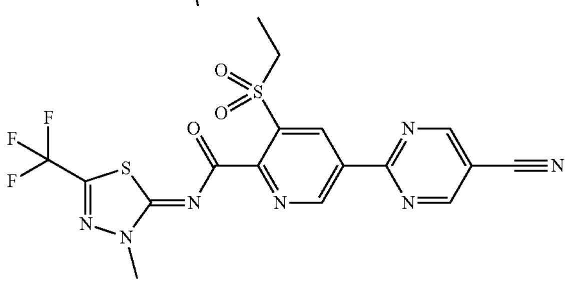 | 0.98 | 484 | 1 | 239-240 |
| P69 | 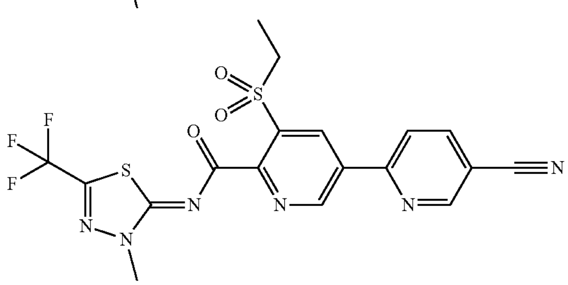 | 0.97 | 483 | 1 | 240-241 |
| P70 | 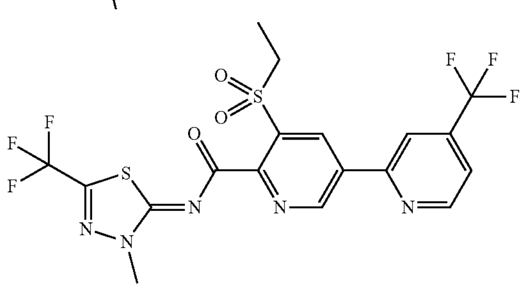 | 1.07 | 526 | 1 | 249-251 |

TABLE P-continued

| P71 | 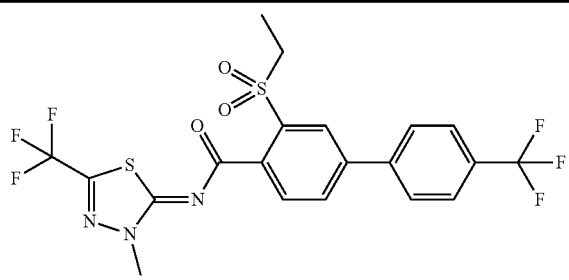 | 1.22 | 524 | 1 | 140-142 |
| P72 | 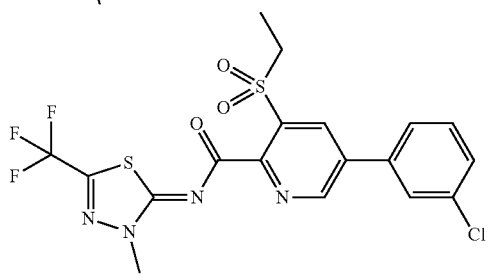 | 1.10 | 491/493 | 1 | 184-186 |

The activity of the compositions according to the invention can be broadened considerably, and adapted to prevailing circumstances, by adding other insecticidally, acaricidally and/or fungicidally active ingredients. The mixtures of the compounds of formula I with other insecticidally, acaricidally and/or fungicidally active ingredients may also have further surprising advantages which can also be described, in a wider sense, as synergistic activity. For example, better tolerance by plants, reduced phytotoxicity, insects can be controlled in their different development stages or better behaviour during their production, for example during grinding or mixing, during their storage or during their use. Suitable additions to active ingredients here are, for example, representatives of the following classes of active ingredients: organophosphorus compounds, nitrophenol derivatives, thioureas, juvenile hormones, formamidines, benzophenone derivatives, ureas, pyrrole derivatives, carbamates, pyrethroids, chlorinated hydrocarbons, acylureas, pyridylmethyleneamino derivatives, macrolides, neonicotinoids and Bacillus thuringiensis preparations.

The following mixtures of the compounds of formula I with active ingredients are preferred (the abbreviation "TX" means "one compound selected from the group consisting of the compounds described in Tables 1 to 12 and P of the present invention"):

an adjuvant selected from the group of substances consisting of petroleum oils (alternative name) (628)+TX, an acaricide selected from the group of substances consisting of 1,1-bis(4-chlorophenyl)-2-ethoxyethanol (IUPAC name) (910)+TX, 2,4-dichlorophenyl benzenesulfonate (IUPAC/Chemical Abstracts name) (1059)+TX, 2-fluoro-N-methyl-N-1-naphthylacetamide (IUPAC name) (1295)+TX, 4-chlorophenyl phenyl sulfone (IUPAC name) (981)+TX, abamectin (1)+TX, acequinocyl (3)+TX, acetoprole [CCN]+TX, acrinathrin (9)+TX, aldicarb (16)+TX, aldoxycarb (863)+TX, alpha-cypermethrin (202)+TX, amidithion (870)+TX, amidoflumet [CCN]+TX, amidothioate (872)+TX, amiton (875)+TX, amiton hydrogen oxalate (875)+TX, amitraz (24)+TX, aramite (881)+TX, arsenous oxide (882)+TX, AVI 382 (compound code)+TX, AZ 60541 (compound code)+TX, azinphos-ethyl (44)+TX, azinphos-methyl (45)+TX, azobenzene (IUPAC name) (888)+TX, azocyclotin (46)+TX, azothoate (889)+TX, benomyl (62)+TX, benoxafos (alternative name) [CCN]+TX, benzoximate (71)+TX, benzyl benzoate (IUPAC name) [CCN]+TX, bifenazate (74)+TX, bifenthrin (76)+TX, binapacryl (907)+TX, bromfenvalerate (alternative name)+TX, bromo-cyclen (918)+TX, bromophos (920)+TX, bromophos-ethyl (921)+TX, bromopropylate (94)+TX, buprofezin (99)+TX, butocarboxim (103)+TX, butoxycarboxim (104)+TX, butylpyridaben (alternative name)+TX, calcium polysulfide (IUPAC name) (111)+TX, camphechlor (941)+TX, carbanolate (943)+TX, carbaryl (115)+TX, carbofuran (118)+TX, carbophenothion (947)+TX, CGA 50'439 (development code) (125)+TX, chinomethionat (126)+TX, chlorbenside (959)+TX, chlordimeform (964)+TX, chlordimeform hydrochloride (964)+TX, chlorfenapyr (130)+TX, chlorfenethol (968)+TX, chlorfenson (970)+TX, chlorfensulfide (971)+TX, chlorfenvinphos (131)+TX, chlorobenzilate (975)+TX, chloromebuform (977)+TX, chloromethiuron (978)+TX, chloropropylate (983)+TX, chlorpyrifos (145)+TX, chlorpyrifos-methyl (146)+TX, chlorthiophos (994)+TX, cinerin I (696)+TX, cinerin II (696)+TX, cinerins (696)+TX, clofentezine (158)+TX, closantel (alternative name) [CCN]+TX, coumaphos (174)+TX, crotamiton (alternative name) [CCN]+TX, crotoxyphos (1010)+TX, cufraneb (1013)+TX, cyanthoate (1020)+TX, cyflumetofen (CAS Reg. No.: 400882-07-7)+TX, cyhalothrin (196)+TX, cyhexatin (199)+TX, cypermethrin (201)+TX, DCPM (1032)+TX, DDT (219)+TX, demephion (1037)+TX, demephion-O (1037)+TX, demephion-S (1037)+TX, demeton (1038)+TX, demeton-methyl (224)+TX, demeton-O (1038)+TX, demeton-O-methyl (224)+TX, demeton-S (1038)+TX, demeton-S-methyl (224)+TX, demeton-S-methylsulfon (1039)+TX, diafenthiuron (226)+TX, dialifos (1042)+TX, diazinon (227)+TX, dichlofluanid (230)+TX, dichlorvos (236)+TX, dicliphos (alternative name)+TX, dicofol (242)+TX, dicrotophos (243)+TX, dienochlor (1071)+TX, dimefox (1081)+TX, dimethoate (262)+TX, dinactin (alternative name) (653)+TX, dinex (1089)+TX, dinex-diclexine (1089)+TX, dinobuton (269)+TX, dinocap (270)+TX, dinocap-4 [CCN]+TX, dinocap-6 [CCN]+TX, dinocton (1090)+TX, dinopenton (1092)+TX, dinosulfon (1097)+TX, dinoterbon (1098)+TX, dioxathion (1102)+TX, diphenyl sulfone (IUPAC name) (1103)+TX, disulfiram (alternative name) [CCN]+TX, disulfoton (278)+TX, DNOC (282)+TX, dofenapyn (1113)+TX, doramectin (alternative name) [CCN]+TX, endosulfan (294)+TX, endothion (1121)+TX, EPN (297)+TX, eprinomectin (alternative name) [CCN]+TX, ethion (309)+TX, ethoate-methyl (1134)+TX, etoxazole (320)+TX, etrimfos (1142)+TX, fenazaflor (1147)+TX, fenazaquin (328)+TX, fenbutatin oxide (330)+TX, fenothiocarb (337)+TX, fenpropathrin (342)+TX, fenpyrad (alternative name)+TX, fenpyroximate (345)+TX, fenson (1157)+TX, fentrifanil (1161)+TX, fenvalerate (349)+TX, fipronil (354)+TX, fluacrypyrim (360)+TX, fluazuron (1166)+TX, flubenzimine (1167)+TX, flucycloxuron (366)+TX, flucythrinate (367)+TX, fluenetil (1169)+TX, flufenoxuron (370)+TX, flumethrin (372)+TX, fluorbenside (1174)+TX, fluvalinate (1184)+TX, FMC 1137 (development code) (1185)+TX, formetanate (405)+TX, formetanate hydrochloride (405)+TX, formothion (1192)+TX, formparanate (1193)+TX, gamma-HCH (430)+TX, glyodin (1205)+TX, halfenprox (424)+TX, heptenophos (432)+TX, hexadecyl cyclopropanecarboxylate (IUPAC/Chemical Abstracts name) (1216)+TX, hexythiazox (441)+TX, iodomethane (IUPAC name) (542)+TX, isocarbophos (alternative name) (473)+TX, isopropyl O-(methoxyaminothiophosphoryl)salicylate (IUPAC name) (473)+TX, ivermectin (alternative name) [CCN]+TX, jasmolin I (696)+TX, jasmolin II (696)+TX, jodfenphos (1248)+TX, lindane (430)+TX, lufenuron (490)+TX, malathion (492)+TX, malonoben (1254)+TX, mecarbam (502)+TX, mephosfolan (1261)+TX, mesulfen (alternative name) [CCN]+TX, methacrifos (1266)+TX, methamidophos (527)+TX, methidathion (529)+TX, methiocarb (530)+TX, methomyl (531)+TX, methyl bromide (537)+TX, metolcarb (550)+TX, mevinphos (556)+TX, mexacarbate (1290)+TX, milbemectin (557)+TX, milbemycin oxime (alternative name) [CCN]+TX, mipafox (1293)+TX, monocrotophos (561)+TX, morphothion (1300)+TX, moxidectin (alternative name) [CCN]+TX, naled (567)+TX, NC-184 (compound code)+TX, NC-512 (compound code)+TX, nifluridide (1309)+TX, nikkomycins (alternative name) [CCN]+TX, nitrilacarb (1313)+TX, nitrilacarb 1:1 zinc chloride complex (1313)+TX, NNI-0101 (compound code)+TX, NNI-0250 (compound code)+TX, omethoate (594)+TX, oxamyl (602)+TX, oxydeprofos (1324)+TX, oxydisulfoton (1325)+TX, pp'-DDT (219)+TX, parathion (615)+TX, permethrin (626)+TX, petroleum oils (alternative name) (628)+TX, phenkapton (1330)+TX, phenthoate (631)+TX, phorate (636)+TX, phosalone (637)+TX, phosfolan (1338)+TX, phosmet (638)+TX, phosphamidon (639)+TX, phoxim (642)+TX, pirimiphos-methyl (652)+TX, polychloroterpenes (traditional name) (1347)+TX, polynactins (alternative name) (653)+TX, proclonol (1350)+TX, profenofos (662)+TX, promacyl (1354)+TX, propargite (671)+TX, propetamphos (673)+TX, propoxur (678)+TX, prothidathion (1360)+TX, prothoate (1362)+TX, pyrethrin I (696)+TX, pyrethrin II (696)+TX, pyrethrins (696)+TX, pyridaben (699)+TX, pyridaphenthion (701)+TX, pyrimidifen (706)+TX, pyrimitate (1370)+TX, quinalphos (711)+TX, quintiofos (1381)+TX, R-1492 (development code) (1382)+TX, RA-17 (development code) (1383)+TX, rotenone (722)+TX, schradan (1389)+TX, sebufos (alternative name)+TX, selamectin (alternative name) [CCN]+TX, SI-0009 (compound code)+TX, sophamide (1402)+TX, spirodiclofen (738)+TX, spiromesifen (739)+TX, SSI-121 (development code) (1404)+TX, sulfiram (alternative name) [CCN]+TX, sulfluramid (750)+TX, sulfotep (753)+TX, sulfur (754)+TX, SZI-121 (development code) (757)+TX, tau-fluvalinate (398)+TX, tebufenpyrad (763)+TX, TEPP (1417)+TX, terbam (alternative name)+TX, tetrachlorvinphos (777)+TX, tetradifon (786)+TX, tetranactin (alternative name) (653)+TX, tetrasul (1425)+TX, thiafenox (alternative name)+TX, thiocarboxime (1431)+TX, thiofanox (800)+TX, thiometon (801)+TX, thioquinox (1436)+TX, thuringiensin (alternative name) [CCN]+TX, triamiphos (1441)+TX, triarathene (1443)+TX, triazophos (820)+TX, triazuron (alternative name)+TX, trichlorfon (824)+TX, trifenofos (1455)+TX, trinactin (alternative name) (653)+TX, vamidothion (847)+TX, vaniliprole [CCN] and YI-5302 (compound code)+TX, an algicide selected from the group of substances consisting of bethoxazin [CCN]+TX, copper dioctanoate (IUPAC name) (170)+TX, copper sulfate (172)+TX, cybutryne [CCN]+TX, dichlone (1052)+TX, dichlorophen (232)+TX, endothal (295)+TX, fentin (347)+TX, hydrated lime [CCN]+TX, nabam (566)+TX, quinoclamine (714)+TX, quinonamid (1379)+TX, simazine (730)+TX, triphenyltin acetate (IUPAC name) (347) and triphenyltin hydroxide (IUPAC name) (347)+TX, an anthelmintic selected from the group of substances consisting of abamectin (1)+TX, crufomate (1011)+TX, doramectin (alternative name) [CCN]+TX, emamectin (291)+TX, emamectin benzoate (291)+TX, eprinomectin (alternative name) [CCN]+TX, ivermectin (alternative name) [CCN]+TX, milbemycin oxime (alternative name) [CCN]+TX, moxidectin (alternative name) [CCN]+TX, piperazine [CCN]+TX, selamectin (alternative name) [CCN]+TX, spinosad (737) and thiophanate (1435)+TX, an avicide selected from the group of substances consisting of chloralose (127)+TX, endrin (1122)+TX, fenthion (346)+TX, pyridin-4-amine (IUPAC name) (23) and strychnine (745)+TX, a bactericide selected from the group of substances consisting of 1-hydroxy-1H-pyridine-2-thione (IUPAC name) (1222)+TX, 4-(quinoxalin-2-ylamino)benzenesulfonamide (IUPAC name) (748)+TX, 8-hydroxyquinoline sulfate (446)+TX, bronopol (97)+TX, copper dioctanoate (IUPAC name) (170)+TX, copper hydroxide (IUPAC name) (169)+TX, cresol [CCN]+TX, dichlorophen (232)+TX, dipyrithione (1105)+TX, dodicin (1112)+TX, fenaminosulf (1144)+TX, formaldehyde (404)+TX, hydrargaphen (alternative name) [CCN]+TX, kasugamycin (483)+TX, kasugamycin hydrochloride hydrate (483)+TX, nickel bis(dimethyldithiocarbamate) (IUPAC name) (1308)+TX, nitrapyrin (580)+TX, octhilinone (590)+TX, oxolinic acid (606)+TX, oxytetracycline (611)+TX, potassium hydroxyquinoline sulfate (446)+TX, probenazole (658)+TX, streptomycin (744)+TX, streptomycin sesquisulfate (744)+TX, tecloftalam (766)+TX, and thiomersal (alternative name) [CCN]+TX, a biological agent selected from the group of substances consisting of Adoxophyes orana GV (alternative name) (12)+TX, Agrobacterium radiobacter (alternative name) (13)+TX, *Amblyseius* spp. (alternative name) (19)+TX, *Anagrapha falcifera* NPV (alternative name) (28)+TX, *Anagrus atomus* (alternative name) (29)+TX, *Aphelinus abdominalis* (alternative name) (33)+TX, *Aphidius colemani* (alternative name) (34)+TX, *Aphidoletes aphidimyza* (alternative name) (35)+TX, *Autographa californica* NPV (alternative name) (38)+TX, *Bacillus firmus* (alternative name) (48)+TX, *Bacillus sphaericus* Neide (scientific name) (49)+TX, *Bacillus thuringiensis* Berliner (scientific name) (51)+TX, *Bacillus thuringiensis* subsp. *aizawai* (scientific name) (51)+TX, *Bacillus thuringiensis* subsp. *israelensis* (scientific name) (51)+TX, *Bacillus thuringiensis* subsp. *japonensis* (scientific name) (51)+TX, *Bacillus thuringiensis* subsp. *kurstaki* (scientific name) (51)+TX, *Bacillus thuringiensis* subsp.

*tenebrionis* (scientific name) (51)+TX, *Beauveria bassiana* (alternative name) (53)+TX, *Beauveria brongniartii* (alternative name) (54)+TX, *Chrysoperla carnea* (alternative name) (151)+TX, *Cryptolaemus montrouzieri* (alternative name) (178)+TX, *Cydia pomonella* GV (alternative name) (191)+TX, *Dacnusa sibirica* (alternative name) (212)+TX, *Diglyphus isaea* (alternative name) (254)+TX, *Encarsia formosa* (scientific name) (293)+TX, *Eretmocerus eremicus* (alternative name) (300)+TX, *Helicoverpa zea* NPV (alternative name) (431)+TX, *Heterorhabditis bacteriophora* and *H. megidis* (alternative name) (433)+TX, *Hippodamia convergens* (alternative name) (442)+TX, *Leptomastix dactylopii* (alternative name) (488)+TX, *Macrolophus caliginosus* (alternative name) (491)+TX, *Mamestra brassicae* NPV (alternative name) (494)+TX, *Metaphycus helvolus* (alternative name) (522)+TX, *Metarhizium anisopliae* var. *acridum* (scientific name) (523)+TX, *Metarhizium anisopliae* var. *anisopliae* (scientific name) (523)+TX, *Neodiprion sertifer* NPV and *N. lecontei* NPV (alternative name) (575)+TX, *Orius* spp. (alternative name) (596)+TX, *Paecilomyces fumosoroseus* (alternative name) (613)+TX, *Phytoseiulus persimilis* (alternative name) (644)+TX, *Spodoptera exigua* multicapsid nuclear polyhedrosis virus (scientific name) (741)+TX, *Steinernema bibionis* (alternative name) (742)+TX, *Steinernema carpocapsae* (alternative name) (742)+TX, *Steinernema feltiae* (alternative name) (742)+TX, *Steinernema glaseri* (alternative name) (742)+TX, *Steinernema riobrave* (alternative name) (742)+TX, *Steinernema riobravis* (alternative name) (742)+TX, *Steinernema scapterisci* (alternative name) (742)+TX, *Steinernema* spp. (alternative name) (742)+TX, *Trichogramma* spp. (alternative name) (826)+TX, *Typhlodromus occidentalis* (alternative name) (844) and *Verticillium lecanii* (alternative name) (848)+TX, a soil sterilant selected from the group of substances consisting of iodomethane (IUPAC name) (542) and methyl bromide (537)+TX, a chemosterilant selected from the group of substances consisting of apholate [CCN]+TX, bisazir (alternative name) [CCN]+TX, busulfan (alternative name) [CCN]+TX, diflubenzuron (250)+TX, dimatif (alternative name) [CCN]+TX, hemel [CCN]+TX, hempa [CCN]+TX, metepa [CCN]+TX, methiotepa [CCN]+TX, methyl apholate [CCN]+TX, morzid [CCN]+TX, penfluron (alternative name) [CCN]+TX, tepa [CCN]+TX, thiohempa (alternative name) [CCN]+TX, thiotepa (alternative name) [CCN]+TX, tretamine (alternative name) [CCN] and uredepa (alternative name) [CCN]+TX, an insect pheromone selected from the group of substances consisting of (E)-dec-5-en-1-yl acetate with (E)-dec-5-en-1-ol (IUPAC name) (222)+TX, (E)-tridec-4-en-1-yl acetate (IUPAC name) (829)+TX, (E)-6-methylhept-2-en-4-ol (IUPAC name) (541)+TX, (E,Z)-tetradeca-4,10-dien-1-yl acetate (IUPAC name) (779)+TX, (Z)-dodec-7-en-1-yl acetate (IUPAC name) (285)+TX, (Z)-hexadec-11-enal (IUPAC name) (436)+TX, (Z)-hexadec-11-en-1-yl acetate (IUPAC name) (437)+TX, (Z)-hexadec-13-en-11-yn-1-yl acetate (IUPAC name) (438)+TX, (Z)-icos-13-en-10-one (IUPAC name) (448)+TX, (Z)-tetradec-7-en-1-al (IUPAC name) (782)+TX, (Z)-tetradec-9-en-1-ol (IUPAC name) (783)+TX, (Z)-tetradec-9-en-1-yl acetate (IUPAC name) (784)+TX, (7E,9Z)-dodeca-7,9-dien-1-yl acetate (IUPAC name) (283)+TX, (9Z,11E)-tetradeca-9,11-dien-1-yl acetate (IUPAC name) (780)+TX, (9Z,12E)-tetradeca-9,12-dien-1-yl acetate (IUPAC name) (781)+TX, 14-methyloctadec-1-ene (IUPAC name) (545)+TX, 4-methylnonan-5-ol with 4-methylnonan-5-one (IUPAC name) (544)+TX, alpha-multistriatin (alternative name) [CCN]+TX, brevicomin (alternative name) [CCN]+TX, codlelure (alternative name) [CCN]+TX, codlemone (alternative name) (167)+TX, cuelure (alternative name) (179)+TX, disparlure (277)+TX, dodec-8-en-1-yl acetate (IUPAC name) (286)+TX, dodec-9-en-1-yl acetate (IUPAC name) (287)+TX, dodeca-8+TX, 10-dien-1-yl acetate (IUPAC name) (284)+TX, dominicalure (alternative name) [CCN]+TX, ethyl 4-methyloctanoate (IUPAC name) (317)+TX, eugenol (alternative name) [CCN]+TX, frontalin (alternative name) [CCN]+TX, gossyplure (alternative name) (420)+TX, grandlure (421)+TX, grandlure I (alternative name) (421)+TX, grandlure II (alternative name) (421)+TX, grandlure III (alternative name) (421)+TX, grandlure IV (alternative name) (421)+TX, hexalure [CCN]+TX, ipsdienol (alternative name) [CCN]+TX, ipsenol (alternative name) [CCN]+TX, japonilure (alternative name) (481)+TX, lineatin (alternative name) [CCN]+TX, litlure (alternative name) [CCN]+TX, looplure (alternative name) [CCN]+TX, medlure [CCN]+TX, megatomoic acid (alternative name) [CCN]+TX, methyl eugenol (alternative name) (540)+TX, muscalure (563)+TX, octadeca-2,13-dien-1-yl acetate (IUPAC name) (588)+TX, octadeca-3,13-dien-1-yl acetate (IUPAC name) (589)+TX, orfralure (alternative name) [CCN]+TX, oryctalure (alternative name) (317)+TX, ostramone (alternative name) [CCN]+TX, siglure [CCN]+TX, sordidin (alternative name) (736)+TX, sulcatol (alternative name) [CCN]+TX, tetradec-11-en-1-yl acetate (IUPAC name) (785)+TX, trimedlure (839)+TX, trimedlure A (alternative name) (839)+TX, trimedlure $B_1$ (alternative name) (839)+TX, trimedlure $B_2$ (alternative name) (839)+TX, trimedlure C (alternative name) (839) and trunc-call (alternative name) [CCN]+TX, an insect repellent selected from the group of substances consisting of 2-(octylthio)ethanol (IUPAC name) (591)+TX, butopyronoxyl (933)+TX, butoxy(polypropylene glycol) (936)+TX, dibutyl adipate (IUPAC name) (1046)+TX, dibutyl phthalate (1047)+TX, dibutyl succinate (IUPAC name) (1048)+TX, diethyltoluamide [CCN]+TX, dimethyl carbate [CCN]+TX, dimethyl phthalate [CCN]+TX, ethyl hexanediol (1137)+TX, hexamide [CCN]+TX, methoquin-butyl (1276)+TX, methylneodecanamide [CCN]+TX, oxamate [CCN] and picaridin [CCN]+TX, an insecticide selected from the group of substances consisting of 1-dichloro-1-nitroethane (IUPAC/Chemical Abstracts name) (1058)+TX, 1,1-dichloro-2,2-bis(4-ethylphenyl)ethane (IUPAC name) (1056), +TX, 1,2-dichloropropane (IUPAC/Chemical Abstracts name) (1062)+TX, 1,2-dichloropropane with 1,3-dichloropropene (IUPAC name) (1063)+TX, 1-bromo-2-chloroethane (IUPAC/Chemical Abstracts name) (916)+TX, 2,2,2-trichloro-1-(3,4-dichlorophenyl)ethyl acetate (IUPAC name) (1451)+TX, 2,2-dichlorovinyl 2-ethylsulfinylethyl methyl phosphate (IUPAC name) (1066)+TX, 2-(1,3-dithiolan-2-yl)phenyl dimethylcarbamate (IUPAC/ Chemical Abstracts name) (1109)+TX, 2-(2-butoxyethoxy)ethyl thiocyanate (IUPAC/ Chemical Abstracts name) (935)+TX, 2-(4,5-dimethyl-1,3-dioxolan-2-yl)phenyl methylcarbamate (IUPAC/ Chemical Abstracts name) (1084)+TX, 2-(4-chloro-3,5-xylyloxy) ethanol (IUPAC name) (986)+TX, 2-chlorovinyl diethyl phosphate (IUPAC name) (984)+TX, 2-imidazolidone (IUPAC name) (1225)+TX, 2-isovalerylindan-1,3-dione (IUPAC name) (1246)+TX, 2-methyl(prop-2-ynyl)aminophenyl methylcarbamate (IUPAC name) (1284)+TX, 2-thiocyanatoethyl laurate (IUPAC name) (1433)+TX, 3-bromo-1-chloroprop-1-ene (IUPAC name) (917)+TX, 3-methyl-1-phenylpyrazol-5-yl dimethylcarbamate (IUPAC name) (1283)+TX, 4-methyl(prop-2-ynyl)amino-3,5-xylyl methylcarbamate (IUPAC name) (1285)+TX, 5,5-dimethyl- 3-oxocyclohex-1-enyl dimethylcarbamate (IUPAC name) (1085)+TX, abamectin (1)+TX, acephate (2)+TX, acetamiprid (4)+TX, acethion (alternative name) [CCN]+TX, acetoprole [CCN]+TX, acrinathrin (9)+TX, acrylonitrile (IUPAC name) (861)+TX, alanycarb (15)+TX, aldicarb (16)+TX, aldoxycarb (863)+TX, aldrin (864)+TX, allethrin (17)+TX, allosamidin (alternative name) [CCN]+TX, allyxycarb (866)+TX, alpha-cypermethrin (202)+TX, alpha-ecdysone (alternative name) [CCN]+TX, aluminium phosphide (640)+TX, amidithion (870)+TX, amidothioate (872)+TX, aminocarb (873)+TX, amiton (875)+TX, amiton hydrogen oxalate (875)+TX, amitraz (24)+TX, anabasine (877)+TX, athidathion (883)+TX, AVI 382 (compound code)+TX, AZ 60541 (compound code)+TX, azadirachtin (alternative name) (41)+TX, azamethiphos (42)+TX, azinphos-ethyl (44)+TX, azinphos-methyl (45)+TX, azothoate (889)+TX, Bacillus thuringiensis delta endotoxins (alternative name) (52)+TX, barium hexafluorosilicate (alternative name) [CCN]+TX, barium polysulfide (IUPAC/Chemical Abstracts name) (892)+TX, barthrin [CCN]+TX, Bayer 22/190 (development code) (893)+TX, Bayer 22408 (development code) (894)+TX, bendiocarb (58)+TX, benfuracarb (60)+TX, bensultap (66)+TX, beta-cyfluthrin (194)+TX, beta-cypermethrin (203)+TX, bifenthrin (76)+TX, bioallethrin (78)+TX, bioallethrin S-cyclopentenyl isomer (alternative name) (79)+TX, bioethanomethrin [CCN]+TX, biopermethrin (908)+TX, bioresmethrin (80)+TX, bis(2-chloroethyl) ether (IUPAC name) (909)+TX, bistrifluron (83)+TX, borax (86)+TX, brofenvalerate (alternative name)+TX, bromfenvinfos (914)+TX, bromocyclen (918)+TX, bromo-DDT (alternative name) [CCN]+TX, bromophos (920)+TX, bromophos-ethyl (921)+TX, bufencarb (924)+TX, buprofezin (99)+TX, butacarb (926)+TX, butathiofos (927)+TX, butocarboxim (103)+TX, butonate (932)+TX, butoxycarboxim (104)+TX, butylpyridaben (alternative name)+TX, cadusafos (109)+TX, calcium arsenate [CCN]+TX, calcium cyanide (444)+TX, calcium polysulfide (IUPAC name) (111)+TX, camphechlor (941)+TX, carbanolate (943)+TX, carbaryl (115)+TX, carbofuran (118)+TX, carbon disulfide (IUPAC/Chemical Abstracts name) (945)+TX, carbon tetrachloride (IUPAC name) (946)+TX, carbophenothion (947)+TX, carbosulfan (119)+TX, cartap (123)+TX, cartap hydrochloride (123)+TX, cevadine (alternative name) (725)+TX, chlorbicyclen (960)+TX, chlordane (128)+TX, chlordecone (963)+TX, chlordimeform (964)+TX, chlordimeform hydrochloride (964)+TX, chlorethoxyfos (129)+TX, chlorfenapyr (130)+TX, chlorfenvinphos (131)+TX, chlorfluazuron (132)+TX, chlormephos (136)+TX, chloroform [CCN]+TX, chloropicrin (141)+TX, chlorphoxim (989)+TX, chlorprazophos (990)+TX, chlorpyrifos (145)+TX, chlorpyrifos-methyl (146)+TX, chlorthiophos (994)+TX, chromafenozide (150)+TX, cinerin I (696)+TX, cinerin II (696)+TX, cinerins (696)+TX, cis-resmethrin (alternative name)+TX, cismethrin (80)+TX, clocythrin (alternative name)+TX, cloethocarb (999)+TX, closantel (alternative name) [CCN]+TX, clothianidin (165)+TX, copper acetoarsenite [CCN]+TX, copper arsenate [CCN]+TX, copper oleate [CCN]+TX, coumaphos (174)+TX, coumithoate (1006)+TX, crotamiton (alternative name) [CCN]+TX, crotoxyphos (1010)+TX, crufomate (1011)+TX, cryolite (alternative name) (177)+TX, CS 708 (development code) (1012)+TX, cyanofenphos (1019)+TX, cyanophos (184)+TX, cyanthoate (1020)+TX, cyclethrin [CCN]+TX, cycloprothrin (188)+TX, cyfluthrin (193)+TX, cyhalothrin (196)+TX, cypermethrin (201)+TX, cyphenothrin (206)+TX, cyromazine (209)+TX, cythioate (alternative name) [CCN]+TX, d-limonene (alternative name) [CCN]+TX, d-tetramethrin (alternative name) (788)+TX, DAEP (1031)+TX, dazomet (216)+TX, DDT (219)+TX, decarbofuran (1034)+TX, deltamethrin (223)+TX, demephion (1037)+TX, demephion-O (1037)+TX, demephion-S (1037)+TX, demeton (1038)+TX, demeton-methyl (224)+TX, demeton-O (1038)+TX, demeton-O-methyl (224)+TX, demeton-S (1038)+TX, demeton-S-methyl (224)+TX, demeton-S-methylsulphon (1039)+TX, diafenthiuron (226)+TX, dialifos (1042)+TX, diamidafos (1044)+TX, diazinon (227)+TX, dicapthon (1050)+TX, dichlofenthion (1051)+TX, dichlorvos (236)+TX, dicliphos (alternative name)+TX, dicresyl (alternative name) [CCN]+TX, dicrotophos (243)+TX, dicyclanil (244)+TX, dieldrin (1070)+TX, diethyl 5-methylpyrazol-3-yl phosphate (IUPAC name) (1076)+TX, diflubenzuron (250)+TX, dilor (alternative name) [CCN]+TX, dimefluthrin [CCN]+TX, dimefox (1081)+TX, dimetan (1085)+TX, dimethoate (262)+TX, dimethrin (1083)+TX, dimethylvinphos (265)+TX, dimetilan (1086)+TX, dinex (1089)+TX, dinex-diclexine (1089)+TX, dinoprop (1093)+TX, dinosam (1094)+TX, dinoseb (1095)+TX, dinotefuran (271)+TX, diofenolan (1099)+TX, dioxabenzofos (1100)+TX, dioxacarb (1101)+TX, dioxathion (1102)+TX, disulfoton (278)+TX, dithicrofos (1108)+TX, DNOC (282)+TX, doramectin (alternative name) [CCN]+TX, DSP (1115)+TX, ecdysterone (alternative name) [CCN]+TX, El 1642 (development code) (1118)+TX, emamectin (291)+TX, emamectin benzoate (291)+TX, EMPC (1120)+TX, empenthrin (292)+TX, endosulfan (294)+TX, endothion (1121)+TX, endrin (1122)+TX, EPBP (1123)+TX, EPN (297)+TX, epofenonane (1124)+TX, eprinomectin (alternative name) [CCN]+TX, esfenvalerate (302)+TX, etaphos (alternative name) [CCN]+TX, ethiofencarb (308)+TX, ethion (309)+TX, ethiprole (310)+TX, ethoate-methyl (1134)+TX, ethoprophos (312)+TX, ethyl formate (IUPAC name) [CCN]+TX, ethyl-DDD (alternative name) (1056)+TX, ethylene dibromide (316)+TX, ethylene dichloride (chemical name) (1136)+TX, ethylene oxide [CCN]+TX, etofenprox (319)+TX, etrimfos (1142)+TX, EXD (1143)+TX, famphur (323)+TX, fenamiphos (326)+TX, fenazaflor (1147)+TX, fenchlorphos (1148)+TX, fenethacarb (1149)+TX, fenfluthrin (1150)+TX, fenitrothion (335)+TX, fenobucarb (336)+TX, fenoxacrim (1153)+TX, fenoxycarb (340)+TX, fenpirithrin (1155)+TX, fenpropathrin (342)+TX, fenpyrad (alternative name)+TX, fensulfothion (1158)+TX, fenthion (346)+TX, fenthion-ethyl [CCN]+TX, fenvalerate (349)+TX, fipronil (354)+TX, flonicamid (358)+TX, flubendiamide (CAS. Reg. No.: 272451-65-7)+TX, flucofuron (1168)+TX, flucycloxuron (366)+TX, flucythrinate (367)+TX, fluenetil (1169)+TX, flufenerim [CCN]+TX, flufenoxuron (370)+TX, flufenprox (1171)+TX, flumethrin (372)+TX, fluvalinate (1184)+TX, FMC 1137 (development code) (1185)+TX, fonofos (1191)+TX, formetanate (405)+TX, formetanate hydrochloride (405)+TX, formothion (1192)+TX, formparanate (1193)+TX, fosmethilan (1194)+TX, fospirate (1195)+TX, fosthiazate (408)+TX, fosthietan (1196)+TX, furathiocarb (412)+TX, furethrin (1200)+TX, gamma-cyhalothrin (197)+TX, gamma-HCH (430)+TX, guazatine (422)+TX, guazatine acetates (422)+TX, GY-81 (development code) (423)+TX, halfenprox (424)+TX, halofenozide (425)+TX, HCH (430)+TX, HEOD (1070)+TX, heptachlor (1211)+TX, heptenophos (432)+TX, heterophos [CCN]+TX, hexaflumuron (439)+TX, HHDN (864)+TX, hydramethylnon (443)+TX, hydrogen cyanide (444)+TX, hydroprene (445)+TX, hyquincarb (1223)+TX, imidacloprid (458)+TX, imiprothrin (460)+TX, indoxacarb (465)+TX, iodomethane (IUPAC name) (542)+TX, IPSP (1229)+TX, isazofos (1231)+TX, isobenzan (1232)+TX, isocarbophos (alternative name)

(473)+TX, isodrin (1235)+TX, isofenphos (1236)+TX, isolane (1237)+TX, isoprocarb (472)+TX, isopropyl O-(methoxy-aminothiophosphoryl)salicylate (IUPAC name) (473)+TX, isoprothiolane (474)+TX, isothioate (1244)+TX, isoxathion (480)+TX, ivermectin (alternative name) [CCN]+TX, jasmolin I (696)+TX, jasmolin II (696)+TX, jodfenphos (1248)+TX, juvenile hormone I (alternative name) [CCN]+TX, juvenile hormone II (alternative name) [CCN]+TX, juvenile hormone III (alternative name) [CCN]+TX, kelevan (1249)+TX, kinoprene (484)+TX, lambda-cyhalothrin (198)+TX, lead arsenate [CCN]+TX, lepimectin (CCN)+TX, leptophos (1250)+TX, lindane (430)+TX, lirimfos (1251)+TX, lufenuron (490)+TX, lythidathion (1253)+TX, m-cumenyl methylcarbamate (IUPAC name) (1014)+TX, magnesium phosphide (IUPAC name) (640)+TX, malathion (492)+TX, malonoben (1254)+TX, mazidox (1255)+TX, mecarbam (502)+TX, mecarphon (1258)+TX, menazon (1260)+TX, mephosfolan (1261)+TX, mercurous chloride (513)+TX, mesulfenfos (1263)+TX, metaflumizone (CCN)+TX, metam (519)+TX, metam-potassium (alternative name) (519)+TX, metam-sodium (519)+TX, methacrifos (1266)+TX, methamidophos (527)+TX, methanesulfonyl fluoride (IUPAC/Chemical Abstracts name) (1268)+TX, methidathion (529)+TX, methiocarb (530)+TX, methocrotophos (1273)+TX, methomyl (531)+TX, methoprene (532)+TX, methoquin-butyl (1276)+TX, methothrin (alternative name) (533)+TX, methoxychlor (534)+TX, methoxyfenozide (535)+TX, methyl bromide (537)+TX, methyl isothiocyanate (543)+TX, methylchloroform (alternative name) [CCN]+TX, methylene chloride [CCN]+TX, metofluthrin [CCN]+TX, metolcarb (550)+TX, metoxadiazone (1288)+TX, mevinphos (556)+TX, mexacarbate (1290)+TX, milbemectin (557)+TX, milbemycin oxime (alternative name) [CCN]+TX, mipafox (1293)+TX, mirex (1294)+TX, monocrotophos (561)+TX, morphothion (1300)+TX, moxidectin (alternative name) [CCN]+TX, naftalofos (alternative name) [CCN]+TX, naled (567)+TX, naphthalene (IUPAC/Chemical Abstracts name) (1303)+TX, NC-170 (development code) (1306)+TX, NC-184 (compound code)+TX, nicotine (578)+TX, nicotine sulfate (578)+TX, nifluridide (1309)+TX, nitenpyram (579)+TX, nithiazine (1311)+TX, nitrilacarb (1313)+TX, nitrilacarb 1:1 zinc chloride complex (1313)+TX, NNI-0101 (compound code)+TX, NNI-0250 (compound code)+TX, nornicotine (traditional name) (1319)+TX, novaluron (585)+TX, noviflumuron (586)+TX, O-5-dichloro-4-iodophenyl O-ethyl ethylphosphonothioate (IUPAC name) (1057)+TX, O,O-diethyl O-4-methyl-2-oxo-2H-chromen-7-yl phosphorothioate (IUPAC name) (1074)+TX, 0,0-diethyl O-6-methyl-2-propylpyrimidin-4-yl phosphorothioate (IUPAC name) (1075)+TX, O,O,O',O'-tetrapropyl dithiopyrophosphate (IUPAC name) (1424)+TX, oleic acid (IUPAC name) (593)+TX, ometohate (594)+TX, oxamyl (602)+TX, oxydemetonmethyl (609)+TX, oxydeprofos (1324)+TX, oxydisulfoton (1325)+TX, pp'-DDT (219)+TX, para-dichlorobenzene [CCN]+TX, parathion (615)+TX, parathion-methyl (616)+TX, penfluron (alternative name) [CCN]+TX, pentachlorophenol (623)+TX, pentachlorophenyl laurate (IUPAC name) (623)+TX, permethrin (626)+TX, petroleum oils (alternative name) (628)+TX, PH 60-38 (development code) (1328)+TX, phenkapton (1330)+TX, phenothrin (630)+TX, phenthoate (631)+TX, phorate (636)+TX, phosalone (637)+TX, phosfolan (1338)+TX, phosmet (638)+TX, phosnichlor (1339)+TX, phosphamidon (639)+TX, phosphine (IUPAC name) (640)+TX, phoxim (642)+TX, phoxim-methyl (1340)+TX, pirimetaphos (1344)+TX, pirimicarb (651)+TX, pirimiphos-ethyl (1345)+TX, pirimiphos-methyl (652)+TX, polychlorodicyclopentadiene isomers (IUPAC name) (1346)+TX, polychloroterpenes (traditional name) (1347)+TX, potassium arsenite [CCN]+TX, potassium thiocyanate [CCN]+TX, prallethrin (655)+TX, precocene I (alternative name) [CCN]+TX, precocene II (alternative name) [CCN]+TX, precocene III (alternative name) [CCN]+TX, primidophos (1349)+TX, profenofos (662)+TX, profluthrin [CCN]+TX, promacyl (1354)+TX, promecarb (1355)+TX, propaphos (1356)+TX, propetamphos (673)+TX, propoxur (678)+TX, prothidathion (1360)+TX, prothiofos (686)+TX, prothoate (1362)+TX, protrifenbute [CCN]+TX, pymetrozine (688)+TX, pyraclofos (689)+TX, pyrazophos (693)+TX, pyresmethrin (1367)+TX, pyrethrin I (696)+TX, pyrethrin II (696)+TX, pyrethrins (696)+TX, pyridaben (699)+TX, pyridalyl (700)+TX, pyridaphenthion (701)+TX, pyrimidifen (706)+TX, pyrimitate (1370)+TX, pyriproxyfen (708)+TX, quassia (alternative name) [CCN]+TX, quinalphos (711)+TX, quinalphos-methyl (1376)+TX, quinothion (1380)+TX, quintiofos (1381)+TX, R-1492 (development code) (1382)+TX, rafoxanide (alternative name) [CCN]+TX, resmethrin (719)+TX, rotenone (722)+TX, RU 15525 (development code) (723)+TX, RU 25475 (development code) (1386)+TX, ryania (alternative name) (1387)+TX, ryanodine (traditional name) (1387)+TX, sabadilla (alternative name) (725)+TX, schradan (1389)+TX, sebufos (alternative name)+TX, selamectin (alternative name) [CCN]+TX, SI-0009 (compound code)+TX, SI-0205 (compound code)+TX, SI-0404 (compound code)+TX, SI-0405 (compound code)+TX, silafluofen (728)+TX, SN 72129 (development code) (1397)+TX, sodium arsenite [CCN]+TX, sodium cyanide (444)+TX, sodium fluoride (IUPAC/Chemical Abstracts name) (1399)+TX, sodium hexafluorosilicate (1400)+TX, sodium pentachlorophenoxide (623)+TX, sodium selenate (IUPAC name) (1401)+TX, sodium thiocyanate [CCN]+TX, sophamide (1402)+TX, spinosad (737)+TX, spiromesifen (739)+TX, spirotetrmat (CCN)+TX, sulcofuron (746)+TX, sulcofuron-sodium (746)+TX, sulfluramid (750)+TX, sulfotep (753)+TX, sulfuryl fluoride (756)+TX, sulprofos (1408)+TX, tar oils (alternative name) (758)+TX, tau-fluvalinate (398)+TX, tazimcarb (1412)+TX, TDE (1414)+TX, tebufenozide (762)+TX, tebufenpyrad (763)+TX, tebupirimfos (764)+TX, teflubenzuron (768)+TX, tefluthrin (769)+TX, temephos (770)+TX, TEPP (1417)+TX, terallethrin (1418)+TX, terbam (alternative name)+TX, terbufos (773)+TX, tetrachloroethane [CCN]+TX, tetrachlorvinphos (777)+TX, tetramethrin (787)+TX, theta-cypermethrin (204)+TX, thiacloprid (791)+TX, thiafenox (alternative name)+TX, thiamethoxam (792)+TX, thicrofos (1428)+TX, thiocarboxime (1431)+TX, thiocyclam (798)+TX, thiocyclam hydrogen oxalate (798)+TX, thiodicarb (799)+TX, thiofanox (800)+TX, thiometon (801)+TX, thionazin (1434)+TX, thiosultap (803)+TX, thiosultap-sodium (803)+TX, thuringiensin (alternative name) [CCN]+TX, tolfenpyrad (809)+TX, tralomethrin (812)+TX, transfluthrin (813)+TX, transpermethrin (1440)+TX, triamiphos (1441)+TX, triazamate (818)+TX, triazophos (820)+TX, triazuron (alternative name)+TX, trichlorfon (824)+TX, trichlormetaphos-3 (alternative name) [CCN]+TX, trichloronat (1452)+TX, trifenofos (1455)+TX, triflumuron (835)+TX, trimethacarb (840)+TX, triprene (1459)+TX, vamidothion (847)+TX, vaniliprole [CCN]+TX, veratridine (alternative name) (725)+TX, veratrine (alternative name) (725)+TX, XMC (853)+TX, xylylcarb (854)+TX, YI-5302 (compound code)+TX, zeta-cypermethrin (205)+TX, zetamethrin (alternative name)+TX, zinc phosphide (640)+TX, zolaprofos (1469) and ZXI 8901 (development code) (858)+TX, cyantraniliprole [736994-63-19+

TX, chlorantraniliprole [500008-45-7]+TX, cyenopyrafen [560121-52-0]+TX, cyflumetofen [400882-07-7]+TX, pyrifluquinazon [337458-27-2]+TX, spinetoram [187166-40-1 +187166-15-0]+TX, spirotetramat [203313-25-1]+TX, sulfoxaflor [946578-00-3]+TX, flufiprole [704886-18-0]+TX, meperfluthrin [915288-13-0]+TX, tetramethylfluthrin [84937-88-2]+TX, triflumezopyrim (disclosed in WO 2012/092115)+TX, fluxametamide (WO 2007/026965)+TX, epsilon-metofluthrin [240494-71-7]+TX, epsilon-momfluorothrin [1065124-65-3]+TX, fluazaindolizine [1254304-22-7]+TX, chloroprallethrin [399572-87-3]+TX, fluxametamide [928783-29-3]+TX, cyhalodiamide [1262605-53-7]+TX, tioxazafen [330459-31-9]+TX, broflanilide [1207727-04-5]+TX, flufiprole [704886-18-0]+TX, cyclaniliprole [1031756-98-5]+TX, tetraniliprole [1229654-66-3]+TX, guadipyr (described in WO2010/060231)+TX, cycloxaprid (described in WO2005/077934)+TX, a molluscicide selected from the group of substances consisting of bis(tributyltin) oxide (IUPAC name) (913)+TX, bromoacetamide [CCN]+TX, calcium arsenate [CCN]+TX, cloethocarb (999)+TX, copper acetoarsenite [CCN]+TX, copper sulfate (172)+TX, fentin (347)+TX, ferric phosphate (IUPAC name) (352)+TX, metaldehyde (518)+TX, methiocarb (530)+TX, niclosamide (576)+TX, niclosamide-olamine (576)+TX, pentachlorophenol (623)+TX, sodium pentachlorophenoxide (623)+TX, tazimcarb (1412)+TX, thiodicarb (799)+TX, tributyltin oxide (913)+TX, trifenmorph (1454)+TX, trimethacarb (840)+TX, triphenyltin acetate (IUPAC name) (347) and triphenyltin hydroxide (IUPAC name) (347)+TX, pyriprole [394730-71-3]+TX, a nematicide selected from the group of substances consisting of AKD-3088 (compound code)+TX, 1,2-dibromo-3-chloropropane (IUPAC/Chemical Abstracts name) (1045)+TX, 1,2-dichloropropane (IUPAC/Chemical Abstracts name) (1062)+TX, 1,2-dichloropropane with 1,3-dichloropropene (IUPAC name) (1063)+TX, 1,3-dichloropropene (233)+TX, 3,4-dichlorotetrahydrothiophene 1,1-dioxide (IUPAC/Chemical Abstracts name) (1065)+TX, 3-(4-chlorophenyl)-5-methylrhodanine (IUPAC name) (980)+TX, 5-methyl-6-thioxo-1,3,5-thiadiazinan-3-ylacetic acid (IUPAC name) (1286)+TX, 6-isopentenylaminopurine (alternative name) (210)+TX, abamectin (1)+TX, acetoprole [CCN]+TX, alanycarb (15)+TX, aldicarb (16)+TX, aldoxycarb (863)+TX, AZ 60541 (compound code)+TX, benclothiaz [CCN]+TX, benomyl (62)+TX, butylpyridaben (alternative name)+TX, cadusafos (109)+TX, carbofuran (118)+TX, carbon disulfide (945)+TX, carbosulfan (119)+TX, chloropicrin (141)+TX, chlorpyrifos (145)+TX, cloethocarb (999)+TX, cytokinins (alternative name) (210)+TX, dazomet (216)+TX, DBCP (1045)+TX, DCIP (218)+TX, diamidafos (1044)+TX, dichlofenthion (1051)+TX, dicliphos (alternative name)+TX, dimethoate (262)+TX, doramectin (alternative name) [CCN]+TX, emamectin (291)+TX, emamectin benzoate (291)+TX, eprinomectin (alternative name) [CCN]+TX, ethoprophos (312)+TX, ethylene dibromide (316)+TX, fenamiphos (326)+TX, fenpyrad (alternative name)+TX, fensulfothion (1158)+TX, fosthiazate (408)+TX, fosthietan (1196)+TX, furfural (alternative name) [CCN]+TX, GY-81 (development code) (423)+TX, heterophos [CCN]+TX, iodomethane (IUPAC name) (542)+TX, isamidofos (1230)+TX, isazofos (1231)+TX, ivermectin (alternative name) [CCN]+TX, kinetin (alternative name) (210)+TX, mecarphon (1258)+TX, metam (519)+TX, metam-potassium (alternative name) (519)+TX, metam-sodium (519)+TX, methyl bromide (537)+TX, methyl isothiocyanate (543)+TX, milbemycin oxime (alternative name) [CCN]+TX, moxidectin (alternative name) [CCN]+TX, Myrothecium verrucaria composition (alternative name) (565)+TX, NC-184 (compound code)+TX, oxamyl (602)+TX, phorate (636)+TX, phosphamidon (639)+TX, phosphocarb [CCN]+TX, sebufos (alternative name)+TX, selamectin (alternative name) [CCN]+TX, spinosad (737)+TX, terbam (alternative name)+TX, terbufos (773)+TX, tetrachlorothiophene (IUPAC/ Chemical Abstracts name) (1422)+TX, thiafenox (alternative name)+TX, thionazin (1434)+TX, triazophos (820)+TX, triazuron (alternative name)+TX, xylenols [CCN]+TX, YI-5302 (compound code) and zeatin (alternative name) (210)+TX, fluensulfone [318290-98-1]+TX, a nitrification inhibitor selected from the group of substances consisting of potassium ethylxanthate [CCN] and nitrapyrin (580)+TX, a plant activator selected from the group of substances consisting of acibenzolar (6)+TX, acibenzolar-S-methyl (6)+TX, probenazole (658) and Reynoutria sachalinensis extract (alternative name) (720)+TX, a rodenticide selected from the group of substances consisting of 2-isovalerylindan-1,3-dione (IUPAC name) (1246)+TX, 4-(quinoxalin-2-ylamino)benzenesulfonamide (IUPAC name) (748)+TX, alpha-chlorohydrin [CCN]+TX, aluminium phosphide (640)+TX, antu (880)+TX, arsenous oxide (882)+TX, barium carbonate (891)+TX, bisthiosemi (912)+TX, brodifacoum (89)+TX, bromadiolone (91)+TX, bromethalin (92)+TX, calcium cyanide (444)+TX, chloralose (127)+TX, chlorophacinone (140)+TX, cholecalciferol (alternative name) (850)+TX, coumachlor (1004)+TX, coumafuryl (1005)+TX, coumatetralyl (175)+TX, crimidine (1009)+TX, difenacoum (246)+TX, difethialone (249)+TX, diphacinone (273)+TX, ergocalciferol (301)+TX, flocoumafen (357)+TX, fluoroacetamide (379)+TX, flupropadine (1183)+TX, flupropadine hydrochloride (1183)+TX, gamma-HCH (430)+TX, HCH (430)+TX, hydrogen cyanide (444)+TX, iodomethane (IUPAC name) (542)+TX, lindane (430)+TX, magnesium phosphide (IUPAC name) (640)+TX, methyl bromide (537)+TX, norbormide (1318)+TX, phosacetim (1336)+TX, phosphine (IUPAC name) (640)+TX, phosphorus [CCN]+TX, pindone (1341)+TX, potassium arsenite [CCN]+TX, pyrinuron (1371)+TX, scilliroside (1390)+TX, sodium arsenite [CCN]+TX, sodium cyanide (444)+TX, sodium fluoroacetate (735)+TX, strychnine (745)+TX, thallium sulfate [CCN]+TX, warfarin (851) and zinc phosphide (640)+TX, a synergist selected from the group of substances consisting of 2-(2-butoxyethoxy)ethyl piperonylate (IUPAC name) (934)+TX, 5-(1,3-benzodioxol-5-yl)-3-hexylcyclohex-2-enone (IUPAC name) (903)+TX, farnesol with nerolidol (alternative name) (324)+TX, MB-599 (development code) (498)+TX, MGK 264 (development code) (296)+TX, piperonyl butoxide (649)+TX, piprotal (1343)+TX, propyl isomer (1358)+TX, S421 (development code) (724)+TX, sesamex (1393)+TX, sesasmolin (1394) and sulfoxide (1406)+TX, an animal repellent selected from the group of substances consisting of anthraquinone (32)+TX, chloralose (127)+TX, copper naphthenate [CCN]+TX, copper oxychloride (171)+TX, diazinon (227)+TX, dicyclopentadiene (chemical name) (1069)+TX, guazatine (422)+TX, guazatine acetates (422)+TX, methiocarb (530)+TX, pyridin-4-amine (IUPAC name) (23)+TX, thiram (804)+TX, trimethacarb (840)+TX, zinc naphthenate [CCN] and ziram (856)+TX, a virucide selected from the group of substances consisting of imanin (alternative name) [CCN] and ribavirin (alternative name) [CCN]+TX, a wound protectant selected from the group of substances consisting of mercuric oxide (512)+TX, octhilinone (590) and thiophanate-methyl (802)+TX, and biologically active compounds selected from the group consisting of azaconazole (60207-31-0]+TX, bitertanol [70585-36-3]+TX, bromuconazole [116255-48-2]+TX, cyproconazole [94361-06-5]+TX, difenoconazole [119446-68-3]+TX, diniconazole [83657-24-3]+TX, epoxiconazole [106325-08-0]+TX, fenbuconazole [114369-43-6]+TX, fluquinconazole [136426-54-5]+TX, flusilazole [85509-19-9]+TX, flutriafol [76674-21-0]+TX, hexaconazole [79983-71-4]+TX, imazalil [35554-44-0]+TX, imibenconazole [86598-92-7]+TX, ipconazole [125225-28-7]+TX, metconazole [125116-23-6]+TX, myclobutanil [88671-89-0]+TX, pefurazoate [101903-30-4]+TX, penconazole [66246-88-6]+TX, prothioconazole [178928-70-6]+TX, pyrifenox [88283-41-4]+TX, prochloraz [67747-09-5]+TX, propiconazole [60207-90-1]+TX, simeconazole [149508-90-7]+TX, tebuconazole [107534-96-3]+TX, tetraconazole [112281-77-3]+TX, triadimefon [43121-43-3]+TX, triadimenol [55219-65-3]+TX, triflumizole [99387-89-0]+TX, triticonazole [131983-72-7]+TX, ancymidol [12771-68-5]+TX, fenarimol [60168-88-9]+TX, nuarimol [63284-71-9]+TX, bupirimate [41483-43-6]+TX, dimethirimol [5221-53-4]+TX, ethirimol [23947-60-6]+TX, dodemorph [1593-77-7]+TX, fenpropidine [67306-00-7]+TX, fenpropimorph [67564-91-4]+TX, spiroxamine [118134-30-8]+TX, tridemorph [81412-43-3]+TX, cyprodinil [121552-61-2]+TX, mepanipyrim [110235-47-7]+TX, pyrimethanil [53112-28-0]+TX, fenpiclonil [74738-17-3]+TX, fludioxonil [131341-86-1]+TX, benalaxyl [71626-11-4]+TX, furalaxyl [57646-30-7]+TX, meta-laxyl [57837-19-1]+TX, R-metalaxyl [70630-17-0]+TX, ofurace [58810-48-3]+TX, oxadixyl [77732-09-3]+TX, benomyl [17804-35-2]+TX, carbendazim [10605-21-7]+TX, debacarb [62732-91-6]+TX, fuberidazole [3878-19-1]+TX, thiabendazole [148-79-8]+TX, chlozolinate [84332-86-5]+TX, dichlozoline [24201-58-9]+TX, iprodione [36734-19-7]+TX, myclozoline [54864-61-8]+TX, procymidone [32809-16-8]+TX, vinclozoline [50471-44-8]+TX, boscalid [188425-85-6]+TX, carboxin [5234-68-4]+TX, fenfuram [24691-80-3]+TX, flutolanil [66332-96-5]+TX, mepronil [55814-41-0]+TX, oxycarboxin [5259-88-1]+TX, penthiopyrad [183675-82-3]+TX, thifluzamide [130000-40-7]+TX, guazatine [108173-90-6]+TX, dodine [2439-10-3] [112-65-2] (free base)+TX, iminoctadine [13516-27-3]+TX, azoxystrobin [131860-33-8]+TX, dimoxystrobin [149961-52-4]+TX, enestroburin {Proc. BCPC, Int. Congr., Glasgow, 2003, 1, 93}+TX, fluoxastrobin [361377-29-9]+TX, kresoxim-methyl [143390-89-0]+TX, metominostrobin [133408-50-1]+TX, trifloxystrobin [141517-21-7]+TX, orysastrobin [248593-16-0]+TX, picoxystrobin [117428-22-5]+TX, pyraclostrobin [175013-18-0]+TX, ferbam [14484-64-1]+TX, mancozeb [8018-01-7]+TX, maneb [12427-38-2]+TX, metiram [9006-42-2]+TX, propineb [12071-83-9]+TX, thiram [137-26-8]+TX, zineb [12122-67-7]+TX, ziram [137-30-4]+TX, captafol [2425-06-1]+TX, captan [133-06-2]+TX, dichlofluanid [1085-98-9]+TX, fluoroimide [41205-21-4]+TX, folpet [133-07-3 ]+TX, tolylfluanid [731-27-1]+TX, bordeaux mixture [8011-63-0]+TX, copperhydroxid [20427-59-2]+TX, copperoxychlorid [1332-40-7]+TX, coppersulfat [7758-98-7]+TX, copperoxid [1317-39-1]+TX, mancopper [53988-93-5]+TX, oxine-copper [10380-28-6]+TX, dinocap [131-72-6]+TX, nitrothal-isopropyl [10552-74-6]+TX, edifenphos [17109-49-8]+TX, iprobenphos [26087-47-8]+TX, isoprothiolane [50512-35-1]+TX, phosdiphen [36519-00-3]+TX, pyrazophos [13457-18-6]+TX, tolclofos-methyl [57018-04-9]+TX, acibenzolar-S-methyl [135158-54-2]+TX, anilazine [101-05-3]+TX, benthiavalicarb [413615-35-7]+TX, blasticidin-S [2079-00-7]+TX, chinomethionat [2439-01-2]+TX, chloroneb [2675-77-6]+TX, chlorothalonil [1897-45-6]+TX, cyflufenamid [180409-60-3]+TX, cymoxanil [57966-95-7]+TX, dichlone [117-80-6]+TX, diclocymet [139920-32-4]+TX, diclomezine [62865-36-5]+TX, dicloran [99-30-9]+TX, diethofencarb [87130-20-9]+TX, dimethomorph [110488-70-5]+TX, SYP-LI90 (Flumorph) [211867-47-9]+TX, dithianon [3347-22-6]+TX, ethaboxam [162650-77-3]+TX, etridiazole [2593-15-9]+TX, famoxadone [131807-57-3]+TX, fenamidone [161326-34-7]+TX, fenoxanil [115852-48-7]+TX, fentin [668-34-8]+TX, ferimzone [89269-64-7]+TX, fluazinam [79622-59-6]+TX, fluopicolide [239110-15-7]+TX, flusulfamide [106917-52-6]+TX, fenhexamid [126833-17-8]+TX, fosetyl-aluminium [39148-24-8]+TX, hymexazol [10004-44-1]+TX, iprovalicarb [140923-17-7]+TX, IKF-916 (Cyazofamid) [120116-88-3]+TX, kasugamycin [6980-18-3]+TX, methasulfocarb [66952-49-6]+TX, metrafenone [220899-03-6]+TX, pencycuron [66063-05-6]+TX, phthalide [27355-22-2]+TX, polyoxins [11113-80-7]+TX, probenazole [27605-76-1]+TX, propamocarb [25606-41-1]+TX, proquinazid [189278-12-4]+TX, pyroquilon [57369-32-1]+TX, quinoxyfen [124495-18-7]+TX, quintozene [82-68-8]+TX, sulfur [7704-34-9]+TX, tiadinil [223580-51-6]+TX, triazoxide [72459-58-6]+TX, tricyclazole [41814-78-2]+TX, triforine [26644-46-2]+TX, validamycin [37248-47-8]+TX, zoxamide (RH7281) [156052-68-5]+TX, mandipropamid [374726-62-2]+TX, isopyrazam [881685-58-1]+TX, sedaxane [874967-67-6]+TX, 3-difluoromethyl-1-methyl-1H-pyrazole-4-carboxylic acid (9-dichloromethylene-1,2,3,4-tetrahydro-1,4-methano-naphthalen-5-yl)-amide (dislosed in WO 2007/048556)+TX, 3-difluoromethyl-1-methyl-1H-pyrazole-4-carboxylic acid (3',4',5'-trifluoro-biphenyl-2-yl)-amide (disclosed in WO 2006/087343)+TX, [(3S,4R,4aR,6S,6aS,12R,12aS,12bS)-3-[(cyclopropylcarbonyl)oxy]-1,3,4,4a,5,6,6a,12,12a,12b-decahydro-6,12-dihydroxy-4,6a,12-trimethyl-11-oxo-9-(3-pyridinyl)-2H,11Hnaphtho[2,1-b]pyrano[3,4-e]pyran-4-yl] methyl-cyclopropanecarboxylate [915972-17-7]+TX and 1,3,5-trimethyl-N-(2-methyl-1-oxopropyl)-N-[3-(2-methylpropyl)-4-[2,2,2-trifluoro-1-methoxy-1-(trifluoromethyp-ethyl]phenyl]-1H-pyrazole-4-carboxamide [926914-55-8]+TX, and microbials including: *Acinetobacter lwoffii*+TX, *Acremonium alternatum*+TX+TX, *Acremonium cephalosporium*+TX+TX, *Acremonium diospyri*+TX, *Acremonium obclavatum*+TX, *Adoxophyes orana granulovirus* (AdoxGV) (Capex®)+TX, *Agrobacterium radiobacter* strain K84 (Galltrol-A®)+TX, *Alternaria alternate*+TX, *Alternaria cassia*+TX, *Alternaria destruens* (Smolder®)+TX, *Ampelomyces quisqualis* (AQ100)+TX, *Aspergillus flavus* AF36 (AF36®)+TX, *Aspergillus flavus* NRRL 21882 (Aflaguard®)+TX, *Aspergillus spp.*+TX, *Aureobasidium pullulans*+TX, *Azospirillum*+TX, (MicroAZ®+TX, TAZO B®)+TX, *Azotobacter*+TX, *Azotobacter chroocuccum* (Azotomeal®)+TX, *Azotobacter cysts* (Bionatural Blooming Blossoms®)+TX, *Bacillus amyloliquefaciens*+TX, *Bacillus cereus*+TX, *Bacillus chitinosporus* strain CM-1+TX, *Bacillus chitinosporus* strain AQ746+TX, *Bacillus licheniformis* strain HB-2 (Biostart™ Rhizoboost®)+TX, *Bacillus licheniformis* strain 3086 (EcoGuard®+TX, Green Releaf®)+TX, *Bacillus circulans*+TX, *Bacillus firmus* (BioSafe®+TX, BioNem-WP®+TX, VOTiVO®)+TX, *Bacillus firmus* strain 1-1582+TX, *Bacillus macerans*+TX, *Bacillus marismortui*+TX, *Bacillus megaterium*+TX, *Bacillus*

*mycoides* strain AQ726+TX, *Bacillus papillae* (Milky Spore Powder®)+TX, *Bacillus pumilus* spp.+TX, *Bacillus pumilus* strain GB34 (Yield Shield®)+TX, *Bacillus pumilus* strain AQ717+TX, *Bacillus pumilus* strain QST 2808 (Sonata®+TX, Ballad Plus®)+TX, *Bacillus spahericus* (VectoLex®)+TX, *Bacillus* spp.+TX, *Bacillus* spp. strain AQ175+TX, *Bacillus* spp. strain AQ177+TX, Bacillus spp. strain AQ178+TX, *Bacillus subtilis* strain QST 713 (CEASE®+TX, Serenade®+TX, Rhapsody®)+TX, *Bacillus subtilis* strain QST 714 (JAZZ®)+TX, *Bacillus subtilis* strain AQ153+TX, *Bacillus subtilis* strain AQ743+TX, *Bacillus subtilis* strain QST3002+TX, *Bacillus subtilis* strain QST3004+TX, *Bacillus subtilis* var. *amyloliquefaciens* strain FZB24 (Taegro®+TX, Rhizopro®)+TX, *Bacillus thuringiensis* Cry 2Ae+TX, *Bacillus thuringiensis* Cry1Ab+TX, *Bacillus thuringiensis aizawai* GC 91 (Agree®)+TX, *Bacillus thuringiensis israelensis* (BMP®+TX, Aquabac®+TX, VectoBac®)+TX, *Bacillus thuringiensis kurstaki* (Javelin®+TX, Deliver®+TX, CryMax®+TX, Bonide®+TX, Scutella WP®+TX, Turilav WP ®+TX, Astuto®+TX, Dipel WP®+TX, Biobit®+TX, Foray®)+TX, *Bacillus thuringiensis kurstaki* BMP 123 (Baritone®)+TX, *Bacillus thuringiensis kurstaki* HD-1 (Bioprotec-CAF/3P®)+TX, *Bacillus thuringiensis* strain BD#32+TX, *Bacillus thuringiensis* strain AQ52+TX, *Bacillus thuringiensis* var. *aizawai* (XenTari®+TX, DiPel®)+TX, bacteria spp. (GROWMEND®+TX, GROWSWEET®+TX, Shootup®)+TX, bacteriophage of *Clavipacter michiganensis* (AgriPhage®)+TX, Bakflor®+TX, *Beauveria bassiana* (Beaugenic®+TX, Brocaril WP®)+TX, *Beauveria bassiana* GHA (Mycotrol ES®+TX, Mycotrol O®+TX, BotaniGuard®)+TX, *Beauveria brongniartii* (Engerlingspilz®+TX, Schweizer Beauveria®+TX, Melocont®)+TX, *Beauveria* spp.+TX, *Botrytis cineria*+TX, *Bradyrhizobium japonicum* (TerraMax®)+TX, *Brevibacillus brevis*+TX, *Bacillus thuringiensis tenebrionis* (Novodor®)+TX, BtBooster+TX, *Burkholderia cepacia* (Deny®+TX, Intercept®+TX, Blue Circle®)+TX, *Burkholderia gladii*+TX, *Burkholderia gladioli*+TX, *Burkholderia* spp.+TX, Canadian thistle fungus (CBH Canadian Bioherbicide®)+TX, *Candida butyri*+TX, *Candida famata*+TX, *Candida fructus*+TX, *Candida glabrata*+TX, *Candida guilliermondii*+TX, *Candida melibiosica*+TX, *Candida oleophila* strain 0+TX, *Candida parapsilosis*+TX, *Candida pelliculosa*+TX, *Candida pulcherrima*+TX, *Candida reukaufii*+TX, *Candida saitoana* (Bio-Coat®+TX, Biocure®)+TX, Candida sake+TX, *Candida* spp.+TX, *Candida tenius*+TX, *Cedecea dravisae*+TX, *Cellulomonas flavigena*+TX, *Chaetomium cochliodes* (Nova-Cide®)+TX, *Chaetomium globosum* (Nova-Cide®)+TX, *Chromobacterium subtsugae* strain PRAA4-1T (Grandevo®)+TX, *Cladosporium cladosporioides*+TX, *Cladosporium oxysporum*+TX, *Cladosporium chlorocephalum*+TX, *Cladosporium* spp.+TX, *Cladosporium tenuissimum*+TX, *Clonostachys rosea* (EndoFine®)+TX, *Colletotrichum acutatum*+TX, *Coniothyrium minitans* (Cotans WG®)+TX, *Coniothyrium* spp.+TX, *Cryptococcus albidus* (YIELDPLUS®)+TX, *Cryptococcus humicola*+TX, *Cryptococcus infirmo-miniatus*+TX, *Cryptococcus laurentii*+TX, *Cryptophlebia leucotreta granulovirus* (Cryptex®)+TX, *Cupriavidus campinensis*+TX, *Cydia pomonella granulovirus* (CYD-X®)+TX, *Cydia pomonella granulovirus* (Madex®+TX, Madex Plus®+TX, Madex Max/Carpovirusine®)+TX, *Cylindrobasidium laeve* (Stumpout®)+TX, *Cylindrocladium*+TX, *Debaryomyces hansenii*+TX, *Drechslera hawaiinensis*+TX, *Enterobacter cloacae*+TX, *Enterobacteriaceae*+TX, *Entomophtora virulenta* (Vektor®)+TX, *Epicoccum nigrum*+TX, *Epicoccum purpurascens*+TX, *Epicoccum* spp.+TX, *Filobasidium floriforme*+TX, *Fusarium acuminatum*+TX, *Fusarium chlamydosporum*+TX, *Fusarium oxysporum* (Fusaclean®/Biofox C®)+TX, *Fusarium proliferatum*+TX, *Fusarium* spp.+TX, *Galactomyces geotrichum*+TX, *Gliocladium catenulatum* (Primastop®+TX, Prestop®)+TX, *Gliocladium roseum*+TX, *Gliocladium* spp. (SoilGard®)+TX, *Gliocladium virens* (Soilgard®)+TX, *Granulovirus* (Granupom®)+TX, *Halobacillus halophilus*+TX, *Halobacillus litoralis*+TX, *Halobacillus trueperi*+TX, *Halomonas* spp.+TX, *Halomonas subglaciescola*+TX, *Halovibrio variabilis +TX, Hanseniaspora uvarum*+TX, *Helicoverpa armigera* nucleopolyhedrovirus (Helicovex®)+TX, *Helicoverpa zea* nuclear polyhedrosis virus (Gemstar®)+TX, Isoflavone—formononetin (Myconate®)+TX, *Kloeckera apiculata*+TX, *Kloeckera* spp.+TX, *Lagenidium giganteum* (Laginex®)+TX, *Lecanicillium longisporum* (Vertiblast®)+TX, *Lecanicillium muscarium* (Vertikil®)+TX, Lymantria Dispar nucleopolyhedrosis virus (Disparvirus®)+TX, *Marinococcus halophilus*+TX, *Meira geulakonigii*+TX, *Metarhizium anisopliae* (Met52®)+TX, *Metarhizium anisopliae* (Destruxin WP®)+TX, *Metschnikowia fruticola* (Shemer®)+TX, *Metschnikowia pulcherrima*+TX, *Microdochium dimerum* (Antibot®)+TX, *Micromonospora coerulea*+TX, *Microsphaeropsis ochracea*+TX, *Muscodor albus* 620 (Muscudor®)+TX, *Muscodor roseus* strain A3-5+TX, *Mycorrhizae* spp. (AMykor®+TX, Root Maximizer®)+TX, *Myrothecium verrucaria* strain AARC-0255 (DiTera®)+TX, BROS PLUS®+TX, *Ophiostoma piliferum* strain D97 (Sylvanex®)+TX, *Paecilomyces farinosus*+TX, *Paecilomyces fumosoroseus* (PFR-97®+TX, PreFeRal®)+TX, *Paecilomyces linacinus* (Biostat WP®)+TX, *Paecilomyces lilacinus* strain 251 (MeloCon WG®)+TX, *Paenibacillus polymyxa*+TX, *Pantoea agglomerans* (BlightBan C9-1®)+TX, *Pantoea* spp.+TX, *Pasteuria* spp. (Econem®)+TX, *Pasteuria nishizawae*+TX, *Penicillium aurantiogriseum*+TX, *Penicillium billai* (Jumpstart®+TX, TagTeam®)+TX, *Penicillium brevicompactum*+TX, *Penicillium frequentans*+TX, *Penicillium griseofulvum*+TX, *Penicillium purpurogenum*+TX, *Penicillium* spp.+TX, *Penicillium viridicatum*+TX, *Phlebiopsis gigantean* (Rotstop®)+TX, phosphate solubilizing bacteria (Phosphomeal®)+TX, *Phytophthora cryptogea*+TX, *Phytophthora palmivora* (Devine®)+TX, *Pichia anomala*+TX, *Pichia guilermondii*+TX, *Pichia membranaefaciens*+TX, *Pichia onychis*+TX, *Pichia stipites*+TX, *Pseudomonas aeruginosa*+TX, *Pseudomonas aureofasciens* (Spot-Less Biofungicide®)+TX, *Pseudomonas cepacia*+TX, *Pseudomonas chloroက*Pseudomonas chlororaphis* (AtEze®)+TX, *Pseudomonas corrugate*+TX, *Pseudomonas fluorescens* strain A506 (BlightBan A506®)+TX, *Pseudomonas putida*+TX, *Pseudomonas reactans*+TX, *Pseudomonas* spp.+TX, *Pseudomonas syringae* (Bio-Save®)+TX, *Pseudomonas viridiflava*+TX, *Pseudomons fluorescens* (Zequanox®)+TX, *Pseudozyma flocculosa* strain PF-A22 UL (Sporodex L®)+TX, *Puccinia canaliculata*+TX, *Puccinia thlaspeos* (Wood Warrior®)+TX, *Pythium paroecandrum*+TX, *Pythium oligandrum* (Polygandron®+TX, Polyversum®)+TX, *Pythium periplocum*+TX, *Rhanella aquatilis*+TX, *Rhanella* spp.+TX, *Rhizobia* (Dormal®+TX, Vault®)+TX, *Rhizoctonia*+TX, *Rhodococcus globerulus* strain AQ719+TX, *Rhodosporidium diobovatum*+TX, *Rhodosporidium toruloides*+TX, *Rhodotorula* spp.+TX, *Rhodotorula glutinis*+TX, *Rhodotorula graminis*+TX, *Rhodotorula mucilagnosa*+TX, *Rhodotorula rubra*+TX, *Saccharomyces cerevisiae*+TX, *Salinococcus roseus*+TX, *Sclerotinia minor*+TX, *Sclerotinia minor* (SARRITOR®)+TX, *Scytalidium* spp.+TX, *Scytalidium uredinicola*+TX, *Spodoptera exigua* nuclear polyhedrosis virus (Spod-X®+TX, Spexit®)+TX, *Serratia*

*marcescens*+TX, *Serratia plymuthica*+TX, *Serratia* spp.+TX, *Sordaria fimicola*+TX, *Spodoptera littoralis* nucleopolyhedrovirus (Littovir®)+TX, *Sporobolomyces roseus*+TX, *Stenotrophomonas maltophilia*+TX, *Streptomyces ahygroscopicus*+TX, *Streptomyces albaduncus*+TX, *Streptomyces exfoliates*+TX, *Streptomyces galbus*+TX, *Streptomyces griseoplanus*+TX, *Streptomyces griseoviridis* (Mycostop®)+TX, *Streptomyces lydicus* (Actinovate®)+TX, *Streptomyces lydicus* WYEC-108 (ActinoGrow®)+TX, *Streptomyces violaceus*+TX, *Tilletiopsis minor*+TX, *Tilletiopsis* spp.+TX, *Trichoderma asperellum* (T34 Biocontrol®)+TX, *Trichoderma gamsii* (Tenet®)+TX, *Trichoderma atroviride* (Plantmate®)+TX, *Trichoderma hamatum* TH 382+TX, *Trichoderma harzianum rifai* (Mycostar®)+TX, *Trichoderma harzianum* T-22 (Trianum-P®+TX, PlantShield HC®+TX, RootShield®+TX, Trianum-G®)+TX, *Trichoderma harzianum* T-39 (Trichodex®)+TX, *Trichoderma inhamatum*+TX, *Trichoderma koningii*+TX, *Trichoderma* spp. LC 52 (Sentinel®)+TX, *Trichoderma lignorum*+TX, *Trichoderma longibrachiatum*+TX, *Trichoderma polysporum* (Binab T®)+TX, *Trichoderma taxi*+TX, *Trichoderma virens*+TX, *Trichoderma virens* (formerly Gliocladium virens GL-21) (SoilGuard®)+TX, *Trichoderma viride*+TX, *Trichoderma viride* strain ICC 080 (Remedier®)+TX, *Trichosporon pullulans*+TX, *Trichosporon* spp.+TX, *Trichothecium* spp.+TX, *Trichothecium roseum*+TX, *Typhula phacorrhiza* strain 94670+TX, *Typhula phacorrhiza* strain 94671+TX, *Ulocladium atrum*+TX, *Ulocladium oudemansii* (Botry-Zen®)+TX, *Ustilago maydis*+TX, various bacteria and supplementary micronutrients (Natural Il®)+TX, various fungi (Millennium Microbes®)+TX, *Verticillium chlamydosporium*+TX, *Verticillium lecanii* (Mycotal®+TX, Vertalec®)+TX, Vip3Aa20 (VIPtera®)+TX, *Virgibaclillus marismortui*+TX, *Xanthomonas campestris* pv. *Poae* (Camperico@)+TX, *Xenorhabdus bovienii*+TX, *Xenorhabdus nematophilus*; and Plant extracts including: pine oil (Retenol®)+TX, azadirachtin (Plasma Neem Oil®+TX, AzaGuard®+TX, MeemAzal®+TX, Molt-X®+TX, Botanical IGR (Neemazad®+TX, Neemix®)+TX, canola oil (Lilly Miller Vegol®)+TX, *Chenopodium ambrosioides* near ambrosioides (Requiem®)+TX, *Chrysanthemum* extract (Crisant®)+TX, extract of neem oil (Trilogy®)+TX, essentials oils of *Labiatae* (Botanic®)+TX, extracts of clove rosemary peppermint and thyme oil (Garden insect killer®)+TX, Glycinebetaine (Greenstim®)+TX, garlic+TX, lemongrass oil (GreenMatch®)+TX, neem oil+TX, *Nepeta cataria* (Catnip oil)+TX, *Nepeta catarina*+TX, nicotine+TX, oregano oil (MossBuster®)+TX, Pedaliaceae oil (Nematon®)+TX, pyrethrum+TX, *Quillaja saponaria* (NemaQ®)+TX, *Reynoutria sachalinensis* (Regalia®+TX, Sakalia®)+TX, rotenone (Eco Roten®)+TX, Rutaceae plant extract (Soleo®)+TX, soybean oil (Ortho ecosense®)+TX, tea tree oil (Timorex Gold®)+TX, thymus oil+TX, AGNIQUE® MMF+TX, BugOil®+TX, mixture of rosemary sesame pepermint thyme and cinnamon extracts (EF 300®)+TX, mixture of clove rosemary and peppermint extract (EF 400®)+TX, mixture of clove pepermint garlic oil and mint (Soil Shot®)+TX, kaolin (Screen®)+TX, storage glucam of brown algae (Laminarin®); and pheromones including: blackheaded fireworm pheromone (3M Sprayable Blackheaded Fireworm Pheromone®)+TX, Codling Moth Pheromone (Paramount dispenser-(CM)/Isomate C-Plus®)+TX, Grape Berry Moth Pheromone (3M MEC-GBM Sprayable Pheromone®)+TX, Leafroller pheromone (3M MEC—LR Sprayable Pheromone®)+TX, Muscamone (Snip7 Fly Bait®+TX, Starbar Premium Fly Bait®)+TX, Oriental Fruit Moth Pheromone (3M oriental fruit moth sprayable pheromone®)+TX, Peachtree Borer Pheromone (Isomate-P®)+TX, Tomato Pinworm Pheromone (3M Sprayable pheromone®)+TX, Entostat powder (extract from palm tree) (Exosex CM®)+TX, (E+TX,Z+TX,Z)-3+TX,8+TX,11 Tetradecatrienyl acetate+TX, (Z+TX,Z+TX,E)-7+TX,11+TX,13-Hexadecatrienal+TX, (E+TX,Z)-7+TX,9-Dodecadien-1-yl acetate+TX, 2-Methyl-1-butanol+TX, Calcium acetate+TX, Scenturion®+TX, Biolure®+TX, Check-Mate®+TX, Lavandulyl senecioate; and Macrobials including: *Aphelinus abdominalis*+TX, *Aphidius ervi* (Aphelinus-System®)+TX, *Acerophagus papaya*+TX, *Adalia bipunctata* (Adalia-System®)+TX, *Adalia bipunctata* (Adaline®)+TX, *Adalia bipunctata* (Aphidalia®)+TX, *Ageniaspis citricola*+TX, *Ageniaspis fuscicollis*+TX, *Amblyseius andersoni* (Anderline®+TX, Andersoni-System®)+TX, *Amblyseius californicus* (Amblyline®+TX, Spical®)+TX, *Amblyseius cucumeris* (Thripex®+TX, Bugline cucumeris®)+TX, *Amblyseius fallacis* (Fallacis®)+TX, *Amblyseius swirskii* (Bugline swirskii®+TX, Swirskii-Mite®)+TX, *Amblyseius womersleyi* (WomerMite®)+TX, *Amitus hesperidum*+TX, *Anagrus atomus*+TX, *Anagrus fusciventris*+TX, *Anagrus kamali*+TX, *Anagrus loecki*+TX, *Anagrus pseudococci* (Citripar®)+TX, *Anicetus benefices*+TX, *Anisopteromalus calandrae*+TX, *Anthocoris nemoralis* (Anthocoris-System®)+TX, *Aphelinus abdominalis* (Apheline®+TX, Aphiline®)+TX, *Aphelinus asychis*+TX, *Aphidius colemani* (Aphipar®)+TX, *Aphidius ervi* (Ervipar®)+TX, *Aphidius gifuensis*+TX, *Aphidius matricariae* (Aphipar-M®)+TX, *Aphidoletes aphidimyza* (Aphidend®)+TX, *Aphidoletes aphidimyza* (Aphidoline®)+TX, *Aphytis lingnanensis*+TX, *Aphytis melinus*+TX, *Aprostocetus hagenowii*+TX, *Atheta coriaria* (Staphyline®)+TX, *Bombus* spp.+TX, *Bombus terrestris* (Natupol Beehive®)+TX, *Bombus terrestris* (Beeline®+TX, Tripol®)+TX, *Cephalonomia stephanoderis*+TX, *Chilocorus nigritus*+TX, *Chrysoperla carnea* (Chrysoline®)+TX, *Chrysoperla carnea* (Chrysopa®)+TX, *Chrysoperla rufilabris*+TX, *Cirrospilus ingenuus*+TX, *Cirrospilus quadristriatus*+TX, *Citrostichus phyllocnistoides*+TX, *Closterocerus chamaeleon*+TX, *Closterocerus* spp.+TX, *Coccidoxenoides perminutus* (Planopar®)+TX, *Coccophagus cowperi*+TX, *Coccophagus lycimnia*+TX, *Cotesia flavipes*+TX, *Cotesia plutellae*+TX, *Cryptolaemus montrouzieri* (Cryptobug®+TX, Cryptoline®)+TX, *Cybocephalus nipponicus*+TX, *Dacnusa sibirica*+TX, *Dacnusa sibirica* (Minusa®)+TX, *Diglyphus isaea* (Diminex®)+TX, *Delphastus catalinae* (Delphastus®)+TX, *Delphastus pusillus*+TX, *Diachasmimorpha krausii*+TX, *Diachasmimorpha longicaudata*+TX, *Diaparsis jucunda*+TX, *Diaphorencyrtus aligarhensis*+TX, *Diglyphus isaea*+TX, *Diglyphus isaea* (Miglyphus®+TX, Digline®)+TX, *Dacnusa sibirica* (Dac-Digline®+TX, Minex®)+TX, *Diversinervus* spp.+TX, *Encarsia citrina*+TX, *Encarsia formosa* (Encarsia max®+TX, Encarline®+TX, EnStrip®)+TX, *Eretmocerus eremicus* (Enermix®)+TX, *Encarsia guadeloupae*+TX, *Encarsia haitiensis*+TX, *Episyrphus balteatus* (Syrphidend®)+TX, *Eretmoceris siphonini*+TX, *Eretmocerus califomicus*+TX, *Eretmocerus eremicus* (Ercal®+TX, Eretline e®)+TX, *Eretmocerus eremicus* (Bemimix®)+TX, *Eretmocerus hayati*+TX, *Eretmocerus mundus* (Bemipar®+TX, Eretline m®)+TX, *Eretmocerus siphonini*+TX, *Exochomus quadripustulatus*+TX, *Feltiella acarisuga* (Spidend®)+TX, *Feltiella acarisuga* (Feltiline®)+TX, *Fopius arisanus*+TX, *Fopius ceratitivorus*+TX, Formononetin (Wirless Beehome®)+TX, *Franklinothrips vespiformis* (Vespop®)+TX, *Galendromus occidentalis*+TX, *Goniozus legneri*+TX,

*Habrobracon hebetor*+TX, *Harmonia axyridis* (Harmo-Beetle®)+TX, *Heterorhabditis* spp. (Lawn Patrol®)+TX, *Heterorhabditis bacteriophora* (NemaShield HB®+TX, Nemaseek®+TX, Terranem-Nam®+TX, Terranem®+TX, Larvanem®+TX, B-Green®+TX, NemAttack®+TX, Nematop®)+TX, *Heterorhabditis megidis* (Nemasys H®+TX, BioNem H®+TX, Exhibitline hm®+TX, Larvanem-M®)+TX, *Hippodamia convergens*+TX, *Hypoaspis aculeifer* (Aculeifer-System®+TX, Entomite-A®)+TX, *Hypoaspis miles* (Hypoline m®+TX, Entomite-M®)+TX, *Lbalia leucospoides*+TX, *Lecanoideus floccissimus*+TX, *Lemophagus errabundus*+TX, *Leptomastidea abnormis*+TX, *Leptomastix dactylopii* (Leptopar®)+TX, *Leptomastix epona*+TX, *Lindorus lophanthae*+TX, *Lipolexis oregmae*+TX, *Lucilia caesar* (Natufly®)+TX, *Lysiphlebus testaceipes*+TX, *Macrolophus caliginosus* (Mirical-N®+TX, Macroline c®+TX, Mirical®)+TX, *Mesoseiulus longipes*+TX, *Metaphycus flavus*+TX, *Metaphycus lounsburyi*+TX, *Micromus angulatus* (Milacewing®)+TX, *Microterys flavus*+TX, *Muscidifurax raptorellus* and *Spalangia cameroni* (Biopar®)+TX, *Neodryinus typhlocybae*+TX, *Neoseiulus califomicus*+TX, *Neoseiulus cucumeris* (THRYPEX®)+TX, *Neoseiulus fallacis*+TX, *Nesideocoris tenuis* (NesidioBug®+TX, Nesibug®)+TX, *Ophyra aenescens* (Biofly®)+TX, *Orius insidiosus* (Thripor-I®+TX, Oriline i®)+TX, *Orius laevigatus* (Thripor-L®+TX, Oriline I®)+TX, *Orius majusculus* (Oriline m®)+TX, *Orius strigicollis* (Thripor-S®)+TX, *Pauesia juniperorum*+TX, *Pediobius foveolatus*+TX, *Phasmarhabditis hermaphrodita* (Nemaslug®)+TX, *Phymastichus coffea*+TX, *Phytoseiulus macropilus*+TX, *Phytoseiulus persimilis* (Spidex®+TX, Phytoline p®)+TX, *Podisus maculiventris* (Podisus®)+TX, *Pseudacteon curvatus*+TX, *Pseudacteon obtusus*+TX, *Pseudacteon tricuspis*+TX, *Pseudaphycus maculipennis*+TX, *Pseudleptomastix mexicana*+TX, *Psyllaephagus pilosus*+TX, *Psyttalia concolor* (complex)+TX, *Quadrastichus* spp.+TX, *Rhyzobius lophanthae*+TX, *Rodolia cardinalis*+TX, *Rumina decollate*+TX, *Semielacher petiolatus*+TX, *Sitobion avenae* (Ervibank®)+TX, *Steinemema carpocapsae* (Nematac C®+TX, Millenium®+TX, BioNem C®+TX, NemAttack®+TX, Nemastar®+TX, Capsanem®)+TX, *Steinemema feltiae* (NemaShield®+TX, Nemasys F®+TX, BioNem F®+TX, Steinernema-System®+TX, NemAttack®+TX, Nemaplus®+TX, Exhibitline sf®+TX, Sciarid®+TX, Entonem®)+TX, *Steinemema kraussei* (Nemasys L®+TX, BioNem L®+TX, Exhibitline srb®)+TX, *Steinernema riobrave* (BioVector®+TX, BioVektor®)+TX, *Steinernema scapterisci* (Nematac S®)+TX, *Steinernema* spp.+TX, *Steinernematid* spp. (Guardian Nematodes®)+TX, *Stethorus punctillum* (Stethorus®)+TX, *Tamarixia radiate*+TX, *Tetrastichus setifer*+TX, *Thripobius semiluteus*+TX, *Torymus sinensis*+TX, *Trichogramma brassicae* (Tricholine b®)+TX, *Trichogramma brassicae* (TrichoStrip®)+TX, *Trichogramma evanescens*+TX, *Trichogramma minutum*+TX, *Trichogramma ostriniae*+TX, *Trichogramma platneri*+TX, *Trichogramma pretiosum*+TX, *Xanthopimpla stemmator*; and other biologicals including: abscisic acid+TX, bioSea®+TX, *Chondrostereum purpureum* (Chontrol Paste®)+TX, *Colletotrichum gloeosporioides* (Collego®)+TX, Copper Octanoate (Cueva®)+TX, Delta traps (Trapline d®)+TX, *Erwinia amylovora* (Harpin) (ProAct®+TX, Ni-HIBIT Gold CST®)+TX, Fern-phosphate (Ferramol®)+TX, Funnel traps (Trapline y®)+TX, Gallex®+TX, Grower's Secret®+TX, Homo-brassonolide+TX, Iron Phosphate (Lilly Miller Worry Free Ferramol Slug & Snail Bait®)+TX, MCP hail trap (Trapline f®)+TX, *Microctonus hyperodae*+TX, *Mycoleptodiscus terrestris* (Des-X®)+TX, BioGain®+TX, Aminomite®+TX, Zenox®+TX, Pheromone trap (Thripline ams®)+TX, potassium bicarbonate (MilStop®)+TX, potassium salts of fatty acids (Sanova®)+TX, potassium silicate solution (SD-Matrix®)+TX, potassium iodide+potassium-thiocyanate (Enzicur®)+TX, SuffOil-X®+TX, Spider venom+TX, *Nosema locustae* (Semaspore Organic Grasshopper Control®)+TX, Sticky traps (Trapline YF®+TX, Rebell Amarillo®)+TX and Traps (Takitrapline y+b®)+TX.

The references in brackets behind the active ingredients, e.g. [3878-19-1] refer to the Chemical Abstracts Registry number. The above described mixing partners are known. Where the active ingredients are included in "The Pesticide Manual" [The Pesticide Manual - A World Compendium; Thirteenth Edition; Editor: C. D. S. TomLin; The British Crop Protection Council], they are described therein under the entry number given in round brackets hereinabove for the particular compound; for example, the compound "abamectin" is described under entry number (1). Where "[CCN]" is added hereinabove to the particular compound, the compound in question is included in the "Compendium of Pesticide Common Names", which is accessible on the internet [A. Wood; *Compendium of Pesticide Common Names*, Copyright 1995-2004]; for example, the compound "acetoprole" is described under the internet address http://www.alanwood.net/pesticides/acetoprole.html.

Most of the active ingredients described above are referred to hereinabove by a so-called "common name", the relevant "ISO common name" or another "common name" being used in individual cases. If the designation is not a "common name", the nature of the designation used instead is given in round brackets for the particular compound; in that case, the IUPAC name, the IUPAC/Chemical Abstracts name, a "chemical name", a "traditional name", a "compound name" or a "develoment code" is used or, if neither one of those designations nor a "common name" is used, an "alternative name" is employed. "CAS Reg. No" means the Chemical Abstracts Registry Number.

The active ingredient mixture of the compounds of formula I selected from Tables 1 to 12 and P with active ingredients described above comprises a compound selected from Tables 1 to 12 and P and an active ingredient as described above preferably in a mixing ratio of from 100:1 to 1:6000, especially from 50:1 to 1:50, more especially in a ratio of from 20:1 to 1:20, even more especially from 10:1 to 1:10, very especially from 5:1 and 1:5, special preference being given to a ratio of from 2:1 to 1:2, and a ratio of from 4:1 to 2:1 being likewise preferred, above all in a ratio of 1:1, or 5:1, or 5:2, or 5:3, or 5:4, or 4:1, or 4:2, or 4:3, or 3:1, or 3:2, or 2:1, or 1:5, or 2:5, or 3:5, or 4:5, or 1:4, or 2:4, or 3:4, or 1:3, or 2:3, or 1:2, or 1:600, or 1:300, or 1:150, or 1:35, or 2:35, or 4:35, or 1:75, or 2:75, or 4:75, or 1:6000, or 1:3000, or 1:1500, or 1:350, or 2:350, or 4:350, or 1:750, or 2:750, or 4:750. Those mixing ratios are by weight.

The mixtures as described above can be used in a method for controlling pests, which comprises applying a composition comprising a mixture as described above to the pests or their environment, with the exception of a method for treatment of the human or animal body by surgery or therapy and diagnostic methods practised on the human or animal body.

The mixtures comprising a compound of formula I selected from Tables 1 to 12 and P and one or more active ingredients as described above can be applied, for example, in a single "ready-mix" form, in a combined spray mixture composed from separate formulations of the single active ingredient components, such as a "tank-mix", and in a combined use of the single active ingredients when applied in a sequential manner, i.e. one after the other with a reasonably short period, such as a few hours or days. The order of applying the compounds of formula I selected from Tables 1 to 12 and P and the active ingredients as described above is not essential for working the present invention.

The compositions according to the invention can also comprise further solid or liquid auxiliaries, such as stabilizers, for example unepoxidized or epoxidized vegetable oils (for example epoxidized coconut oil, rapeseed oil or soya oil), antifoams, for example silicone oil, preservatives, viscosity regulators, binders and/or tackifiers, fertilizers or other active ingredients for achieving specific effects, for example bactericides, fungicides, nematocides, plant activators, molluscicides or herbicides.

The compositions according to the invention are prepared in a manner known per se, in the absence of auxiliaries for example by grinding, screening and/or compressing a solid active ingredient and in the presence of at least one auxiliary for example by intimately mixing and/or grinding the active ingredient with the auxiliary (auxiliaries). These processes for the preparation of the compositions and the use of the compounds I for the preparation of these compositions are also a subject of the invention.

The application methods for the compositions, that is the methods of controlling pests of the abovementioned type, such as spraying, atomizing, dusting, brushing on, dressing, scattering or pouring—which are to be selected to suit the intended aims of the prevailing circumstances—and the use of the compositions for controlling pests of the abovementioned type are other subjects of the invention. Typical rates of concentration are between 0.1 and 1000 ppm, preferably between 0.1 and 500 ppm, of active ingredient. The rate of application per hectare is generally 1 to 2000 g of active ingredient per hectare, in particular 10 to 1000 g/ha, preferably 10 to 600 g/ha.

A preferred method of application in the field of crop protection is application to the foliage of the plants (foliar application), it being possible to select frequency and rate of application to match the danger of infestation with the pest in question. Alternatively, the active ingredient can reach the plants via the root system (systemic action), by drenching the locus of the plants with a liquid composition or by incorporating the active ingredient in solid form into the locus of the plants, for example into the soil, for example in the form of granules (soil application). In the case of paddy rice crops, such granules can be metered into the flooded paddy-field.

The compounds of the invention and compositions thereof are also be suitable for the protection of plant propagation material, for example seeds, such as fruit, tubers or kernels, or nursery plants, against pests of the abovementioned type. The propagation material can be treated with the compound prior to planting, for example seed can be treated prior to sowing. Alternatively, the compound can be applied to seed kernels (coating), either by soaking the kernels in a liquid composition or by applying a layer of a solid composition. It is also possible to apply the compositions when the propagation material is planted to the site of application, for example into the seed furrow during drilling. These treatment methods for plant propagation material and the plant propagation material thus treated are further subjects of the invention. Typical treatment rates would depend on the plant and pest/fungi to be controlled and are generally between 1 to 200 grams per 100 kg of seeds, preferably between 5 to 150 grams per 100 kg of seeds, such as between 10 to 100 grams per 100 kg of seeds.

The term seed embraces seeds and plant propagules of all kinds including but not limited to true seeds, seed pieces, suckers, corns, bulbs, fruit, tubers, grains, rhizomes, cuttings, cut shoots and the like and means in a preferred embodiment true seeds.

The present invention also comprises seeds coated or treated with or containing a compound of formula I. The term "coated or treated with and/or containing" generally signifies that the active ingredient is for the most part on the surface of the seed at the time of application, although a greater or lesser part of the ingredient may penetrate into the seed material, depending on the method of application. When the said seed product is (re)planted, it may absorb the active ingredient. In an embodiment, the present invention makes available a plant propagation material adhered thereto with a compound of formula (I). Further, it is hereby made available, a composition comprising a plant propagation material treated with a compound of formula (I).

Seed treatment comprises all suitable seed treatment techniques known in the art, such as seed dressing, seed coating, seed dusting, seed soaking and seed pelleting. The seed treatment application of the compound formula (I) can be carried out by any known methods, such as spraying or by dusting the seeds before sowing or during the sowing/planting of the seeds.

BIOLOGICAL EXAMPLES

Example B1

Activity Against *Spodoptera Littoralis* (Egyptian Cotton Leaf Worm)

Cotton leaf discs were placed on agar in 24-well microtiter plates and sprayed with aqueous test solutions prepared from 10,000 ppm DMSO stock solutions. After drying the leaf discs were infested with five L1 larvae. The samples were assessed for mortality, anti-feedant effect, and growth inhibition in comparison to untreated samples 3 days after infestation. Control of *Spodoptera littoralis* by a test sample is when at least one of mortality, anti-feedant effect, and growth inhibition is higher than the untreated sample.

The following compounds gave an effect of at least 80% control in at least one of the three categories (mortality, anti-feedancy or growth inhibition) at an application rate of 200 ppm: P2, P3, P4, P5, P6, P8, P9, P11, P14, P16, P17, P18, P19, P20, P21, P22, P23, P24, P25, P26, P27, P28, P29, P31, P32, P33, P34, P35, P36, P37, P38, P39, P40, P41, P42, P43, P44, P45, P46, P47, P48, P49, P50, P51, P52, P53, P54, P56, P57, P58, P59, P60, P61, P62, P63, P64, P65, P66, P69 and P70.

Example B2

Activity Against *Spodoptera Littoralis* (Egyptian Cotton Leaf Worm)

Test compounds were applied by pipette from 10,000 ppm DMSO stock solutions into 24-well plates and mixed with agar. Lettuce seeds were placed on the agar and the multi well plate was closed by another plate which contains also agar. After 7 days the roots have absorbed the compound and the lettuce has grown into the lid plate. The lettuce leafs were now cut off into the lid plate. *Spodoptera* eggs were pipetted through a plastic stencil on a humid gel blotting paper and the plate closed with it. The samples were assessed for mortality, anti-feedant effect and growth inhibition in comparison to untreated samples 6 days after infestation.

The following compounds gave an effect of at least 80% control in at least one of the three categories (mortality, anti-feedancy or growth inhibition) at an application rate of 12.5 ppm: P2, P3, P8, P9, P11 and P17, P19, P20, P22, P23, P25, P26, P28, P30, P31, P32, P33, P40, P42, P43, P44, P45, P46, P47, P48, P49, P50, P51, P52, P53, P54, P60 and P61.

Example B3

Activity Against *Plutella Xylostella* (Diamond Back Moth)

24-well microtiter plates with artificial diet were treated with aqueous test solutions prepared from 10,000 ppm DMSO stock solutions by pipetting. After drying, the plates were infested with L2 larvae (10 to 15 per well). The samples were assessed for mortality and growth inhibition in comparison to untreated samples 5 days after infestation.

The following compounds gave an effect of at least 80% in at least one of the two categories (mortality or growth inhibition) at an application rate of 200 ppm: P2, P3, P4, P5, P6, P8, P9, P11, P14, P16, P17, P18, P19, P20, P22, P23, P25, P26, P27, P28, P29, P31, P32, P33, P34, P35, P36, P37, P38, P40, P41, P42, P43, P44, P45, P46, P47, P48, P49, P50, P51, P52, P53, P54, P56, P57, P60, P61, P62, P63, P64, P65, P66, P67, P68, P69 and P70.

Example B4

Activity Against Diabrotica Balteata (Corn Root Worm)

Maize sprouts, placed on an agar layer in 24-well microtiter plates were treated with aqueous test solutions prepared from 10,000 ppm DMSO stock solutions by spraying. After drying, the plates were infested with L2 larvae (6 to 10 per well). The samples were assessed for mortality and growth inhibition in comparison to untreated samples 4 days after infestation.

The following compounds gave an effect of at least 80% in at least one of the two categories (mortality or growth inhibition) at an application rate of 200 ppm: P2, P4, P5, P6, P8, P9, P11, P12, P13, P14, P15, P16, P17, P18, P19, P20, P22, P23, P25, P26, P27, P28, P29, P30, P31, P32, P33, P34, P35, P36, P37, P38, P39, P40, P41, P42, P43, P44, P45, P46, P47, P48, P49, P50, P51, P52, P53, P54, P56, P57, P58, P59, P60, P61, P63, P64, P65, P66, P67, P68, P69 and P70.

Example B5

Activity Against *Myzus Persicae* (Green Peach Aphid)

Sunflower leaf discs were placed on agar in a 24-well microtiter plate and sprayed with aqueous test solutions prepared from 10,000 ppm DMSO stock solutions. After drying, the leaf discs were infested with an aphid population of mixed ages. The samples were assessed for mortality 6 days after infestation.

The following compounds resulted in at least 80% mortality at an application rate of 200 ppm: P2, P5, P6, P8, P11, P16, P17, P18, P19, P20, P40, P42, P45, P46, P51, P53, P54, P56, P60, P63, P64 and P66.

Example B6

Activity Against *Euschistus Heros* (Neotropical Brown Stink Bug)

Soybean leaf on agar in 24-well microtiter plates were sprayed with aqueous test solutions prepared from 10,000 ppm DMSO stock solutions. After drying the leaf were infested with N-2 nymphs. The samples were assessed for mortality 5 days after infestation. The following compounds resulted in at least 80% mortality at an application rate of 200 ppm: P2, P5, P6, P8, P11, P16, P17, P18, P19, P20, P23, P25, P26, P28, P29, P32, P33, P34, P40, P41, P42, P43, P44, P45, P46, P47, P48, P49, P50, P51, P52, P54, P61, P62, P63, P64, P65, P66, P67, P68 and P69.

Example B7

Activity Against *Myzus Persicae* (Green Peach Aphid)

Roots of pea seedlings infested with an aphid population of mixed ages were placed directly in the aqueous test solutions prepared from 10,000 DMSO stock solutions. The samples were assessed for mortality 6 days after placing seedlings in test solutions. The following compound resulted in at least 80% mortality at a test rate of 24 ppm: P17, P42 and P63.

Example B8

Activity Against *Tetranychus Urticae* (Two-Spotted Spider Mite)

Bean leaf discs on agar in 24-well microtiter plates were sprayed with aqueous test solutions prepared from 10,000 ppm DMSO stock solutions. After drying the leaf discs were infested with a mite population of mixed ages. The samples were assessed for mortality on mixed population (mobile stages) 8 days after infestation. The following compound resulted in at least 80% mortality at an application rate of 200 ppm: P8, P29, P31, P45 and P70.

Example B9

Activity Against *Aedes Aegypti* (Yellow Fever Mosquito)

Test solutions, at an application rate of 200ppm in ethanol, were applied to 12-well tissue culture plates. Once the deposits were dry, five, two to five days old adult female Aedes aegypti were added to each well, and sustained with a 10% sucrose solution in a cotton wool plug. Assessment of knockdown was made one hour after introduction, and mortality was assessed at 24 and 48 hours after introduction. The following compounds gave at least 80% control of Aedes aegypti after 48h and/or 24 h: P2, P8, P9, P11, P16.

Example B10

Activity Against *Bemisia Tabaci* (Cotton White Fly)

Cotton leaf discs were placed on agar in 24-well microtiter plates and sprayed with aqueous test solutions prepared from 10,000 ppm DMSO stock solutions. After drying the leaf discs were infested with adult white flies. The samples were checked for mortality 6 days after incubation.

The following compound resulted in at least 80% mortality at an application rate of 200 ppm: P20, P39 and P57.

The invention claimed is:
1. A compound of formula I

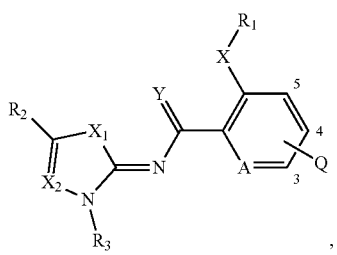

(I)

wherein
A is CH or N;
Q is attached to the 3- or 4-position; and is phenyl which can be mono- or polysubstituted by substituents selected from the group consisting of halogen, cyano, $C_1$-$C_4$alkyl, $C_1$-$C_4$haloalkyl, $C_1$-$C_4$haloalkoxy, $C_1$-$C_4$alkoxy, $C_1$-$C_4$haloalkylsulfanyl, $C_1$-$C_4$haloalkylsulfinyl, $C_1$-$C_4$haloalkylsulfonyl and —C(O)$C_1$-$C_4$haloalkyl; or
Q is a five- to ten-membered monocyclic or fused bicyclic ring system linked via a carbon atom to the ring which contains the group A, said ring system can be aromatic, partially saturated or fully saturated and contains 1 to 4 hetero atoms selected from the group consisting of nitrogen, oxygen and sulfur, it not being possible for each ring system to contain more than 2 oxygen atoms and more than 2 sulfur atoms, said five- to ten-membered ring system can be mono- to polysubstituted by substituents independently selected from the group consisting of halogen, cyano, $C_1$-$C_4$alkyl, $C_1$-$C_4$haloalkyl, $C_1$-$C_4$haloalkoxy, $C_1$-$C_4$alkoxy, $C_1$-$C_4$alkylsulfanyl, $C_1$-$C_4$alkylsulfinyl, $C_1$-$C_4$alkylsulfonyl, —C(O)$C_1$-$C_4$alkyl, $C_1$-$C_4$haloalkylsulfanyl, $C_1$-$C_4$haloalkylsulfinyl, $C_1$-$C_4$haloalkyl sulfonyl and —C(O)$C_1$-$C_4$haloalkyl; or
Q is a five- to six-membered, aromatic, partially saturated or fully saturated ring system linked via a nitrogen atom to the ring which contains the group A, said ring system can be mono- or polysubstituted by substituents selected from the group consisting of halogen, cyano, $C_1$-$C_4$alkyl, $C_1$-$C_4$haloalkyl, $C_1$-$C_4$haloalkoxy, $C_1$-$C_4$alkoxy, $C_1$-$C_4$alkylsulfanyl, $C_1$-$C_4$alkylsulfinyl, $C_1$-$C_4$alkylsulfonyl, —C(O)$C_1$-$C_4$alkyl, $C_1$-$C_4$haloalkylsulfanyl, $C_1$-$C_4$haloalkylsulfinyl, $C_1$-$C_4$haloalkylsulfonyl and —C(O)$C_1$-$C_4$haloalkyl; and said ring system contains 1, 2 or 3 heteroatoms selected from the group consisting of nitrogen, oxygen and sulfur, where said ring system may not contain more than one oxygen atom and not more than one sulfur atom; or
Q is $C_3$-$C_6$cycloalkyl, or $C_3$-$C_6$cycloalkyl mono- or polysubstituted by substituents selected from the group consisting of halogen, cyano, $C_1$-$C_4$alkyl, $C_1$-$C_4$haloalkyl, $C_3$-$C_6$cycloalkyl and phenyl, wherein said phenyl can be mono- or polysubstituted by substituents selected from the group consisting of halogen, cyano, $C_1$-$C_4$alkyl, $C_1$-$C_4$haloalkyl, $C_1$-$C_4$haloalkoxy, $C_1$-$C_4$alkoxy, $C_1$-$C_4$haloalkylsulfanyl, $C_1$-$C_4$haloalkylsulfinyl, $C_1$-$C_4$haloalkylsulfonyl and —C(O)$C_1$-$C_4$haloalkyl; or Q is $C_2$-$C_6$alkenyl, or $C_2$-$C_6$alkenyl mono- or polysubstituted by substituents selected from the group consisting of halogen, cyano, $C_1$-$C_4$alkyl, $C_1$-$C_4$haloalkyl, $C_1$-$C_4$alkoxy, $C_3$-$C_6$cycloalkyl and phenyl, wherein said phenyl can be mono- or polysubstituted by substituents selected from the group consisting of halogen, cyano, $C_1$-$C_4$alkyl, $C_1$-$C_4$haloalkyl, $C_1$-$C_4$haloalkoxy, $C_1$-$C_4$alkoxy, $C_1$-$C_4$haloalkylsulfanyl, $C_1$-$C_4$haloalkylsulfinyl, $C_1$-$C_4$haloalkylsulfonyl and —C(O)$C_1$-$C_4$haloalkyl; or Q is $C_2$-$C_6$alkynyl, or $C_2$-$C_6$alkynyl mono- or polysubstituted by substituents selected from the group consisting of halogen, cyano, $C_1$-$C_4$alkyl, $C_1$-$C_4$haloalkyl, $C_3$-$C_6$cycloalkyl, tri($C_1$-$C_4$alkyl)silyl and phenyl, wherein said phenyl can be mono- or polysubstituted by substituents selected from the group consisting of halogen, cyano, $C_1$-$C_4$alkyl, $C_1$-$C_4$haloalkyl, $C_1$-$C_4$haloalkoxy, $C_1$-$C_4$alkoxy, $C_1$-$C_4$halo-alkylsulfanyl, $C_1$-$C_4$haloalkylsulfinyl, $C_1$-$C_4$haloalkylsulfonyl and —C(O)$C_1$-$C_4$haloalkyl; or Q is $C_1$-$C_6$haloalkylsulfanyl, $C_1$-$C_6$haloalkylsulfinyl, $C_1$-$C_6$haloalkylsulfonyl, $C_1$-$C_6$haloalkoxy, —C(O)$C_1$-$C_4$haloalkyl, $C_1$-$C_6$alkylsulfanyl, $C_1$-$C_6$alkylsulfinyl, or $C_1$-$C_6$alkylsulfonyl;

X is S, SO or $SO_2$;
$R_1$ is $C_1$-$C_4$alkyl, $C_1$-$C_4$haloalkyl, $C_3$-$C_6$cycloalkyl, $C_3$-$C_6$cycloalkyl-$C_1$-$C_4$alkyl; or
$R_1$ is $C_3$-$C_6$cycloalkyl mono- or polysubstituted by substituents selected from the group consisting of halogen, cyano and $C_1$-$C_4$alkyl; or
$R_1$ is $C_3$-$C_6$cycloalkyl-$C_1$-$C_4$alkyl mono- or polysubstituted by substituents selected from the group consisting of halogen, cyano and $C_1$-$C_4$alkyl; or
$R_1$ is $C_2$-$C_6$alkenyl, $C_2$-$C_6$haloalkenyl or $C_2$-$C_6$alkynyl;
$X_1$ is O, S or $CR_6$=CH, wherein $R_6$ is hydrogen, halogen, $C_1$-$C_6$haloalkyl or $C_1$-$C_6$haloalkyl substituted by one or two substituents selected from the group consisting of hydroxyl, methoxy and cyano; or $R_6$ is $C_1$-$C_4$haloalkylsulfanyl, $C_1$-$C_4$haloalkylsulfinyl, $C_1$-$C_4$haloalkylsulfonyl, O($C_1$-$C_4$haloalkyl), or —C(O)$C_1$-$C_4$haloalkyl;
or $X_1$ is N—$R_4$, wherein $R_4$ is $C_1$-$C_4$alkyl;
$X_2$ is N or C—$R_5$, wherein $R_5$ is hydrogen, $C_1$-$C_4$alkyl, $C_1$-$C_4$haloalkyl, halogen or cyano;
$R_2$ is hydrogen, halogen, cyano, $C_1$-$C_6$haloalkyl, or $C_1$-$C_6$haloalkyl substituted by one or two substituents selected from the group consisting of hydroxyl, methoxy and cyano; or
$R_2$ is $C_1$-$C_4$haloalkylsulfanyl, $C_1$-$C_4$haloalkylsulfinyl, $C_1$-$C_4$haloalkylsulfonyl, O($C_1$-$C_4$haloalkyl), or —C(O) $C_1$-$C_4$haloalkyl;
$R_3$ is $C_1$-$C_4$alkyl, $C_2$-$C_6$alkenyl, $C_2$-$C_6$alkynyl, $C_1$-$C_4$alkoxy-$C_1$-$C_4$alkyl or $C_3$-$C_6$cycloalkyl;
Y is O or S;
and agrochemically acceptable salts, stereoisomers, enantiomers, tautomers and N-oxides of those compounds.

2. A compound of formula I according to claim 1, represented by the compounds of formula I-1

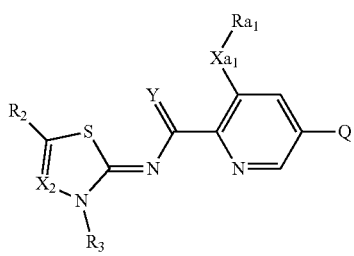

(I-1)

wherein
Y, $R_2$, $R_3$, $X_2$ and Q are as defined under formula I in claim 1;
$Xa_1$ is S, SO or $SO_2$; and
$Ra_1$ is methyl, ethyl, n-propyl, i-propyl or cyclopropylmethyl.

3. A compound of formula I-1 according to claim 2, wherein
Q is selected from the group consisting of J-1 to J-45 (where the arrow represents the point of attachment of the heterocycle to the radical Q):

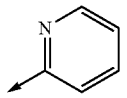 J-1

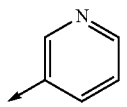 J-2

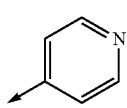 J-3

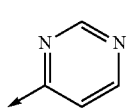 J-4

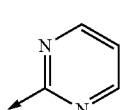 J-5

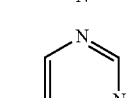 J-6

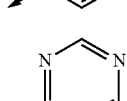 J-7

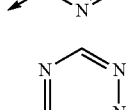 J-8

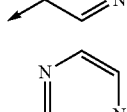 J-9

-continued

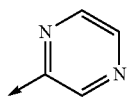 J-10

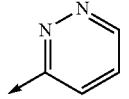 J-11

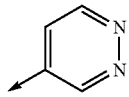 J-12

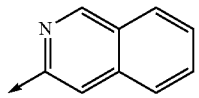 J-13

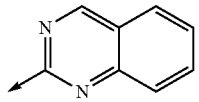 J-14

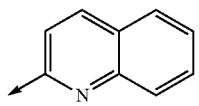 J-15

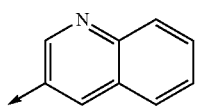 J-16

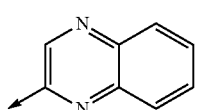 J-17

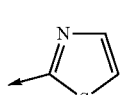 J-18

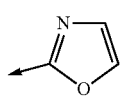 J-19

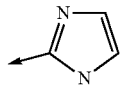 J-20

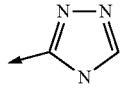 J-21

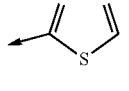 J-22

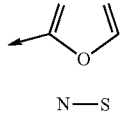 J-23

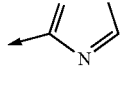 J-24

-continued

J-25 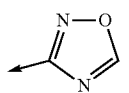

J-26 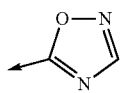

J-27 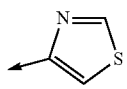

J-28 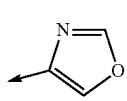

J-29 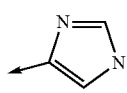

J-30 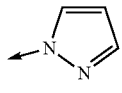

J-31 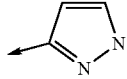

J-32 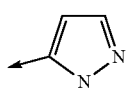

J-33 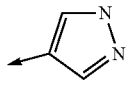

J-34 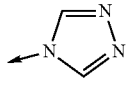

J-35 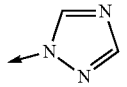

J-36 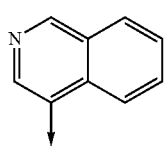

J-37 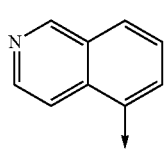

J-38 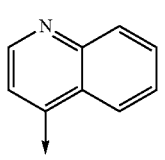

-continued

J-39 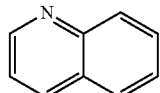

J-40 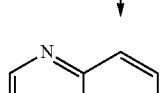

J-41 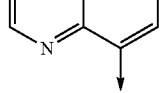

J-42 

J-43 

J-44  and

J-45 , wherein each group J-1 to J-45 is mono- di- or trisubstituted with Rx, wherein each Rx is independently selected from the group consisting of hydrogen, halogen, cyano, $C_1$-$C_4$alkyl, $C_1$-$C_4$haloalkyl, $C_1$-$C_4$haloalkoxy, $C_1$-$C_4$alkoxy, $C_1$-$C_4$alkylsulfanyl, $C_1$-$C_4$alkylsulfinyl, $C_1$-$C_4$alkylsulfonyl, —C(O)$C_1$-$C_4$alkyl, $C_1$-$C_4$haloalkylsulfanyl, $C_1$-$C_4$haloalkylsulfinyl, $C_1$-$C_4$haloalkylsulfonyl and —C(O)$C_1$-$C_4$haloalkyl.

4. A compound of formula I according to claim 1, represented by the compounds of formula I-2

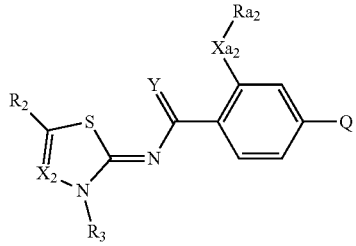

(I-2)

wherein
Y, $R_2$, $R_3$, $X_2$ and Q are as defined under formula I in claim 1;
$Xa_2$ is S, SO or $SO_2$; and Ra$_2$ is methyl, ethyl, n-propyl, i-propyl or cyclopropylmethyl.
5. A compound of formula I-2 according to claim 4, wherein
Q is selected from the group consisting of J-1 to J-45 (where the arrow represents the point of attachment)
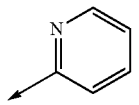 J-1
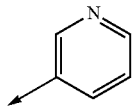 J-2
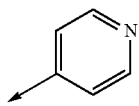 J-3
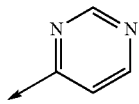 J-4
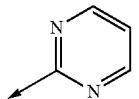 J-5
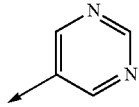 J-6
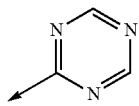 J-7
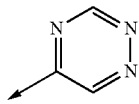 J-8
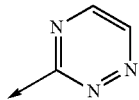 J-9
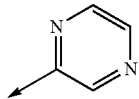 J-10
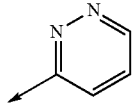 J-11
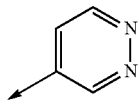 J-12
-continued
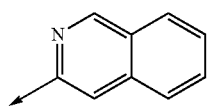
J-13
J-14
J-15
J-16
J-17
J-18
J-19
J-20
J-21
J-22
J-23
J-24
J-25
J-26
J-27

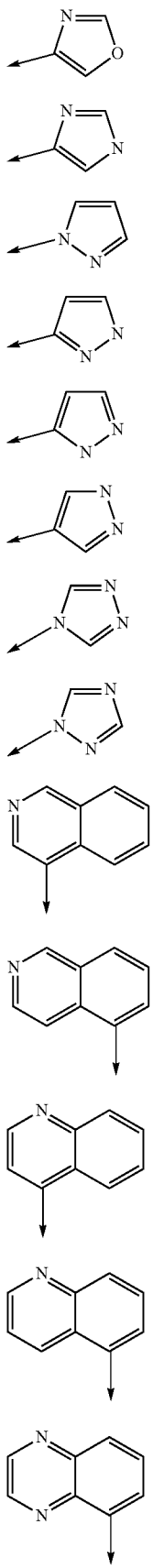

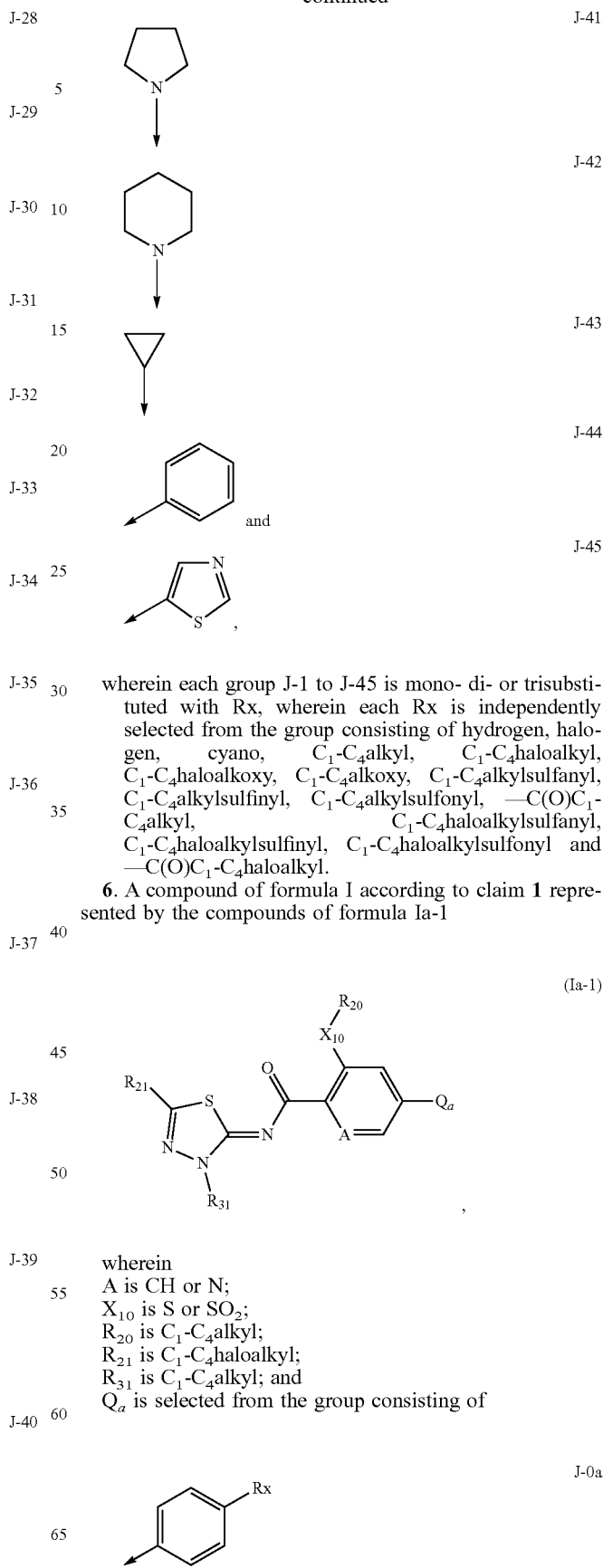

wherein each group J-1 to J-45 is mono- di- or trisubstituted with Rx, wherein each Rx is independently selected from the group consisting of hydrogen, halogen, cyano, C₁-C₄alkyl, C₁-C₄haloalkyl, C₁-C₄haloalkoxy, C₁-C₄alkoxy, C₁-C₄alkylsulfanyl, C₁-C₄alkylsulfinyl, C₁-C₄alkylsulfonyl, —C(O)C₁-C₄alkyl, C₁-C₄haloalkylsulfanyl, C₁-C₄haloalkylsulfinyl, C₁-C₄haloalkylsulfonyl and —C(O)C₁-C₄haloalkyl.

6. A compound of formula I according to claim 1 represented by the compounds of formula Ia-1 wherein
A is CH or N;
X₁₀ is S or SO₂;
R₂₀ is C₁-C₄alkyl;
R₂₁ is C₁-C₄haloalkyl;
R₃₁ is C₁-C₄alkyl; and
Q_a is selected from the group consisting of

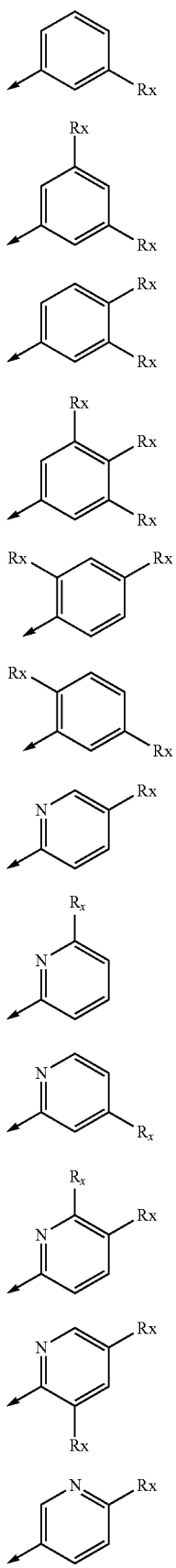
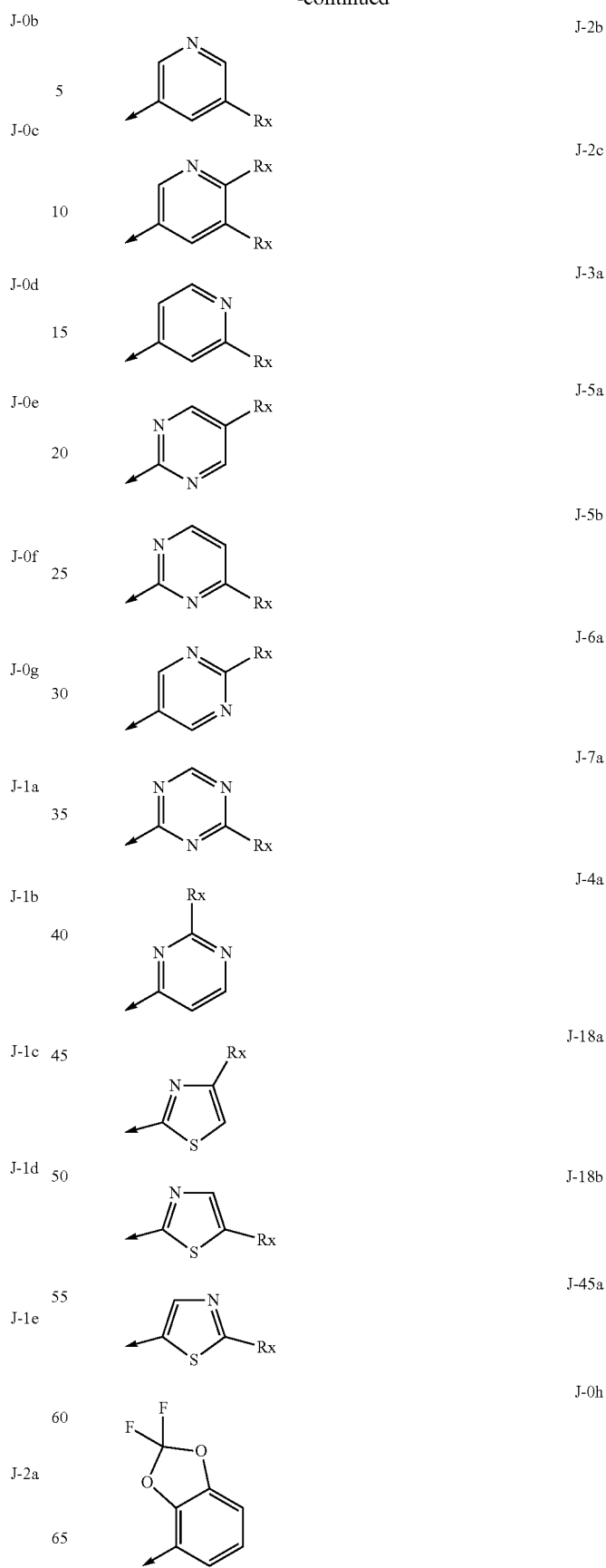

-continued

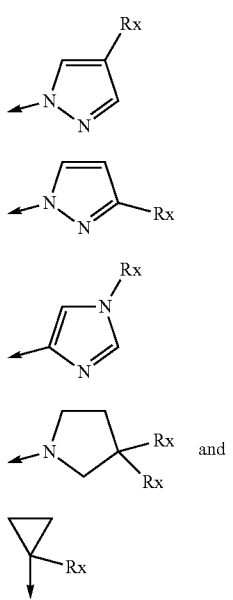

J-30a

J-30b

J-33a

J-41a

J-43a wherein each group $Q_a$ is mono- di- or trisubstituted with Rx, wherein each Rx is independently selected from the group consisting of hydrogen, halogen, cyano, $C_1$-$C_4$alkyl, $C_1$-$C_4$haloalkyl, $C_1$-$C_4$haloalkoxy, $C_1$-$C_4$alkoxy, $C_1$-$C_4$alkylsulfanyl, $C_1$-$C_4$alkylsulfinyl, $C_1$-$C_4$alkylsulfonyl, —C(O)$C_1$-$C_4$alkyl, $C_1$-$C_4$haloalkylsulfanyl, $C_1$-$C_4$haloalkylsulfinyl, $C_1$-$C_4$haloalkylsulfonyl and —C(O)$C_1$-$C_4$haloalkyl.

7. A compound of formula I according to claim 1 represented by the compounds of formula Ia-2

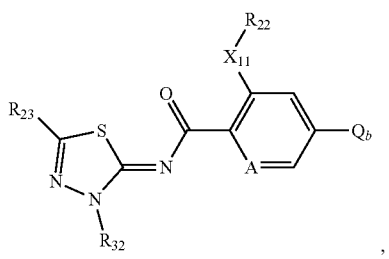

(Ia-2)

wherein
A is CH or N;
$X_{11}$ is S or $SO_2$;
$R_{22}$ is $C_1$-$C_4$alkyl;
$R_{23}$ is $C_1$-$C_4$haloalkyl;
$R_{32}$ is $C_1$-$C_4$alkyl; and
$Q_b$ is selected from the group consisting of

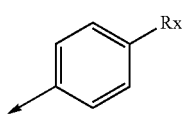

J-0a

-continued

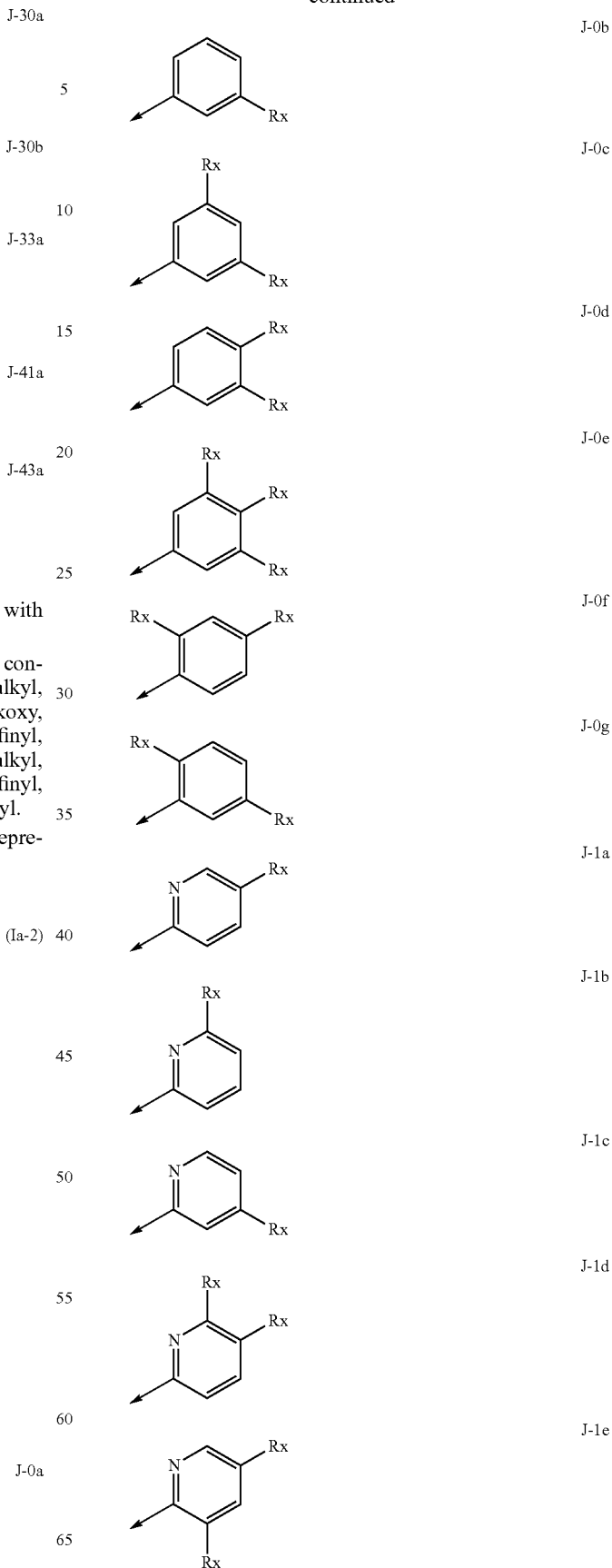

J-0b

J-0c

J-0d

J-0e

J-0f

J-0g

J-1a

J-1b

J-1c

J-1d

J-1e

-continued

J-2a 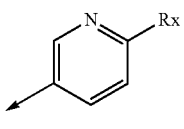

J-2b 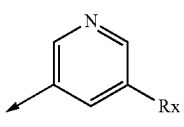

J-3a 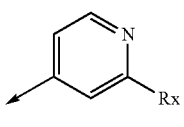

J-5a 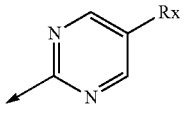

J-5b 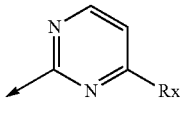

J-6a 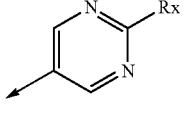

J-4a 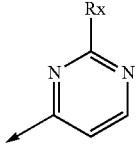

J-18a 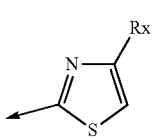

J-18b 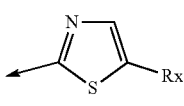

J-45a 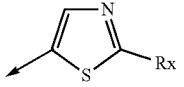

J-0h 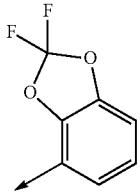

J-30a 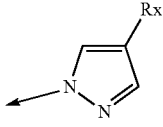

-continued

J-30b 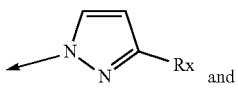 and

J-43a 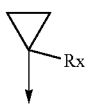

wherein each Rx is independently selected from the group consisting of hydrogen, halogen, cyano, $C_1$-$C_4$alkyl, $C_1$-$C_4$haloalkyl, $C_1$-$C_4$haloalkoxy, $C_1$-$C_4$alkoxy, $C_1$-$C_4$alkylsulfanyl, $C_1$-$C_4$alkylsulfinyl, $C_1$-$C_4$alkylsulfonyl, —C(O)$C_1$-$C_4$alkyl, $C_1$-$C_4$haloalkylsulfanyl, $C_1$-$C_4$haloalkylsulfinyl, $C_1$-$C_4$haloalkylsulfonyl and —C(O)$C_1$-$C_4$haloalkyl.

8. A compound of formula I according to claim 1 represented by the compounds of formula Ia-3

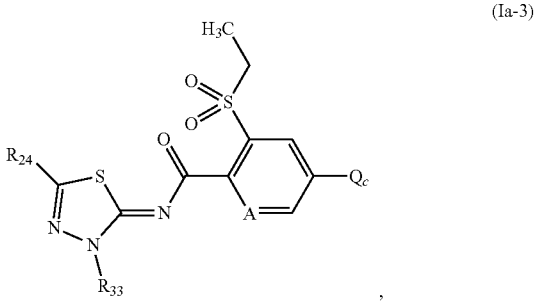

(Ia-3)

wherein

A is CH or N;

$R_{24}$ is $C_1$-$C_4$haloalkyl;

$R_{33}$ is $C_1$-$C_4$alkyl; and $Q_c$ is selected from the group consisting of J-0a 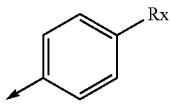

J-0b 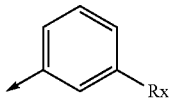

J-0c 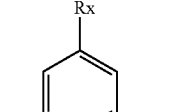

J-0d 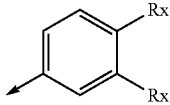

-continued

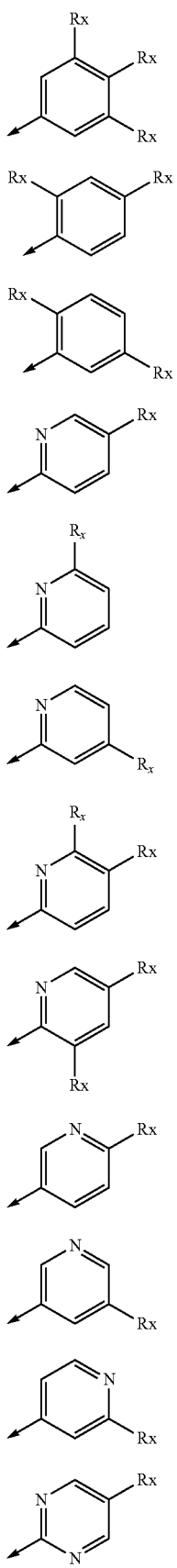

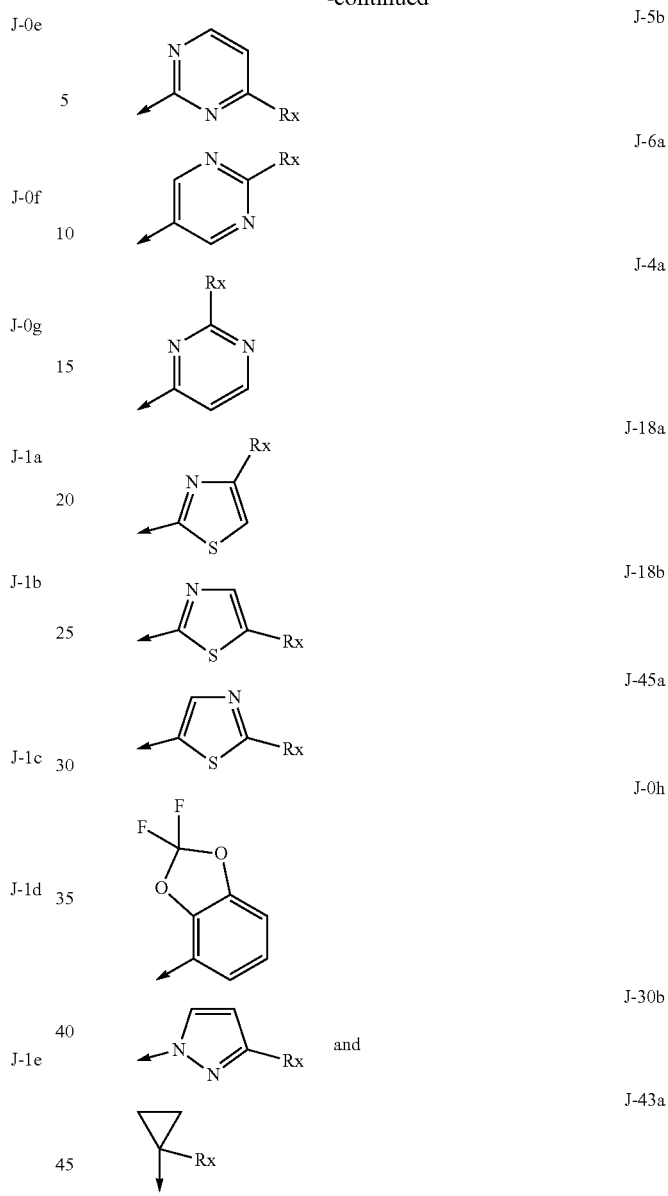

wherein Rx is independently selected from the group consisting of hydrogen, halogen, cyano, $C_1$-$C_4$alkyl, $C_1$-$C_4$haloalkyl, $C_1$-$C_4$alkoxy, $C_1$-$C_4$haloalkoxy, $C_1$-$C_4$alkylsulfanyl and $C_1$-$C_4$alkylsulfonyl.

9. A pesticidal composition, which comprises at least one compound of formula I according to claim 1 or a tautomer thereof, in each case in free form or in agrochemically utilizable salt form, as active ingredient and at least one auxiliary.

10. A method for controlling pests, which comprises applying a composition according to claim 9 to the pests or their environment with the exception of a method for treatment of the human or animal body by surgery or therapy and diagnostic methods practised on the human or animal body.

11. A method for the protection of plant propagation material from the attack by pests, which comprises treating the propagation material or the site, where the propagation material is planted, with a composition according to claim 9.

12. A compound of formula II

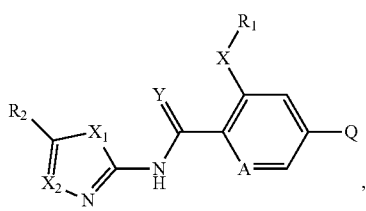

wherein
A is CH or N;
Q is phenyl which can be mono- or polysubstituted by substituents selected from the group consisting of halogen, cyano, $C_1$-$C_4$alkyl, $C_1$-$C_4$haloalkyl, $C_1$-$C_4$haloalkoxy, $C_1$-$C_4$alkoxy, $C_1$-$C_4$haloalkylsulfanyl, $C_1$-$C_4$haloalkylsulfinyl, $C_1$-$C_4$haloalkylsulfonyl and —C(O)$C_1$-$C_4$haloalkyl; or
Q is a five- to ten-membered monocyclic or fused bicyclic ring system linked via a carbon atom to the ring which contains the group A, said ring system can be aromatic, partially saturated or fully saturated and contains 1 to 4 hetero atoms selected from the group consisting of nitrogen, oxygen and sulfur, it not being possible for each ring system to contain more than 2 oxygen atoms and more than 2 sulfur atoms, said five- to ten-membered ring system can be mono- to polysubstituted by substituents independently selected from the group consisting of halogen, cyano, $C_1$-$C_4$alkyl, $C_1$-$C_4$haloalkyl, $C_1$-$C_4$haloalkoxy, $C_1$-$C_4$alkoxy, $C_1$-$C_4$alkylsulfanyl, $C_1$-$C_4$alkylsulfinyl, $C_1$-$C_4$alkylsulfonyl, —C(O)$C_1$-$C_4$alkyl, $C_1$-$C_4$haloalkylsulfanyl, $C_1$-$C_4$haloalkylsulfinyl, $C_1$-$C_4$haloalkylsulfonyl and —C(O)$C_1$-$C_4$haloalkyl; or
Q is a five- to six-membered, aromatic, partially saturated or fully saturated ring system linked via a nitrogen atom to the ring which contains the group A, said ring system can be mono- or polysubstituted by substituents selected from the group consisting of halogen, cyano, $C_1$-$C_4$alkyl, $C_1$-$C_4$haloalkyl, $C_1$-$C_4$haloalkoxy, $C_1$-$C_4$alkoxy, $C_1$-$C_4$alkylsulfanyl, $C_1$-$C_4$alkylsulfinyl, $C_1$-$C_4$alkylsulfonyl, —C(O)$C_1$-$C_4$alkyl, $C_1$-$C_4$haloalkylsulfanyl, $C_1$-$C_4$haloalkylsulfinyl, $C_1$-$C_4$haloalkylsulfonyl and —C(O)$C_1$-$C_4$haloalkyl; and said ring system contains 1, 2 or 3 heteroatoms selected from the group consisting of nitrogen, oxygen and sulfur, where said ring system may not contain more than one oxygen atom and not more than one sulfur atom; or
Q is $C_3$-$C_6$cycloalkyl, or $C_3$-$C_6$cycloalkyl mono- or polysubstituted by substituents selected from the group consisting of halogen, cyano, $C_1$-$C_4$alkyl, $C_1$-$C_4$haloalkyl, $C_3$-$C_6$cycloalkyl and phenyl, wherein said phenyl can be mono- or polysubstituted by substituents selected from the group consisting of halogen, cyano, $C_1$-$C_4$alkyl, $C_1$-$C_4$haloalkyl, $C_1$-$C_4$haloalkoxy, $C_1$-$C_4$alkoxy, $C_1$-$C_4$haloalkylsulfanyl, $C_1$-$C_4$haloalkylsulfinyl, $C_1$-$C_4$haloalkylsulfonyl and —C(O)$C_1$-$C_4$haloalkyl; or
Q is $C_2$-$C_6$alkenyl, or $C_2$-$C_6$alkenyl mono- or polysubstituted by substituents selected from the group consisting of halogen, cyano, $C_1$-$C_4$alkyl, $C_1$-$C_4$haloalkyl, $C_1$-$C_4$alkoxy, $C_3$-$C_6$cycloalkyl and phenyl, wherein said phenyl can be mono- or polysubstituted by substituents selected from the group consisting of halogen, cyano, $C_1$-$C_4$alkyl, $C_1$-$C_4$haloalkyl, $C_1$-$C_4$haloalkoxy, $C_1$-$C_4$alkoxy, $C_1$-$C_4$haloalkylsulfanyl, $C_1$-$C_4$haloalkylsulfinyl, $C_1$-$C_4$haloalkylsulfonyl and —C(O)$C_1$-$C_4$haloalkyl; or
Q is $C_2$-$C_6$alkynyl, or $C_2$-$C_6$alkynyl mono- or polysubstituted by substituents selected from the group consisting of halogen, cyano, $C_1$-$C_4$alkyl, $C_1$-$C_4$haloalkyl, $C_3$-$C_6$cycloalkyl, tri($C_1$-$C_4$alkyl)silyl and phenyl, wherein said phenyl can be mono- or polysubstituted by substituents selected from the group consisting of halogen, cyano, $C_1$-$C_4$alkyl, $C_1$-$C_4$haloalkyl, $C_1$-$C_4$haloalkoxy, $C_1$-$C_4$alkoxy, $C_1$-$C_4$halo-alkylsulfanyl, $C_1$-$C_4$haloalkylsulfinyl, $C_1$-$C_4$haloalkylsulfonyl and —C(O)$C_1$-$C_4$haloalkyl; or
Q is $C_1$-$C_6$haloalkylsulfanyl, $C_1$-$C_6$haloalkylsulfinyl, $C_1$-$C_6$haloalkylsulfonyl, $C_1$-$C_6$haloalkoxy, —C(O)$C_1$-$C_4$haloalkyl, $C_1$-$C_6$alkylsulfanyl, $C_1$-$C_6$alkylsulfinyl, or $C_1$-$C_6$alkylsulfonyl;
X is S, SO or $SO_2$;
$R_1$ is $C_1$-$C_4$alkyl, $C_1$-$C_4$haloalkyl, $C_3$-$C_6$cycloalkyl, $C_3$-$C_6$cycloalkyl-$C_1$-$C_4$alkyl; or
$R_1$ is $C_3$-$C_6$cycloalkyl mono - or polysubstituted by substituents selected from the group consisting of halogen, cyano and $C_1$-$C_4$alkyl; or
$R_1$ is $C_3$-$C_6$cycloalkyl-$C_1$-$C_4$alkyl mono- or polysubstituted by substituents selected from the group consisting of halogen, cyano and $C_1$-$C_4$alkyl; or
$R_1$ is $C_2$-$C_6$alkenyl, $C_2$-$C_6$haloalkenyl or $C_2$-$C_6$alkynyl;
$X_1$ is O, S or $CR_6$=CH, wherein $R_6$ is hydrogen, halogen, $C_1$-$C_6$haloalkyl or $C_1$-$C_6$haloalkyl substituted by one or two substituents selected from the group consisting of hydroxyl, methoxy and cyano; or $R_6$ is $C_1$-$C_4$haloalkylsulfanyl, $C_1$-$C_4$haloalkylsulfinyl, $C_1$-$C_4$haloalkylsulfonyl, O($C_1$-$C_4$haloalkyl), or —C(O)$C_1$-$C_4$haloalkyl;
or $X_1$ is N—$R_4$, wherein $R_4$ is $C_1$-$C_4$alkyl;
$X_2$ is N or C—$R_5$, wherein $R_5$ is hydrogen, $C_1$-$C_4$alkyl, $C_1$-$C_4$haloalkyl, halogen or cyano;
$R_2$ is hydrogen, halogen, cyano, $C_1$-$C_6$haloalkyl, or $C_1$-$C_6$haloalkyl substituted by one or two substituents selected from the group consisting of hydroxyl, methoxy and cyano; or
$R_2$ is $C_1$-$C_4$haloalkylsulfanyl, $C_1$-$C_4$haloalkylsulfinyl, $C_1$-$C_4$haloalkylsulfonyl, O($C_1$-$C_4$haloalkyl), or —C(O)$C_1$-$C_4$haloalkyl;
Y is O or S;
and agrochemically acceptable salts, stereoisomers, enantiomers, tautomers and N-oxides of those compounds.

13. A compound of formula XXI-int

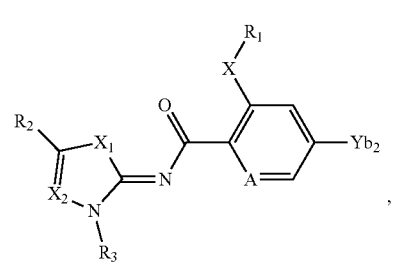

wherein
A is CH or N;
X is S, SO or $SO_2$;
$R_1$ is $C_1$-$C_4$alkyl, $C_1$-$C_4$haloalkyl, $C_3$-$C_6$cycloalkyl, $C_3$-$C_6$cycloalkyl-$C_1$-$C_4$alkyl; or
$R_1$ is $C_3$-$C_6$cycloalkyl mono- or polysubstituted by substituents selected from the group consisting of halogen, cyano and $C_1$-$C_4$alkyl; or
$R_1$ is $C_3$-$C_6$cycloalkyl-$C_1$-$C_4$alkyl mono- or polysubstituted by substituents selected from the group consisting of halogen, cyano and $C_1$-$C_4$alkyl; or
$R_1$ is $C_2$-$C_6$alkenyl, $C_2$-$C_6$haloalkenyl or $C_2$-$C_6$alkynyl;
$X_1$ is O, S or $CR_6$=CH, wherein $R_6$ is hydrogen, halogen, $C_1$-$C_6$haloalkyl or $C_1$-$C_6$haloalkyl substituted by one or two substituents selected from the group consisting of hydroxyl, methoxy and cyano; or $R_6$ is $C_1$-$C_4$haloalkylsulfanyl, $C_1$-$C_4$haloalkylsulfinyl, $C_1$-$C_4$haloalkylsulfonyl, $O(C_1$-$C_4$haloalkyl), or —C(O)$C_1$-$C_4$haloalkyl;
or $X_1$ is N—$R_4$, wherein $R_4$ is $C_1$-$C_4$alkyl;
$X_2$ is N or C—$R_5$, wherein $R_5$ is hydrogen, $C_1$-$C_4$alkyl, $C_1$-$C_4$haloalkyl, halogen or cyano;

$R_2$ is hydrogen, halogen, cyano, $C_1$-$C_6$haloalkyl, or $C_1$-$C_6$haloalkyl substituted by one or two substituents selected from the group consisting of hydroxyl, methoxy and cyano; or
$R_2$ is $C_1$-$C_4$haloalkylsulfanyl, $C_1$-$C_4$haloalkylsulfinyl, $C_1$-$C_4$haloalkylsulfonyl, $O(C_1$-$C_4$haloalkyl), or —C(O)$C_1$-$C_4$haloalkyl;
$R_3$ is $C_1$-$C_4$alkyl, $C_2$-$C_6$alkenyl, $C_2$-$C_6$alkynyl, $C_1$-$C_4$alkoxy-$C_1$-$C_4$alkyl or $C_3$-$C_6$cycloalkyl; and
and $Yb_2$ is —$B(OH)_2$, —$B(OR_{b2})_2$, in which $R_{b2}$ is a $C_1$-$C_6$alkyl or $Yb_2$ is

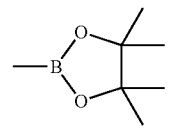

(a 4,4,5,5-tetramethyl-1,3,2-dioxaborolane group).

* * * * *